US008268605B2

(12) United States Patent
Sorge et al.

(10) Patent No.: US 8,268,605 B2
(45) Date of Patent: *Sep. 18, 2012

(54) COMPOSITIONS AND METHODS UTILIZING DNA POLYMERASES

(75) Inventors: Joseph A. Sorge, Wilson, WY (US); Connie Jo Hansen, San Diego, CA (US); Holly Hogrefe, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 09/896,923

(22) Filed: Jun. 29, 2001

(65) Prior Publication Data

US 2003/0157483 A1    Aug. 21, 2003

Related U.S. Application Data

(63) Continuation-in-part of application No. 09/698,341, filed on Oct. 27, 2000, now Pat. No. 6,946,273.

(60) Provisional application No. 60/162,600, filed on Oct. 29, 1999.

(51) Int. Cl.
*C12N 9/12* (2006.01)
(52) U.S. Cl. ...................................... 435/194; 536/23.2
(58) Field of Classification Search .................. 435/194, 435/183, 91.2; 530/350, 23.2
See application file for complete search history.

(56) References Cited

U.S. PATENT DOCUMENTS

| 5,545,552 | A | * | 8/1996 | Mathur ....................... 435/252.3 |
| 5,674,679 | A | | 10/1997 | Fuller ............................... 435/6 |
| 5,882,904 | A | * | 3/1999 | Riedl et al. ................... 435/91.2 |
| 6,027,913 | A | | 2/2000 | Sommer | |
| 2004/0081965 | A1 | | 4/2004 | Sorge et al. | |

FOREIGN PATENT DOCUMENTS

| WO | 97/39150 | 10/1997 |
| WO | 99/06538 | 2/1998 |
| WO | WO 01/23411 A2 | 4/2001 |
| WO | WO 01/32887 A1 | 5/2001 |
| WO | WO 01/38546 A1 | 5/2001 |
| WO | WO 01/92501 | 12/2001 |
| WO | WO 03/054139 | 7/2003 |
| WO | WO 2004/039947 | 5/2004 |

OTHER PUBLICATIONS

Ngo et al., Computational Complexity, Protein Structure Prediction, and the Levinthal Paradox, in the Protein Folding Problem and Tertiary Structure Prediction, 1994, Merz et al. (ed.), Birkhauser, Boston, MA, pp. 433 and 492-495.*
Gardner and Jack, Nucleic Acids Research, vol. 27, pp. 2545-2553, Jun. 1999.*
Gardner, Andrew and Jack, William, "Determinants of nucleotide sugar recognition in an archaeon DNA polymerase", *Nucleic Acids Research*, (1999), vol. 27, No. 12, 2545-2553.
Tabor, Stanley and Richardson, Charles C., "A single residue in DNA polymerases of the *Escherichia coli* DNA polymerase I family is critical for distinguishing between deoxy- and dideoxyribonucleotides", *Proc. Natl. Acad. Sci. USA*, (1995) vol. 92, 6339-6343.
International Search Report based on PCT/US02/20562 dated Sep. 22, 2003.
Supplemental European Search Report from EP02803260, dated Dec. 13, 2004.
Syvanen, A., "From Gels to Chips: 'Minisequencing' Primer Extension for Analysis of Point Mutations and Single Nucleotide Polymorphisms," *Human Mutation* 13:1-10 (1999).
Dong, Qun et al., "Mutational Studies of Human DNA Polymerase," Journal of Biological Chemistry, vol. 268, No. 32, 24163-24174, 1993.
U.S. Appl. No. 10/839,456, filed May 5, 2004. Office Action mailed Dec. 13, 2007.
Office Action mailed May 13, 2009 in U.S. Appl. No. 11/435,018.
Supplemental Partial European Search Report received in EP1766065, dated Jul. 6, 2009, pp. 1-5.

* cited by examiner

*Primary Examiner* — Richard Hutson

(57) ABSTRACT

The invention features a novel isolated Family B DNA polymerase, a *Thermococcus* polymerase JDF-3, and mutant recombinant forms thereof. Mutant polymerases of the invention are deficient in 3' to 5' exonuclease activity and/or exhibit reduced discrimination against non-conventional nucleotides relative to the wild-type form of the polymerase.

95 Claims, 26 Drawing Sheets

FIG. 1.
JDF-3 DNA polymerase nucleotide sequence: 2331 nucleotides (SEQ ID NO: 1)

```
ATGATCCTTGACGTTGATTACATCACCGAGAATGGAAAGCCCGTCATCAGGGTCTTCAAGAAGGAGAACGG
CGAGTTCAGGATTGAATACGACCGCGAGTTCGAGCCCTACTTCTACGCGCTCCTCAGGGACGACTCTGCCA
TCGAAGAAATCAAAAAGATAACCGCGGAGAGGCACGGCAGGGTCGTTAAGGTTAAGCGCGCGGAGAAGGTG
AAGAAAAAGTTCCTCGGCAGGTCTGTGGAGGTCTGGGTCCTCTACTTCACGCACCCGCAGGACGTTCCGGC
AATCCGCGACAAAATAAGGAAGCACCCCGCGGTCATCGACATCTACGAGTACGACATACCCTTCGCCAAGC
GCTACCTCATAGACAAGGGCCTAATCCCGATGGAAGGTGAGGAAGAGCTTAAACTCATGTCCTTCGACATC
GAGACGCTCTACCACGAGGGAGAAGAGTTTGGAACCGGGCCGATTCTGATGATAAGCTACGCCGATGAAAG
CGAGGCGCGCGTGATAACCTGGAAGAAGATCGACCTTCCTTACGTTGAGGTTGTCTCCACCGAGAAGGAGA
TGATTAAGCGCTTCTTGAGGGTCGTTAAGGAGAAGGACCCGGACGTGCTGATAACATACAACGGCGACAAC
TTCGACTTCGCCTACCTGAAAAAGCGCTGTGAGAAGCTTGGCGTGAGCTTTACCCTCGGGAGGGACGGGAG
CGAGCCGAAGATACAGCGCATGGGGACAGGTTTGCGGTCGAGGTGAAGGGCAGGGTACACTTCGACCTTT
ATCCAGTCATAAGGCGCACCATAAACCTCCCGACCTACACCCTTGAGGCTGTATACGAGGCGGTTTTCGGC
AAGCCCAAGGAGAAGGTCTACGCCGAGGAGATAGCCACCGCCTGGGAGACCGGCGAGGGCTTGAGAGGGT
CGCGCGCTACTCGATGGAGGACGCGAGGGTTACCTACGAGCTTGGCAGGGAGTTCTTCCCGATGGAGGCCC
AGCTTTCCAGGCTCATCGGCCAAGGCCTCTGGACGTTTCCCGCTCCAGCACCGGCAACCTCGTCGAGTGG
TTCCTCCTAAGGAAGGCCTACGAGAGGAACGAACTCGCTCCCAACAAGCCCGACGAGAGGGAGCTGGCGAG
GAGAAGGGGGGGCTACgCCGGTGGCTACGTCAAGGAGCCGGAGCGGGGACTGTGGGACAATATCGTGTATC
TAGACTTTCGTAGTCTCTACCCTTCAATCATAATCACCCACAACGTCTCGCCAGATACGCTCAACCGCGAG
GGGTGTAGGAGCTACGACGTTGCCCCCGAGGTCGGTCACAAGTTCTGCAAGGACTTCCCCGGCTTCATTCC
GAGCCTGCTCGGAAACCTGCTGGAGGAAAGGCAGAAGATAAAGAGGAAGATGAAGGCAACTCTCGACCCGC
TGGAGAAGAATCTCCTCGATTACAGGCAACGCGCCATCAAGATTCTCGCCAACAGCTACTACGGCTACTAC
GGCTATGCCAGGGCAAGATGGTACTGCAGGGAGTGCGCCGAGAGCGTTACGGCATGGGGAAGGGAGTACAT
CGAAATGGTCATCAGAGAGCTTGAGGAAAGTTCGGTTTTAAAGCCCTCTATGCAGACACAGACGGTCTCC
ATGCCACCATTCCTGGAGCGGACGCTGAAACAGTCAAGAAAAGGCAATGGAGTTCTTAAACTATATCAAT
CCCAAACTGCCCGGCCTTCTCGAACTCGAATACGAGGGCTTCTACGTCAGGGGCTTCTTCGTCACGAAGAA
AAAGTACGCGGTCATCGACGAGGAGGGCAAGATAACCACGCGCGGGCTTGAGATAGTCAGGCGCGACTGGA
GCGAGATAGCGAAGGAGACGCAGGCGAGGGTTTTGGAGGCGATACTCAGGCACGGTGACGTTGAAGAGGCC
GTCAGAATTGTCAGGGAAGTCACCGAAAGCTGAGCAAGTACGAGGTTCCGCCGAGAAGCTGGTTATCCA
CGAGCAGATAACGCGCGAGCTCAAGGACTACAAGGCCACCGGCCCGCACGTAGCCATAGCGAAgCGTTTGG
CCGCCAGAGGTGTTAAAATCCGGCCCGGAACTGTGATAAGCTACATCGTTCTGAAGGGCTCCGGAAGGATA
GGCGACAGGGCGATTCCCTTCGACGAGTTCGACCCGACGAAGCACAAGTACGATGCGGACTACTACATCGA
GAACCAGGTTCTGCCGGCAGTTGAGAGAATCCTCAGGGCCTTCGGCTACCGCAAGGAAGACCTGCGCTACC
AGAAGACGAGGCAGGTCGGGCTTGGCGCGTGGCTGAAGCCGAAGGGGAAGAAGAAGTGA
```

FIG. 2.
JDF-3 DNA polymerase amino acid sequence (SEQ ID NO: 2)
Theoretical molecular weight: 90.3 kD

```
MILDVDYITENGKPVIRVFKKENGEFRIEYDREFEPYFYALLRDDSAIEEIKKITAERHGRVVKVKRAEKV
KKKFLGRSVEVWVLYFTHPQDVPAIRDKIRKHPAVIDIYEYDIPFAKRYLIDKGLIPMEGEEELKLMSFDI
ETLYHEGEEFGTGPILMISYADESEARVITWKKIDLPYVEVVSTEKEMIKRFLRVVKEKDPDVLITYNGDN
FDFAYLKKRCEKLGVSFTLGRDGSEPKIQRMGDRFAVEVKGRVHFDLYPVIRRTINLPTYTLEAVYEAVFG
KPKEKVYAEEIATAWETGEGLERVARYSMEDARVTYELGREFFPMEAQLSRLIGQGLWDVSRSSTGNLVEW
FLLRKAYERNELAPNKPDERELARRRGGYAGGYVKEPERGLWDNIVYLDFRSLYPSIIITHNVSPDTLNRE
GCRSYDVAPEVGHKFCKDFPGFIPSLLGNLLEERQKIKRKMKATLDPLEKNLLDYRQRAIKILANSYYGYY
GYARARWYCRECAESVTAWGREYIEMVIRELEEKFGFKVLYADTDGLHATIPGADAETVKKKAMEFLNYIN
PKLPGLLELEYEGFYVRGFFVTKKKYAVIDEEGKITTRGLEIVRRDWSEIAKETQARVLEAILRHGDVEEA
VRIVREVTEKLSKYEVPPEKLVIHEQITRELKDYKATGPHVAIAKRLAARGVKIRPGTVISYIVLKGSGRI
GDRAIPFDEFDPTKHKYDADYYIENQVLPAVERILEAFGYRKEDLRYQKTRQVGLGAWLKPKGKKK
```

FIG. 3.
JDF-3 DNA polymerase with intein sequence (SEQ ID NO: 3)

| | |
|---|---|
| MILDVDYITENGKPVIRVFKKENGEFRIEYDREFEPYFYALLRDDSAIEE<br>IKKITAERHGRVVKVKRAEKVKKKFLGRSVEVWVLYFTHPQDVPAIRDKI<br>RKHPAVIDIYEYDIPFAKRYLIDKGLIPMEGEEELKLMSFDIETLYHEGE<br>EFGTGPILMISYADESEARVITWKKIDLPYVEVVSTEKEMIKRFLRVVKE<br>KDPDVLITYNGDNFDFAYLKKRCEKLGVSFTLGRDGSEPKIQRMGDRFAV<br>EVKGRVHFDLYPVIRRTINLPTYTLEAVYEAVFGKPKEKVYAEEIATAWE<br>TGEGLERVARYSMEDARVTYELGREFFPMEAQLSRLIGQGLWDVSRSSTG<br>NLVEWFLLRKAYERNELAPNKPDERELARRRGGYAGGYVKEPERGLWDNI<br>VYLDFRSLYPSIIITHNVSPDTLNREGCRSYDVAPEVGHKFCKDFPGFIP<br>SLLGNLLEERQKIKRKMKATLDPLEKNLLDYRQRAIKILAN | Extein 1 |
| SLLPGEWVA<br>VIEGGKLRPVRIGELVDGLMEASGERVKRDGDTEVLEVEGLYASPSTGSP<br>RKPAQCR*KP**GTAMPGKFTE*LSTPEGGLSVTRGHSLFAYRDASLWR*<br>RGRRRFKPGDLLAVPSG*PSRRGGRGSTSLNCSSNCPRRKRPTCHRHSGK<br>GRKNFFRGMLRTLRWIFGEEKTGGRPGATWSTLRGLGYVKLRKIGYGVVD<br>REGLGKVPRFYERLVEVIRYNGNRGEFIADFNALRPVLRLMMPEKELEEW<br>LVGTRNGFRIRPFIEVDWKFAKLLGYYVSEGSAGKWKNRTGGWSYSVRLY<br>NEDGSVLDDMERLARSSLGA*ARGELRRDFKEDGLHNLRGALRFTGREQE<br>GSVAYLHVP*GGPLGLP*GVLHRRRRRSPEQDGSALHQERASG*RPRPAP<br>ELAGRLSDKRPPRQRGLQGLRERGTALYRVPEAEERLTYSHVIPREVLEE<br>TSAGPSRRT*VTGNSGSWWKAGSSTRKGPVG*AGSSTGI*SSTGSRKSGR<br>KATRGTSTT*ALRRTRTSGGLWVPLRRQX | Intein 1 |
| SYYGYYGYARARWYCRECAES<br>VTAWGREYIEMVIRELEEKFGFKVLYADTDGLHATIPGADAETVKKKAME<br>FLNYINPKLPGLLELEYEGFYVRGFFVTKKKYAVIDEEGKITTRGLEIVR<br>RDWSEIAKETQARVLEAILRHGDVEEAVRIVREVTEHLSKYEVPPEKLVI<br>HEQITRELKDYKATGPHVAIAKRLAARGVKIRPGTVISYIVLKGSGRIGD<br>RAIPFDEFDPTKHKYDADYYIENQVLPAVERILRAFGYRKEDLRYQKTRQ<br>VGLGAWLKPKGKKK | Extein 2 |

FIG. 4.
JDF-3 DNA polymerase genomic sequence (SEQ ID NO: 4)

AATTCCACTGCCGTGTTTAACCTTTCCACCGTTGAACTTGAGGGTGATTT
TCTGAGCCTCCTCAATCACTTAATCGAGACCGCGGATTACCTTGAACTGG
TACACGTTCAACGATTCGGTTCTTGTAATGGTCGATACTGGGCCGTGCTG
GATTTTCTAAACGTCTCAAGAACGGCTTTCATCAACGGAAACTGCCACGT  5' untranslated sequence
CTCCGCCGTCGTGAGGGTTAAACCTGAAGTTCAAGACTTTGCAACGGAAT
GGCGAGAGAACGGCGACTACCCCAGTGGAAGAGCTTTTGAAAGCCAAAGC
CGAGCTTCAGCGAATGTGCGGTGCCCTTGTTCAAGAGTTGTGAGCCCTTG
ATTGTTGTTTTCTCCTCTTTTCTGATAACATCGATGGCGAAGTTTATTAG
TTCTCAGTTCGATAATCAGGCAGGTGTTGGTC ATGATCCTTGACGTTGAT
TACATCACCGAGAATGGAAAGCCCGTCATCAGGGTCTTCAAGAAGGAGAA
CGGCGAGTTCAGGATTGAATACGACCGCGAGTTCGAGCCCTACTTCTACG
CGCTCCTCAGGGACGACTCTGCCATCGAAGAAATCAAAAGATAACCGCG
GAGAGGCACGGCAGGGTCGTTAAGGTTAAGCGCGCGGAGAAGGTGAAGAA
AAAGTTCCTCGGCAGGTCTGTGGAGGTCTGGGTCCTCTACTTCACGCACC
CGCAGGACGTTCCGGCAATCCGCGACAAAATAAGGAAGCACCCCGCGGTC
ATCGACATCTACGAGTACGACATACCCTTCGCCAAGCGCTACCTCATAGA
CAAGGGCCTAATCCCGATGGAAGGTGAGGAAGAGCTTAAACTCATGTCCT
TCGACATCGAGACGCTCTACCACGAGGAGAAGAGTTTGGAACCGGGCCG
ATTCTGATGATAAGCTACGCCGATGAAAGCGAGGCGCGCGTGATAACCTG
GAAGAAGATCGACCTTCCTTACGTTGAGGTTGTCTCCACCGAGAAGGAGA
TGATTAAGCGCTTCTTGAGGGTCGTTAAGGAGAAGGACCCGGACGTGCTG
ATAACATACAACGGCGACAACTTCGACTTCGCCTACCTGAAAAAGCGCTG
TGAGAAGCTTGGCGTGAGCTTTACCCTCGGGAGGGACGGGAGCGAGCCGA  Extein 1
AGATACAGCGCATGGGGACAGGTTTGCGGTCGAGGTGAAGGGCAGGGTA
CACTTCGACCTTTATCCAGTCATAAGGCGCACCATAAACCTCCCGACCTA
CACCCTTGAGGCTGTATACGAGGCGGTTTTCGGCAAGCCCAAGGAGAAGG
TCTACGCCGAGGAGATAGCCACCGCCTGGGAGACCGGCGAGGGGCTTGAG
AGGGTCGCGCGCTACTCGATGGAGGACGCGAGGGTTACCTACGAGCTTGG
CAGGGAGTTCTTCCCGATGGAGGCCCAGCTTTCCAGGCTCATCGGCCAAG
GCCTCTGGGACGTTTCCCGCTCCAGCACCGGCAACCTCGTCGAGTGGTTC
CTCCTAAGGAAGGCCTACGAGAGGAACGAACTCGCTCCCAACAAGCCCGA
CGAGGGGAGCTGGCGAGGAGAAGGGGCGGCTACGCCGGTGGCTACGTCA
AGGAGCCGGAGCGGGGACTGTGGGACAATATCGTGTATCTAGACTTTCGT
AGTCTCTACCCTTCAATCATAATCACCCACAACGTCTCGCCAGATACGCT
CAACCGCGAGGGTGTAGGAGCTACGACGTTGCCCCCGAGGTCGGTCACA
AGTTCTGCAAGGACTTCCCCGGCTTCATTCCGAGCCTGCTCGGAAACCTG
CTGGAGGAAAGGCAGAAGATAAAGAGGAAGATGAAGGCAACTCTCGACCC
GCTGGAGAAGAATCTCCTCGATTACAGGCAACGCGCCATCAAGATTCTCG
CCAAC AGCCTTCTTCCCGGGGAGTGGGTTGCGGTCATTGAAGGGGGGAAA
CTCAGGCCCGTCCGCATCGGCGAGCTGGTTGATGGACTGATGGAAGCCAG
CGGGGAGAGGGTGAAAAGAGACGGCGACACCGAGGTCCTTGAAGTCGAGG
GGCTTTACGCCTCTCCTTCGACAGGGAGTCCAAGAAAGCCCGCACAATGC
CGGTGAAAGCCGTGATAAGGCACCGCTATGCCGGGAAGTTTACAGAATA
GCTCTCAACTCCGGAAGGAGGATTAAGCGTGACGCGCGGCCACAGCCTCT  Intein 1
TCGCGTACCGGGACGCGAGCTTGTGGAGGTGACGGGGGAGGAGGAGGTTC
AAGCCCGGCGACCTCCTGGCGGTGCCAAGCGGATAACCCTCCCGGAGAGG

FIG. 4 (cont)

AGGGAGAGGCTAACATCGTTGAACTGCTCCTCGAACTGCCCGAGGAGGA
AACGGCCGACATGTCATCGACATTCCGGCAAGGGTAGAAAGAACTTCTTC
AGGGGAATGCTCAGAACCCTCCGCTGGATTTTCGGGGAGGAGAAGACCGG  Intein 1
AGGGCGGCCAGGCGCTACCTGGAGCACCTTGCGTGGGCTCGGCTACGTGA
AGCTGAGGAAAATCGGCTACGGGGTGGTTGATAGGGAGGGACTGGGAAAG
GTACCGCGCTTCTACGAGAGGCTCGTGGAGGTAATCCGCTACAACGGCAA
CAGGGGGGAGTTCATCGCCGATTTCAACGCGCTCCGCCCCGTCCTCCGCC
TGATGATGCCCGAGAAGGAGCTTGAAGAGTGGCTCGTTGGGACGAGGAAC
GGGTTCAGGATAAGGCCGTTCATAGAGGTTGATTGGAAGTTCGCAAAGCT
CCTCGGCTACTACGTGAGCGAGGGAGCGCCGGGAAGTGGAAAAACCGGA
CCGGGGGCTGGAGCTACTCGGTGAGGCTTTACAACGAGGACGGGAGCGTT
CTCGACGACATGGAGAGACTCGCGAGGAGTTCTTTGGGGGCGTGAGCGCG
GGGGGAACTACGTCGAGATTTCAAAGAAGATGGCCTACATAATCTTCGAG
GGGCTCTGCGGTTCACCGGCCGAGAACAAGAGGGTTCCGTGGCTTATCTT
CACGTCCCTGAGGAGGTCCGCTGGGCCTTCCTTGAGGGGTACTTCATCG
GCGACGGCGACGTTCACCCGAGCAAGATGGTTCGGCTCTCCACCAAGAGC
GAGCTTCTGGCTAACGGCCTCGTCCTGCTCCTGAACTCGCTGGGCGTCTC
AGCGATAAACGTCCGCCACGACAGCGGGGTTTACAGGGTCTACGTGAACG
AGGAACTGCCCTTTACAGAGTACCGGAAGCGGAAGAACGCCTCACTTACT
CCCACGTCATACCGAGGGAAGTGCTGGAGGAGACTTCGGCCGGGCCTTCC
AGAAGAACATGAGTCACGGGAAATTCAGGGAGCTGGTGGAAAGCGGGGAG
CTCGACGCGGAAAGGGCCGGTAGGATAGGCTGGCTCCTCGACGGGGATAT
AGTCCTCGACAGGGTCTCGGAAGTCAGGAAGGAAAGCTACGAGGGGTACG
TCTACGACCTGAGCGTTGAGGAGGACGAGAACTTCTGGCGGGCTTTGGGT
TCCTCTACGCGCACAACNN

```
                       AGCTACTACGGCTACTACGGCTATGCCAGGG
CAAGATGGTACTGCAGGGAGTGCGCCGAGAGCGTTACGGCATGGGGAAGG
GAGTACATCGAAATGGTCATCAGAGAGCTTGAGGAAAAGTTCGGTTTTAA
AGTCCTCTATGCAGACACAGACGGTCTCCATGCCACCATTCCTGGAGCGG
ACGCTGAAACAGTCAAGAAAAAGGCAATGGAGTTCTTAAACTATATCAAT
CCCAAACTGCCCGGCCTTCTCGAACTCGAATACGAGGGCTTCTACGTCAG
GGGCTTCTTCGTCACGAAGAAAAAGTACGCGGTCATCGACGAGGAGGGCA
AGATAACCACGCGCGGGCTTGAGATAGTCAGGCGCGACTGGAGCGAGATA
GCGAAGGAGACGCAGGCGAGGGTTTTGGAGGCGATACTCAGGCACGGTGA   Extein 2
CGTTGAAGAGGCCGTCAGAATTGTCAGGGAAGTCACCGAAAGCTGAGCA
AGTACGAGGTTCCGCCGGAGAAGCTGGTTATCCACGAGCAGATAACGCGC
GAGCTCAAGGACTACAAGGCCACCGGCCCGCACGTAGCCATAGCGAAGCG
TTTGGCCGCCAGAGGTGTTAAAATCCGGCCCGGAACTGTGATAAGCTACA
TCGTTCTGAAGGGCTCCGGAAGGATAGGCGACAGGGCGATTCCCTTCGAC
GAGTTCGACCCGACGAAGCACAAGTACGATGCGGACTACTACATCGAGAA
CCAGGTTCTGCCGGCAGTTGAGAGAATCCTCAGGGCCTTCGGCTACCGCA
AGGAAGACCTGCGCTACCAGAAGACGAGGCAGGTCGGGCTTGGCGCGTGG
CTGAAGCCGAAGGGGAAGAAGAAGTGA
```

```
                          GGAATTATCTGGTTTCTTTTCCC
AGCATTAAATGCTTCCGACATTGCCTTATTTATGAAAACTCCTGTTGTGCC
TGAGTTTGTGCCAGAAAACAGCCTGTTCTGACGGCGCTTTTTCTTGCCAG
GTCTCTTGAGTTTCGCAAGGGTCTTCTCGACCAGCTCAATGGTCTTGTCG
TCATTGTTTNNNNNNNNNNNNNNNNNNNNNCCCGGGGACTTCATACTGGC
GGTAATAGACAGGGATTCCTTCCTCAAGGACTTCCCGGGAGGCATTGGAG
TTTTTTGGTGGGGCTTTCACAGGATTTGCTCATCTTGTGGATTTCTCGTT
CGATTGAATCTGTCCACTTGAGGGTGTAGGTCGAGACGGTGGAGCGCGTA
```

FIG. 4 (con't)

```
TTCCGGGAGCGGGTCTTGAGGCTCCATTTTTCAGTCCTCCTCCGGCGAAG  3' Untranslated sequence
AAGTGGAACTCAAGCCGGGTGTTAGCTTATGTTATGTTCCCAACTCCTCC
AGCACCTCCAGGATCCCCTCAATCCCGGAACCTCGAAGCCCTCTCGTGG
ATCTTTCTAACTTCCTCTGCCTCCGGGTTTATCCAGACCGCCCACATGCC
GGCTCTCAGCGCACCCTCGAAATCCTCCGCGTAGGTGTCGCCGATGTGGA
TTGCCTCGTCCGGCTCGACCCCGAAGCATCGAGCGGTTTTCTGAACATCT
CGGGCATCGGCTTATACGCCAGAACCTCGTCGGCGAAGAAGGTTCCCTCA
ATGTAGTCCATCAGGCCGAACCTCTCGAGGGGGGCCCGGTACCCAATTC
GCCCTATAGTGAGTCGATTACAATTCACTGGCCGTCGTTTTACAACGTCG
TGACTGGGAAAACCCTGGCGTTACCCAACTTAAGTCGCTTTGCAGCACAT
CCCCC
```

Sequencing with Purified Mutants

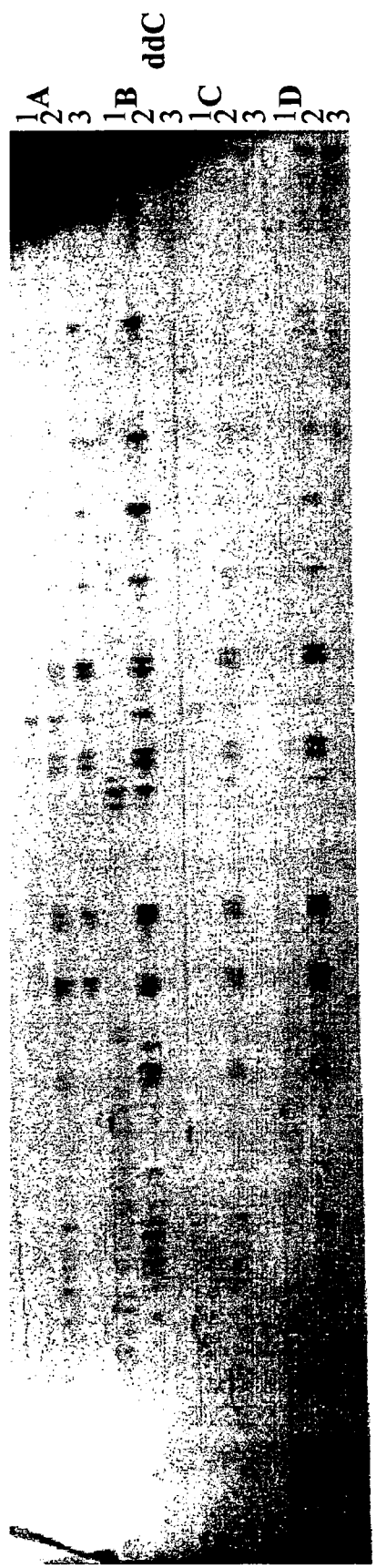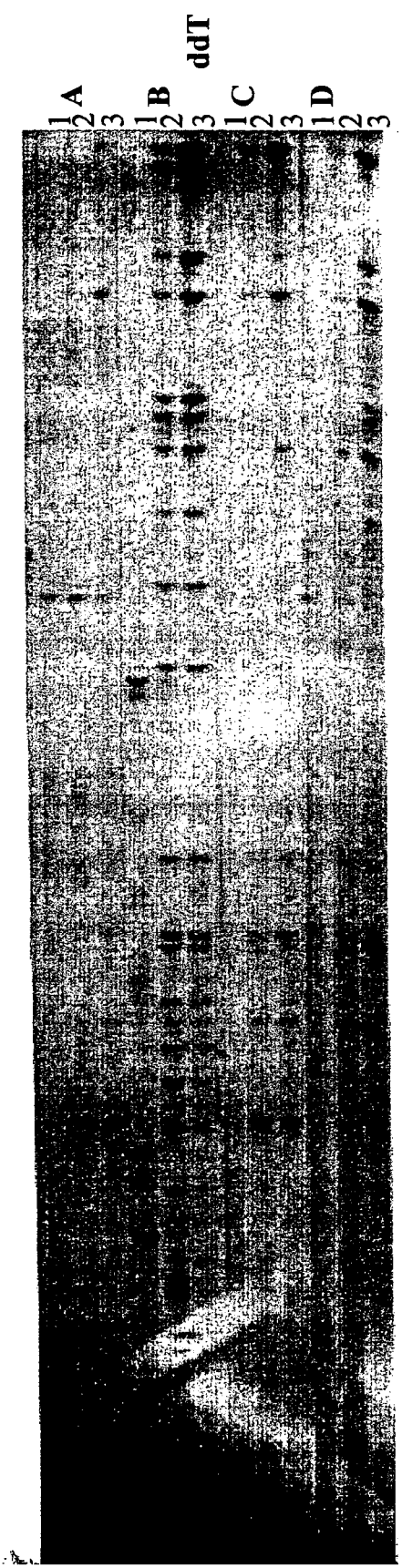
FIG. 7B

Figure 14

```
4    140  YRQRAIKILANSYYGYCGYARARWYCRECAESVTAWGREYIEMVIRELEEKFGFKVLYAD
10   141  YRQRAIKILANSYYGYYGYARARWYCRECAESVTAWGREYIEMVIRELEEKFGFKVLYAD
13   141  YRQRAIKILANSYYGYYGYARARWYCRECAESVTAWGREYIEMVIRELEEKFGFKVLYAD
16   141  YRQRAIKILANSYYGYYGYARARWYCRECAESVTAWGREYIEMVIRELEEKFGFKVLYAD
18   141  YRQRAIKILANSYYGYYGYARARWYCRECAESVTAWGREYIEMVIRELEEKFGFKVLYAD
19   141  YRQRAIKILANSYYGYYGYARARWYCRECAESVTAWGREYIEMVIRELEEKFGFKVLYAD
28   141  YRQRAIKILANSYYGYYGYARARWYCRECAESVTAWGREYIEMVIRELEEKFGFKVLYAD
34   141  YRQRAIKILANSYYGYYGYARARWYCRECAESVTAWGREYIEMVIRELEEKFGFKVLYAD
41   141  YRQRAIKILANSYYGYYGYARARWYCRECAESVTAWGREYIEMVIRELEEKFGFKVLYAD
33   141  YRQRAIKILANSYYGYYGYARARWYCRECAESVTAWGREYIEMVIRELEEKFGFKVLYAD
48   141  YRQRAIKILANSYYGYYGYARARWYCRECAESVTAWGREYIEMVIRELEEKFGFKVLYAD
55   142  YRQRAIKILANSYYGYYGYARARWYCRECAESVTAWGREYIEMVIRELEEKFGFKVLYAD
64   144  YRQRAIKILANSYYGNYGYARARWYCRECAESVTAWGREYIEMVIRELEEKFGFKVLYAD
Jdf3 481  YRQRAIKILANSYYGYYGYARARWYCRECAESVTAWGREYIEMVIRELEEKFGFKVLYAD 4    200  TDGLHATIPGADAETVKKKAMEFLNYINPKLPGLLELEYEGFYVRGFFVTKKKYAVIDEE
10   201  TDGLHATIPGADAETVKKKAMEFLNYINPKLPGLLELEYEGFYVRGFFVTKKKYAVIDEE
13   201  TDGLHATIPGADAETVKKKAMEFLNYINPKLPGLLELEYEGFYVRGFFVTKKKYAVIDEE
16   201  TDGLHATIPGADAETVKKKAMEFLNYINPKLPGLLELKYEGFYVRGFFVTKKKYAVIDEE
18   201  TDGLHATIPGADAETVKKKAMEFLNYINPKLPGLLELEYEGFYVRGFFVTKKKYAVIDEE
19   201  TDGLHATIPGADAETVKKKAMEFLNYINKLPGLLELEYEGFYVRGFFVTKKKXAVIDEE
28   201  TDGLHATIPGADAETVKKKAMEFLNYINPKLPGLLELEYEGFYVRGFFVTKKKYAVIDEE
34   201  TDGLHATIPGADAETVKKKAMEFLNYINPKLPGLLELEYEGFYVRGFFVTKKKYAVIDEE
41   201  TDGLHATIPGADAETVKKKAMEFLNYINPKLPGLLELEYEGFYVRGFFVTKKKYAVIDEE
33   201  TDGLHATIPGADAETVKKKAMEFLNYINPKLPGLLEPEYEGFYVRGFFVTKKKYAVIDEE
48   201  TDGLHATIPGADAETVKKKAMEFLNYINPKLPGLLELEYEGFYVRGFFVTKKKYAVIDEE
55   202  TDGLHATIPGADAETVKKKAMEFLNYINPKLPGLLELEYEGFYVRGFFVTKKKYAVIDEE
64   204  TDGLHATIPGADAETVKKKAMEFLNYINPKLPGLLELEYEGFYVRGFFVTKKKYAVIDEE
Jdf3 541  TDGLHATIPGADAETVKKKAMEFLNYINPKLPGLLELEYEGFYVRGFFVTKKKYAVIDEE 4    260  GKITTRGLEIVRRDWSEIAKETQARVLEAVLRHGDVEEAVRIVREVTEKLSKYEVPPEKL
10   261  GKITTRGLEIVRRDWSEIAKETQARVLEAILRHGDVEEAVRIVREVTEKLSKYEVPPEEL
13   261  GKITTRGLEIVRRDWSEIAKETQARVLEAILRHGDVEEAVRIVRKVTEKLSKYEVPPEKL
16   261  GKITTRGLEIVRRDWSEIAKETQARVLEAILRHDDVEEAVRIVREVTEKLSKYEVPPEKL
18   261  GKITTRGLEIVRRDWSEIAKETQARVLEAILRHGDVEEAVRIVREVTEKLSKYEVPPEKL
19   261  GKITTRGLEIVRRDWSKIAKETQARVLEAILRHGDVEEAIRIVREVTEKLSKYEVPPEKL
28   261  GKIATRGLEIVRRDWSEIAKETQARVLEAILRHGDVEEAVRIVREVTEKLSKYEVPPEKL
34   261  GKITTRGLEIVRRDWSEIAKETQARVLEAILRHGDVEEAVRIVREVTEKLNKYEVPPEKL
41   261  GKITTRGLEIVRRDWSEIAKETQARVLEAILRHGDVEEAVRIVREVTEKLSKYEVPPEKL
33   261  GKITTRGLEIVRRDWSEIAKETQARVLEAILRHGDVEEAVRIVREVTEKLSKYEVPPEKL
48   261  GKITTRGLEIVRRDWSEIAKETQARVLEAILRHGDVEEAVRIVREVTEKLSKYEVPPVKL
55   262  GKITTRGLEIVRRDWSEIAKETQARVLEAILRHGDVEEAVRIVREVTEKLSKYEVPPGEA
64   264  GKITTRGLEIVRRDWSEIAKETQARVLEAILRHGDVEEAVRIVREVTEKLSKYEVPPEKL
Jdf3 601  GKITTRGLEIVRRDWSEIAKETQARVLEAILRHGDVEEAVRIVREVTEKLSKYEVPPEKL
```

Figure 15 pBL34A+R6G- pBL31G+TAMpBL28T+R110- pBL25C+ROX- 1  2  3  4  5

COMPOSITIONS AND METHODS UTILIZING DNA POLYMERASES

This application is a continuation-in-part of application U.S. Ser. No. 09/698,341, pending.

FIELD OF THE INVENTION

The present invention relates to compositions and methods utilizing DNA polymerase enzymes with reduced discrimination for non-conventional nucleotides. The enzymes of the invention are useful in many applications calling for the detectable labeling of nucleic acids and are particularly useful in DNA sequencing applications.

BACKGROUND OF THE INVENTION

Detectable labeling of nucleic acids is required for many applications in molecular biology, including applications for research as well as clinical diagnostic techniques. A commonly used method of labeling nucleic acids uses one or more unconventional nucleotides and a polymerase enzyme that catalyzes the template-dependent incorporation of the unconventional nucleotide(s) into the newly synthesized complementary strand.

The ability of a DNA polymerase to incorporate the correct deoxynucleotide is the basis for high fidelity DNA replication in vivo. Amino acids within the active site of polymerases form a specific binding pocket that favors the placement of the correct complementary nucleotide opposite the template nucleotide. If a mismatched nucleotide, ribonucleotide, or nucleotide analog fills that position, the precise alignment of the amino acids contacting the incoming nucleotide may be distorted into a position unfavorable for DNA polymerization. Because of this, the unconventional nucleotides or nucleotide analogs used to label DNA tend to be incorporated into the elongated strand less efficiently than do the standard deoxynucleotide triphosphates (dNTPs; the so-called "standard" dNTPs include deoxyadenosine triphosphate (dATP), deoxycytosine triphosphate (dCTP), deoxyguanosine triphosphate (dGTP), and deoxythymidine triphosphate (dTTP)).

The reduced efficiency with which unconventional nucleotides are incorporated by the polymerase increases the amount of the unconventional nucleotide necessary for DNA labeling. The reduced efficiency of incorporation of a particular nucleotide can also adversely affect the performance of techniques or assays, such as DNA sequencing, that depend upon unbiased incorporation of unconventional nucleotides for homogeneous signal strength.

The identity and exact arrangement of the amino acids of a DNA polymerase that contact an incoming nucleotide triphosphate determine the nature of the nucleotides, both conventional and unconventional, that may be incorporated by that polymerase enzyme. Changes in the exact placement of the amino acids that contact the incoming nucleotide triphosphate at any stage of binding or chain elongation can dramatically alter the polymerase's capacity for utilization of unusual or unconventional nucleotides. Sometimes changes in distant amino acids can influence the incorporation of nucleotide analogs due to indirect global or structural effects. Polymerases with increased capacity to incorporate nucleotide analogs are useful for labeling DNA or RNA strands with nucleotides modified with signal moieties such as dyes, reactive groups or unstable isotopes.

In addition to labeled nucleotides, an extremely important class of modified nucleotides is the dideoxynucleotides. The so-called "Sanger" or "dideoxy" DNA sequencing method (Sanger et al., 1977, Proc. Natl. Acad. Sci. USA 74: 5463, which is incorporated herein by reference) relies upon the template-directed incorporation of nucleotides onto an annealed primer by a DNA polymerase from a mixture containing deoxy- and dideoxynucleotides. The incorporation of a dideoxynucleotide results in chain termination, the inability of the enzyme to catalyze further extension of that strand. Electrophoretic separation of reaction products results in a "ladder" of extension products wherein each extension product ends in a particular dideoxynucleotide complementary to the nucleotide opposite it in the template. The distance of the dideoxynucleotide analog from the primer is indicated by the length of the extension product. When four reactions, each containing one of the four dideoxynucleotide analogs ddA, ddC, ddG, or ddT (ddNTPs) are separated on the same gel, the sequence of the template may be read directly from the ladder patterns. Extension products may be detected in several ways, including for example, the inclusion of isotopically- or fluorescently-labeled primers, deoxynucleotide triphosphates or dideoxynucleotide triphosphates in the reaction.

Fluorescent labeling has the advantages of faster data collection, since detection may be performed while the gel is running, and longer reads of sequence data from a single reaction and gel. Further, fluorescent sequence detection has allowed sequencing to be performed in a single reaction tube containing four differentially-labeled fluorescent dye terminators (the so-called dye-terminator method, Lee et al., 1992, Nucleic Acids Res. 20: 2471, incorporated herein by reference).

A desirable quality of a polymerase useful for DNA sequencing is improved incorporation of dideoxynucleotides. Improved incorporation of dideoxynucleotides can make processes such as DNA sequencing more cost effective by reducing the requirement for expensive radioactive or fluorescent dye-labeled dideoxynucleotides. Moreover, unbiased dideoxynucleotide incorporation provides improved signal uniformity, leading to increased accuracy of base determination. The even signal output further allows subtle sequence differences caused by factors like allelic variation to be detected. Allelic variation, which produces two different half strength signals at the position of relevance, can easily be concealed by the varied signal strengths caused by polymerases with non-uniform ddNTP utilization.

Incorporation of ribonucleotides by the native form of DNA polymerase is a rare event. Mutants that incorporate higher levels of ribonucleotides can be used for applications such as sequencing by partial ribosubstitution. In this system, a mixture of ribonucleotides and deoxynucleotides corresponding to the same base are incorporated by the mutant polymerase (Barnes, 1978 J. Mol. Biol. 119:83-99). When the ribosequencing reactions are exposed to alkaline conditions and heat, fragmentation of the extended strand occurs. If the reactions for all four bases are separated on a denaturing acrylamide gel, they produce a sequencing ladder. there is a need in the art for polymerase mutants with higher utilization of ribonucleotides for this alternative method of sequencing.

Alternatively, the incorporation of ribonucleotides followed by alkaline hydrolysis could be utilized in a system that requires random cleavage of DNA molecules such as DNA shuffling ((Stemmer, 1994, Nature, 370: 389-391) which has also been called molecular breeding, sexual PCR and directed evolution).

Another desirable quality in a DNA labeling enzyme is thermal stability. DNA polymerases exhibiting thermal stability have revolutionized many aspects of molecular biology and clinical diagnostics since the development of the polymerase chain reaction (PCR), which uses cycles of thermal denaturation, primer annealing, and enzymatic primer extension to amplify DNA templates. The prototype thermostable DNA polymerase is Taq polymerase, originally isolated from the thermophilic eubacterium *Thermus aquaticus*. So-called "cycle sequencing" reactions using thermostable DNA polymerases have the advantage of requiring smaller amounts of starting template relative to conventional (i.e., non-cycle) sequencing reactions.

There are three major families of DNA polymerases, termed families A, B and C. The classification of a polymerase into one of these three families is based on structural similarity of a given polymerase to *E. coli* DNA polymerase I (Family A), II (Family B) or III (family C). As examples, Family A DNA polymerases include, but are not limited to Klenow DNA polymerase, *Thermus aquaticus* DNA polymerase I (Taq polymerase) and bacteriophage T7 DNA polymerase; Family B DNA polymerases, formerly known as α-family polymerases (Braithwaite and Ito, 1991, Nuc. Acids Res. 19:4045), include, but are not limited to human α, δ and ε DNA polymerases, T4, RB69 and φ29 bacteriophage DNA polymerases, and *Pyrococcus furiosus* DNA polymerase (Pfu polymerase); and family C DNA polymerases include, but are not limited to *Bacillus subtilis* DNA polymerase III, and *E. coli* DNA polymerase III α and ε subunits (listed as products of the dnaE and dnaQ genes, respectively, by Brathwaite and Ito, 1993, Nucleic Acids Res. 21: 787). An alignment of DNA polymerase protein sequences of each family across a broad spectrum of archaeal, bacterial, viral and eukaryotic organisms is presented in Braithwaite and Ito (1993, supra), which is incorporated herein by reference.

The term used to describe the tendency of DNA polymerases to not to carry the incorporation of unnatural nucleotides into the nascent DNA polymer is "discrimination". In Family A DNA polymerases, the effective discrimination against incorporation of dideoxynucleotide analogs is largely associated with a single amino acid residue. The majority of enzymes from the Family A DNA polymerases have a phenylalanine (phe or F) residue at the position equivalent to F762 in *E. coli* Klenow fragment of DNA polymerase and demonstrate a strong discrimination against dideoxynucleotides. A few polymerases (e.g. T7 DNA polymerase) have a tyrosine (tyr or Y) residue at the corresponding position and exhibit relatively weak discrimination against dideoxynucleotides. Family A polymerases with tyrosine at this position readily incorporate dideoxynucleotides at levels equal to or only slightly different from the levels at which they incorporate deoxynucleotides. Conversion of the tyrosine or phenylalanine residues in the site responsible for discrimination reverses the dideoxynucleotide discrimination profile of the Family A enzymes (Tabor and Richardson, 1995, Proc. Natl. Acad. Sci. USA 92:6449).

Among the thermostable DNA polymerases, a mutant form of the Family A DNA polymerase from *Thermus aqaticus*, known as AmpliTaq FS® (Perkin Elmer), contains a F667Y mutation at the position equivalent to F762 of Klenow DNA polymerase and exhibits increased dideoxynucleotide uptake (i.e., reduced discrimination against ddNTPs) relative to the wild-type enzyme. The reduced discrimination for dideoxynucleotide uptake makes it more useful for fluorescent and labeled dideoxynucleotide sequencing than the wild-type enzyme.

The F667Y mutant of Taq DNA polymerase is not suited, however, for use with fluorescein-labeled dideoxynucleotides, necessitating the use of rhodamine dye terminators. Rhodamine dye terminators that are currently utilized with Taq sequencing reactions, however, stabilize DNA secondary structure, causing compression of signal. Efforts to eliminate compression problems have resulted in systems that use high amounts of the nucleotide analog deoxyinosine triphosphate (dITP) in place of deoxyguanosine triphosphate. While incorporation of (dITP) reduces the compression of the signal, the presence of dITP in the reaction produces additional complications including lowered reaction temperatures and increased reaction times. Additionally, the use of rhodamine dyes in sequencing requires undesirable post-reaction purification (Brandis, 1999 Nuc. Acid Res. 27:1912).

Family B DNA polymerases exhibit substantially different structure compared to Family A DNA polymerases, with the exception of the position of acidic residues involved in catalysis in the so-called palm domain (Wang et al., 1997, Cell 89:1087; Hopfner et al., 1999, Proc. Natl. Acad. Sci. USA 96:3600). The unique structure of Family B DNA polymerases may permit a completely different spectrum of interactions with nucleotide analogs, perhaps allowing utilization of analogs which are unsuitable for use with Family A DNA polymerases due to structural constraints. Thermostable Family B DNA polymerases have been identified in hyperthermophilic archaea. These organisms grow at temperatures higher than 901 C. and their enzymes demonstrate greater themostability (Mathur et al., 1992, Stratagies 5:11) than the thermophilic eubacterial Family A DNA polymerases. Family B polymerases from hyperthermophilic archaea may be well suited starting substrates for modification(s) to reduce discrimination against non-conventional nucleotides.

Although the crystal structures of three Family B DNA polymerases have been solved (Wang et al., 1997, supra; Hopfner, K.-P. et al., 1999, Proc. Natl. Acad. Sci. 96: 3600; Zhao, 1999, Structure Fold Des., 7:1189), the structures of DNA-polymerase or dNTP-polymerase co-complexes have not yet been reported. At present, identification of amino acid residues contributing to nucleotide analog discrimination can only be inferred from extrapolation to Family A-dNTP structures or from mutagenesis studies carried out with related Family B DNA polymerases (e.g., human polα, phage T4, phage φ29, *T. litoralis* DNA polymerase).

Sequence comparison of the Family B DNA polymerases indicate six conserved regions numbered I-VI (Braithwaite and Ito, 1993, supra). The crystal structure of bacteriophage RB69 DNA polymerase (Family B) proposed by Wang et al. (Wang et al., 1997, supra) shows that Y416 in region II (which corresponds to Y409 in the Family B DNA polymerase of *Thermococcus* species JDF-3) has the same position as Y115 in HIV reverse transcriptase (RT) and E710 in the Klenow fragment (Family A polymerases). Modeling of the dNTP and primer template complex in RB69 was carried out using the atomic coordinates of the reverse transcriptase-DNA cocrystal. This model predicts the RB69 Y416 packs under the deoxyribose portion of the dNTP. Tyrosine at this position has been implicated in ribose selectivity, contributing to polymerase discrimination between ribonucleotides and deoxribonucleotides in mammalian reverse transcriptases (Y115) (Gao et al., 1997, Proc. Natl. Acad. Sci. USA 94:407; Joyce, 1994, Proc. Natl. Acad. Sci. USA 94:1619) and in Family A DNA polymerases where modification of the corresponding invariable glutamate residue (E710) reduces discrimination against ribonucleotides (Gelfand et al., 1998, Pat. No. EPO823479; Astatke et al, 1998, Proc. Natl. Acad. Sci. USA 96:3402).

Mutagenesis studies done in Family B DNA polymerases also implicate the region containing the analogous Y in region II in dNTP incorporation and ribose selectivity. Mutations at the corresponding Y865 in human DNA polymerase α affect polymerase fidelity and sensitivity to dNTP nucleotide inhibitors such as AZT-TP, which has a bulky 3'-azido group in place of the 3'-OH group, BuPdGTP, which contains a butylphenyl group attached to the amino group at the C-2 position in the guanine base of dGTP (resulting in a bulkier and more hydrophobic purine base nucleotide) and aphidicolin, a competitive inhibitor of pyrimidine deoxynucleotide triphosphate. Interestingly, the mutants showed no difference in their uptake of ddCTP (Dong et al., 1993, J. Biol. Chem. 268: 26143). Additionally, mutants of bacteriophage T4 DNA polymerase, which have converted L412 to methionine (M) or isoleucine (I) just one amino acid before the analogous Y (Y411), show extreme and mild sensitivity, respectively, to the inorganic pyrophosphate analog phosphonoacetic acid (PAA). Alterations in PAA sensitivity have been shown to predict polymerase interactions with nucleotide analogs. L412 in T4 DNA polymerase corresponds to L410 in *Thermococcus* species JDF-3 DNA polymerase. The L412M T4 DNA polymerase mutant was inhibited with 50-fold less ddGTP than wild-type polymerase while the $K_m$s for dGTP was similar. As stated by the authors in that study, "[d]espite the sensitivity of the L412M DNA polymerase to ddGTP, there was no difference found in the incorporation of ddNTPs by wild-type and L412M DNA polymerase." (Reha-Krantz et al., 1993, J. Virol. 67:60). In bacteriophage φ29, mutations in region II (LYP where Y is analogous to *Thermococcus* species JDF3 DNA polymerase Y409) produce mixed results when challenged with PAA; P255S was hypersensitive to PAA while L253V was shown to be less sensitive than the wild-type enzyme (Blasco et al., 1993, J. Biol. Chem. 268: 24106). These data support the role of the LYP region (region II) in polymerase-nucleotide interactions, but improved incorporation of ddNTPs was not achieved in these references.

In another study, extensive mutation of region II in the archaeal Family B DNA polymerase from *Thermococcus litoralis* DNA polymerase (VENT™ polymerase, New England Biolabs) was performed. In that study, 26 different site-directed mutants were made for the sole intent of examining nucleotide analog discrimination (Gardner and Jack, 1999, Nucleic Acids Res. 27: 2545). Site-directed mutagenesis of VENT™ DNA polymerase demonstrated that three mutations at Y412 (which corresponds to JDF-3 DNA polymerase Y409) could alter nucleotide binding (Gardner and Jack, 1999, supra). Y412V was most significant with a 2 fold increase in dideoxynucleotide incorporation and a 200 fold increase in the incorporation of ribonucleotide ATP. The mutation Y412F showed no change in analog incorporation.

Region III of the Family B polymerases (also referred to as motif B) has also been demonstrated to play a role in nucleotide recognition. This region, which corresponds to AA 487 to 495 of JDF-3 Family B DNA polymerase, has a consensus sequence $KX_3NSXYG$ (Jung et al., 1990, supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563), and is functionally, but not structurally (Wang et al., 1997, supra), analogous to $KX_3(F/Y)GX_2YG$ in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem 267: 8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F763 in the Klenow fragment; F667 in Taq) which confers ddNTP discrimination in Family A DNA polymerases ($KX_3$(F/Y)$GX_2YG$) (Tabor and Richardson, 1995, supra).

Directed mutagenesis studies in region III of VENT™ DNA polymerase also targeted an alanine analogous to A485 of the *Thermococcus* species JDF-3 DNA polymerase. These mutants (A→C, A→S, A→L, A→I, A→F and A→V) exhibited a range of specific activities from 0.12 to 1.2 times the polymerase activity of the progenitor enzyme (Gardner and Jack, 1999, Nucl. Acids Res. 27:2545). The dideoxynucleotide incorporation ranged from 4 to 15 times the unmutated enzyme. Interestingly, the mutant with the highest dideoxynucleotide incorporation (15×) had a specific activity of only 0.12× of the original enzyme.

Site-directed mutagenesis studies on the Family B DNA polymerase from *Thermococcus barossii* modified each residue independently in the sequence ILANSF (SEQ ID NO:49), which corresponds to AA residues 488-493 of the JDF-3 DNA polymerase, to tyrosine (Reidl et al., U.S. Pat. No. 5,882,904). That study indicated that an L489Y mutant exhibits approximately 3 times greater incorporation of dideoxynucleotides relative to an enzyme bearing the wild-type leucine residue at this site.

One area of active research involves the use of nucleic acid arrays, often referred to as nucleic acid or DNA "chips", in the simultaneous analyses of multiple different nucleic acid sequences. Many of these applications, such as those described in U.S. Pat. No. 5,882,904 (Reidl et al., issued Mar. 16, 1999) will benefit from DNA polymerases exhibiting reduced discrimination against non-conventional nucleotides, particularly fluorescently-labeled non-conventional nucleotides. Applications being addressed in the chip format include DNA sequencing and mutation detection, among others. For example, the "mini-sequencing" methods (e.g., Pastinen et al., 1997, Genome Res. 7: 606; Syvanen, 1999, Human Mutation 13: 1-10) and the arrayed primer extension (APEX) mutation detection method (Shumaker et al., 1996, Hum. Mutat. 7: 346) and methods like them can benefit from DNA polymerases with reduced discrimination against fluorescently-labeled or other non-conventional nucleotides. There is a need in the art for a non-discriminating DNA polymerase for use in chip or gel based mini-sequencing systems. Such a system would advantageously permit detection of multiplexed single nucleotide polymorphisms (SNPs) and allow for quantitative genotyping. Identification of sequence variation permits the diagnosis and treatment of genetic disorders, predisposition to multifactorial diseases, and sensitivity to new or existing pharmaceutical products.

With the completion of the human genome project, considerable attention is now focused on analyzing genetic variations between individuals, and specifically, single nucleotide polymorphisms (SNPs) which have been estimated to occur one in every 1000 bp (Halushka et al., 1999). The importance of SNPs is that they serve as genetic markers that enable identification of disease related loci (Lai et al., 1998). They can also be used to investigate the underlying cause of genetic diseases and could eventually help pave the way to personalized medicine.

Current assays used in SNP detection include hybridization to allele-specific oligonucleotide (ASO) probes (Saiki et al., 1989), oligonucleotide ligation assay (OLA) (Landegren et al., 1988), restriction fragment length polymorphism (RFLP) (Shi et al., 2001), TaqMan assay (Livak et al., 1995), molecular beacon assay (Tyagi et al., 1998), and primer extension assay (Tyagi et al., 1998; Gilles et al., 1999; Fu et al., 1998) on a variety of platforms including gel electrophoresis (Chen et al., 1997), MALDI-TOF mass spectrometry (Fu et al., 1998), solid phase minisequencing (Syvanen et al., 1990), semiconductor microchips (Gilles et al., 1999), and flow cytometric analysis (Taylor et al., 2001).

The principle of minisequencing is to anneal primers immediately adjacent to the SNP positions to be analyzed and to extend these primers with ddNTPs complementary to the SNP (Syvanen et al., 1990, hereby incorporated as reference) using a DNA polymerase that readily incorporates ddNTPs. Minisequencing is unique since it is based on the high accuracy (high specificity) of polymerase mediated nucleotide incorporation reactions rather than the thermostability of matched and mismatched species which affects most other SNP detection methods. Thus, compared to hybridization-based methods, minisequencing is insensitive to small variations in reaction conditions, temperature, and to flanking DNA sequence. Moreover, minisequencing allows discrimination between homozygous and heterozygous genotypes (Chen et al., 1997). These characteristics are important in multiplexing and/or high throughput SNP detection. With the completion of the genome project and considerable interest in high throughput SNP detection, a significant market exists for enzymes that efficiently incorporate ddNTPs and dye labeled-ddNTPs in single base extension assays (minisequencing).

DNA polymerases constitute a core component of minisequencing protocols. Efficient ddNTP and dye-ddNTP incorporation and high fidelity are essential characteristics of minisequencing enzymes. Commercially available DNA polymerases that are suitable for sequencing and minisequencing have been derived from either Taq (Taq F667Y mutants such as ThermoSequenase and AmpliTaqFS) or bacteriophage T7 DNA polymerase (Sequenase), which are both family A DNA polymerases. A tyrosine (Y) residue in the nucleotide binding pocket of T7 (native) or Taq (engineered F667Y mutant) DNA polymerase confers efficient ddNTP incorporation (Tabor et al., 1995). In two recent mutagenesis studies employing archaeal (family B) DNA polymerases, mutations were identified that reduced ddNTP discrimination; however, the archaeal DNA polymerase mutants incorporated ddNTPs less efficiently than the Taq F667Y mutant (Gardner et al., 1999; Evans et al., 2000).

There is a need in the art for DNA polymerases with reduced discrimination against unconventional nucleotides. There is particularly a need in the art for thermostable DNA polymerases exhibiting reduced discrimination against dideoxynucleotides, and further, for DNA polymerases exhibiting reduced discrimination against fluorescently labeled dideoxynucleotides.

SUMMARY OF THE INVENTION

The present invention relates to compositions and methods utilizing DNA polymerase enzymes exhibiting reduced discrimination against non-conventional nucleotides. Enzymes with this quality are useful in many applications calling for the detectable labeling of nucleic acids and are particularly useful in DNA sequencing applications.

The invention further relates to a Family B DNA polymerase having one or more mutations at a site or sites corresponding to L408, P410, S345, and/or A485 of SEQ ID NO: 2, or a fragment thereof which retains the ability to direct the template-dependent polymerization of nucleic acid. The invention also encompasses mutants and modified versions (e.g., reversibly inactivated versions of a Family B polymerase prepared, for example, by chemical modification or antibody complexing) of a Family B polymerase mutated at sites corresponding to L408, P410 and or A485 of SEQ ID NO: 2.

In one embodiment, the DNA polymerase has a dual mutation comprising comprising a serine to proline mutation at a site corresponding to S345 of SEQ ID NO: 2; and a proline to leucine mutation at a site corresponding to P410 of SEQ ID NO: 2.

The invention encompasses purified thermostable DNA polymerase having an amino acid sequence presented in SEQ ID NO: 2 from residue 1 to 776.

In one embodiment, the thermostable DNA polymerase is isolated from *Thermococcus* species JDF-3.

In another embodiment, the thermostable polymerase is isolated from a recombinant organism transformed with a vector that codes for the expression of *Thermococcus* species JDF-3 DNA polymerase.

The invention further encompasses a recombinant vector comprising the nucleotide sequence presented in SEQ ID NO: 1.

The invention further encompasses an isolated recombinant polypeptide comprising the amino acid sequence of SEQ ID NO: 2 or a functional fragment thereof.

The invention further encompasses an isolated recombinant DNA polymerase from *Thermococcus* species JDF-3 that is 3' to 5' exonuclease deficient.

In one embodiment, the isolated recombinant DNA polymerase of has an aspartic acid to threonine or alanine mutation at the amino acid corresponding to D141 of SEQ ID NO: 2 or a glutamic acid to alanine mutation at the amino acid corresponding to E143 of SEQ ID NO: 2.

In another embodiment, the isolated recombinant DNA polymerase has an aspartic acid to threonine or alanine mutation at the amino acid corresponding to D141 of SEQ ID NO: 2 and a glutamic acid to alanine mutation at the amino acid corresponding to E143 of SEQ ID NO: 2.

The invention further encompasses an isolated recombinant DNA polymerase having reduced discrimination against non-conventional nucleotides.

In one embodiment, the DNA polymerase is a Family B DNA polymerase.

In another embodiment, the DNA polymerase further comprises a mutation selected from the group consisting of: a leucine to histidine mutation at a site corresponding to L408 of SEQ ID NO: 2; a leucine to phenylalanine mutation at a site corresponding to L408 of SEQ ID NO: 2; a proline to leucine mutation at a site corresponding to P410 of SEQ ID NO: 2; and an alanine to threonine mutation at a site corresponding to A485 of SEQ ID NO: 2.

The invention further encompasses an isolated recombinant DNA polymerase having the alanine to threonine mutation at the site corresponding to A485 of SEQ ID NO:2 further comprising a mutation selected from the group consisting of: a leucine to histidine mutation at a site corresponding to L408 of SEQ ID NO: 2; a leucine to phenylalanine mutation at a site corresponding to L408 of SEQ ID NO: 2; and a proline to leucine mutation at a site corresponding to P410 of SEQ ID NO: 2.

The invention further encompasses an isolated recombinant DNA polymerase having the a proline to leucine mutation at a site corresponding to P410 of SEQ ID NO: 2, further comprising of serine to proline mutation at a site corresponding to S345 of SEQ ID NO: 2

In another embodiment, the DNA polymerase has reduced discrimination against a non-conventional nucleotide selected from the group consisting of: dideoxynucleotides, ribonucleotides and conjugated nucleotides.

In another embodiment, conjugated nucleotide is selected from the group consisting of radiolabeled nucleotides, fluorescently labeled nucleotides, biotin labeled nucleotides, chemiluminescently labeled nucleotides and quantum dot labeled nucleotides.

The invention further encompasses an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase.

In one embodiment, the Family B DNA polymerase is 3' to 5' exonuclease deficient.

In another embodiment, the Family B DNA polymerase has a mutation at an amino acid corresponding to D141 or E143 of SEQ ID NO: 2.

In another embodiment, the Family B DNA polymerase has an aspartic acid to threonine or alanine mutation at a site corresponding to D141 of SEQ ID NO: 2.

In another embodiment, the Family B DNA polymerase has a glutamic acid to alanine mutation at a site corresponding to E143 of SEQ ID NO: 2.

In another embodiment, the Family B DNA polymerase has a glutamic acid to alanine mutation at a site corresponding to E143 of SEQ ID NO: 2 and has an aspartic acid to threonine or alanine mutation at the amino acid corresponding to D141 of SEQ ID NO: 2.

In another embodiment, the Family B DNA polymerase is thermostable.

In another embodiment, the Family B DNA polymerase is archaeal.

In another embodiment, the Family B DNA polymerase comprises a leucine to histidine mutation at a site corresponding to L408 of SEQ ID NO: 2.

In another embodiment, the Family B DNA polymerase comprises a leucine to phenylalanine mutation at a site corresponding to L408 of SEQ ID NO: 2.

In another embodiment, the Family B DNA polymerase comprises a proline to leucine mutation at a site corresponding to P410 of SEQ ID NO: 2.

In another embodiment, the Family B DNA polymerase comprises an alanine to threonine mutation at a site corresponding to A485 of SEQ ID NO: 2.

In another embodiment, the Family B DNA polymerase comprising an alanine to threonine mutation at a site corresponding to A485 of SEQ ID NO: 2 comprises a leucine to histidine mutation at a site corresponding to L408 of SEQ ID NO: 2.

In another embodiment, the Family B DNA polymerase comprising an alanine to threonine mutation at a site corresponding to A485 of SEQ ID NO: 2 comprises a leucine to phenylalanine mutation at a site corresponding to L408 of SEQ ID NO: 2.

In another embodiment, the Family B DNA polymerase comprising an alanine to threonine mutation at a site corresponding to A485 of SEQ ID NO: 2 comprises a proline to leucine mutation at a site corresponding to P410 of SEQ ID NO: 2.

In another embodiment, the Family B DNA polymerase comprising a proline to leucine mutation at a site corresponding to P410 of SEQ ID NO: 2, further having a serine to proline mutation at a site corresponding to S345 of SEQ ID NO: 2.

In another embodiment, the Family B DNA polymerase comprises a serine to proline mutation at a site corresponding to S345 of SEQ ID NO: 2, and may further comprise a mutation at a site corresponding to T604 of SEQ ID NO: 2.

In another embodiment, the Family B DNA polymerase comprises a tyrosine to cysteine mutation at a site corresponding to Y497 of SEQ ID NO: 2, and may further comprise an isoleucine to valine mutation at a site corresponding to I630 of SEQ ID NO:2.

In another embodiment, the Family B DNA polymerase comprises a glutamic acid to lysine mutation at a site corresponding to E645 of SEQ ID NO: 2.

In another embodiment, the Family B DNA polymerase comprises a glutamic acid to lysine mutation at a site corresponding to E578 of SEQ ID NO: 2, and may further comprise an arginine to methionine mutation at a site corresponding to R465 of SEQ ID NO: 2.

In another embodiment, the Family B DNA polymerase comprises a leucine to glutamine mutation at a site corresponding to L396 of SEQ ID NO: 2, and may further comprise a mutation at a site corresponding to V401, N424, P569, E617, or V640 of SEQ ID NO: 2.

In another embodiment, the Family B DNA polymerase comprises a serine to asparagene mutation at a site corresponding to S651 of SEQ ID NO: 2.

In another embodiment, the Family B DNA polymerase comprises a leucine to proline mutation at a site corresponding to L396 of SEQ ID NO: 2, and may further comprise a mutation at a site corresponding to E459 of SEQ ID NO: 2.

In another embodiment, the Family B DNA polymerase comprises a leucine to proline mutation at a site corresponding to L456 of SEQ ID NO: 2, and may further comprise a mutation at a site corresponding to E658 of SEQ ID NO: 2.

In another embodiment, the Family B DNA polymerase comprises a leucine to histidine mutation at a site corresponding to L408 of SEQ ID NO: 2, and may further comprise a mutation at a site corresponding to V437, or L478 of SEQ ID NO: 2. The L408H mutation was isolated both in the dideoxynucleotide and the dye-dideoxynucleotide screens described herein.

In another embodiment, the Family B DNA polymerase comprises an tyrosine to asparagine mutation at a site corresponding to Y496 of SEQ ID NO: 2.

In another embodiment, the Family B DNA polymerase has reduced discrimination against a non-conventional nucleotide selected from the group consisting of: dideoxynucleotides, ribonucleotides and conjugated nucleotides.

In another embodiment, the conjugated nucleotide is selected from the group consisting of radiolabeled nucleotides, fluorescently labeled nucleotides, biotin labeled nucleotides, chemiluminescently labeled nucleotides and quantum dot labeled nucleotides.

In another embodiment, an isolated recombinant DNA polymerase having reduced discrimination against non-conventional nucleotides or an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase further comprises a mutation at an amino acid residue in the polymerase that corresponds to a mutation selected from the group consisting of: a Y to V mutation at amino acid 409 of SEQ ID NO:2; an A to C, S, L, I, F, or V mutation at amino acid 485 of SEQ ID NO: 2; a Y to S mutation at amino acid 494 of SEQ ID NO: 2; a Y to L mutation at amino acid 496 of SEQ ID NO: 2; and an A to Y mutation at amino acid 490 of SEQ ID NO: 2.

In another embodiment, an isolated recombinant DNA polymerase having reduced discrimination against non-conventional nucleotides or an isolated recombinant Family B DNA polymerase comprising an alanine to threonine mutation at the site corresponding to A485 of SEQ ID NO: 2 or a mutation at a site corresponding to L408 or P410 of SEQ ID NO: 2, wherein the DNA polymerase has reduced discrimination against non-conventional nucleotides relative to the wild-type form of that polymerase further comprises a mutation at an amino acid of the polymerase corresponding to one of amino acids 483 to 496, inclusive, of SEQ ID NO: 2.

In one embodiment, the mutation is at an amino acid of the polymerase corresponding to one of amino acids 485, 490, 494, or 496 of SEQ ID NO: 2.

The invention further encompasses an isolated recombinant Family B DNA polymerase comprising an alanine to threonine mutation at an amino acid corresponding to A485T of SEQ ID NO: 2 and at least one substitution in the polymerase of an amino acid corresponding to L408, Y409, or P410, respectively, of SEQ ID NO: 2.

The invention further encompasses an isolated recombinant Family B DNA polymerase comprising an amino acid other than A at an amino acid of the polymerase corresponding to A485 of SEQ ID NO: 2, and at least one substitution in the polymerase of an amino acid corresponding to L408, Y409, or P410, respectively, of SEQ ID NO: 2.

The invention further encompasses a recombinant vector comprising a nucleic acid sequence encoding the Family B DNA polymerase.

The invention further encompasses a method of labeling a complementary strand of DNA, the method comprising the step of contacting a template DNA molecule with a recombinant Family B DNA polymerase from *Thermococcus* species JDF-3, wherein the DNA polymerase has reduced discrimination against non-conventional nucleotides, and a non-conventional nucleotide, under conditions and for a time sufficient to permit the DNA polymerase to synthesize a complementary DNA strand and to incorporate the non-conventional nucleotide into the synthesized complementary DNA strand.

The invention further encompasses a method of labeling a complementary strand of DNA, the method comprising the step of contacting a template DNA molecule with a recombinant Family B DNA polymerase comprising an alanine to threonine mutation at a site corresponding to A485 of SEQ ID NO: 2 or a mutation at a site corresponding to L408 or P410 of SEQ ID NO: 2, wherein the DNA polymerase has reduced discrimination against non-conventional nucleotides, and a non-conventional nucleotide, under conditions and for a time sufficient to permit the DNA polymerase to synthesize a complementary DNA strand and to incorporate the non-conventional nucleotide into the synthesized complementary DNA strand.

In one embodiment, the recombinant Family B DNA polymerase is 3' to 5' exonuclease deficient.

In another embodiment, the recombinant Family B polymerase comprises a leucine to histidine mutation at a site corresponding to amino acid L408 of SEQ ID NO: 2.

In another embodiment, the recombinant Family B polymerase comprises a leucine to phenylalanine mutation at a site corresponding to amino acid L408 of SEQ ID NO: 2.

In another embodiment, the recombinant Family B polymerase comprises a proline to leucine mutation at a site corresponding to amino acid P410 of SEQ ID NO: 2.

In another embodiment, the recombinant Family B polymerase comprises an alanine to threonine mutation at a site corresponding to amino acid A485 of SEQ ID NO: 2.

In another embodiment, the recombinant Family B polymerase comprising an alanine to threonine mutation at a site corresponding to amino acid A485 of SEQ ID NO: 2 comprises a leucine to histidine mutation at an amino acid corresponding to L408 of SEQ ID NO: 2.

In another embodiment, the recombinant Family B polymerase comprising an alanine to threonine mutation at a site corresponding to amino acid A485 of SEQ ID NO: 2 comprises a leucine to phenylalanine mutation at an amino acid corresponding to L408 of SEQ ID NO: 2.

In another embodiment, the recombinant Family B polymerase comprising an alanine to threonine mutation at a site corresponding to amino acid A485 of SEQ ID NO: 2 comprises a proline to leucine mutation at an amino acid corresponding to P410 of SEQ ID NO: 2.

In another embodiment, the recombinant Family B polymerase has reduced discrimination against a non-conventional nucleotide selected from the group consisting of: dideoxynucleotides, ribonucleotides, and conjugated nucleotides.

In another embodiment, the conjugated nucleotide is selected from the group consisting of radiolabeled nucleotides, fluorescently labeled nucleotides, biotin labeled nucleotides, chemiluminescently labeled nucleotides and quantum dot labeled nucleotides.

The invention further encompasses a method of sequencing DNA comprising the steps of contacting a DNA strand to be sequenced with a sequencing primer, a recombinant Family B DNA polymerase from *Thermococcus* species JDF-3, wherein the DNA polymerase has reduced discrimination against non-conventional nucleotides, and a chain-terminating nucleotide analog, under conditions that permit the DNA polymerase to synthesize a complementary DNA strand, and to incorporate nucleotides into the synthesized complementary DNA strand, wherein incorporation of a chain-terminating nucleotide analog results in the termination of chain elongation, such that the nucleotide sequence of the template DNA strand is determined.

The invention further encompasses a method of sequencing DNA comprising the steps of contacting a DNA strand to be sequenced with a sequencing primer, a recombinant Family B DNA polymerase comprising an alanine to threonine mutation at a site corresponding to A485 of SEQ ID NO: 2 or a mutation at a site corresponding to L408, S345 or P410 of SEQ ID NO: 2, where the DNA polymerase has reduced discrimination against non-conventional nucleotides, and a chain-terminating nucleotide analog, under conditions that permit the DNA polymerase to synthesize a complementary DNA strand, and to incorporate nucleotides into the synthesized complementary DNA strand, wherein incorporation of a chain-terminating nucleotide analog results in the termination of chain elongation, such that the nucleotide sequence of the template DNA strand is determined.

In one embodiment, the recombinant DNA polymerase is deficient in 3' to 5' exonuclease activity.

In another embodiment, the recombinant Family B polymerase has a leucine to histidine mutation at a site corresponding to amino acid L408 of SEQ ID NO: 2.

In another embodiment, the recombinant Family B polymerase has a leucine to phenylalanine mutation at a site corresponding to amino acid L408 of SEQ ID NO: 2.

In another embodiment, the recombinant Family B polymerase has a proline to leucine mutation at a site corresponding to amino acid P410 of SEQ ID NO: 2.

In another embodiment, the Family B DNA polymerase comprising a proline to leucine mutation at a site corresponding to P410 of SEQ ID NO: 2, further having a serine to proline mutation at a site corresponding to S345 of SEQ ID NO: 2.

In another embodiment, the recombinant Family B polymerase has an alanine to threonine mutation at a site corresponding to amino acid A485 of SEQ ID NO: 2.

In another embodiment, the recombinant Family B polymerase having an alanine to threonine mutation at a site corresponding to amino acid A485 of SEQ ID NO: 2 has a leucine to histidine mutation at a site corresponding to L408 of SEQ ID NO: 2.

In another embodiment, the recombinant Family B polymerase having an alanine to threonine mutation at a site corresponding to amino acid A485 of SEQ ID NO: 2 has a leucine to phenylalanine mutation at a site corresponding to L408 of SEQ ID NO: 2.

In another embodiment, the recombinant Family B polymerase having an alanine to threonine mutation at a site corresponding to amino acid A485 of SEQ ID NO: 2 has a proline to leucine mutation at a site corresponding to P410 of SEQ ID NO: 2.

In another embodiment, the chain-terminating nucleotide analog is a dideoxynucleotide.

In another embodiment, the dideoxynucleotide is detectably labeled.

In another embodiment, the dideoxynucleotide is fluorescently labeled.

In another embodiment, the dideoxynucleotide is labeled with a moiety selected from the group consisting of fluorescein and rhodamine.

The invention also encompasses a kit for performing the methods disclosed herein.

The invention also encompasses methods of making a recombinant DNA polymerase as disclosed here, comprising culturing a host cell containing a nucleic acid sequence encoding said polymerase under conditions which permit production of said DNA polymerase.

The invention encompasses a mixture of a mutant DNA polymerase described herein and another DNA polymerase such as Taq DNA polymerase (preferably the mutant form, F667Y). Such a mixture is useful in that it may increase signal uniformity generated from polymerization of a labeled nucleotide into a synthetic nucleotide.

The invention provides a composition for identifying a nucleotide at a given position of a template DNA molecule, the composition comprising a Family B DNA polymerase having reduced discrimination against non-conventional nucleotides and a first primer, wherein the first primer anneals to the immediate 3' of the nucleotide at the given position of the template DNA molecule.

In one embodiment, the Family B DNA polymerase is a JDF-3 DNA polymerase.

In a preferred embodiment, the JDF-3 DNA polymerase has a sequence of SEQ ID NO: 2 and further comprises one or more amino acid mutations at D141, E143, A485, L408 or P410.

In a preferred embodiment, the JDF-3 DNA polymerase has one or more amino acid mutations selected from the group consisting of: D141A or D141T, E143A, L408H or L408F, A485T, and P410L.

In a preferred embodiment, the JDF-3 DNA polymerase comprises four amino acid mutations at D141A, E 143A, P410L and A485T.

Preferably, the Family B DNA polymerase in the above embodiments is deficient in 3' to 5' exonuclease activity.

The above embodiments of the present invention may further comprise at least one chain-terminating nucleotide analog, wherein the chain-terminating nucleotide analog is incorporated into the first primer by the Family B DNA polymerase in a template-dependent manner.

In a preferred embodiment, at least one chain-terminating nucleotide analog is labeled with a first detectable label.

In another preferred embodiment, more than one chain-terminating nucleotide analog is labeled, each chain-terminating nucleotide analog being labeled with a different first detectable label.

Preferably, the chain-terminating nucleotide analog in the above embodiments is a dideoxynucleotide.

More preferably, the dideoxynucleotide is selected from the group consisting of: ddATP, ddTTP, ddCTP and ddGTP.

In a preferred embodiment, the first primer is labeled with a second detectable label.

In another preferred embodiment, the first and second detectable labels generate a signal for identifying the nucleotide at the given position of the template DNA molecule.

The above compositions for identifying a nucleotide may further comprise a second primer.

In one embodiment, the first primer is labeled with a second detectable label and the second primer is labeled with a third detectable label, the second and third detectable labels generate a signal for identifying the nucleotide at the given position of the template DNA molecule.

In a preferred embodiment, the second primer anneals to the immediate 5' of the nucleotide at the given position of the template DNA molecule.

In one embodiment, the above composition further comprises a DNA ligase.

In a preferred embodiment, each above composition further comprises a reaction buffer for the Family B DNA polymerase.

In another preferred embodiment, the template DNA molecule is the product of a polymerase chain reaction or a plasmid DNA.

In another preferred embodiment, the first or second or third detectable label is one selected from the group consisting of: a fluorescent label, an isotope, a chemiluminescent label, a quantum dot label, an antigen, or an affinity moiety.

In another preferred embodiment, the first detectable label is a rhodamine label or a cyanine label.

The invention further provides each of the above compositions in kit format.

In a preferred embodiment, the kit further comprises a control template and/or at least one control primer.

In a more preferred embodiment, the kit further comprises a control template and four control primers.

The invention provides a method of identifying a nucleotide at a given position of a template DNA molecule in a sample, the method comprising:
  (a) contacting a first primer with the template DNA molecule, wherein the contacting allows the first primer to anneal to the immediate 3' of the nucleotide at the given position of the template DNA molecule, so as to form a duplex between the first primer and the template DNA molecule;
  (b) incubating the duplex from step (a), in the presence of a Family B DNA polymerase and at least one chain-terminating nucleotide analog, the Family B DNA polymerase having reduced discrimination against non-conventional nucleotides and the terminator is labeled with a first detectable label, wherein the incubating allows the incorporation of a labeled chain-terminating nucleotide analog into the first primer by the DNA polymerase in a template-dependent manner; and
  (c) determining the presence or identity of the duplex from step (b) by a signal generated from the first detectable label.

In a preferred embodiment, the Family B DNA polymerase is a JDF-3 DNA polymerase.

In another embodiment, the JDF-3 DNA polymerase has a sequence of SEQ ID NO: 2 and further comprises one or more amino acid mutations at D141, E143, A485, L408 or P410.

In another embodiment, the JDF-3 DNA polymerase has one or more amino acid mutations selected from the group consisting of: D141A or D141T, E143A, L408H or L408F, A485T, and P410L.

In yet another embodiment, the JDF-3 DNA polymerase comprises four amino acid mutations at D141A, E 143A, P410L and A485T.

Preferably, the Family B DNA polymerase is deficient in 3' to 5' exonuclease activity.

In one embodiment, at least one chain-terminating nucleotide analog is labeled with a first detectable label.

In another embodiment, more than one chain-terminating nucleotide analog is labeled, each chain-terminating nucleotide analog being labeled with a different first detectable label.

Preferably, the chain-terminating nucleotide analog is a dideoxynucleotide.

More preferably, the dideoxynucleotide is selected from the group consisting of: ddATP, ddTTP, ddCTP and ddGTP.

In one embodiment, the first primer is labeled with a second detectable label.

In another embodiment, the first and second detectable labels generate a signal for identifying the nucleotide at the given position of the template DNA molecule.

In a preferred embodiment, the template DNA molecule is the product of a polymerase chain reaction or a plasmid.

In a preferred embodiment, the method of the present invention further comprises removing PCR primers and dNTPs from the PCR product before step (a).

The invention provides a method of identifying a nucleotide at a given position of a template DNA molecule in a sample, the method comprising:
(a) contacting a first primer and s second primer with the template DNA molecule, wherein the contacting allows the first primer to anneal to the immediate 3' of the nucleotide at the given position of the template DNA molecule and the second primer to anneal to the immediate 5' of the nucleotide at the given position of the template DNA molecule, so as to form a complex between the template DNA molecule and the first and second primers, the first primer being labeled with a second detectable label and the second primer being labeled with a third detectable label.
(b) incubating the complex from step (a), in the presence of a DNA ligase., wherein the incubating allows the ligation between the first and second primers so as to form a single molecule; and
(c) determining the presence or identity of the single molecule from step (b) by a signal generated from the second and third detectable labels.

In a preferred embodiment, the first or second or third detectable label is one selected from the group consisting of: a radiolabel, a fluorescent label, a chemiluminescent label, a calorimetric label and an enzymatic label.

In another embodiment, the first detectable label is a rhodamine label or a cyanine label.

As used herein, "discrimination" refers to the tendency of DNA polymerase to not incorporate non-conventional nucleotides into a nascent DNA polymer. DNA polymerase has the ability to sense nucleotide structure, including but not limited to nucleotide base complementarity, and structural features of the sugar and heterocyclic base, thereby allowing DNA polymerase to preferentially utilize conventional deoxynucleotides rather than non-conventional nucleotides for incorporation into a nascent polymer. DNA polymerase strongly prefers to incorporate the conventional deoxynucleotides dATP, dCTP, dGTP and dTTP into DNA polymers; the polymerase is unlikely to progress with an unconventional nucleotide in its binding pocket.

As used herein, "reduced discrimination" refers to a reduction of at least 50% in the tendency of a DNA polymerase to exclude a non-conventional nucleotide from (that is, to not incorporate non-conventional nucleotides into) a nascent DNA polymer, relative to a parental or wild type DNA polymerase which does not exhibit reduced discrimination. The preference of DNA polymerase to incorporate the conventional deoxynucleotides dATP, dCTP, dGTP and TTP rather than non-conventional nucleotides into DNA polymers is thereby reduced compared to the natural level of preference, such that non-conventional nucleotides are more readily incorporated into DNA polymers by DNA polymerase. According to the invention, a polymerase exhibiting reduced discrimination will exhibit reduced discrimination against at least one non-conventional nucleotides, but may not exhibit reduced discrimination against all non-conventional nucleotides.

According to the invention, discrimination is quantitated by measuring the concentration of a non-conventional nucleotide required to inhibit the incorporation of the corresponding conventional nucleotide by 50%. This concentration is referred to herein as the "$I_{50\%}$" for a non-conventional nucleotide. Discrimination against a given non-conventional nucleotide is "reduced" if the $I_{50}$% for that non-conventional nucleotide is reduced by at least two fold (50%) relative to an identical assay containing, in place of the mutant DNA polymerase, a parental DNA polymerase.

Alternatively, reduced discrimination may be quantitated by determining the amount of a non-conventional nucleotide (for example, a dideoxynucleotide, ribonucleotide, or cordycepin) required in a reaction with a mutant polymerase having reduced discrimination to generate a sequencing ladder identical to a sequencing ladder produced using the wild-type or parental enzyme. The sequencing ladder can be examined, for example, in the range of 1 to 400 bases from the primer terminus, and the ladders will be identical in the number of extension products generated as well as the lengths of extension products generated in the sequencing reaction. For this type of assay, a constant amount of dNTPs and varying amounts of non-conventional nucleotides are used to generate a sequencing ladder with both the wild-type (or parental) enzyme and the mutant polymerase (for ribonucleotides, a sequencing ladder is generated by alkali cleavage of the polymerization products). See Gardner & Jack, 1999, supra. A mutant exhibits reduced discrimination if it requires at least two-fold (50%) less, five-fold (80%) less, ten-fold (100%) less, etc. of the amount of the non-conventional nucleotide used by the wild-type or parental polymerase to produce a sequencing ladder identical (with respect to the number and length of extension products generated) to that generated by the wild-type or parental enzyme.

As used herein, the term "parental" or "progenitor" refers to a polymerase used as the starting material in generating a mutant polymerase having reduced discrimination. The term "parental" is meant to encompass not only a so-called "wild-type" enzyme as it occurs in nature, but also intermediate forms, for example, an exonuclease deficient enzyme that is used as the starting material for generating an enzyme with reduced discrimination against non-conventional nucleotides.

As used herein, "non-conventional nucleotide" refers to a) a nucleotide structure that is not one of the four conventional deoxynucleotides dATP, dCTP, dGTP, and dTTP recognized by and incorporated by a DNA polymerase, b) a synthetic nucleotide that is not one of the four conventional deoxynucleotides in (a), c) a modified conventional nucleotide, or d) a ribonucleotide (since they are not normally recognized or incorporated by DNA polymerases) and modified forms of a ribonucleotide. Non-conventional nucleotides include but are not limited to those listed in Table III, which are commercially available, for example, from New England Nuclear. Any one of the above non-conventional nucleotides may be a "conjugated nucleotide", which as used herein refers to nucleotides bearing a detectable label, including but not limited to a fluorescent label, isotope, chemiluminescent label, quantum dot label, antigen, or affinity moiety.

As used herein, the term "cell", "cell line" and "cell culture" can be used interchangeably and all such designations include progeny. Thus, the words "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, the term "organism transformed with a vector" refers to an organism carrying a recombinant gene construct.

As used herein, "thermostable" refers to a property of a DNA polymerase, such that the enzyme active at elevated temperatures and is resistant to DNA duplex-denaturing temperatures in the range of about 93° C. to about 97° C. "Active" means the enzyme retains the ability to effect primer extension reactions when subjected to elevated or denaturing temperatures for the time necessary to effect denaturation of double-stranded nucleic acids. Elevated temperatures as used herein refer to the range of about 70° C. to about 75° C., whereas non-elevated temperatures as used herein refer to the range of about 35° C. to about 50° C.

As used herein, "archaeal" refers to an organism or to a DNA polymerase from an organism of the kingdom Archaea.

As used herein, "primer" refers to an oligonucleotide, whether natural or synthetic, which is substantially complementary (i.e., at least 7 out of 10, preferably 9 out of 10, more preferably 9 out of 10 bases are fully complementary) and can anneal to a complementary template DNA to form a duplex between the primer and the template DNA. A primer may serve as a point of initiation of nucleic acid synthesis by a polymerase following annealing to a DNA strand to be sequenced. A primer is typically a single-stranded oligodeoxyribonucleotide. The appropriate length of a primer depends on the intended use of the primer, but for DNA sequencing applications typically ranges from about 15 to about 40 nucleotides in length.

As used herein, "Family B DNA polymerase" refers to any DNA polymerase that is classified as a member of the Family B DNA polymerases, where the Family B classification is based on structural similarity to E. coli DNA polymerase II. The Family B DNA polymerases, formerly known as α-family polymerases, include, but are not limited to those listed as such in Table I.

As used herein, "Family A DNA polymerase" refers to any DNA polymerase that is classified as a member of the Family A DNA polymerases, where the Family A classification is based on structural similarity to E. coli DNA polymerase I. Family A DNA polymerases include, but are not limited to those listed as such in Table I.

As used herein, "3' to 5' exonuclease deficient" or "3' to 5' exo−" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, or a "substantial" lack of activity. "Substantial" lack of activity means that the 3' exonuclease activity of the mutant polymerase relative to the parental polymerase is 0.03%, and also may be 0.05%, 0.1%, 1%, 5%, 10%, or 20%, but is not higher than 50% of the 3' exonuclease activity of the parental or wild type polymerase.

As used herein, "mutation" refers to a change introduced into a starting parental DNA sequence that changes the amino acid sequence encoded by the DNA. The consequences of a mutation include but are not limited to the creation of a new character, property, function, or trait not found in the protein encoded by the parental DNA.

As used herein, "wild-type" refers to the typical state of an organism, strain, gene, protein or characteristic as it occurs in nature. The wild-type is therefore the natural state that is distinguished from a mutant, which was derived from the wild type by introduction of change(s) to the wild-type.

As used herein, "corresponding" refers to sequence similarity in a comparison of two or more nucleic acids or polypeptides, where functionally equivalent domains or sub-sequences are identified; such functionally equivalent domains or sub-sequences or amino acids within such a domain or sub-sequence are said to "correspond". That is, two or more sequences are compared through a comparative alignment analysis in which an entire sequence is examined for regions of sequence that are similar or identical, and thus regions likely to be functionally equivalent to regions from the other sequence(s) are identified.

As used herein in reference to comparisons of an amino acid, amino acid sequence, or protein domain, the term "similar" refers to amino acids or domains that although not identical, represent "conservative" differences. By "conservative" is meant that the differing amino acid has like characteristics with the amino acid in the corresponding or reference sequence. Typical conservative substitutions are among Ala, Val, Leu and Ile; among Ser and Thr; among the acidic residues Asp and Glu; among Asn and Gln; and among the basic residues Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "functionally equivalent" means that a given motif, region, or amino acid within a motif or region performs the same function with regard to the overall function of the enzyme as a motif, region or amino acid within a motif or region performs in another enzyme.

As used herein, "chain terminating nucleotide analog" refers to a nucleotide analog that once incorporated cannot serve as a substrate for subsequent extension by a DNA polymerase, thereby terminating the elongation of a DNA polymer by a DNA polymerase. Such a nucleotide analog typically lacks a hydroxyl group on its sugar moiety to which DNA polymerase can synthesize a phosphodiester bond with an incoming nucleotide. Chain terminating nucleotide analogs are a subset of non-conventional nucleotides, and include but are not limited to dideoxynucleotides.

As used herein, "detectably labeled" refers to a structural modification that incorporates a functional group (label) that can be readily detected by various means. Compounds that can be detectably labeled include but are not limited to nucleotide analogs. Detectable nucleotide analog labels include but are not limited to fluorescent compounds, isotopic compounds, chemiluminescent compound, quantum dot labels, biotin, enzymes, electron-dense reagents, and haptens or proteins for which antisera or monoclonal antibodies are available. The various means of detection include but are not limited to spectroscopic, photochemical, biochemical, immunochemical, or chemical means.

As used herein in reference to a polynucleotide or polypeptide, the term "isolated" means that a naturally occurring sequence has been removed from its normal cellular environment or is synthesized in a non-natural environment (e.g., artificially synthesized). Thus, the sequence may be in a cell-free solution or placed in a different cellular environment. The term does not imply that the sequence is the only nucleotide or polypeptide chain present, but that it is essentially free (about 90-95% pure at least) of non-nucleotide or non-polypeptide material, respectively, naturally associated with it.

As used herein, the term "recombinant" refers to a polynucleotide or polypeptide that is altered by genetic engineering (i.e., by modification or manipulation of the genetic material encoding that polynucleotide or polypeptide).

The invention encompasses full length mutant DNA polymerases, as described herein, as well as a functional fragment of a mutant polymerase, that is, a fragment of a DNA polymerase that is less than the entire amino acid sequence of the mutant polymerase and retains the ability, under at least one set of conditions, to catalyze the polymerization of a polynucleotide. Such a functional fragment may exist as a separate entity, or it may be a constituent of a larger polypeptide, such as a fusion protein.

As used herein, the term "complementary DNA strand" refers to that DNA molecule synthesized from a template DNA molecule by a DNA polymerase in a primer extension reaction.

As used herein, the term "template DNA molecule" refers to that strand of a nucleic acid from which a complementary nucleic acid strand is synthesized by a DNA polymerase, for example, in a primer extension reaction. A "template DNA molecule", also refers to a template DNA strand whose sequence needs to be identified. The sequence may need to be identified for a single nucleotide at a given position of the template DNA molecule (i.e., by mini-sequencing) or for a fragment of or the whole DNA molecule (i.e., by sequencing). The term "sequence", according to the present invention, refers to the identification of a nucleotide at a given position or at more than one position of a template DNA molecule.

Further features and advantages of the invention will become more fully apparent in the following description of the embodiments and drawings thereof, and from the claims.

BRIEF DESCRIPTION OF THE DRAWINGS

FIG. 1 shows the DNA sequence encoding Thermococcus species JDF-3 DNA polymerase (intein removed) (SEQ ID NO: 1).

FIG. 2 shows the amino sequence of Thermococcus species JDF-3 DNA polymerase (intein removed) (SEQ ID NO: 2).

FIG. 3 shows the amino acid sequence of the genomic clone encoding Thermococcus species JDF-3 DNA polymerase (SEQ ID NO: 3). The position of an intein, removed by post-translational processing, is shown.

FIG. 4 shows the DNA sequence of the genomic clone encoding Thermococcus species JDF-3 DNA polymerase (SEQ ID NO: 4). DNA sequences are shown which correspond to 5' and 3' untranslated regions, polymerase-coding regions (exteins), and an intein-coding region.

Figure 14:
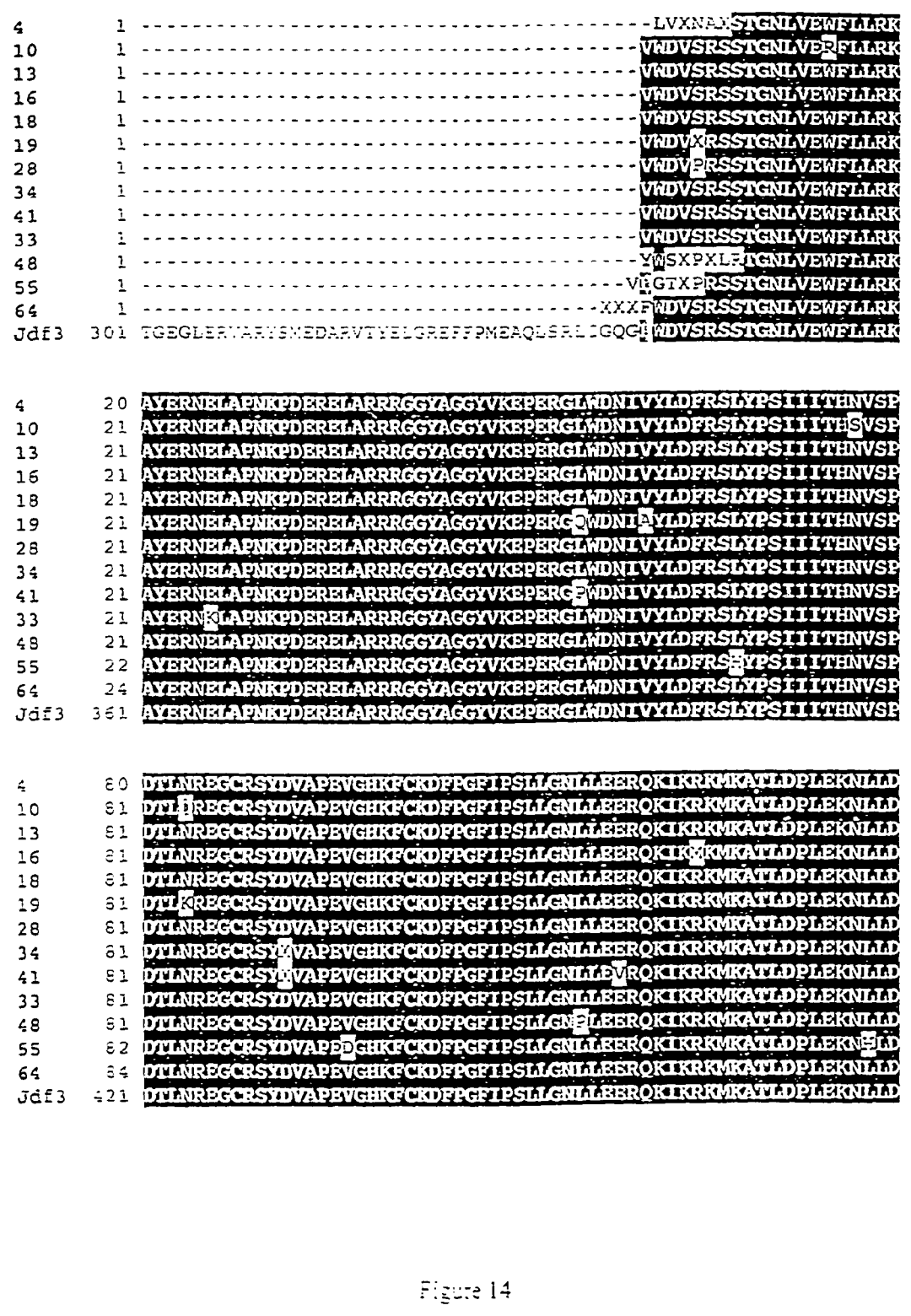

FIG. 14 shows the sequence alignment of dye-dideoxy-nucleotide selected JDF-3 mutants (amino acids 301-480). Nucleic acid residues highlighted by white boxes indicate the location of a mutation. The mutation S345P is one of two mutations present in mutant 28. Sequence assignments are as follows: 4: SEQ ID NO: 21; 10: SEQ ID NO: 22; 13: SEQ ID NO: 23; 16; SEQ ID NO: 24, 18: SEQ ID NO: 25; 19: SEQ ID NO: 26; 28: SEQ ID NO: 27: 34; SEQ ID NO: 28; 41: SEQ ID NO: 29; 33: SEQ ID NO: 30; 48: SEQ ID NO: 31; 55: SEQ ID NO: 32: 64: SEQ ID NO: 33; jdf3: SEQ ID NO: 34.

FIG. 15 shows the sequence alignment of dye-dideoxy-nucleotide selected JDF-3 (amino acids 481-660). Nucleic acid residues highlighted by white boxes indication the location of a mutation.

DESCRIPTION

Figure 5:
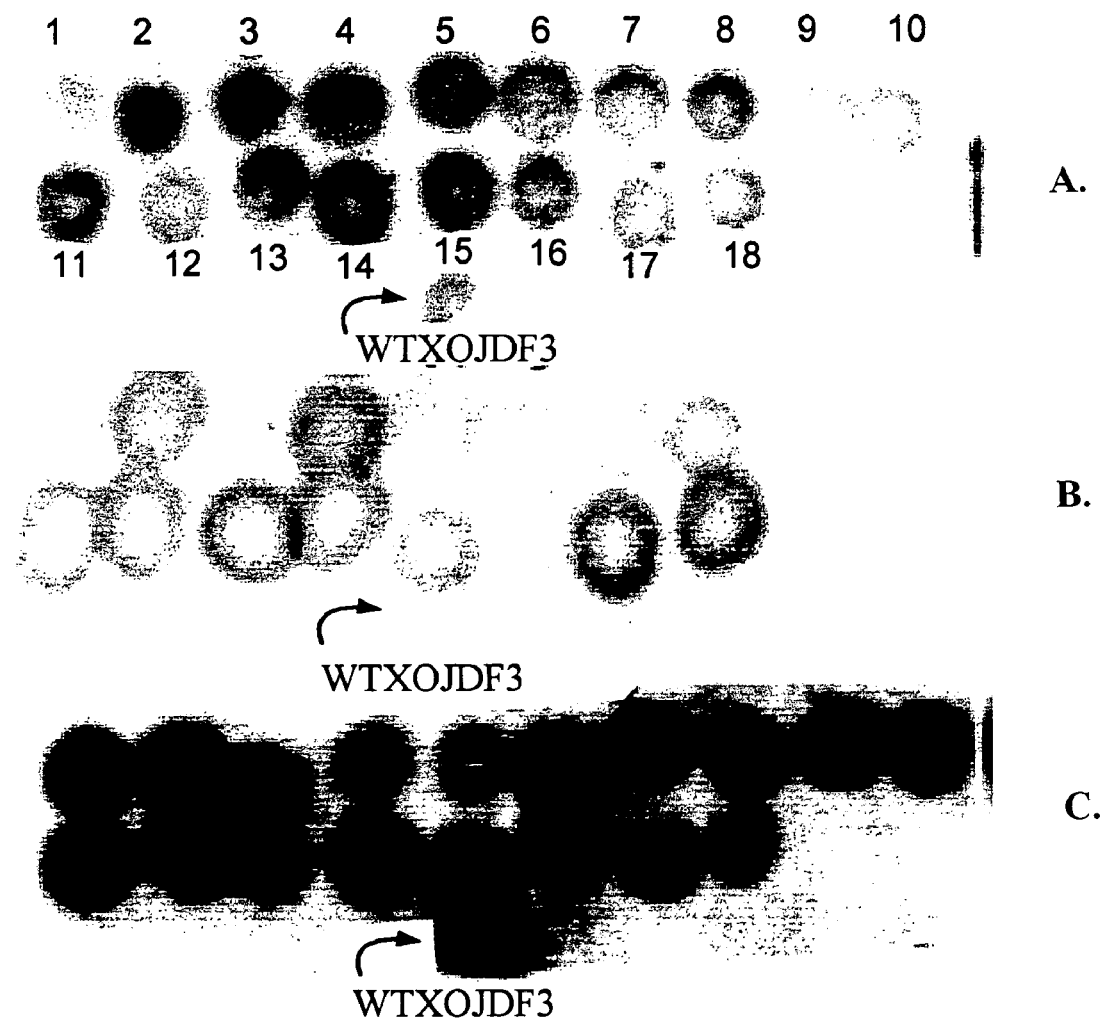
FIG. 5 shows nucleotide incorporation by JDF-3 mutants. Lambda phage clones which incorporated $^{33}$P-labeled ddNTPs in the primary library screen were rescreened to assess $^{33}$P-ddNTP incorporation in the presence of: (panel A) 0.5 mM $MnCl_2$ or (panel B) 1.5 mM $MgCl_2$. Polymerase activity was measured using $^{33}$P-dNTPs in the presence of 1.5 mM $MgCl_2$ (panel C). Nucleotide utilization is shown for clones 1-18 and for the parental #550 clone.

The invention is based on the discovery of Family B DNA polymerases that bear one or more genetic alterations resulting in reduced discrimination against non-conventional nucleotides relative to their unmodified wild-type forms. All references described herein are incorporated by reference herein in their entirety.

Family B DNA Polymerase Exhibiting Reduced Discrimination Against Non-Conventional Nucleotides:

A. DNA Polymerases Useful According to the Invention

According to the invention, DNA polymerases of Family B may be mutated to generate enzymes exhibiting reduced discrimination against non-conventional nucleotides. Table I includes a non-limiting list of known DNA polymerases categorized by family.

TABLE I

| DNA POLYMERASES BY FAMILY | |
|---|---|
| | Reference |
| FAMILY A DNA POLYMERASES | |
| Bacterial DNA Polymerases | |
| a) *E. coli* DNA polymerase 1 | (1) |
| b) *Streptococcus pneumoniae* DNA polymerase I | (2) |
| c) *Thermus aquaticus* DNA polymerase I | (3) |
| d) *Thermus flavus* DNA polymerase I | (4) |
| e) *Thermotoga maritima* DNA polymerase I | |
| Bacteriophage DNA Polymerases | |
| a) T5 DNA polymerase | (5) |
| b) T7 DNA polymerase | (6) |

TABLE I-continued

DNA POLYMERASES BY FAMILY

| | Reference |
|---|---|
| c) Spo1 DNA polymerase | (7) |
| d) Spo2 DNA polymerase | (8) |
| Mitochondrial DNA polymerase | |
| Yeast Mitochondrial DNA polymerase II | (9, 10, 11) |
| FAMILY B DNA POLYMERASES | |
| Bacterial DNA polymerase | |
| E. coli DNA polymerase II | (15) |
| Bacteriophage DNA polymerase | |
| a) PRD1 DNA polymerase | (16, 17) |
| b) φ29 DNA polymerase | (18) |
| c) M2 DNA polymerase | (19) |
| d) T4 DNA polymerase | (20) |
| Archaeal DNA polymerase | |
| a) *Thermococcus litoralis* DNA polymerase (Vent) | (21) |
| b) *Pyrococcus furiosus* DNA polymerase | (22) |
| c) *Sulfolobus solfataricus* DNA polymerase | (23) |
| d) *Thermococcus gorgonarius* DNA polymerase | (64) |
| e) Thermococcus species TY | (65) |
| f) Pyrococcus species strain KOD1 | (66) |
| g) *Sulfolobus acidocaldarius* | (67) |
| h) Thermococcus species 9°N-7 | (68) |
| i) *Pyrodictium occultum* | (69) |
| j) *Methanococcus voltae* | (70) |
| k) Desulfurococcus strain TOK (D. Tok Pol) | (71) |
| Eukaryotic Cell DNA polymerase | |
| (1) DNA polymerase alpha | |
| a) Human DNA polymerase (alpha) | (24) |
| b) *S. cerevisiae* DNA polymerase (alpha) | (25) |
| c) *S. pombe* DNA polymerase I (alpha) | (26) |
| d) *Drosophila melanogaster* DNA polymerase (alpha) | (27) |
| e) *Trypanosoma brucei* DNA polymerase (alpha) | (28) |
| (2) DNA polymerase delta | |
| a) Human DNA polymerase (delta) | (29, 30) |
| b) Bovine DNA polymerase (delta) | (31) |
| c) *S. cerevisiae* DNA polymerase III (delta) | (32) |
| d) *S. pombe* DNA polymerase III (delta) | (33) |
| e) *Plasmodium falciparum* DNA polymerase (delta) | (34) |
| (3) DNA polymerase epsilon | |
| *S. cerevisiae* DNA polymerase II (epsilon) | (35) |
| (4) Other eukaryotic DNA polymerase | |
| *S. cerevisiae* DNA polymerase Rev3 | (36) |
| Viral DNA polymerases | |
| a) Herpes Simplex virus type 1 DNA polymerase | (37) |
| b) Equine herpes virus type 1 DNA polymerase | (38) |
| c) Varicella-Zoster virus DNA polymerase | (39) |
| d) Epstein-Barr virus DNA polymerase | (40) |
| e) Herpesvirus saimiri DNA polymerase | (41) |
| f) Human cytomegalovirus DNA polymerase | (42) |
| g) Murine cytomegalovirus DNA polymerase | (43) |
| h) Human herpes virus type 6 DNA polymerase | (44) |
| i) Channel Catfish virus DNA polymerase | (45) |
| j) Chlorella virus DNA polymerase | (46) |
| k) Fowlpox virus DNA polymerase | (47) |
| l) Vaccinia virus DNA polymerase | (48) |
| m) *Choristoneura biennis* DNA polymerase | (49) |
| n) *Autographa california* nuclear polymerase virus (AcMNPV) DNA polymerase | (50) |
| o) *Lymantria dispar* nuclear polyhedrosis virus DNA polymerase | (51) |
| p) Adenovirus-2 DNA polymerase | (52) |
| q) Adenovirus-7 DNA polymerase | (53) |
| r) Adenovirus-12 DNA polymerase | (54) |
| Eukaryotic linear DNA plasmid encoded DNA polymerases | |
| a) S-1 Maize DNA polymerase | (55) |
| b) kalilo neurospora intermedia DNA polymerase | (56) |
| c) pA12 ascobolus immersus DNA polymerase | (57) |
| d) pCLK1 *Claviceps purpurea* DNA polymerase | (58) |
| e) maranhar neurospora crassa DNA polymerase | (59) |
| f) pEM *Agaricus bitorquis* DNA polymerase | (60) |
| g) pGKL1 *Kluyveromyces lactis* DNA polymerase | (61) |
| h) pGKL2 *Kluyveromyces lactis* DNA polymerase | (62) |
| i) pSKL *Saccharomyces kluyveri* DNA polymerase | (63) |

B. Plasmids

The starting sequences for the generation of Family B DNA polymerases according to the invention may be contained in a plasmid vector. A non-limiting list of cloned Family B DNA polymerases and their GenBank Accession numbers are listed in Table II.

TABLE II

Accession Information for Cloned Family B Polymerases

```
Vent Thermococcus litoralis (SEQ ID NO: 62)
ACCESSION   AAA72101
PID    g348689
VERSION    AAA72101.1  GI:348689
DBSOURCE   locus THCVDPE accession M74198.1

MILDTDYITK DGKPIIRIFK KENGEFKIEL DPHFQPYIYA LLKDDSAIEE IKAIKGERHG    60

KTVRVLDAVK VRKKFLGREV EVWKLIFEHP QDVPAMRGKI REHPAVVDIY EYDIPFAKRY   120

LIDKGLIPME GDEELKLLAF DIETFYHEGD EFGKGEIIMI SYADEEEARV ITWKNIDLPY   180

VDVVSNEREM IKRFVQVVKE KDPDVIITYN GDNFDLPYLI KRAEKLGVRL VLGRDKEHPE   240

PKIQRMGDSF AVEIKGRIHF DLFPVVRRTI NLPTYTLEAV YEAVLGKTKS KLGAEEIAAI   300

WETEESMKKL AQYSMEDARA TYELGKEFFP MEAELAKLIG QSVWDVSRSS TGNLVEWYLL   360

RVAYARNELA PNKPDEEEYK RRLRTTYLGG YVKEPEKGLW ENIIYLDFRS LYPSIIVTHN   420

VSPDTLEKEG CKNYDVAPIV GYRFCKDFPG FIPSILGDLI AMRQDIKKKM KSTIDPIEKK   480

MLDYRQRAIK LLANSYYGYM GYPKARWYSK ECAESVTAWG RHYIEMTIRE IEEKFGFKVL   540

YADTDGFYAT IPGEKPELIK KKAKEFLNYI NSKLPGLLEL EYEGFYLRGF FVTKKRYAVI   600
```

TABLE II-continued

Accession Information for Cloned Family B Polymerases

```
DEEGRITTRG LEVVRRDWSE IAKETQAKVL EAILKEGSVE KAVEVVRDVV EKIAKYRVPL    660

EKLVIHEQIT RDLKDYKAIG PHVAIAKRLA ARGIKVKPGT IISYIVLKGS GKISDRVILL    720

TEYDPRKHKY DPDYYIENQV LPAVLRILEA FGYRKEDLRY QSSKQTGLDA WLKR          774

THEST THERMOCOCCUS SP. (STRAIN TY) (SEQ ID NO: 63)
ACCESSION   O33845
PID     g3913524
VERSION     O33845 GI:3913524
DBSOURCE    swissprot: locus DPOL_THEST, accession O33845

MILDTDYITK DGKPIIRIFK KENGEFKIEL DPHFQPYIYA LLKDDSAIDE IKAIKGERHG     60

KIVRVVDAVK VKKKFLGRDV EVWKLIFEHP QDVPALRGKI REHPAVIDIY EYDIPFAKRY   120

LIDKGLIPME GDEELKLMAF DIETFYHEGD EFGKGEIIMI SYADEEEARV ITWKNIDLPY   180

VDVVSNEREM IKRFVQIVRE KDPDVLITYN GDNFDLPYLI KRAEKLGVTL LLGRDKEHPE   240

PKIHRMGDSF AVEIKGRIHF DLFPVVRRTI NLPTYTLEAV YEAVLGKTKS KLGAEEIAAI   300

WETEESMKKL AQYSMEDARA TYELGKEFFP MEAELAKLIG QSVWDVSRSS TGNLVEWYLL   360

RVAYERNELA PNKPDEEEYR RRLRTTYLGG YVKEPERGLW ENIAYLDFRC HPADTKVIVK   420

GKGIVNISDV KEGDYILGID GWQRVKKVWK YHYEGKLINI NGLKCTPNHK VPVVTENDRQ   480

TRIRDSLAKS FLSGKVKGKI ITTKLFEKIA EFEKNKPSEE EILKGELSGI ILAEGTLLRK   540

DIEYFDSSRG KKRISHQYRV EITIGENEKE LLERILYIFD KLFGIRPSVK KKGDTNALKI   600

TTAKKAVYLQ IEELLKNIES LYAPAVLRGF FERDATVNKI RSTIVVTQGT NNKWKIDIVA   660

KLLDSLGIPY SRYEYKYIEN GKELTKHILE ITGRDGLILF QTLVGFISSE KNEALEKAIE   720

VREMNRLKNN SFYNLSTFEV SSEEYYKGEVY DLTLEGNPYY FANGILTHNS LYPSIIVTHN   780

VSPDTLEREG CKNYDVAPIV GYKFCKDFPG FIPSILGELI TMRQEIKKKM KATIDPIEKK   840

MLDYRQRAVK LLANSILPNE WLPIIENGEV KFVKIGEFID RYMEEQKDKV RTVDNTEVLE   900

VDNIFAFSLN KESKKSEIKK VKALIRHKYK GEAYEVELNS GRKIHITRGH SLFTIRNGKI   960

KEIWGEEVKV GDLIIVPKKV KLNEKEAVIN IPELISKLPD EDTADVVMTT PVKGRKNFFK  1020

GMLRTLKWIF GEESKRIRTF NRYLFHLEEL GFVKLLPRGY EVTDWEGLKR YRQLYEKLVK  1080

NLRYNGNKRE YLVRFNDIKD SVSCFPRKEL EEWKIGTXKG FRXKCILKVD EDFGKFLGYY  1140

VSEGYAGAQK NKTGGMSYSV KLYNENPNVL KDMKNIAEKF FGKVRVGKNC VDIPKKMAYL  1200

LAKSLCGVTA ENKRIPSIIF DSSEPVRWAF LRAYFVGDGD IHPSKRLRLS TKSELLANQL  1260

VFLLNSLGVS SIKIGFDSGV YRVYINEDLP FLQTSRQKNT YYPNLIPKEV LEEIFGRKFQ  1320

KNITFEKFKE LADSGKLDKR KVKLLDFLLN GDIVLDRVKN VEKREYEGYV YDLSVEDNEN  1380

FLVGFGLLYA HNSYYGYMGY PKARWYSKEC AESVTAWGRH YIEMTIKEIE EKFGFKVLYA  1440

DSVTGDTEII VKRNGRIEFV PIEKLFERVD YRIGEKEYCI LEDVEALTLD NRGKLIWKKV  1500

PYVMRHRAKK KVYRIWITNS WYIDVTEDHS LIVAEDGLKE ARPMEIEGKS LIATKDDLSG  1560

VEYIKPHAIE EISYNGYVYD IEVEGTHRFF ANGILVHNTD GFYATIPGEK PETIKKKAKE  1620

FLKYINSKLP GLLELEYEGF YLRGFFVAKK RYAVIDEEGR ITTRGLEVVR RDWSEIAKET  1680

QAKVLEAILK EDSVEKAVEI VKDVVEEIAK YQVPLEKLVI HEQITKDLSE YKAIGPHVAI  1740

AKRLAAKGIK VRPGTIISYI VLRGSGKISD RVILLSEYDP KKHKYDPDYY IENQVLPAVL  1800

RILEAFGYRK EDLKYQSSKQ VGLDAWLKK                                    1829
```

Pab *Pyrococcus abyssi* (SEQ ID NO: 64)
ACCESSION   P77916
PID     g3913529

TABLE II-continued

Accession Information for Cloned Family B Polymerases

VERSION    P77916 GI:3913529
DBSOURCE   swissprot: locus DPOL_PYRAB, accession P77916

```
MIIDADYITE DGKPIIRIFK KEKGEFKVEY DRTFRPYIYA LLKDDSAIDE VKKITAERHG      60
KIVRITEVEK VQKKFLGRPI EVWKLYLEHP QDVPAIREKI REHPAVVDIF EYDIPFAKRY     120
LIDKGLTPME GNEELTFLAV DIETLYHEGE EFGKGPIIMI SYADEEGAKV ITWKSIDLPY     180
VEVVSSEREM IKRLVKVIRE KDPDVIITYN GDNFDFPYLL KRAEKLGIKL PLGRDNSEPK     240
MQRMGDSLAV EIKGRIHFDL FPVIRRTINL PTYTLEAVYE AIFGKSKEKV YAHEIAEAWE     300
TGKGLERVAK YSMEDAKVTF ELGKEFFPME AQLARLVGQP VWDVSRSSTG NLVEWFLLRK     360
AYERNELAPN KPDEREYERR LRESYEGGYV KEPEKGLWEG IVSLDFRSLY PSIIITHNVS     420
PDTLNRENCK EYDVAPQVGH RFCKDFPGFI PSLLGNLLEE RQKIKKRMKE SKDPVEKKLL     480
DYRQRAIKIL ANSYYGYYGY AKARWYCKEC AESVTAWGRQ YIDLVRRELE SRGFKVLYID     540
TDGLYATIPG AKHEEIKEKA LKFVEYINSK LPGLLELEYE GFYARGFFVT KKKYALIDEE     600
GKIVTRGLEI VRRDWSEIAK ETQAKVLEAI LKHGNVDEAV KIVKEVTEKL SKYEIPPEKL     660
VIYEQITRPL SEYKAIGPHV AVAKRLAAKG VKVKPGMVIG YIVLRGDGPI SKRAIAIEEF     720
DPKKHKYDAE YYIENQVLPA VERILRAFGY RKEDLKYQKT KQVGLGAWLK F             771
```

PYRHO *Pyrococcus horikoshii* (SEQ ID NO: 65)
ACCESSION    O59610
PID          g3913526
VERSION      O59610 GI:3913526
DBSOURCE     swissprot: locus DPOL_PYRHO, accession O59610

```
MILDADYITE DGKPIIRIFK KENGEFKVEY DRNFRPYIYA LLRDDSAIDE IKKITAQRHG      60
KVVRIVETEK IQRKFLGRPI EVWKLYLEHP QDVPAIRDKI REHPAVVDIF EYDIPFAKRY     120
LIDKGLTPME GNEKLTFLAV DIETLYHEGE EFGKGPVIMI SYADEEGAKV ITWKKIDLPY     180
VEVVSSEREM IKRLIRVIKE KDPDVIITYN GDNFDFPYLL KRAEKLGIKL LLGRDNSEPK     240
MQKMGDSLAV EIKGRIHFDL FPVIRRTINL PTYTLEAVYE AIFGKPKEKV YADEIAKAWE     300
TGEGLERVAK YSMEDAKVTY ELGREFFPME AQLARLVGQP VWDVSRSSTG NLVEWFLLRK     360
AYERNELAPN KPDEKEYERR LRESYEGGYV KEPEKGLWEG IVSLDFRSLY PSIIITHNVS     420
PDTLNREGCE EYDVAPKVGH RFCKDFPGFI PSLLGQLLEE RQKIKKRMKE SKDPVEKKLL     480
DYRQRAIKIL ANSILPDEWL PIVENEKVRF VKIGDFIDRE IEENAERVKR DGETEILEVK     540
DLKALSFNRE TKKSELKKVK ALIRHRYSGK VYSIKLKSGR RIKITSGHSL FSVKNGKLVK     600
VRGDELKPGD LVVVPGRLKL PESKQVLNLV ELLLKLPEEE TSNIVMMIPV KGRKNFFKGM     660
LKTLYWIFGE GERPRTAGRY LKHLERLGYV KLKRRGCEVL DWESLKRYRK LYETLIKNLK     720
YNGNSRAYMV EFNSLRDVVS LMPIEELKEW IIGEPRGPKI GTFIDVDDSF AKLLGYYISS     780
GDVEKDRVKF HSKDQNVLED IAKLAEKLFG KVRRGRGYIE VSGKISHAIF RVLAEGKRIP     840
EFIFTSPMDI KVAFLKGLNG NAEELTFSTK SELLVNQLIL LLNSIGVSDI KIEHEKGVYR     900
VYINKKESSN GDIVLDSVES IEVEKYEGYV YDLSVEDNEN FLVGFGLLYA HNSYYGYYGY     960
AKARWYCKEC AESVTAWGRQ YIDLVRRELE ARGFKVLYID TDGLYATIPG VKDWEEVKRR    1020
ALEFVDYINS KLPGVLELEY EGFYARGFFV TKKKYALIDE EGKIVTRGLE IVRRDWSEIA    1080
KETQARVLEA ILKHGNVEEA VKIVKDVTEK LTNYEVPPEK LVIYEQITRP INEYKAIGPH    1140
VAVAKRLMAR GIKVKPGMVI GYIVLRGDGP ISKRAISIEE FDPRKHKYDA EYYIENQVLP    1200
AVERILKAFG YKREDLRWQK TKQVGLGAWI KVKKS                              1235
```

PYRSE *PYROCOCCUS* SP. (STRAIN GE23) (SEQ ID NO: 66)

TABLE II-continued

Accession Information for Cloned Family B Polymerases

```
ACCESSION   P77932
PID   g3913530
VERSION   P77932 GI:3913530
DBSOURCE   swissprot: locus DPOL_PYRSE, accession P77932

MIIDADYITE DGKPIIRIFK KEKGEFKVEY DRTFRPYIYA LLKDDSAIDE VKKITAERHG    60

KIVRITEVEK VQKKFLGRPI EVWKLYLEHP QDVPAIREKI REHPAVVDIF EYDIPFAKRY   120

LIDKGLTPME GNEELTFLAV DIETLYHEGE EFGKGPIIMI SYADEEGAKV ITWKSIDLPY   180

VEVVSSEREM IKRLVKVIRE KDPDVIITYN GDNFDFPYLL KRAEKLGIKL PLGRDNSEPK   240

MQRMGDSLAV EIKGRIHFDL FPVIRRTINL PTYTLEAVYE AIFGKSKEKV YAHEIAEAWE   300

TGKGLERVAK YSMEDAKVTF ELGKEFFPME AQLARLVGQP VWDVSRSSTG NLVEWFLLRK   360

AYERNELAPN KPDEREYERR LRESYEGGYV KEPEKGLWEG IVSLDFRSLY PSIIITHNVS   420

PDTLNRENCK EYDVAPQVGH RFCKDFPGFI PSLLGNLLEE RQKIKKRMKE SKDPVEKKLL   480

DYRQRAIKIL ANSYYGYYGY AKARWYCKEC AESVTAWGRQ YIDLVRRELE SSGFKVLYID   540

TDGLYATIPG AKPNEIKEKA LKFVEYINSK LPGLLELEYE GFYARGFFVT KKKYALIDEE   600

GKIVTRGLEI VRRDWSEIAK ETQAKVLEAI LKHGNVDEAV KIVKEVTEKL SKYEIPPEKL   660

VIYEQITRPL SEYKAIGPHV AVAKRLAAKG VKVKPGMVIG YIVLRGDGPI SKRAIAIEEF   720

DPKKHKYDAE YYIENQVLPA VERILRAFGY RKEDLRYQKT KQVGLGAWLK F            771

DeepVent Pyrococcus sp. (SEQ ID NO: 67)
ACCESSION   AAA67131
PID   g436495
VERSION   AAA67131.1 GI:436495
DBSOURCE   locus PSU00707 accession U00707.1

MILDADYITE DGKPIIRIFK KENGEFKVEY DRNFRPYIYA LLKDDSQIDE VRKITAERHG    60

KIVRIIDAEK VRKKFLGRPI EVWRLYFEHP QDVPAIRDKI REHSAVIDIF EYDIPFAKRY   120

LIDKGLIPME GDEELKLLAF DIETLYHEGE EFAKGPIIMI SYADEEEAKV ITWKKIDLPY   180

VEVVSSEREM IKRFLKVIRE KDPDVIITYN GDSFDLPYLV KRAEKLGIKL PLGRDGSEPK   240

MQRLGDMTAV EIKGRIHFDL YHVIRRTINL PTYTLEAVYE AIFGKPKEKV YAHEIAEAWE   300

TGKGLERVAK YSMEDAKVTY ELGREFFPME AQLSRLVGQP LWDVSRSSTG NLVEWYLLRK   360

AYERNELAPN KPDEREYERR LRESYAGGYV KEPEKGLWEG LVSLDFRSLY PSIIITHNVS   420

PDTLNREGCR EYDVAPEVGH KFCKDFPGFI PSLLKRLLDE RQEIKRKMKA SKDPIEKKML   480

DYRQRAIKIL ANSYYGYYGY AKARWYCKEC AESVTAWGRE YIEFVRKELE EKFGFKVLYI   540

DTDGLYATIP GAKPEEIKKK ALEFVDYINA KLPGLLELEY EGFYVRGFFV TKKKYALIDE   600

EGKIITRGLE IVRRDWSEIA KETQAKVLEA ILKHGNVEEA VKIVKEVTEK LSKYEIPPEK   660

LVIYEQITRP LHEYKAIGPH VAVAKRLAAR GVKVRPGMVI GYIVLRGDGP ISKRAILAEE   720

FDLRKHKYDA EYYIENQVLP AVLRILEAFG YRKEDLRWQK TKQTGLTAWL NIKKK        775

Pfu Pyrococcus furiosus (SEQ ID NO: 68)
ACCESSION   P80061
PID   g399403
VERSION   P80061 GI:399403
DBSOURCE   swissprot: locus DPOL_PYRFU, accession P80061

MILDVDYITE EGKPVIRLFK KENGKFKIEH DRTFRPYIYA LLRDDSKIEE VKKITGERHG    60

KIVRIVDVEK VEKKFLGKPI TVWKLYLEHP QDVPTIREKV REHPAVVDIF EYDIPFAKRY   120

LIDKGLIPME GEEELKILAF DIETLYHEGE EFGKGPIIMI SYADENEAKV ITWKNIDLPY   180

VEVVSSEREM IKRFLRIIRE KDPDIIVTYN GDSFDFPYLA KRAEKLGIKL TIGRDGSEPK   240

MQRIGDMTAV EVKGRIHFDL YHVITRTINL PTYTLEAVYE AIFGKPKEKV YADEIAKAWE   300
```

TABLE II-continued

Accession Information for Cloned Family B Polymerases

```
SGENLERVAK YSMEDAKATY ELGKEFLPME IQLSRLVGQP LWDVSRSSTG NLVEWFLLRK    360

AYERNEVAPN KPSEEEYQRR LRESYTGGFV KEPEKGLWEN IVYLDFRALY PSIIITHNVS    420

PDTLNLEGCK NYDIAPQVGH KFCKDIPGFI PSLLGHLLEE RQKIKTKMKE TQDPIEKILL    480

DYRQKAIKLL ANSFYGYYGY AKARWYCKEC AESVTAWGRK YIELVWKELE EKFGFKVLYI    540

DTDGLYATIP GGESEEIKKK ALEFVKYINS KLPGLLELEY EGFYKRGFFV TKKRYAVIDE    600

EGKVITRGLE IVRRDWSEIA KETQARVLET ILKHGDVEEA VRIVKEVIQK LANYEIPPEK    660

LAIYEQITRP LHEYKAIGPH VAVAKKLAAK GVKIKPGMVI GYIVLRGDGP ISNRAILAEE    720

YDPKKHKYDA EYYIENQVLP AVLRILEGFG YRKEDLRYQK TRQVGLTSWL NIKKS         775
```

JDF-3 *Thermococcus* sp. (SEQ ID NO: 69)
Unpublished
Baross gi|2097756|pat|US|5602011|12 Sequence 12 from U.S. Pat. No. 5,602,011
9degN THERMOCOCCUS SP. (STRAIN 9ON-7).
ACCESSION   Q56366
PID     g3913540
VERSION   Q56366 GI:3913540
DBSOURCE   swissprot: locus DPOL_THES9, accession Q56366

```
MILDTDYITE NGKPVIRVFK KENGEFKIEY DRTFEPYFYA LLKDDSAIED VKKVTAKRHG     60

TVVKVKRAEK VQKKFLGRPI EVWKLYFNHP QDVPAIRDRI RAHPAVVDIY EYDIPFAKRY    120

LIDKGLIPME GDEELTMLAF DIETLYHEGE EFGTGPILMI SYADGSEARV ITWKKIDLPY    180

VDVVSTEKEM IKRFLRVVRE KDPDVLITYN GDNFDFAYLK KRCEELGIKF TLGRDGSEPK    240

IQRMGDRFAV EVKGRIHFDL YPVIRRTINL PTYTLEAVYE AVFGKPKEKV YAEEIAQAWE    300

SGEGLERVAR YSMEDAKVTY ELGREFFPME AQLSRLIGQS LWDVSRSSTG NLVEWFLLRK    360

AYKRNELAPN KPDERELARR RGGYAGGYVK EPERGLWDNI VYLDFRSLYP SIIITHNVSP    420

DTLNREGCKE YDVAPEVGHK FCKDFPGFIP SLLGDLLEER QKIKRKMKAT VDPLEKKLLD    480

YRQRAIKILA NSFYGYYGYA KARWYCKECA ESVTAWGREY IEMVIRELEE KFGFKVLYAD    540

TDGLHATIPG ADAETVKKKA KEFLKYINPK LPGLLELEYE GFYVRGFFVT KKKYAVIDEE    600

GKITTRGLEI VRRDWSEIAK ETQARVLEAI LKHGDVEEAV RIVKEVTEKL SKYEVPPEKL    660

VIHEQITRDL RDYKATGPHV AVAKRLAARG VKIRPGTVIS YIVLKGSGRI GDRAIPADEF    720

DPTKHRYDAE YYIENQVLPA VERILKAFGY RKEDLRYQKT KQVGLGAWLK VKGKK         775
```

KOD *Pyrococcus* sp. (SEQ ID NO: 70)
ACCESSION   BAA06142
PID     g1620911
VERSION   BAA06142.1 GI:1620911
DBSOURCE   locus PYWKODPOL accession D29671.1

```
MILDTDYITE DGKPVIRIFK KENGEFKIEY DRTFEPYFYA LLKDDSAIEE VKKITAERHG     60

TVVTVKRVEK VQKKFLGRPV EVWKLYFTHP QDVPAIRDKI REHPAVIDIY EYDIPFAKRY    120

LIDKGLVPME GDEELKMLAF DIETLYHEGE EFAEGPILMI SYADEEGARV ITWKNVDLPY    180

VDVVSTEREM IKRFLRVVKE KDPDVLITYN GDNFDFAYLK KRCEKLGINF ALGRDGSEPK    240

IQRMGDRFAV EVKGRIHFDL YPVIRRTINL PTYTLEAVYE AVFGQPKEKV YAEEITTAWE    300

TGENLERVAR YSMEDAKVTY ELGKEFLPME AQLSRLIGQS LWDVSRSSTG NLVEWFLLRK    360

AYERNELAPN KPDEKELARR RQSYEGGYVK EPERGLWENI VYLDFRCHPA DTKVVVKGKG    420

IINISEVQEG DYVLGIDGWQ RVRKVWEYDY KGELVNINGL KCTPNHKLPV VTKNERQTRI    480

RDSLAKSFLT KKVKGKIITT PLFYEIGRAT SENIPEEEVL KGELAGILLA EGTLLRKDVE    540

YFDSSRKKRR ISHQYRVEIT IGKDEEEFRD RITYIFERLF GITPSISEKK GTNAVTLKVA    600
```

TABLE II-continued

Accession Information for Cloned Family B Polymerases

```
KKNVYLKVKE IMDNIESLHA PSVLRGFFEG DGSVNRVRRS IVATQGTKNE WKIKLVSKLL    660

SQLGIPHQTY TYQYQENGKD RSRYILEITG KDGLILFQTL IGFISERKNA LLNKAISQRE    720

MNNLENNGFY RLSEFNVSTE YYEGKVYDLT LEGTPYYFAN GILTHNSLYP SIIITHNVSP    780

DTLNREGCKE YDVAPQVGHR FCKDFPGFIP SLLGDLLEER QKIKKKMKAT IDPIERKLLD    840

YRQRAIKILA NSILPEEWLP VLEEGEVHFV RIGELIDRMM EENAGKVKRE GETEVLEVSG    900

LEVPSFNRRT NKAELKRVKA LIRHDYSGKV YTIRLKSGRR IKITSGHSLF SVRNGELVEV    960

TGDELKPGDL VAVPRRLELP ERNHVLNLVE LLLGTPEEET LDIVMTIPVK GKKNFFKGML   1020

RTLRWIFGEE KRPRTARRYL RHLEDLGYVR LKKIGYEVLD WDSLKNYRRL YEALVENVRY   1080

NGNKREYLVE FNSIRDAVGI MPLKELKEWK IGTLNGFRMR KLIEVDESLA KLLGYYVSEG   1140

YARKQRNPKN GWSYSVKLYN EDPEVLDDME RLASRFFGKV RRGRNYVEIP KKIGYLLFEN   1200

MCGVLAENKR IPEFVFTSPK GVRLAFLEGY FIGDGDVHPN KRLRLSTKSE LLANQLVLLL   1260

NSVGVSAVKL GHDSGVYRVY INEELPFVKL DKKKNAYYSH VIPKEVLSEV FGKVFQKNVS   1320

PQTFRKMVED GRLDPEKAQR LSWLIEGDVV LDRVESVDVE DYDGYVYDLS VEDNENFLVG   1380

FGLVYAHNSY YGYYGYARAR WYCKECAESV TAWGREYITM TIKEIEEKYG FKVIYSDTDG   1440

FFATIPGADA ETVKKKAMEF LKYINAKLPG ALELEYEGFY KRGFFVTKKK YAVIDEEGKI   1500

TTRGLEIVRR DWSEIAKETQ ARVLEALLKD GDVEKAVRIV KEVTEKLSKY EVPPEKLVIH   1560

EQITRDLKDY KATGPHVAVA KRLAARGVKI RPGTVISYIV LKGSGRIGDR AIPFDEFDPT   1620

KHKYDAEYYI ENQVLPAVER ILRAFGYRKE DLRYQKTRQV GLSAWLKPKG T            1671

Tgo Thermococcus gorgonarius. (SEQ ID NO: 71)
ACCESSION   4699806
PID     g4699806
VERSION   GI:4699806
DBSOURCE    pdb: chain 65, release Feb. 23, 1999

MILDTDYITE DGKPVIRIFK KENGEFKIDY DRNFEPYIYA LLKDDSAIED VKKITAERHG     60

TTVRVVRAEK VKKKFLGRPI EVWKLYFTHP QDVPAIRDKI KEHPAVVDIY EYDIPFAKRY   120

LIDKGLIPME GDEELKMLAF DIETLYHEGE EFAEGPILMI SYADEEGARV ITWKNIDLPY   180

VDVVSTEKEM IKRFLKVVKE KDPDVLITYN GDNFDFAYLK KRSEKLGVKF ILGREGSEPK   240

IQRMGDRFAV EVKGRIHFDL YPVIRRTINL PTYTLEAVYE AIFGQPKEKV YAEEIAQAWE   300

TGEGLERVAR YSMEDAKVTY ELGKEFFPME AQLSRLVGQS LWDVSRSSTG NLVEWFLLRK   360

AYERNELAPN KPDERELARR RESYAGGYVK EPERGLWENI VYLDFRSLYP SIIITHNVSP   420

DTLNREGCEE YDVAPQVGHK FCKDFPGFIP SLLGDLLEER QKVKKKMKAT IDPIEKKLLD   480

YRQRAIKILA NSFYGYYGYA KARWYCKECA ESVTAWGRQY IETTIREIEE KFGFKVLYAD   540

TDGFFATIPG ADAETVKKKA KEFLDYINAK LPGLLELEYE GFYKRGFFVT KKKYAVIDEE   600

DKITTRGLEI VRRDWSEIAK ETQARVLEAI LKHGDVEEAV RIVKEVTEKL SKYEVPPEKL   660

VIYEQITRDL KDYKATGPHV AVAKRLAARG IKIRPGTVIS YIVLKGSGRI GDRAIPFDEF   720

DPAKHKYDAE YYIENQVLPA VERILRAFGY RKEDLRYQKT RQVGLGAWLK PKT          773

THEFM Thermococcus fumicolans (SEQ ID NO: 72)
ACCESSION   P74918
PID     g3913528
VERSION   P74918 GI:3913528
DBSOURCE    swissprot: locus DPOL_THEFM, accession P74918

MILDTDYITE DGRPVIRVFK KENGEFKIEY DRDFEPYIYA LLKDDSAIED VKKITASRHG     60

TTVRVVRAGK VKKKFLGRPI EVWKLYFTHP QDVPAIRDKI REHPAVVDIY EYDIPFAKRY   120
```

TABLE II-continued

Accession Information for Cloned Family B Polymerases

```
LIDKGLIPME GDEELKMLAF DIETLYHEGE EFAEGPILMI SYADEEGARV ITWKKIDLPY    180

VDVVSTEKEM IKRFLKVVKE KDPDVLITYN GDNFDFAYLK KRSEKLGVKF ILGRDGSEPK    240

IQRMGDRFAV EVKGRIHFDL YPVIRHTINL PTYTLEAVYE AIFGQPKEKV YAEEIAQAWE    300

TGEGLERVAR YSMEDAKVTY ELGREFFPME AQLSRLVGQS FWDVSRSSTG NLVEWYLLRK    360

AYERNELAPN KPSGRELERR RGGYAGGYVK EPERGLWENI AYLDFRCHPA DTKVIVKGKG    420

VVNISEVREG DYVLGIDGWQ KVQRVWEYDY EGELVNINGL KCTPNHKLPV VRRTERQTAI    480

RDSLAKSFLT KKVKGKLITT PLFEKIGKIE REDVPEEEIL KGELAGIILA EGTLLRKDVE    540

YFDSSRGKKR VSHQYRVEIT VGAQEEDFQR RIVYIFERLF GVTPSVYRKK NTNAITFKVA    600

KKEVYLRVRE IMDGIENLHA PSVLRGFFEG DGSVNKVRKT VVVNQGTNNE WKIEVVSKLL    660

NKLGIPHRRY TYDYTEREKT MTTHILEIAG RDGLILFQTI VGFISTEKNM ALEEAIRNRE    720

VNRLENNAFY TLADFTAKTE YYKGKVYDLT LEGTPYYFAN GILTHNSLYP SIIISHNVSP    780

DTLNREGCGE YDEAPQVGHR FCKDFPGFIP SLLGDLLDER QKVKKHMKAT VDPIEKKLLD    840

YRQRAIKILA NSFYGYYGYA KARWYCKECA ESVTAWGRQY IETTMREIEE KFGFKVLYAD    900

SVTGDTEVTI RRNGRIEFVP IEKLFERVDH RVGEKEYCVL GGVEALTLDN RGRLVWKKVP    960

YVMRHKTDKR IYRVWFTNSW YLDVTEDHSL IGYLNTSKVK PGKPLKERLV EVKPEELGGK   1020

VKSLITPNRP IARTIKANPI AVKLWELIGL LVGDGNWGGQ SNWAKYYVGL SCGLDKAEIE   1080

RKVLNPLREA SVISNYYDKS KKGDVSILSK WLAGFMVKYF KDENGNKAIP SFMFNLPREY   1140

IEAFLRGLFS ADGTVSLRRG IPEIRLTSVN RELSDAVRKL LWLVGVSNSL FTETKPNRYL   1200

EKESGTHSIH VRIKNKHRFA DRIGFLIDRK STKLSENLGG HTNKKRAYKY DFDLVYPRKI   1260

EEITYDGYVY DIEVEGTHRF FANGILVHNT DGFFATIPGA DAETVKKKAR EFLNYINPKL   1320

PGLLELEYEG FYRRGFFVTK KKYAVIDEEG KITTRGLEIV RRDWSEVAKE TQARVLEAIL   1380

RHGDVEEAVR IVKEVTEKLS KYEVPPEKLV IHEQITRELK DYKATGPHVA IAKRLAARGI   1440

KVRPGTVISY IVLKGSGRIG DRTIPFDEFD PTKHRYDAEY YIENQVLPAV ERILKAFGYK   1500

KEDLRYQKTR QVGLGAWLKM GKK                                          1523
```

METTH *Methanobacterium thermoautotrophicum* (SEQ ID NO: 73)
ACCESSION   O27276
PID   g3913522
VERSION   O27276 GI:3913522
DBSOURCE   swissprot: locus DPOL_METTH, accession O27276

```
MEDYRMVLLD IDYVTVDEVP VIRLFGKDKS GGNEPIIAHD RSFRPYIYAI PTDLDECLRE     60

LEELELEKLE VKEMRDLGRP TEVIRIEFRH PQDVPKIRDR IRDLESVRDI REHDIPFYRR    120

YLIDKSIVPM EELEFQGVEV DSAPSVTTDV RTVEVTGRVQ STGSGAHGLD ILSFDIEVRN    180

PHGMPDPEKD EIVMIGVAGN MGYESVISTA GDHLDFVEVV EDERELLERF AEIVIDKKPD    240

ILVGYNSDNF DFPYITRRAA ILGAELDLGW DGSKIRTMRR GFANATAIKG TVHVDLYPVM    300

RRYMNLDRYT LERVQELFG EEKIDLPGDR LWEYWDRDEL RDELFRYSLD DVVATHRIAE    360

KILPLNLELT RLVGQPLFDI SRMATGQQAE WFLVRKAYQY GELVPNKPSQ SDFSSRRGRR    420

AVGGYVKEPE KGLHENIVQF DFRSLYPSII ISKNISPDTL TDDEESECYV APEYGYRFRK    480

SPRGFVPSVI GEILSERVRI KEEMKGSDDP MERKILNVQQ EALKRLANTM YGVYGYSRFR    540

WYSMECAEAI TAWGRDYIKK TIKTAEEFGF HTVYADTDGF YATYRG                   586
```

Metja *Methanococcus jannaschii* (SEQ ID NO: 74)
ACCESSION   Q58295
PID   g3915679
VERSION   Q58295 GI:3915679

TABLE II-continued

Accession Information for Cloned Family B Polymerases

DBSOURCE    swissprot: locus DPOL_METJA, accession Q58295

| | | | | | |
|---|---|---|---|---|---|
| MGMSMGKIKI | DALIDNTYKT | IEDKAVIYLY | LINSILKDRD | FKPYFYVELH | KEKVENEDIE | 60
| KIKEFLLKND | LLKFVENIEV | VKKIILRKEK | EVIKIIATHP | QKVPKLRKIK | ECEIVKEIYE | 120
| HDIPFAKRYL | IDNEIIPMTY | WDFENKKPVS | IEIPKLKSVA | FDMEVYNRDT | EPNPERDPIL | 180
| MASFWDENGG | KVITYKEFNH | PNIEVVKNEK | ELIKKIIETL | KEYDVIYTYN | GDNFDFPYLK | 240
| ARAKIYGIDI | NLGKDGEELK | IKRGGMEYRS | YIPGRVHIDL | YPISRRLLKL | TKYTLEDVVY | 300
| NLFGIEKLKI | PHTKIVDYWA | NNDKTLIEYS | LQDAKYTYKI | GKYFFPLEVM | FSRIVNQTPF | 360
| EITRMSSGQM | VEYLLMKRAF | KENMIVPNKP | DEEEYRRRVL | TTYEGGYVKE | PEKGMFEDII | 420
| SMDFRCHPKG | TKVVVKGKGI | VNIEDVKEGN | YVLGIDGWQK | VKKVWKYEYE | GELINVNGLK | 480
| CTPNHKIPLR | YKIKHKKINK | NDYLVRDIYA | KSLLTKFKGE | GKLILCKDFE | TIGNYEKYIN | 540
| DMDEDFILKS | ELIGILLAEG | HLLRRDIEYF | DSSRGKKRIS | HQYRVEITVN | EDEKDFIEKI | 600
| KYIFKKLFNY | ELYVRRKKGT | KAITLGCAKK | DIYLKIEEIL | KNKEKYLPNA | ILRGFFEGDG | 660
| YVNTVRRAVV | VNQGTNNYDK | IKFIASLLDR | LGIKYSFYTY | SYEERGKKLK | RYVIEIFSKG | 720
| DLIKFSILIS | FISRRKNNLL | NEIIRQKTLY | KIGDYGFYDL | DDVCVSLESY | KGEVYDLTLE | 780
| GRPYYFANGI | LTHNSLYPSI | IISYNISPDT | LDCECCKDVS | EKILGHWFCK | KKEGLIPKTL | 840
| RNLIERRINI | KRRMKKMAEI | GEINEEYNLL | DYEQKSLKIL | ANSILPDEYL | TIIEEDGIKV | 900
| VKIGEYIDDL | MRKHKDKIKF | SGISEILETK | NLKTFSFDKI | TKKCEIKKVK | ALIRHPYFGK | 960
| AYKIKLRSGR | TIKVTRGHSL | FKYENGKIVE | VKGDDVRFGD | LIVVPKKLTC | VDKEVVINIP | 1020
| KRLINADEEE | IKDLVITKHK | DKAFFVKLKK | TLEDIENNKL | KVIFDDCILY | LKELGLIDYN | 1080
| IIKKINKVDI | KILDEEKFKA | YKKYFDTVIE | HGNFKKGRCN | IQYIKIKDYI | ANIPDKEFED | 1140
| CEIGAYSGKI | NALLKLDEKL | AKFLGFFVTR | GRLKKQKLKG | ETVYEISVYK | SLPEYQKEIA | 1200
| ETFKEVFGAG | SMVKDKVTMD | NKIVYLVLKY | IFKCGDKDKK | HIPEELFLAS | ESVIKSFLDG | 1260
| FLKAKKNSHK | GTSTFMAKDE | KYLNQLMILF | NLVGIPTRFT | PVKNKGYKLT | LNPKYGTVKD | 1320
| LMLDEVKEIE | AFEYSGYVYD | LSVEDNENFL | VNNIYAHNSV | YGYLAFPRAR | FYSRECAEIV | 1380
| TYLGRKYILE | TVKEAEKFGF | KVLYIDTDGF | YAIWKEKISK | EELIKKAMEF | VEYINSKLPG | 1440
| TMELEFEGYF | KRGIFVTKKR | YALIDENGRV | TVKGLEFVRR | DWSNIAKITQ | RRVLEALLVE | 1500
| GSIEKAKKII | QDVIKDLREK | KIKKEDLIIY | TQLTKDPKEY | KTTAPHVEIA | KKLMREGKRI | 1560
| KVGDIIGYII | VKGTKSISER | AKLPEEVDID | DIDVNYYIDN | QILPPVLRIM | EAVGVSKNEL | 1620
| KKEGAQLTLD | KFFK | | | | | 1634

POC *Pyrodictium occultum* (SEQ ID NO: 75)
ACCESSION   B56277
PID         g1363344
VERSION     B56277 GI:1363344
DBSOURCE    pir: locus B56277

| | | | | | |
|---|---|---|---|---|---|
| MTETIEFVLL | DSSYEILGKE | PVVILWGITL | DGKRVVLLDH | RFRPYFYALI | ARGYEDMVEE | 60
| IAASIRRLSV | VKSPIIDAKP | LDKRYFGRPR | KAVKITTMIP | ESVRHYREAV | KKIEGVEDSL | 120
| EADIRFAMRY | LIDKRLYPFT | VYRIPVEDAG | RNPGFRVDRV | YKVAGDPEPL | ADITRIDLPP | 180
| MRLVAFDIEV | YSRRGSPNPA | RDPVIIVSLR | DSEGKERLIE | AEGHDDRRVL | REFVEYVRAF | 240
| DPDIIVGYNS | NHFDWPYLME | RARRLGIKLD | VTRRVGAEPT | TSVYGHVSVQ | GRLNVDLYDY | 300
| AEEMPEIKMK | TLEEVAEYLG | VMKKSERVII | EWWRIPEYWD | DEKKRQLLER | YALDDVRATY | 360
| GLAEKMLPFA | IQLSTVTGVP | LDQVGAMGVG | FRLEWYLMRA | AYDMNELVPN | RVERRGESYK | 420

TABLE II-continued

Accession Information for Cloned Family B Polymerases

```
GAVVLKPLKG VHENVVVLDF SSMYPSIMIK YNVGPDTIVD DPSECPKYGG CYVAPEVGHR    480

FRRSPPGFFK TVLENLLKLR RQVKEKMKEF PPDSPEYRLY DERQKALKVL ANASYGYMGW    540

SHARWYCKRC AEAVTAWGRN LILTAIEYAR KLGLKVIYGD TDSLFVVYDK EKVEKLIEFV    600

EKELGFEIKI DKIYKKVFFT EAKKRYVGLL EDGRIDIVGF EAVRGDWCEL AKEVQEKAAE    660

IVLNTGNVDK AISYIREVIK QLREGKVPIT KLIIWKTLSK RIEEYEHDAP HVMAARRMKE    720

AGYEVSPGDK VGYVIVKGSG SVSSRAYPYF MVDPSTIDVN YYIDHQIVPA ALRILSYFGV    780

TEKQLKAAAT VQRSLFDFFA SKK                                           803
```

ApeI *Aeropyrum pernix* (SEQ ID NO: 76)
ACCESSION   BAA81109
PID   g5105797
VERSION   BAA81109.1 GI:5105797
DBSOURCE   locus AP000063 accession AP000063.1

```
MRGSTPVIIL WGRGADGSRV VVFYGEFRPY FYVLPDGSVG LDQLAAMIRR LSRPSSPILS     60

VERVRRRFIG REVEALKVTT LVPASVREYR EAVRRLGGVR DVLEADIPFA LRFIIDFNLY    120

PMRWYVAEVR EVAVPHGYSV DRAYTLSGDI REDETRIQED PLKGLRVMAF DIEVYSKMRT    180

PDPKKDPVIM IGLQQAGGEI EILEAEDRSD KKVIAGFVER VKSIDPDVIV GYNQNRFDWP    240

YLVERARVLG VKLAVGRRSV EPQPGLYGHY SVSGRLNVDL LDFAEELHEV KVKTLEEVAD    300

YLGVVKIGER VTLEWWQIGE YWDDPSKREI LRKYLRDDVR STMGLAEKFL PFGAELSQVS    360

GLPLDQVMAA SVGFRLEWRL IREAAKLGEL VPNRVERSEG RYAGAIVLRP KPGVHEDIAV    420

LDFASMYPNI MVKYNVGPDT LVRPGEEYGE EEVYTAPEVG HKFRKSPPGF FKKILERFLS    480

WRRQIRSEMK KHPPDSPEYK LLDERQKAIK LLANASYGYM GWPHARWYCR ECAEAVTAWG    540

RSIIRTAIRK AGELGLEVIY GDTDSLFVKN DPEKVERLIR FVEEELGFDI KVDKVYRRVF    600

FTEAKKRYVG LTVDGKIDVV GFEAVRGDWS ELAKETQFKV AEIVLKTGSV DEAVDYVRNI    660

IEKLRRGQVD MRKLVIWKTL TRPPSMYEAR QPHVTAALLM ERAGIKVEPG AKIGYVVTKG    720

SGPLYTRAKP YFMASKEEVD VEYYVDKQVV PAALRILQYF GVTEKRLKGG GRQSTLLDFM    780

RRGK                                                               784
```

ARCFU *Archaeoglobus fulgidus* (SEQ ID NO: 77)
ACCESSION   O29753
PID   g3122019
VERSION   O29753 GI:3122019
DBSOURCE   swissprot: locus DPOL_ARCFU, accession O29753

```
MERVEGWLID ADYETIGGKA VVRLWCKDDQ GIFVAYDYNF DPYFYVIGVD EDILKNAATS     60

TRREVIKLKS FEKAQLKTLG REVEGYIVYA HHPQHVPKLR DYLSQFGDVR EADIPFAYRY    120

LIDKDLACMD GIAIEGEKQG GVIRSYKIEK VERIPRMEFP ELKMLVFDCE MLSSFGMPEP    180

EKDPIIVISV KTNDDDEIIL TGDERKIISD FVKLIKSYDP DIIVGYNQDA FDWPYLRKRA    240

ERWNIPLDVG RDGSNVVFRG GRPKITGRLN VDLYDIAMRI SDIKIKKLEN VAEFLGTKIE    300

IADIEAKDIY RYWSRGEKEK VLNYARQDAI NTYLIAKELL PMHYELSKMI RLPVDDVTRM    360

GRGKQVDWLL LSEAKKIGEI APNPPEHAES YEGAFVLEPE RGLHENVACL DFASMYPSIM    420

IAFNISPDTY GCRDDCYEAP EVGHKFRKSP DGFFKRILRM LIEKRRELKV ELKNLSPESS    480

EYKLLDIKQQ TLKVLTNSFY GYMGWNLARW YCHPCAEATT AWGRHFIRTS AKIAESMGFK    540

VLYGDTDSIF VTKAGMTKED VDRLIDKLHE ELPIQIEVDE YYSAIFFVEK KRYAGLTEDG    600

RLVVKGLEVR RGDWCELAKK VQREVIEVIL KEKNPEKALS LVKDVILRIK EGKVSLEEVV    660

IYKGLTKKPS KYESMQAHVK AALKAREMGI IYPVSSKIGY VIVKGSGNIG DRAYPIDLIE    720
```

TABLE II-continued

Accession Information for Cloned Family B Polymerases

```
DFDGENLRIK TKSGIEIKKL DKDYYIDNQI IPSVLRILER FGYTEASLKG SSQMSLDSFF      780

S                                                                     781

Desulfurococcus sp. Tok. (SEQ ID NO: 78)
ACCESSION   6435708
PID         g64357089
VERSION     GI:6435708
DBSOURCE    pdb. chain 65, release Jun. 2, 1999

MILDADYITE DGKPVIRVFK KEKGEFKIDY DRDFEPYIYA LLKDDSAIED IKKITAERHG       60

TTVRVTRAER VKKKFLGRPV EVWKLYFTHP QDVPAIRDKI REHPAVVDIY EYDIPFAKRY      120

LIDRGLIPME GDEELRMLAF DIETLYHEGE EFGEGPILMI SYADEEGARV ITWKNIDLPY      180

VESVSTEKEM IKRFLKVIQE KDPDVLITYN GDNFDFAYLK KRSEMLGVKF ILGRDGSEPK      240

IQRMGDRFAV EVKGRIHFDL YPVIRRTINL PTYTLETVYE PVFGQPKEKV YAEEIARAWE      300

SGEGLERVAR YSMEDAKATY ELGKEFFPME AQLSRLVGQS LWDVSRSSTG NLVEWFLLRK      360

AYERNDVAPN KPDERELARR TESYAGGYVK EPEKGLWENI VYLDYKSLYP SIIITHNVSP      420

DTLNREGCRE YDVAPQVGHR FCKDFPGFIP SLLGDLLEER QKVKKKMKAT VDPIERKLLD      480

YRQRAIKILA NSYYGYYAYA NARWYCRECA ESVTAWGRQY IETTMREIEE KFGFKVLYAD      540

TDGFFATIPG ADAETVKNKA KEFLNYINPR LPGLLELEYE GFYRRGFFVT KKKYAVIDEE      600

DKITTRGLEI VRRDWSEIAK ETQARVLEAI LKHGDVEEAV RIVKEVTEKL SRHEVPPEKL      660

VIYEQITRDL RSYRATGPHV AVAKRLAARG IKIRPGTVIS YIVLKGPGRV GDRAIPFDEF      720

DPAKHRYDAE YYIENQVLPA VERILRAFGY RKEDLRYQKT KQAGLGAWLK PKT             773
```

Plasmids acceptable for the expression of modified forms of Family B DNA polymerases may be selected from a large number known in the art by one of skill in the art. A plasmid vector for expression of a modified DNA polymerase according to the invention will preferably comprise sequences directing high level expression of a DNA polymerase, and will more preferably comprise sequences directing inducible, high level expression of a DNA polymerase As one example of an inducible high level expression system, plasmids placing a modified DNA polymerase coding sequence according to the invention under the control of a bacteriophage T7 promoter may be introduced to bacteria containing an inducible T7 RNA polymerase gene within their chromosome. Induction of the T7 RNA polymerase gene subsequently induces high level expression of the T7 promoter-driven modified DNA polymerase gene (see for example, Gardner & Jack, Nucleic Acids Res. 27: 2545).

C. Mutagenesis

The cloned wild-type form of a Family B DNA polymerase may be mutated to generate forms exhibiting reduced discrimination against non-conventional nucleotides by a number of methods.

First, methods of random mutagenesis which will result in a panel of mutants bearing one or more randomly-situated mutations exist in the art. Such a panel of mutants may then be screened for those exhibiting reduced discrimination relative to the wild-type polymerase (see "Methods of Evaluating Mutants for Reduced Discrimination", below). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Second, there are a number of site-directed mutagenesis methods known in the art which allow one to mutate a particular site or region in a straightforward manner. There are a number of kits available commercially for the performance of site-directed mutagenesis, including both conventional and PCR-based methods. Examples include the EXSITE™ PCR-Based Site-directed Mutagenesis Kit available from Stratagene (Catalog No. 200502; PCR based) and the QUIKCHANGE™ Site-directed mutagenesis Kit from Stratagene (Catalog No. 200518; non-PCR-based), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one annealed a mutagenic primer (i.e., a primer capable of annealing to the site to be mutated but bearing one or mismatched nucleotides at the site to be mutated) to the single-stranded template and then polymerized the complement of the template starting from the 3' end of the mutagenic primer. The resulting duplexes were then transformed into host bacteria and plaques were screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accomodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease DpnI (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

The method is described in detail as follows:

PCR-based Site Directed Mutagenesis of the 3'-5' Exonuclease domain

Plasmid template DNA (approximately 0.5 pmole) is added to a PCR cocktail containing: 1× mutagenesis buffer (20 mM Tris HCl, pH 7.5; 8 mM MgCl2; 40 ug/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 uM each dNTP, 2.5 U Taq DNA polymerase, and 2.5 U of Taq Extender (Available from Stratagene; See Nielson et al. (1994) Strategies 7: 27, and U.S. Pat. No. 5,556,772). The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

D. Non-Conventional Nucleotides Useful According to the Invention

There is a wide variety of non-conventional nucleotides available in the art. Any or all of them are contemplated for use with a DNA polymerase of the invention. A non-limiting list of such non-conventional nucleotides is presented in Table III.

TABLE III

Non-Conventional Nucleotides

| DIDEOXYNUCLEOTIDE ANALOGS | |
|---|---|
| Fluorescein Labeled | Fluorophore Labeled |
| Fluorescein-12-ddCTP | Eosin-6-ddCTP |
| Fluorescein-12-ddUTP | Coumarin-5-ddUTP |
| Fluorescein-12-ddATP | Tetramethylrhodamine-6-ddUTP |
| Fluorescein-12-ddGTP | Texas Red-5-ddATP |
| Fluorescein-N6-ddATP | LISSAMINE ™-rhodamine-5-ddGTP |
| FAM Labeled | TAMRA Labeled |
| FAM-ddUTP | TAMRA-ddUTP |
| FAM-ddCTP | TAMRA-ddCTP |
| FAM-ddATP | TAMRA-ddATP |
| FAM-ddGTP | TAMRA-ddGTP |
| ROX Labeled | JOE Labeled |
| ROX-ddUTP | JOE-ddUTP |
| ROX-ddCTP | JOE-ddCTP |
| ROX-ddATP | JOE-ddATP |
| ROX-ddGTP | JOE-ddGTP |
| R6G Labeled | R110 Labeled |
| R6G-ddUTP | R110-ddUTP |
| R6G-ddCTP | R110-ddCTP |
| R6G-ddATP | R110-ddATP |
| R6G-ddGTP | R110-ddGTP |
| BIOTIN Labeled | DNP Labeled |
| Biotin-N6-ATP | DNP-N6-ddATP |

| DEOXYNUCLEOTIDE ANALOGS | |
|---|---|
| TTP Analogs | dATP-Analogs |
| Fluorescein-12-dUTP | Coumarin-5-dATP |
| Coumarin-5-dUTP | Diethylaminocoumarin-5-dATP |
| Tetramethylrhodamine-6-dUTP | Fluorescein-12-dATP |
| Tetraethylrhodamine-6-dUTP | Fluorescein Chlorotriazinyl-4-dATP |
| Texas Red-5-dUTP | LISSAMINE ™-rhodamine-5-dATP |
| LISSAMINE ™-rhodamine-5-dUTP | Naphthofluorescein-5-dATP |
| Naphthofluorescein-5-dUTP | Pyrene-8-dATP |
| Fluorescein Chlorotriazinyl-4-dUTP | Tetramethylrhodamine-6-dATP |
| Pyrene-8-dUTP | Texas Red-5-dATP |
| Diethylaminocoumarin-5-dUTP | DNA-N6-dATP |
|  | Biotin-N6-dATP |
| dCTP Analogs | dGTP Analogs |
| Coumarin-5-dCTP | Coumarin-5-dGTP |
| Fluorescein-12-dCTP | Fluorescein-12-dGTP |
| Tetramethylrhodamine-6-dCTP | Tetramethylrhodamine-6-dGTP |
| Texas Red-5-dCTP | Texas Red-5-dGTP |
| LISSAMINE ™-rhodamine-5-dCTP | LISSAMINE ™-rhodamine-5-dGTP |
| Naphthofluorescein-5-dCTP | Diethylaminocoumarin-5-dCTP |
| Fluorescein Chlorotriazinyl-4-dCTP | |
| Pyrene-8-dCTP | |
| Fluorescein-N4-dCTP | |
| Biotin-N4-dCTP | |
| DNP-N4-dCTP | |

| RIBONUCLEOTIDE ANALOGS | |
|---|---|
| CTP Analogs | UTP Analogs |
| Coumarin-5-CTP | Fluorescein-12-UTP |
| Fluorescein-12-CTP | Coumarin-5-UTP |
| Tetramethylrhodainine-6-CTP | Tetramethylrhodamine-6-UTP |
| Texas Red-5-CTP | Texas Red-5-UTP |

TABLE III-continued

Non-Conventional Nucleotides

LISSAMINE ™-rhodamine-5-CTP  LISSAMTNE ™ 5-UTP
Naphthofluorescein-5-CTP  Naphthofluorescein-5-UTP
Fluorescein Chlorotriazinyl-4-CTP  Fluorescein Chlorotriazinyl-4-UTP
Pyrene-8-CTP  Pyrene-8-UTP
Fluorescein-N4-CTP
Biotin-N4-CTP
ATP Analogs
Coumarin-5-ATP
Fluorescein-12-ATP
Tetramethylrhodamine-6-ATP
Texas Red-5-ATP
LISSAMINE ™-rhodamine-5-ATP
Fluorescein-N6-ATP
Biotin-N6-ATP
DNP-N6-ATP Additional non-conventional nucleotides useful according to the invention include, but are not limited to 7-deaza-dATP, 7-deaza-dGTP, 5'-methyl-2'-deoxycytidine-5'-triphosphate. Further non-conventional nucleotides or variations on those listed above are discussed by Wright & Brown, 1990, Pharmacol. Ther. 47: 447. It is specifically noted that ribonucleotides qualify as non-conventional nucleotides, since ribonucleotides are not generally incorporated by DNA polymerases. Modifications of Family B DNA polymerases that result in the ability, or enhanced ability, of the polymerase to incorporate labeled or unlabeled ribonucleotides are specifically contemplated herein.

E. Methods of Evaluating Mutants for Reduced Discrimination

Random or site-directed mutants generated as known in the art or as described herein and expressed in bacteria may be screened for reduced discrimination against non-conventional nucleotides by several different assays. In one method, Family B DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) *Gene* 97:119-123). For this approach, lambda phage clones are plated at a density of 10-20 plaques per square centimeter. Proteins present in the plaques are transferred to filters and moistened with polymerase screening buffer (50 mM Tris (pH 8.0), 7 mM $MgCl_2$, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35 µl of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 ug/ml bovine serum albumin (BSA), and 0.1% Triton X-100; Pfii Magnesium-free buffer may be obtained from Stratagene (Catalog No. 200534)), 125 ng/ml activated calf thymus or salmon sperm DNA, 1.29 µCi/ml α-$^{33}$P ddNTP or dideoxynucleotides (at a dNTP:dye-ddNTP ratio of 1:15). Initial screening was done in the presence of $MnCl_2$, but the preferred method was to screen in 1×Taq Polymerase buffer (1.5 mM $MgCl_2$) The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the activity of the polymerase with regard to that particular unconventional nucleotide or combination of unconventional nucleotides used in the assay. Unconventional nucleotides corresponding to all four conventional nucleotides may be included in the reactions, or, alternatively, only one unconventional nucleotide may be included to assess the effect of the mutation(s) on utilization of a given unconventional nucleotide. One approach is to use unconventional nucleotides corresponding to all four nucleotides in a first screen to identify clones that incorporate more than a reference wild-type clone, and then to monitor the incorporation of individual unconventional nucleotides in a subsequent screen. In the preferred screening mode, only the dideoxynucleotides and dideoxynucleotide analogs of ddATP, ddCTP, and ddTTP would be used since ddGTP is not discriminated against by some DNA polymerases and increases the background signal of any screen In order to screen for clones with enhanced ability to incorporate dideoxynucleotides, clones identified in first screens utilizing only dideoxynucleotides may then be characterized by their sensitivity to low levels of each of the four dideoxynucleotides in a DNA polymerase nucleotide incorporation assay employing all four dNTPs, a; H-TTP tracer, and a low level of each ddNTP. Since incorporation of dideoxynucleotides stops DNA chain elongation, superior ability to incorporate dideoxynucleotides diminishes the incorporation of tritium labeled deoxynucleotides relative to wild-type DNA polymerase. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

In order to measure incorporation of individual ddNTPs, cocktails are prepared which consist of varying concentrations of the ddNTP of interest, and a total of 200 µM of each nucleotide triphosphate. For example, the incorporation of ddATP by wild type JDF-3 polymerase may be measured at 0, 40, 80, 120 and 160 µM ddATP. In these reactions, dATP concentrations would be adjusted to 200, 160, 120, 80, and 40 µM, respectively, so that the total amount of adenine nucleotide triphosphate is 200 µM. In comparison, mutants may be assayed using ddATP concentrations of 0, 5, 10, and 20 µM ddATP, and adjusted dATP concentrations of 200, 195, 190, and 180 µM, respectively (dATP+ddATP=200 µM). Additional cocktails are prepared to similarly measure ddCTP, ddGTP, and ddTTP incorporation.

Incorporation of nucleotides under the concentration parameters described above may be measured in extension reactions by adding, for example, 1 µl of appropriately diluted bacterial extract (i.e., heat-treated and clarified extract of bacterial cells (see Example 1, part M) expressing a cloned polymerase or mutated cloned polymerase) to 10 ul of each nucleotide cocktail, followed by incubation at 72° C. for 30 minutes. Extension reactions are quenched on ice, and then 5

µl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above).

Cpms bound is proportional to the amount of polymerase activity present per volume of bacterial extract. The volume of bacterial extract (generally about 0.25-1 µl) which brings about incorporation of approximately 10,000 cpms is determined for use in subsequent nucleotide analog incorporation testing.

Genes for mutant DNA polymerases generated by random mutagenesis may be sequenced to identify the sites and number of mutations. For those mutants comprising more than one mutation, the effect of a given mutation may be evaluated by introduction of the identified mutation to the exo⁻ progenitor gene by site-directed mutagenesis in isolation from the other mutations borne by the particular mutant. Screening assays of the single mutant thus produced will then allow the determination of the effect of that mutation alone.

F. Expression of Mutated Family B DNA Polymerase According to the Invention

Methods known in the art may be applied to express and isolate the mutated forms of Family B DNA polymerase according to the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter (see Gardner & Jack, 1999, supra).

Appropriate host strains of bacteria may be selected from those available in the art by one of skill in the art. As a non-limiting example, $E.$ $coli$ strain BL-21 is commonly used for expression of exogenous proteins since it is protease deficient relative to other strains of $E.$ $coli$. BL-21 strains bearing an inducible T7 RNA polymerase gene include WJ56 and ER2566 (Gardner & Jack, 1999, supra). For situations in which codon usage for the particular polymerase gene differs from that normally seen in $E.$ $coli$ genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, PCR Meth. & App. 2: 275) is well suited for the isolation of thermostable DNA polymerases expressed in $E.$ $coli$, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure thermostable DNA polymerase. Further, as detailed in Example 1, part N, below, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

G. Preparation of $Thermococcus$ species JDF-3 Thermostable DNA Polymerase With Reduced Discrimination To prepare thermostable Family B polymerases which exhibit reduced discrimination for dideoxynucleotide triphosphates (ddNTPs), the DNA sequence encoding a 3' to 5' exonuclease-deficient (D141A) Family B polymerase from the hyperthermophilic archaeon $Thermococcus$ species JDF-3 was subjected to random mutagenesis using "error-prone PCR" as described herein, and cloned into the bacteriophage lambda Zap®II. The polymerase from JDF-3 was chosen due to superior processivity, polymerization rate and ddNTP incorporation relative to the Family B DNA polymerase from $Pyrococcus$ $furiosus$ (Pfu) (see Table IV, below). The library of mutants was plated on $E.$ $coli$ hosts and the proteins present in the lytic plaques were transferred to a solid support that was then immersed in a buffer containing DNA template and all four $\alpha$-$^{33}$p labeled dideoxynucleotides. Mutants that incorporated the labeled dideoxynucleotide produced signals that corresponded to their ability to incorporate the $\alpha$-$^{33}$P ddNTPs. Isolated clones were then characterized by their sensitivity to low levels of each of the four dideoxynucleotides in a DNA polymerase nucleotide incorporation assay employing all four dNTPs and a; H-TTP tracer. Since incorporation of dideoxynucleotides stops DNA chain elongation, superior ability to incorporate dideoxynucleotides diminishes the incorporation of tritium labeled deoxynucleotides. The unmutated progenitor DNA polymerase rarely incorporates dideoxynucleotides and is only 50% inhibited at high ddNTP levels (100-160 micromolar each ddNTP). The mutant enzymes show 50% inhibition at 5 to 40 micromolar concentrations of ddNTP and improved incorporation was observed for all four ddNTPs (ddATP, ddCTP, ddTTP and ddGTP; see Tables V and VI in Example 1, below).

The incorporation of non-conventional nucleotides was also evaluated through use of purified mutant polymerases in cycle sequencing, with $\alpha$-$^{33}$p labeled ddNTPs present at 0.021 µM and dNTPs present at 2.1 µM each. The mutants readily utilized all four dideoxynucleotides and produced sequencing ladders that compared favorably to Thermo Sequenase®, which uses an F667Y Taq DNA polymerase mutant (VanderHom et al., 1997, BioTechniques 22: 758).

The domains of relevance in 17 of the 40 purified mutants were sequenced. Most randomly mutated clones contained more than one mutation in the regions sequenced but all mutants contained mutations at one of three sites. Mutations predicted to confer an enhanced ddNTP uptake phenotype were introduced into the progenitor exonuclease deficient DNA polymerase sequence by site-directed mutagenesis to eliminate ancillary mutations which were not expected to contribute to the improved dideoxynucleotide uptake phenotype.

Sixteen of the seventeen JDF-3 DNA polymerase mutations were found in region II (motif A) on either side of the tyrosine in the consensus sequence 404 DxxSLYPSII 413.

These mutations consisted of DFRSLYLSII (P410 L), DFRSHYPSII (L408H) and DFRSFYPSII (L408F). Therefore, the LYP motif of region II appears to be important in ddNTP discrimination in the JDF-3 Family B polymerase.

The prior art modification of the tyrosine corresponding to Y409 in JDF3 Family B DNA polymerase is recognized for its positioning in the nucleotide binding pocket. As shown herein, however, modification of the residues neighboring Y409 (L408H or L408F or P410L) had the unexpected effect of profoundly altering nucleotide binding, particularly with respect to ddNTP incorporation.

The only JDF-3 DNA polymerase mutation leading to enhanced incorporation of non-conventional nucleotides occurring outside of region II is an alanine (ala or A) to threonine (thr or T) conversion at position 485 in region III (A485T). This site is two residues upstream of $KX_3NSXYG$ (Jung et al., 1990, supra; Blasco et al., 1992, supra; Dong et al., 1993, J. Biol. Chem. 268:21163; Zhu et al., 1994, Biochem. Biophys. Acta 1219:260; Dong and Wang, 1995, J. Biol. Chem. 270:21563) (referred to as region III or motif B) which is functionally, but not structurally (Wang et al., 1997, supra), analogous to $KX_3(F/Y)GX_2YG$ in helix O of the Family A DNA polymerases. In Family A DNA polymerases, such as the Klenow fragment and Taq DNA polymerases, the O helix contains amino acids that play a major role in dNTP binding (Astatke et al., 1998, J. Mol. Biol. 278:147; Astatke et al., 1995, J. Biol. Chem. 270:1945; Polesky et al., 1992, J. Biol. Chem 267:8417; Polesky et al., 1990, J. Biol. Chem. 265:14579; Pandey et al., 1994, J. Biol. Chem. 269:13259; Kaushik et al., 1996, Biochem. 35:7256). Specifically, helix O contains the F (F762 in the Klenow fragment; F667 in Taq) which confers ddNTP discrimination in Family A DNA polymerases ($KX_3(F/MY)GX_2YG$) (Tabor and Richardson, 1995, supra).

The effect of the A485T mutation on ddNTP incorporation in the JDF-3 DNA polymerase is surprising since the RB69 and *Thermococcus gorgonarius* crystal structures (Hopfner et al., 1999, supra) show it facing away from the proposed active site of the nucleotide binding surface. Moreover, the type of side chain conferring ribose selectivity in archaeal Family B DNA polymerases (A: small, non-polar) is different from that of the bulky, aromatic Y and F residues that dictate ddNTP discrimination in Family A DNA polymerases (Tabor and Richardson, 1995, supra). Additionally, this position (A485) is not well conserved among either DNA polymerase family and is not included in the consensus sequence for this domain (Braithwaite and Ito, 1993, supra), implying a lack of critical importance in dNTP recognition.

A JDF-3 double mutant was constructed that contains mutations P410L and A485T. In dideoxynucleotide cycle sequencing, the banding pattern intensity demonstrated by the double mutant was extremely uniform, suggesting little if any preference for any dNTP over its corresponding ddNTP (See FIG. 8 and Example 1Q). This polymerase characteristic improves the accuracy of base calling in automated sequencing. We presume that combinations of P410L and A485 mutations, L408H and A485 mutations, and L408F and A485 mutations would result in enzymes that exhibit improved ddNTP incorporation. The efficiency of dideoxynucleotide incorporation by such double mutant enzymes may also be characterized or quantitated by measurement of the $I_{50\%}$ as described herein to determine the relative degree of improvement in incorporation.

EXAMPLES

The following examples are offered by way of illustration only and are by no means intended to limit the scope of the claimed invention.

Example 1

A. Cloning a DNA Polymerase Gene from *Thermococcus* Species JDF-3 DNA Polymerase A *Thermococcus* species was cultured from submarine samples taken from the Juan de Fuca ridge. Genomic DNA was isolated and used to prepare a genomic DNA library in ZAP II (Stratagene) using standard procedures. The lambda library was plated on XL1-Blue MRF' *E. coli* and screened for clones with DNA polymerase activity using a variation of the method described by Sagner et al. (Sagner, G., Ruger, R., and Kessler, C. (1991) *Gene* 97:119-123). Plaques containing active polymerase were cored and stored in SM buffer. Positive primary plaques were re-plated and re-assayed to allow purification of isolated clones. Secondary clones were excised according to the instructions provided with the ZAP II system (Stratagene), and the DNA sequence of the insert determined (FIG. 1).

The translated amino acid sequence of the JDF-3 DNA polymerase is shown in FIG. 2. Amino acid sequence alignments show that JDF-3 DNA polymerase exhibits homology to the class of DNA polymerases referred to as Family B.

Recombinant JDF-3 DNA polymerase was purified as described below (see "Purification of JDF-3" (method 1)). The biochemical properties of JDF-3 DNA polymerase have been compared to those of other commercially available archaeal DNA polymerases. The results shown in Table IV and V indicated that, compared to other enzymes, JDF-3 exhibits higher processivity, a faster polymerization rate ($K_{cat}$), and a greater tendency to utilize ddNTPs. JDF-3 DNA polymerase was therefore chosen for development of a DNA sequencing enzyme.

TABLE IV

Polymerase Activities of Archaeal Family B DNA Polymerases

| Polymerase | Specific Activity (U/mg) × 10⁴ Activated DNA | Primed M13 | DNA (nM) | dNTP (µM each) |
|---|---|---|---|---|
| Pfu | 2.6 ± .07 | 2.0 ± .02 | 0.7 | 16 ± 2 |
| exo⁻ Pfu | 4.1 ± .07 | 2.3 | 0.5 | 12 |
| JDF-3 | 1.2 ± .07 | 5.2 | 2.0 | 16 ± 2 |
| Vent | 1.8[a] | 0.7[a] | 0.1[a] | 57[a] |

[a]H. Kong, R. B. Kucera, and W. E Jack, *J. Biol. Chem.* 268, 1965 (1993).

B. Intein Removal from the Gene Encoding JDF-3 DNA Polymerase

By alignment to Family B DNA polymerase sequences, the JDF-3 DNA polymerase clone was found to contain an intein sequence (FIGS. 3 and 4). To improve expression of recombinant JDF-3 polymerase, the intein was removed by inverse PCR. PCR primers were designed to prime immediately upstream and downstream to the sequence coding for the intein termini, and were oriented such that the 3' ends of the primers were pointed away from the intein. The primers were also modified with 5'-phosphate groups to facilitate ligation. The plasmid/insert sequence was PCR amplified and circularized by standard methods.

C. Construction of a JDF-3 DNA Polymerase Mutant with Diminished 3'-5' Exonuclease Activity DNA polymerases lacking 3'-5' exonuclease (proofreading) activity are preferred for applications requiring nucleotide analog incorporation (e.g., DNA sequencing) to prevent removal of nucleotide analogs after incorporation. The 3'-5' exonuclease activity associated with proofreading DNA polymerases can be reduced or abolished by mutagenesis. Sequence comparisons have identified three conserved motifs (exo I, II, III) in the 3'-5' exonuclease domain of DNA polymerases (reviewed V. Derbyshire, J. K. Pinsonneault, and C. M. Joyce, *Methods Enzymol.* 262, 363 (1995)). Replacement of any of the conserved aspartic or glutamic acid residues with alanine has been shown to abolish the exonuclease activity of numerous DNA polymerases, including archaeal DNA polymerases such as Vent (H. Kong, R. B. Kucera, and W. E. Jack, *J. Biol. Chem.* 268, 1965 (1993)) and Pfu (Stratagene, unpublished). Conservative substitutions lead to reduced exonuclease activity, as shown for mutants of the archaeal 9° N-7 DNA polymerase (M. W. Southworth, H. Kong, R. B. Kucera, J. Ware, H. Jannasch, and F. B. Perler, *Proc. Natl. Acad. Sci.* 93, 5281 (1996)).

JDF-3 DNA polymerase mutants exhibiting substantially reduced 3'-5' exonuclease activity were prepared by introducing amino acid substitutions at the conserved 141D or 143E residues in the exo I domain. Using the CHAMELEON® Double-Stranded, Site-Directed Mutagenesis Kit (Stratagene), the following JDF-3 mutants were constructed: D141A, D141N, D141S, D141T, D141E and E143A.

To analyze JDF-3 mutant proteins, the DNA sequence encoding JDF-3 DNA polymerase was PCR amplified using primers GGG AAA CAT <u>ATG</u> ATC CTT GAC GTT GAT TAC (where NdeI site in bold and start codon underlined) and GGG AAA GGA TCC TCA CTT CTT CTT CCC CTT C (where BamHI site shown in bold type). The PCR products were digested, purified, and ligated into a high expression level vector using standard methods. Plasmid clones were transformed into BL21(DE3). Recombinant bacterial clones were grown using standard procedures and JDF-3 polymerase mutants were expressed in the absence of induction. The exonuclease and polymerase activities of recombinant clones were assayed using bacterial lysates. Typically, crude extracts were heated at 70° C. for 15-30 minutes and then centrifuged to obtain a cleared lysate.

There are several methods of measuring 3' to 5' exonuclease activity known in the art, including that of Kong et al. (Kong et al., 1993, J. Biol. Chem. 268: 1965) and that of Southworth et al. (Southworth et al., 1996, Proc. Natl. Acad. Sci. U.S.A. 93: 5281), the full contents of both of which are hereby incorporated by reference. The exonuclease activity of wild type and active mutant polymerases as measured by the Kong et al. method were as follows;

Exo Activity (U/mg):

| | |
|---|---|
| Wt | 915 |
| D141A | 7 |
| D141N | 953 |
| D141S | 954 |
| D141T | 0.5 |
| D141E | 940 |
| E143A | 0.3 |

The combination exonuclease mutant D141A+E143A was made as described in section L.

The E143A JDF-3 mutant (clone #550) exhibited significantly reduced 3'-5' exo activity and was chosen for further mutagenesis to improve incorporation of ddNTP and other nucleotide analogs. Other JDF-3 mutants with substantially reduced exonuclease activity could have been used for this purpose, such as the JDF-3 D141T mutant. for experiment or applications requiring the absolute elimination of 3' to 5' exonuclease activity, the double mutant D141A+E143A was preferred.

D. Error-Prone PCR Amplification of the JDF-3 DNA Polymerase Gene

Random mutations were introduced into exo⁻ JDF-3 by amplifying the entire gene (clone #550) under conditions which did not support high fidelity replication. To broaden the spectrum of potential mutations, three different PCR enzymes were used under error-prone conditions.

In the preferred mode, ten reactions of 100 μl each were amplified with each PCR enzyme.

i. Amplification with Taq DNA polymerase:

Reaction Mixture

| 1x | magnesium free Taq Buffer (Stratagene catalog #200530) |
|---|---|
| 1 mM | each TTP and dCTP |
| 0.2 mM | each dGTP and dATP |
| 2 ng/μl | Primer 923 (also called 490) |
| 2 ng/μl | Primer 721 |
| 0.05 u/μl | Taq2000 (Stratagene catalog #600195) |
| 1.5 mM | MgCl₂ |
| 0.5 mM | MnCl₂ |
| 0.1 pM | plasmid DNA (clone #550) |

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 to 4 thirty times.

ii. Amplification with exo⁻ JDF-3 DNA polymerase

Reaction Mixture

| 1x | magnesium free Taq Buffer (Stratagene catalog #200530) |
|---|---|
| 450 μM | each deoxynucleotide (dGTP, dATP, TTP and dCTP) |
| 2 ng/μl | Primer 923 (also called 490) |
| 2 ng/μl | Primer 721 |
| 0.1 μl | exo⁻ JDF-3 DNA polymerase |
| 0.5 mM | MnCl₂ |
| 0.1 pM | plasmid DNA (clone #550) |

Cycling Parameters

PCRs were carried out using Stratagene's ROBOCYCLER™40 Temperature Cycler with a Hot Top assembly. The following cycling conditions were used:

1) 95° C. for 1 minute
2) 95° C. for 1 minute
3) 54° C. for 1 minute
4) 72° C. for 2.5 minutes
5) Repeat steps 2 through 4 thirty times.

iii. Amplifiction with exo⁻ Pfu DNA polymerase
Reaction Mixture

| | |
|---|---|
| 1x | TAQPLUS ® Precision Buffer (Stratagene catalog #600210) |
| 200 µM | each deoxynucleotide (dGTP, dATP, TTP, dCTP) |
| 2 ng/µl | Primer 923 (also called 490) |
| 2 ng/µl | Primer 721 |
| 0.05 u/µl | exo⁻ Pfu DNA polymerase (Stratagene catalog number 600163) |
| 0.1 pM | plasmid DNA (clone #550) |

Cycling Parameters

PCRs were carried out using Perkin-Elmer's 9600 Temperature Cycler. The following cycling conditions were used:
 1) 95° C. for 1 minute
 2) 95° C. for 1 minute
 3) 53° C. for 1 minute
 4) 72° C. for 5 minutes
 5) Repeat steps 2 through 4 thirty times.
Forward Primers Earlier versions of the mutant libraries were made with the forward primer 461, which contains an EcoR I site. When products amplified with primers 461 and 923 were restriction digested and cloned into the lambda vector as described in the following section, JDF-3 DNA polymerase was synthesized as a fusion protein with the first 39 amino acids of the vector-encoded β-galactosidase (lacZ) protein.

```
Primer 461
 5' TCAGATGAATTCGATGATCCTTGACGTTGATTAC 3'
        EcoR I    JDF-3 specific sequence
```

The clones isolated using primer 461 were designed as p#.

The preferred mode of amplification and cloning utilizes the forward primer 721, which also contains an EcoR I site followed by three consecutive in-frame stop codons and a ribosome binding site. This arrangement allows the JDF-3 DNA polymerase to be translated without any vector-derived residues at the amino terminus. The clones isolated from libraries constructed with the forward primer 721 were designated as 1-# to differentiate them from the p# series of clones.

```
Primer 721    5' GAGAGAATTCATAATGATAAGGAGGAAAAAATTATGATCCYUGACGTTGATTAC3'
                      EcoR I   3x STOP                JDF-3 specific sequence Reverse Primers
Primer 923 (490) 5' TCAGATCTCGAGTCACTTCTTCTTCCCCTTC 3'
                         Xho I  JDF-3 specific sequence
```

E. Preparing PCR Products for Cloning

PCR products were purified and concentrated with the STRATAPREP™ PCR Purification kit (Stratagene catalog number 400771). The PCR products were then digested with 50 units of Xho I and 50 units of EcoR I in 1.5× Universal buffer (10× Universal Buffer: 1M KOAc, 250 mM Tris-Acetate (pH 7.6), 100 mM MgOAc, 5 mM β-mercaptoethanol and 100 µg/ml BSA) for one hour at 37° C. The digested samples were run on a 1% agarose, 1×TBE gel and visualized with ethidium bromide staining. The 2.3 kb amplification product was gel isolated and purified with the STRATAPREP™ DNA Gel Extraction Kit (Stratagene catalog number 400766).

F. Cloning PCR Inserts into the Uni-Zap®XR Lambda Vector 200 ng of purified amplification product was ligated with 1 µg of UNI-ZAP®XR Lambda Vector (Stratagene catalog #239213), which had been predigested with EcoR I and ho I and then dephosphorylated with alkaline phosphatase (Stratagene catalog number 237211). The DNAs were ligated using 2 units of T4 DNA ligase (Stratagene catalog number 600011) and 0.5 mM ATP in 1× ligase buffer (50 mM Tris-HCL (pH 7.5), 7 mM $MgCl_2$, 1 mM DTT) in reaction volumes of 10 to 15 µl. Ligations were carried out at 16° C. for a minimum of 16 hours.

G. Lambda Packaging and Bacterial Infection

Two microliters of each ligation reaction were packaged with GIGAPACK® III Gold Packaging extract (Stratagene catalog #200201) for 90 minutes at room temperature before being stopped with 500 µl SM buffer (50 mM Tris pH 7.5, 100 mM NaCl, 8 mM $MgSO_4$ and 0.01% gelatin) and 20 µl of chloroform. The packaged lambda vectors were plated on E. coli XL1-Blue MRF' host cells.

H. Dideoxynucleotide Screening

Mutant polymerase libraries were screened using a variation of the technique used by Sagner et al (Sagner, G., Ruger, R., and Kessler, C. (1991) *Gene* 97:119-123). Lambda phage clones were plated at a density of 10-20 plaques per square centimeter. Proteins present in the plaques were transferred to filters and moistened with polymerase screening buffer (50 mM Tris (pH 8.0), 7 mM $MgCl_2$, 3 mM β-ME). The filters were kept between layers of plastic wrap and glass while the host cell proteins were heat-inactivated by incubation at 65° C. for 30 minutes. The heat-treated filters were transferred to fresh plastic wrap and approximately 35 µl of the polymerase assay cocktail was added for every square centimeter of filter. Polymerase assay cocktail consisted of 1× cloned Pfu magnesium-free buffer (Stratagene catalog #200534), 125 ng/ml activated calf thymus or salmon sperm DNA, 1.29 µCi/ml α-$^{33}$P ddNTP (Amersham), and 0.5 mM $MnCl_2$. Initial screening was done in the presence of $MnCl_2$, but the preferred method was to screen in 1×Taq Polymerase buffer (1.5 mM $MgCl_2$). The filters were sandwiched between plastic wrap and glass again and incubated at 65° C. for one hour, and then at 70° C. for one hour and 15 minutes. The filters were washed three times in 2×SSC for five minutes each time before being rinsed twice in 100% ethanol and dried on a vacuum dryer. The filters were exposed to X-ray film for approximately 16 hours. Plaques corresponding to strong signals were cored and placed in SM buffer. The positive primary plaques were replated at more dilute concentrations and assayed under essentially similar conditions to allow the purification of isolated plaques.

Dye-Dideoxynucleotide Screening

To detect mutant polymerases with improved capacity for dye-deoxynucleotide and dye-dideoxynucleotide utilization, the JDF-3 mutant DNA polymerase library was screened as described previously with the following exceptions:

Polymerase assay cocktail for Flu-12-dUTP screening:

0.9×Taq Buffer (Stratagene Catalog #200435), 65 µM dATP, 65 µM dCTP, 65 µM dGTP, 65 µMdTTP, 0.3 µM Fluresceince-12-dUTP (Stratagene in-house production), 0.75 µg/µl activated calf thymus DNA.

Polymerase Assay Cocktail for ROX ddNTP

1×Taq Buffer, 0.9 μM dATP, 0.9 μM dCTP, 0.9 μM dGTP, 0.9 μl TTP, 0.6 μM ROX ddATP (New England Nuclear (NEN) NEN478), 0.06 μM ROX ddGTP (NEN NEL479), 0.06 μM ROX ddCTP (NEN NEL477), 0.06 μM ROX ddUTP (NEN NEL476), 0.84 μg/μl activated calf thymus DNA. (Note: A screening system without ROX ddGTP is the preferred method since DNA polymerases do not discriminate against ddGTP).

Polymerase Assay Cocktail for Fluroesceine ddUTP

1×Taq Buffer, 70 μM dATP, 70 μM dTTP, 70 μM dCTP, 15 μM dTTP, 1 μM Fluroesceine-12-ddUTP (NEN NEL401), 0.84 μg/μl activated calf thymus DNA.

Antibody Binding to Fluroesceine

The filters were blocked overnight with 1% non-fat dry milk dissolved in TBST (50 mM Tris pH 8.0, 150 mM NaCl, 0.05% Tween-20) at 4° C. The filters were washed briefly in TBST before alkaline phosphatase conjugated anti-fluoresceine antibody from the Illuminator kit (Stratagene catalog #300360) was added at a 1/10,000 dilution in 50 ml TBST. The antibody was detected with NBT/BCIP at concentrations of 0.3 mg/ml and 0.15 mg/ml respectively in a buffer composed of 100 mM Tris pH 9.5, 100 mM NaCl, and 5 mM $MgCl_2$.

Antibody Binding to Rhodamine

Anti-ROX antibody (Zymed cat. no. 71-3600 rabbit Rhodamine (5-ROX polyclonal, 1 mg/ml)) was diluted to 1:1000 in TBST. The blocked filters were blotted briefly to remove excess moisture then laid on plastic wrap and covered with 2.5 ml of the diluted antibody solution. An additional sheet of plastic wrap was laid over the filters before incubation at room temperature for 1 hour. The filters were washed briefly three times with TBST, then washed three times with gentle agitation for 15 minutes each time. The washed filters were incubated with alkaline phosphatase conjugated goat anti-rabbit antibodies diluted 1:5000 in TBST. The filters were incubated with the antibody for one hour then detected with NBT/BCIP as described previously.

I. Dideoxynuclcotide Qualification

Lambda phage clones which incorporated $^{33}$P-labeled ddNTPs in the primary library screen were re-screened to verify polymerase activity and to assess the contribution of the divalent metal ion to $^{33}$P-ddNTP incorporation. The clones selected during this round of screening were designated as p#. These clones all contained an amino-terminal tag, as discussed in the section entitled "Forward Primers". FIG. 5 shows that clones p1, p2, p3, p6, p7, p8, p9, p10, p11, p12, p14, p 15, and p16 exhibited wild type levels of DNA polymerase activity, based upon similarity in signal strength to the parental #550 clone (FIG. 5, panel 3). Although initial screening was carried out in the presence of 0.5 mM $MnCl_2$, all of the clones except p9 and p10 were able to incorporate $^{33}$P-labeled ddNTPs to at least some extent in the presence of 1.5 mM $MgCl_2$ (panel 2), with clones p2, p4, p8, p11, p12, p13, p14, p15, p17, and p18 producing the highest signals.

Eighteen mutants were chosen for evaluation. One microliter of phage isolated from each purified plaque was placed on each of three *E. coli* XLI-Blue MRF' lawns. Phage containing a parental copy of exo⁻ JDF3 DNA (#550 clone) were also spotted on the grid. The plaques formed by the phage were transferred to filters and treated as described in the preceding screening section with the exception of the final buffer composition. The buffers used for each filter (filters 1-3) are as follows:

Filter 1: Dideoxynucleotide Screen with Manganese Chloride

| 1x | Taq DNA polymerase magnesium-free buffer |
|---|---|
| 1.28 μCi/ml | $^{33}$P ddNTPs |
| 0.5 μg/μl | Activated Calf Thymus DNA (Sigma) |
| 0.5 mM | $MnCl_2$ |

Filter 2: Dideoxynucleotide Screen with Magnesium Chloride

| 1x | Taq DNA polymerase buffer (containing 1.5 mM $MgCl_2$, catalog #200435) |
|---|---|
| 1.28 μCi/ml | $^{33}$P ddNTP |
| 0.5 μg/μl | Activated Calf Thymus DNA (Sigma) |

Filter 3: Deoxynucleotide Screen with Magnesium Chloride

| 1x | Taq DNA polymerase buffer |
|---|---|
| 0.072 | mM dGTP, dCTP and TTP |
| 40 | μM dATP |
| 0.5 | μg/ml Activated Calf Thymus DNA (Sigma) |
| 0.01 | μCi α-$^{33}$P dATP. |

Results are shown in FIG. 5.

Dye-Dideoxynucleotide Qualification

As described in the previous segments, primary lambda clones were spotted on an *E. coli* lawn and re-screened with the appropriate antibody or antibodies.

J. Excision of Lambda Clones

When incubated with helper phage under suitable conditions, Lambda Zap™ vectors are designed to produce phagemid copies of the part of the vector containing pBluescript (SK−) and the insert. This process yields a plasmid (pBluescript SK−) vector carrying the same insert that was contained in the lambda clone. Excision of clones with the desired phenotype was carried out according to the instructions in the EXASSIST™ system (Stratagene catalog #200253).

K. Sequence Analysis of Mutants

The mutants were sequenced by Sequetech Corporation (Mountain View, Calif.) using the following primers:

```
Primer 3 (or primer G)
5' CCAGCTTTCCAGACTAGTCGGCCAAGGCC 3'

Primer 5 (or JDF3-1128)
5' AACTCTCGACCCGCTG 3'
```

L. Dideoxynucleotide Mutagenesis

To conclusively identify the amino acids contributing to reduced ddNTP discrimination, individual point mutations were introduced into the exo⁻ JDF-3 #550 clone using the QUIKCHANGE™ Site-Directed Mutagenesis Kit (Stratagene catalog #200518). The following mutants were prepared: L408H, L408F, P410L, A485T, S345P, D373Y, A619V, and L631V. In addition, a double mutant (P410L/A485T) was constructed by introducing the A485T mutation into the exo⁻ JDF-3 P410L mutant clone. To completely eliminate all 3' to 5' exonuclease activity, the mutation D141A was added to all clones. A pre-existing 5' to 3' exonuclease mutation (E143A) was present in the parental template JDF-3 550.

Dye-Dideoxynucleotide Mutagenesis

To conclusively identify amino acids responsible for contributing to reduced discrimination of dye nucleotides, the mutation S345P was generated alone and in combination with the P410L and P410L+A485T.

M. Preparation of Heat-Treated Bacterial Extracts

E. coli SOLR cells containing the excised plasmid were grown overnight at 37° C. The cells contained in 500 µl of culture were collected by microcentrifugation. The cell pellets were resuspended in 50 µl of 50 mM Tris (pH 8.0). Lysozyme was added to a final concentration of 1 µg/µl, and the cells were lysed during a 10 minute incubation at 37° C., followed by 10 minutes at 65° C. The heat-inactivated cell material was collected by microcentrifugation and the supernatants were assayed for dNTP and ddNTP incorporation as described below.

N. Purification of JDF-3 and JDF-3 polymerase mutants

One method for purifying exo⁻ JDF-3 DNA polymerase involves ammonium sulfate fractionation, followed by Q Sepharose and DNA cellulose columns. A second method has been developed to allow rapid purification of JDF-3 polymerase mutants, and entails adsorption of contaminants on a HiTrap Q column, followed by gradient elution from a HiTrap heparin column (section iii).

i. Preparation of Bacterial Lysate.

Frozen cell paste (3-14 grams) was resuspended with 3× volume of lysis buffer, consisting of 50mM Tris-HCl (pH 8.0), 1 mM EDTA, and 10 mM β-mercaptoethanol. Lysozyme was added to 0.2 mg/ml and PMSF was added to 1 mM final concentration. The cells were lysed on ice over a period of 1 hour. The lysate was then sonicated for 2 minutes (90% duty, level of 2×2.5, 1×3.0). Following sonication, the lysate was heated at 65° C. for 15 minutes to denature bacterial proteins. The heated lysate was then centrifuged for 30 minutes at 14.5K rpm in a Sorvall RC-2B centrifuge using a Sorvall SS-34 rotor, and the supernatant was recovered.

ii. Ammonium Sulfate Fractionation and Q Sepharose/DNA Cellulose Chromatography (Method 1)

Ammonium sulfate was added to the bacterial lysate to a final concentration of 45%. The ammonium sulfate was added over a period of 15 minutes, and the mixture was stirred for an additional 30 minutes. The mixture was centrifuged as described above, and the supernatant was recovered. Additional ammonium sulfate was then added to bring the final concentration to 65%. The mixture was centrifuged as described above, and the supernatant removed. The pellet was resuspended in 10 ml of buffer A consisting of 50 mM Tris-HCl (pH 7.5), 1 mM EDTA, 10 mM β-mercaptoethanol, 0.1% (v/v) Tween 20, and 10% (v/v) glycerol. The supernatant was dialyzed overnight against 2 changes of buffer A (3 liters each).

The dialysate was loaded onto a 2.6×9.4 cm Q-Sepharose Fast Flow column (50 mls), pre-equilibrated in buffer A. The column was washed with buffer A until the absorbence ($OD_{280}$) approached baseline. The column was then eluted with a gradient from 0 to 1 M NaCl/buffer A. Fractions were collected, and analyzed by SDS-PAGE and DNA polymerase activity assays (see below). Active protein typically eluted between 130 and 240 mM NaCl. Active fractions were pooled and dialyzed overnight against 2 changes of buffer B (3 liters each), consisting of 50 mM Tris-HCl (pH 7.5), 1 mM EDTA, 10 mM β-mercaptoethanol, 0.1% (v/v) Tween 20, 10%(v/v) glycerol, and 50 mM NaCl.

The Q-Sepharose eluate was then loaded onto a 1.6×4.9 cm (10 mls) DNA cellulose column, equilibrated in buffer B. The column was washed with buffer B until the absorbence ($OD_{280}$) approached baseline. The column was then eluted with a gradient from 50 to 1000 mM NaCl/buffer A. Fractions were collected, and analyzed by SDS-PAGE and DNA polymerase activity assays. Active protein typically eluted between 280 and 360 mM NaCl. Active fractions were pooled and dialyzed overnight against JDF-3 final dialysis buffer, consisting of 25 mM Tris-HCl (pH 7.5), 100 mM KCl, 0.1 mM EDTA, 1 mM DTT, 0.1% (v/v) Tween 20, 0.1% (v/v) Igepal 630, 10 µg/ml BSA, and 50% (v/v) glycerol.

iii. HiTrap Q/HiTrap Heparin Chromatography (Method 2)

The preferable method for rapid purification of multiple mutants is as follows. Bacterial cell lysates were prepared as described for method 1, except that Tween 20 and Igepal CA 630 were added to a final concentration of 0.01% (v/v) just prior to the heat denaturation step, and a heat denaturation temperature of 72° C. was used.

The lysate was loaded onto a 1.6×2.5 cm (5 mls) HiTrap Q column (pre-packed column from Pharmacia), pre-equilibrated in buffer C consisting of 50 mM Tris-HCl (pH 8.2), 1 mM EDTA, 10 mM β-mercaptoethanol, 0.1% (v/v) Tween 20, and 0.1% (v/v) Igepal CA 630. The column was washed with buffer C until the absorbence ($OD_{280}$) approached baseline. The flow through fractions ($OD_{280}$ absorbence above background) were collected and then loaded onto a 1.6×2.5 cm (5 mls) HiTrap heparin column (pre-packed column from Pharmacia), pre-equilibrated in buffer D consisting of 50 mM Tris-HCl (pH 8.2), 1 mM EDTA, 1 mM DTT, 0.1% (v/v) Tween 20, 0.1% (v/v) Igepal CA 630, and 10% glycerol (v/v). The column was washed with buffer D until the absorbence ($OD_{280}$) approached baseline. The column was then eluted with a gradient from 0 to 1 M KCl/buffer D. Fractions were collected, and analyzed by SDS-PAGE and DNA polymerase activity assays. Active protein typically eluted between 390 and 560 mM NaCl. Active fractions were pooled and dialyzed overnight against JDF-3 final dialysis buffer (see above). Purified polymerases were stored at −20 C.

iv. Analysis of Purified Proteins

The concentrations of JDF-3 and mutant DNA polymerases were determined relative to a BSA standard (Pierce), using Pierce's Coumassie Blue Protein assay reagent. In addition, the purity and relative protein concentrations of different polymerase preparations were verified by SDS-PAGE. Polymerase samples were electrophoresed on 4-20% Tris-glycine gels (Novex), and the gels were silver-stained using standard procedures.

O. Nucleotide Incorporation Assay

DNA polymerase activity was measured using purified JDF-3 polymerase mutants or heat-treated bacterial extracts prepared from various mutant clones. DNA polymerase activity was measured by monitoring the incorporation of $^3$H-TTP into activated calf thymus DNA. A typical DNA polymerase reaction cocktail contained:

10 mM Tris-HCl, pH 8.8
1.5 mM $MgCl_2$
50 mM KCl
0.001% gelatin
200 µM each dATP, dCTP, dGTP
195 µM TTP
  5 µM [$^3$H]TTP (NEN #NET-221H, 20.5Ci/mmole; partially evaporated to remove ETOH)
  250 µg/ml of activated calf thymus DNA (e.g., Pharmacia #27-4575-01)

Incorporation was measured by adding 1 µl of polymerase samples to 10 µl aliquots of polymerase cocktail. DNA polymerase samples were diluted in a suitable storage buffer (e.g., 25 mM Tris-HCl (pH 7.5), 100 mM KCl, 0.1 mM EDTA, 1 mM DTT, 0.1% (v/v) Tween 20, 0.1% (v/v) Igepal 630, 10 µg/ml BSA, and 50% (v/v) glycerol). Polymerization reactions were conducted for 30 minutes at 72° C. Extension reactions were quenched on ice, and then 5 μl aliquots were spotted immediately onto DE81 ion-exchange filters (2.3 cm; Whatman #3658323). Unincorporated [³H]TTP was removed by 6 washes with 2×SCC (0.3 M NaCl, 30 mM sodium citrate, pH 7.0), followed by a brief wash with 100% ethanol. Incorporated radioactivity was measured by scintillation counting. Reactions that lacked enzyme were also set up along with sample incubations to determine "total cpms" (omit filter wash steps) and "minimum cpms" (wash filters as above).

mutants at 3 different ddNTP concentrations, 12 reaction cocktails were prepared consisting of:
- 10 mM Tris-HCl, pH 8.8
- 1.5 mM MgCl$_2$
- 50 mM KCl
- 0.001% gelatin
- 5 μM [³H]TTP (NEN #NET-221H, 20.5Ci/mmole; partially evaporated to remove EtOH)
- 250 μg/ml of activated calf thymus DNA (e.g., Pharmacia #27-4575-01)

To each of 12 reaction cocktails was added the appropriate amounts of dNTPs and ddNTPs as summarized below:

| Cocktail | DGTP | dDATP | dCTP | TTP | ddGTP | ddATP | ddCTP | ddTTP |
|---|---|---|---|---|---|---|---|---|
| G-0 | 200 μM | 200 μM | 200 μM | 195 μM | 0 | 0 | 0 | 0 |
| G-5 | 195 μM | 200 μM | 200 μM | 195 μM | 5 | 0 | 0 | 0 |
| G-10 | 190 μM | 200 μM | 200 μM | 195 μM | 10 | 0 | 0 | 0 |
| G-20 | 180 μM | 200 μM | 200 μM | 195 μM | 20 | 0 | 0 | 0 |
| A-0 | 200 μM | 200 μM | 200 μM | 195 μM | 0 | 0 | 0 | 0 |
| A-5 | 200 μM | 195 μM | 200 μM | 195 μM | 0 | 5 | 0 | 0 |
| A-10 | 200 μM | 190 μM | 200 μM | 195 μM | 0 | 10 | 0 | 0 |
| A-20 | 200 μM | 180 μM | 200 μM | 195 μM | 0 | 20 | 0 | 0 |
| C-0 | 200 μM | 200 μM | 200 μM | 195 μM | 0 | 0 | 0 | 0 |
| C-5 | 200 μM | 200 μM | 195 μM | 195 μM | 0 | 0 | 5 | 0 |
| C-10 | 200 μM | 200 μM | 190 μM | 195 μM | 0 | 0 | 10 | 0 |
| C-20 | 200 μM | 200 μM | 180 μM | 195 μM | 0 | 0 | 20 | 0 |
| T-0 | 200 μM | 200 μM | 200 μM | 195 μM | 0 | 0 | 0 | 0 |
| T-5 | 200 μM | 200 μM | 200 μM | 190 μM | 0 | 0 | 0 | 5 |
| T-10 | 200 μM | 200 μM | 200 μM | 185 μM | 0 | 0 | 0 | 10 |
| T-20 | 200 μM | 200 μM | 200 μM | 175 μM | 0 | 0 | 0 | 20 |

Cpms bound is proportional to amount of polymerase activity present per volume of bacterial extract. The volume of bacterial extract (0.25-1 μl) which brought about incorporation of approximately 10,000 cpms was determined for use in subsequent nucleotide analog incorporation testing.

P. Quantitating ddNTP Incorporation Efficiency

JDF-3 polymerase mutants were evaluated to assess relative ddNTP incorporation efficiency. Nucleotide incorporation was measured in the presence of varying concentrations of each ddNTP terminator (ddATP, ddCTP, ddGTP, and ddTTP). Since ddNTP incorporation produces non-extendable termini, polymerization is strongly inhibited for polymerases that incorporate ddNTPs efficiently. Comparisons of ddNTP concentrations that bring about 50% inhibition of nucleotide incorporation ($I_{50\%}$) can be used to compare ddNTP incorporation efficiency of different polymerases or polymerase mutants. Comparisons of $I_{50\%}$ values for ddATP, ddCTP, ddGTP, and ddTTP can be used to identify mutants with reduced selectivity for particular bases. Such mutants would be expected to produce more uniform DNA sequencing ladders.

To measure incorporation of individual ddNTPs, cocktails were prepared which consisted of varying concentrations of the ddNTP of interest, and a total of 200 μM of each nucleotide triphosphate. For example, the incorporation of ddATP by wild type JDF-3 polymerase was measured at 0, 40, 80, 120 and 160 μM ddATP. In these reactions, dATP concentrations were adjusted to 200, 160, 120, 80, and 40 μM, respectively, so that the total amount of adenine nucleotide triphosphate was 200 μM. In comparison, mutants were assayed using ddATP concentrations of 0, 5, 10, and 20 μM ddATP, and adjusted dATP concentrations of 200, 195, 190, and 180 μM, respectively (dATP+ddATP=200 μM). Additional cocktails were prepared to measure ddCTP, ddGTP, and ddTTP incorporation. To assess ddNTP incorporation by JDF-3

Incorporation was measured by adding 1 μl of appropriately diluted bacterial extract (10,000 cpms) to 10 μl of each polymerase cocktail. Polymerization reactions were conducted for 30 minutes at 72° C. The extension reactions were counted as described above.

Reactions that lacked enzyme were also set up along with sample incubations to determine "minimum cpms" (wash filters as above). To determine % activity as a function of ddNTP concentration, background ("minimum cpms" value) was first subtracted from each of the sample cpms. "Total cpms", which are equivalent to 100% activity (0 ddNTPs), are determined by averaging the corrected cpms for the 4 reactions lacking ddNTPs (A-0, G-0, C-0, and T-0). Percent remaining activity was then calculated by dividing corrected sample cpms (with ddNTPs) by the corrected total cpms (average 0 ddNTPs).

Percent activity was plotted as a function of ddNTP concentration. $I_{50\%}$ values for each ddNTP (ddNTP concentration which inhibits nucleotide incorporation by 50%) were determined for each mutant. Comparisons allowed the identification of mutants with improved ddNTP incorporation relative to wild type JDF-3.

Initial studies used purified enzymes, and $I_{50\%}$ values were determined from inhibition plots employing 40-160 μM ddNTPs. The results in Table V show that mutants p8 (P410L), p11 (P410L), and p12(A485T) are inhibited by lower concentrations of ddNTPs than the parental exo JDF-3 polymerase. Greater sensitivity indicates that the mutants incorporate all four ddNTPs more efficiently than the original JDF-3 polymerase.

For enzymes which preferentially incorporate TTP over ddTTP (exo⁻ JDF-3, exo⁻ Pfu), the use of increasingly higher concentrations of ddTTP (80-160 μM) and correspondingly lower concentrations of TTP (115-35 μM), in combination with a constant amount of [³H]TTP (5 μM), leads to an increase in cpms incorporated with increasing ddNTP concentration. Therefore, in these initial experiments (where ddTTP>120 μM), $I_{50\%}$ values for TTP are artificially high. While they can be used to compare ddTTP incorporation among different polymerase mutants, they can not be used to assess reduced/enhanced preference for ddTTP relative to ddCTP, ddGTP, or ddATP.

TABLE V $I_{50\%}$ Values for Purified JDF-3 and JDF-3 Mutants.

| Purified Polymerase | Primary Mutation | $I_{50\%}$ Values (μM) | | | |
|---|---|---|---|---|---|
| | | ddATP | ddGTP | ddCTP | ddTTP |
| Exo⁻ JDF-3 | — | 160 | 110 | >160 | >>160 |
| Exo⁻ Pfu | — | >160 | >160 | >160 | >>160 |
| JDF-3 mutant p8 | P410L | 30 | 25 | 40 | 40 |
| JDF-3 mutant p11 | P410L | 30 | 30 | 60 | >160 |
| JDF-3 mutant p12 | A485T | 40 | 25 | 25 | 150 |

To allow a larger number of mutant clones to be screened, subsequent experiments employed bacterial extracts containing JDF-3 polymerase mutants. In addition, sensitivity was improved by using lower concentrations of each ddNTP inhibitor (5-20 μM). The results in Table VI demonstrate that all of the mutants selected from the primary filter screen exhibited improved incorporation of ddNTPs. Improvements in ddNTP incorporation were as high as >20-fold. All of the mutants containing a mutation at amino acid 408 (L408H/F), 410 (P410L), or 485 (A485T) (referred to as the "primary mutation") exhibited reduced discrimination against all four ddNTPs. Most, but not all, mutants with the L408H/F primary mutation produced very similar $I_{50\%}$ values (<2-fold difference) for all four ddNTPs, indicating that base selectivity is diminished or absent.

TABLE VI $I_{50\%}$ Values for JDF-3 Mutants (Bacterial Extracts).

| JDF-3 mutant clones | Primary mutation | $I_{50\%}$ Values (μM) | | | |
|---|---|---|---|---|---|
| | | ddATP | ddGTP | ddCTP | ddTTP |
| Exo⁻ JDF-3 | — | >80 | >80 | >80 | >80 |
| 1-1, 1-4, 1-18 | L408H | 8 to >20 | 4 to 5 | 6 to 13 | 5.5. to 10 |
| 1-25, 1-28, 1-29, 1-17 | L408F | 4.5 to >20 | 3.5 to 10 | 4 to 6.5 | 4 to 8 |
| p8 | P410L | 18.5 | 12 | 9.5 | >20 |
| 1-5, 1-6, 1-17 | P410L | 10 to >20 | 3.5 to 9 | 16.5 to >20 | 11 to >20 5 to >20 |
| 1-41, 1-38, 1-37, 1-3, 1-19, 1-30, 1-27, 1, 20 1-26, 1-32, 1-16, 1-12 | Not determined | 7 to >20 | 3.5 to 12 | 4 to >20 | |

Q. Sequencing with Purified JDF-3 Polymerase Mutants
i. Sequencing with Radioactively Labeled Dideoxynucleotides 1 to 2 μl of purified enzyme was substituted into the Thermo Sequenase radiolabeled terminator cycle sequencing kit (Amersham-Pharmacia #US79750). The samples were processed according to the manufacturer's instructions using the control primer and template provided with the kit. Three microliters of each sequencing reaction were loaded onto a 6% acylamide-7M urea, 1×TBE CASTAWAY™ Precast gel (Stratagene catalog #s 401090 and 401094). When the bromophenol blue indicator dye reached the end of the gel, the gel was fixed, dried and exposed to film for 24-72 hours (FIG. 6).

Figure 6:
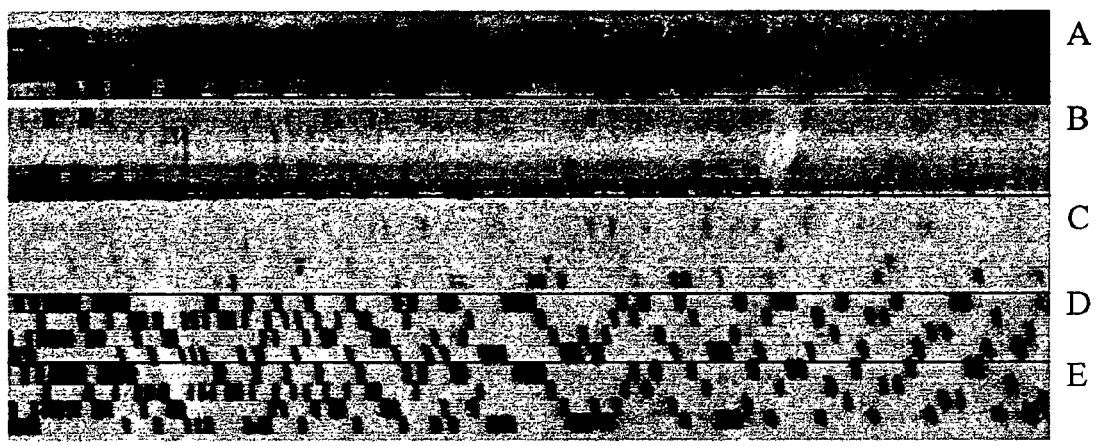
FIG. 6 shows $^{33}$P-ddNTP cycle sequencing reactions performed using JDF-3 polymerase mutants. Purified JDF-3 mutants were substituted into the Thermo Sequenase radiolabeled terminator cycle sequencing kit. DNA sequencing ladders were generated as per the kit's instructions using the following polymerases: (A) Thermo Sequenase (B) JDF-3 #550 clone (parental) (C) JDF-3 A485T mutant (clone p12) (D) JDF-3 P410L mutant (clone p11) (E) JDF-3 P410 L mutant (clone p8). The top of the original sequencing gel is shown on the side. The lanes are: (bottom) ddGTP, ddATP, ddTTP, ddCTP (top). Clones p8, p11, and p12 contain ancillary mutations and an amino-terminal tag.

The results in FIG. 6 show that clones p11 (panel D) and p8 (panel E) exhibit a dramatic improvement in the incorporation of all four ddNTPs compared to the parental #550 clone (panel B). Mutants p11 and p8 both contain the primary P410L mutation and an amino tag, but differ with respect to the number and types of ancillary mutations. Mutant p12 (panel C) produced a faint sequencing ladder, presumably due to the use of an insufficient amount of enzyme or the presence of ancillary mutations which reduce thermal stability. There is evidence of termination products in all lanes, suggesting an improvement in the incorporation of all four ddNTPs relative to the parental clone. Mutant p12 contains the primary mutation A485T in addition to ancillary mutations. In contrast to JDF-3 mutants identified here, the parental clone shows a strong preference to incorporate ddGTP, as evidenced both in primer extension (FIG. 6) and ddNTP inhibition assays (Tables V and VI).

ii. Sequencing with a Radioactively Labeled Primer and Fluorescent Dideoxynucleotides Different DNA polymerases and polymerase mutants will exhibit varying degrees of discrimination against the dye moieties on the dideoxynucleotide analogs. An assessment of usage of dye-labeled dideoxynucleotide analogs by the JDF-3 polymerase mutants was carried out. The procedure used was as follows:

a. Primer Labeling

The sequencing primer SK was radioactively labeled with the KINACE-II™ Kinasing Kit (Stratagene catalog #200390). The incubation reaction (40 μl) contained the following components:

| 1X | kinase buffer #1 |
|---|---|
| 0.75 | μCi/μl γ-³³P ATP |
| 0.375 | u/μl T4 polynucleotide kinase |
| 2.5 | pmol/μl SK primer |

The reaction was incubated at 37° C. for 45 minutes. The primer was purified away from free nucleotides with a size exclusion matrix (NUC TRAP® Stratagene catalog number 400701).

b. Dye Labeled-Dideoxynucleotide: DNTP Ratios

Fluorescent dideoxynucleotides were purchased from New England Nuclear (NEN):

| R6G-ddATP | NEN catalog number NEL-490 |
|---|---|
| R110-ddTP | NEN catalog number NEL-495 |
| TAMRA-ddUTP | NEN catalog number NEL-472 |
| ROX-ddCTP | NEN catalog number NEL-477 |

Incorporation was measured using 3 different concentrations of dye labeled
dideoxynucleotides (ddNTPs) and a constant amount of deoxynucleotides (dNTPs; 2.14 µM):

| | |
|---|---|
| Condition 3) 1:1 | (2-14 µM each dNTP:2.14 µM dye-labeled ddNTP) |
| Condition 2) 1:0.1 | (2.14 µM each dNTP:0.214 µM dye-labeled ddNTP) |
| Condition 1) 1:0.01 | (2.14 µM each dNTP:0.0214 µM dye-labeled ddNTP) | c. Preparation of the DNA Sequencing Reaction Mixtures

Four polymerases were tested for utilization of dye-labeled ddNTPs, exo⁻ JDF-3 (#550 clone), Thermo Sequenase (4u/µl), JDF-3 P410L (clone p8 with ancillary mutations and an amino-terminal tag) and JDF-3 L408H (clone 1-1). A mixture containing the following reagents was assembled:

| | |
|---|---|
| 13.7 µl | H₂O |
| 1 µl | labeled SK primer (2 pmol/µl) |
| 1 µl | pBluescript KS (0.2 µg/µl) |
| 1 µl | polymerase (~1.5 u/µl) |
| 2 µl | 10X buffer (reaction buffer 1 for all but L408H which uses 1.5 mM MgCl₂, buffer (see below) |

10× Reaction Buffer 1

| | |
|---|---|
| 260 mM | Tris pH 9.5 |
| 65 mM | MgCl₂ |

10×1.5 mM MgCl₂ Buffer

| | |
|---|---|
| 24 | mM MgCl₂ |
| 260 | mM Tris pH 9.5 |

2.5 µl of each dye-labeled ddNTP terminator (ddGTP, ddATP, ddTTP and ddGTP was aliquotted separately into one of four tubes. 4.5 µl of each polymerase reaction was added to each of the four tubes, to give a final reaction volume of 7 µl.

d. Cycle Sequencing Reactions

The samples were cycled in a RoboCycler®96 Temperature Cycler with a Hot Top Assembly (Stratagene Catalog #400870 and #400894) using the following conditions:
1) 1 minute at 95° C.
2) 1 minute at 95° C.
3) 1 minute at 50° C.
4) 2 minutes at 72° C.
5) Repeat steps 2-4 thirty times.

Figure 7:
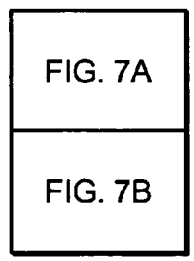
FIG. 7 shows cycle sequencing reactions performed using dye-labeled ddNTPs and JDF-3 polymerase mutants. DNA sequencing ladders were generated using (1) 2.14 µM dNTP: 0.0214 µM ddNTP; (2) 2.14 µM dNTP: 0.214 µM ddNTP; or (3) 2.14 µM dNTP: 2.14 µM ddNTP. The following purified DNA polymerases were used: (A) JDF-3 #550 clone (parental) (B) Thermo Sequenase (C) JDF-3 P410L mutant (clone p8, contains ancillary mutations and an amino tag) (D) JDF-3 L408H mutant (clone 1-1). The top of the original sequencing gel is shown on the right hand side.
Figure 7A:
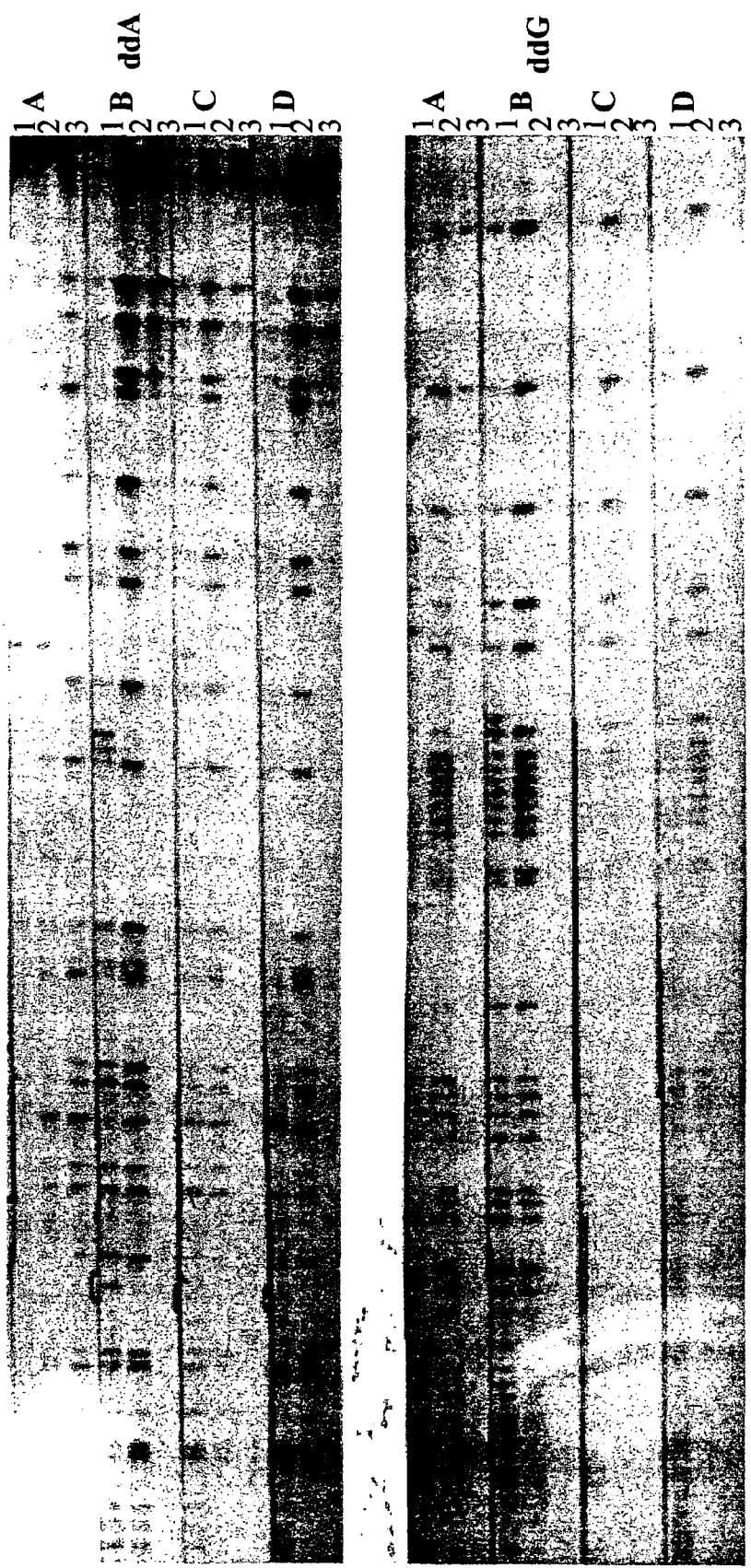

4 µl of stop solution (95% formamide, 20 mM EDTA, 0.05% bromophenol blue, 0.05% xylene cyanol FF) was added to each of the amplified reactions before heating them to 99° C. for five minutes. The samples were electrophoresed on a 6% CASTAWAY™ gel as described above. The gels were dried and then exposed to film for 72 hours (FIG. 7). The results of studies designed to assess utilization of dye-labeled ddNTPs by the different polymerase clones are shown in FIG. 7. Clones p8 (panel C) and 1-1 (panel D) exhibited significantly improved incorporation of R6G-ddATP and R110-ddGTP, compared to the parental clone (panel A). Improvement was evidenced by the synthesis of sequencing ladders at 0.1×(1) and 0.1×(2) dye-ddNTP/dNTP ratios. Optimization of reaction conditions and/or dye moieties may be performed to realize improvements in the incorporation of ddTTP and ddCTP.

iii. Sequencing with Double-Mutant exo⁻ JDF-3 DNA polymerase.

To verify that changes at residues 408, 410, and 485 were sufficient to improve ddNTP incorporation, individual mutations were introduced into the parental 550 (JDF-3 exo⁻ DNA polymerase) clone by site-directed mutagenesis. In addition, point mutations were combined to examine whether they resulted in further improvements in dideoxynucleotide incorporation over polymerases bearing single mutations.

DNA sequencing reactions consisting of 1× reaction buffer, 0.15 pmol/µl long −20 primer, and 10 ng/µg pBluescript KS were prepared as follows:

| | |
|---|---|
| 81 µl | H₂O |
| 9 µl | −20 long primer (2 pmol/µl) |
| 6 µl | pBluescript KS (0.2 µg/µl) |
| **µl | polymerase |
| 12 µl | 10X buffer (260 mM Tris pH 9.5, 65 mM MgCl₂) |

18 µl of the cocktail listed above was aliquotted into the appropriate number of tubes (one per polymerase). Each polymerase (2 µl) was added to an aliquot of cocktail and the tubes were mixed well. Each resulting polymerase mixture (4.5 µl) was then added to each of four tubes, already containing 0.06 mM of one of the four −$^{33}$P-dideoxynucleotides (ddATP, ddTTP, ddGTP or ddTTP; 1500Ci/mmol; 450 µCi/ml) and 6 mM each deoxynucleotide in a volume of 2.5 µl.

The sequencing reactions were cycled in a ROBOCYCLER®96 temperature cycler with a Hot Top Assembly using the following conditions:
1) 1 minute at 95° C.
2) 45 seconds at 95° C.
3) 45 seconds at 60° C.
4) 1.5 minutes at 72° C.
5) Repeat steps 2-4 thirty times.

Stop solution (µl; 95% formamide, 20 mM EDTA, 0.05% bromophenol blue, 0.05% xylene cyanol FF) was added to each reaction before heating to 99° C. for five minutes. Each sample (4 µl) was loaded onto a 6% acrylamide denaturing CastAway gel. The gel was run and treated as described previously.

Figure 8:
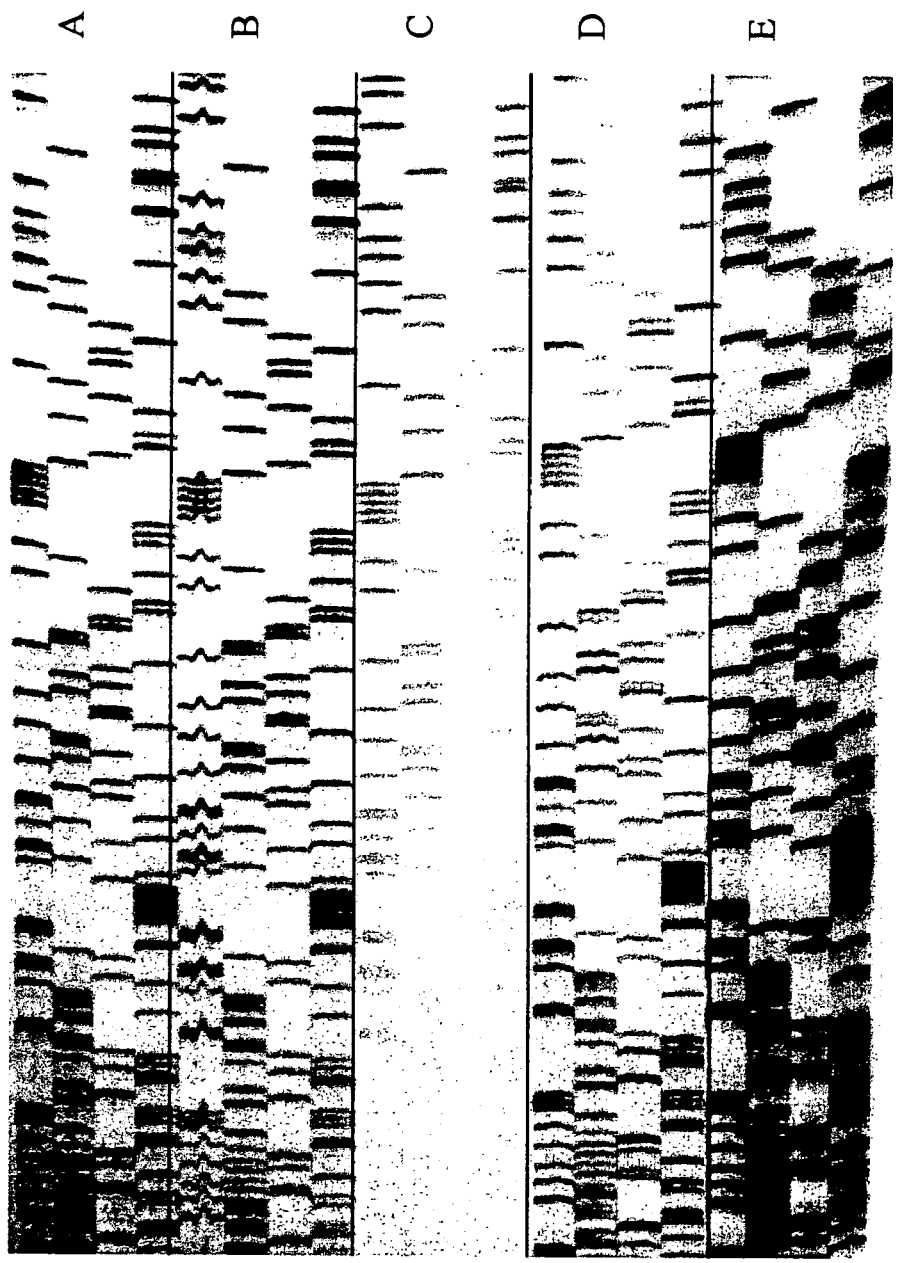
FIG. 8 shows cycle sequencing reactions performed using the JDF-3 P410L/A485T double mutant and α-$^{33}$P Dideoxynucleotides. DNA sequencing ladders were generated using the JDF-3 P410L/A485T double mutant at (A) 2 µl (B) 1 µl (C) 0.5 µl, the JDF-3 P410L mutant (clone p8, contains ancillary mutations and an amino-terminal tag)(D), or Thermo Sequenase (E). The top of the original sequencing gel is shown on the left side. The lanes are: (bottom) ddGTP, ddATP, ddTTP, ddCTP (top).

FIG. 8 shows that the P410L/A485T double mutant exhibits exceptionally even signals. Band uniformity was improved compared to mutant p8 (P410L mutation plus ancillary mutations that do not include A485T) and mutant A485T (data not shown). Mutant p8 exhibited a tendency to preferentially incorporate ddGTP and ddCTP in a sequence-dependent fashion. The optimal amount of enzyme may be higher than the quantity tested in this experiment. Sequence produced by the commercially available Family A DNA polymerase mutant, Thermo Sequenase, is shown in panel E.

iv. Ribonucleotide Incorporation by JDF-3 Polymerase Mutants.

A primer annealed to single stranded DNA template was extended in a mixture containing all ribonucleotides or all deoxynucleotides with the mutant and progenitor polymerases.

M13mp18+ single stranded DNA was annealed to 95× molar excess of the 38mer primer by heating the mixture to 95° C. and cooling slowly at room temperature.

38mer primer: 5' GGTTTTCCCAGTCACGACGTTG-TAAAACGACGGCCAGT 3'

Preliminary assays were carried out to determine what dilutions of enzyme would be necessary to examine the incorporation activity at non-maximal levels. The final assay solutions were composed as described below:

Ribonucleotide Mixture

| | |
|---|---|
| 20 ng/µl | annealed primer/template |
| 1x | Cloned Pfu buffer (Stratagene catalog #200532) |
| 200 µM each | GTP, UTP, ATP |
| 50 µM | CTP |
| 1 µM | 5-$^3$H CTP 20.2 Ci/mmole |
| 0.05-0.3 units | JDF-3 polymerase* |

Deoxyribonucleotide Mixture

| | |
|---|---|
| 20 ng/µl | annealed primer template |
| 1x | Cloned Pfu buffer |
| 200 µM each | dGTP, dATP, dCTP |
| 50 µM | TTP (deoxyribonucleotide) |
| 1 µM | Thymidine 5'-triphosphate, [methyl-$^3$H] 20.5 Ci/mmole |
| 0.05-0.3 units | JDF-3 polymerase* |

*Added separately

Nine microliters of the polymerase-free mixtures were placed in 0.2 ml tubes before the polymerases were added. The samples were incubated at 72° C. in a ROBOCYCLER®96 temperature cycler with Hot Top Assembly (Stratagene Catalog Nos. 400870 and 400894). The deoxyribonucleotide mixture was removed at 2 minutes and placed at approximately 2° C. The ribonucleotide mixture was incubated for 30 minutes. Seven microliters of the assay mixture were spotted onto DE81 filter circles (Whatmann) and dried prior to being washed three times in 2×SSC (0.3M NaCl, 0.03M sodium citrate) for five minutes each wash. The filters were rinsed twice in ethanol and allowed to dry before being quantified with a scintillation counter.

Figure 9:
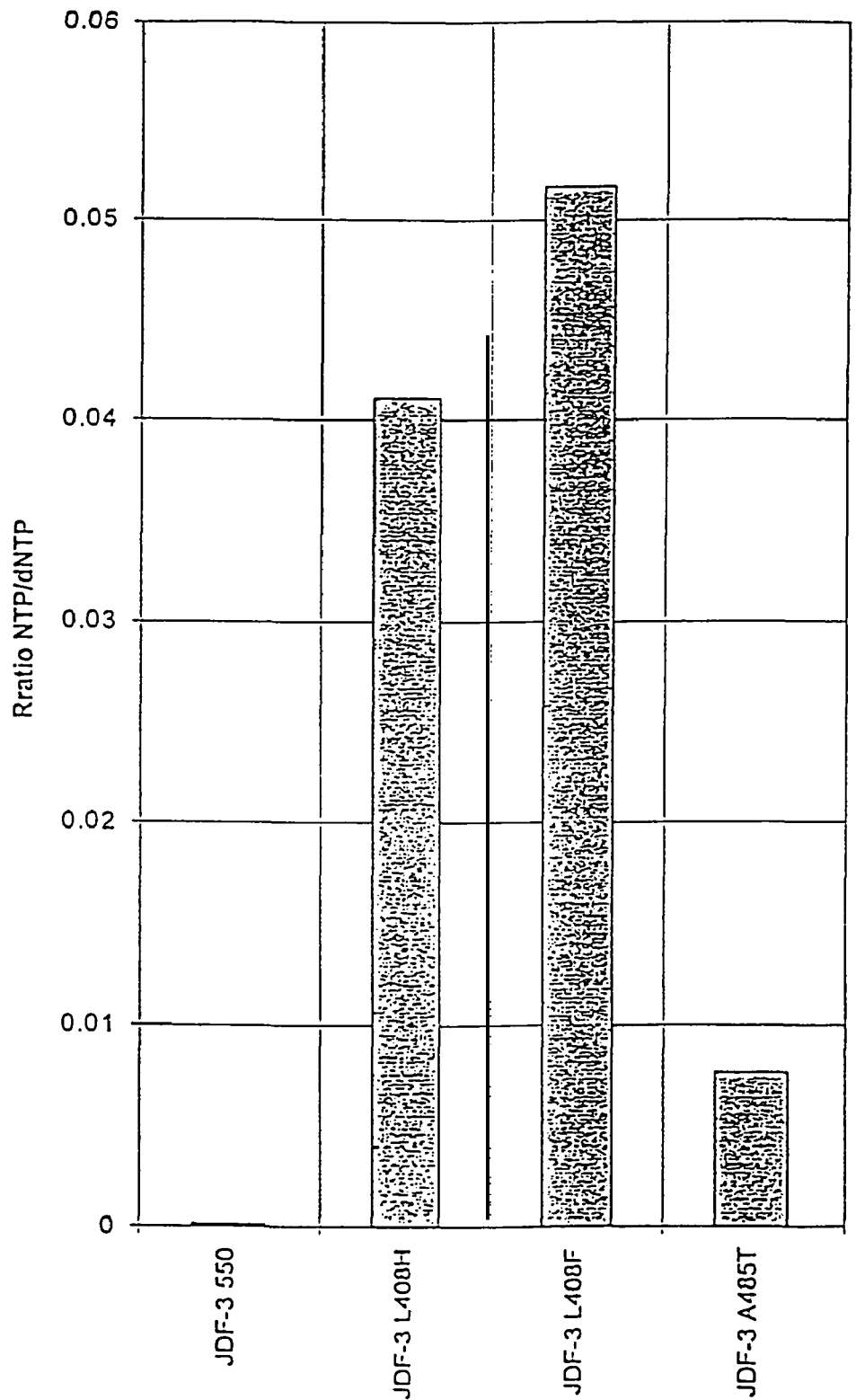
FIG. 9 shows the result of ribonucleotide incorporation assays using exo JDF-3 (550) and mutants of this progenitor clone. The ratios of ribonucleotide versus deoxynucleotide incorporation are plotted for JDF-3 550, JDF-3 L408H, JDF-3 L408F and JDF-3 A485T.
Figure 10:
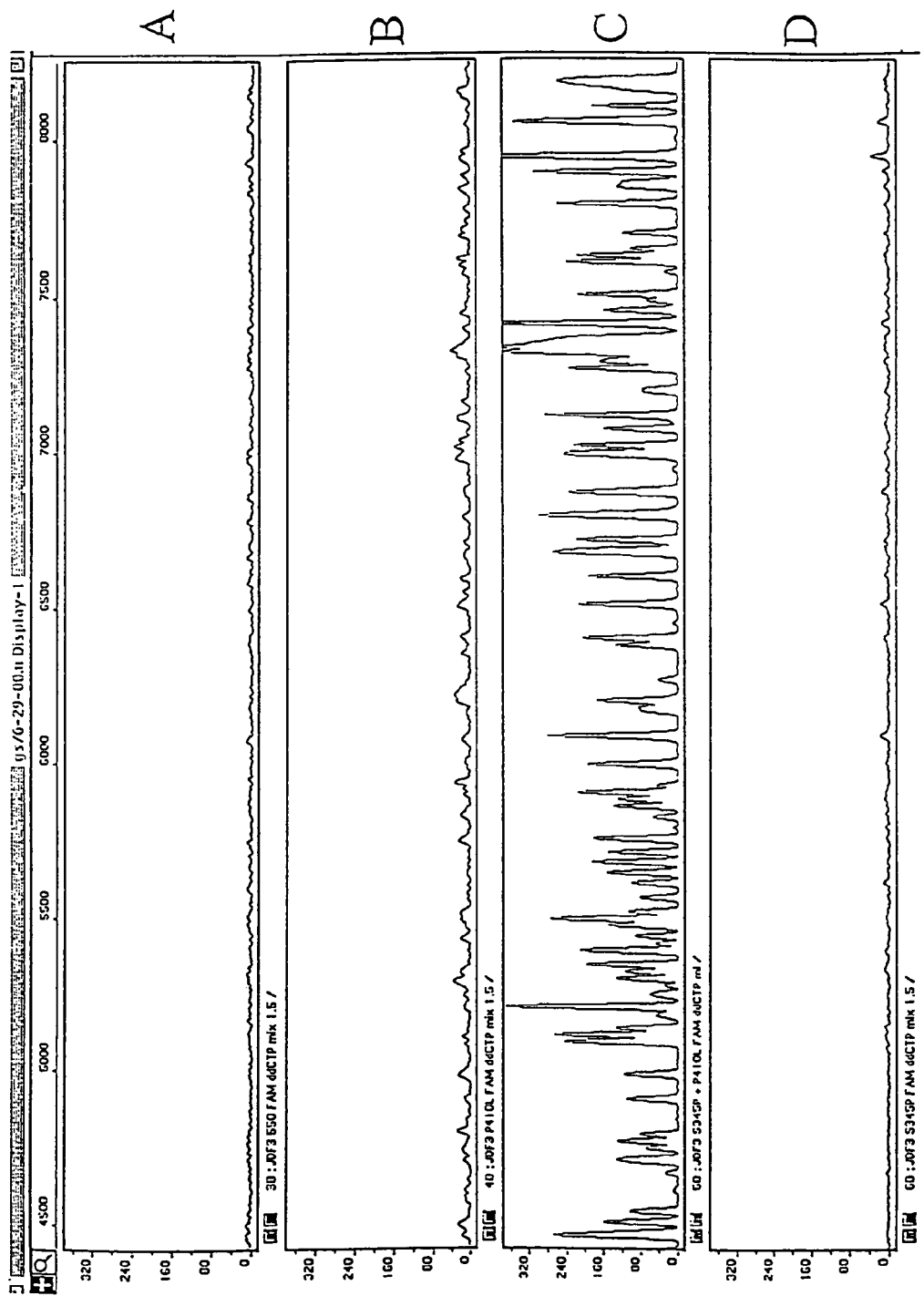
FIG. 10 shows the traces of the sequence generated by four versions of JDF-3 DNA polymerase and FAM ddCTP. Panel A shows the minimal trace produced by the progenitor polymerase JDF-3 550, Panel B demonstrates the slightly improved trace made by JDF-3 P410L, Panel C shows the sequence generated by the double mutant S345P and P410L, and Panel D shows the trace created by JDF-3 S345P.
Figure 11:
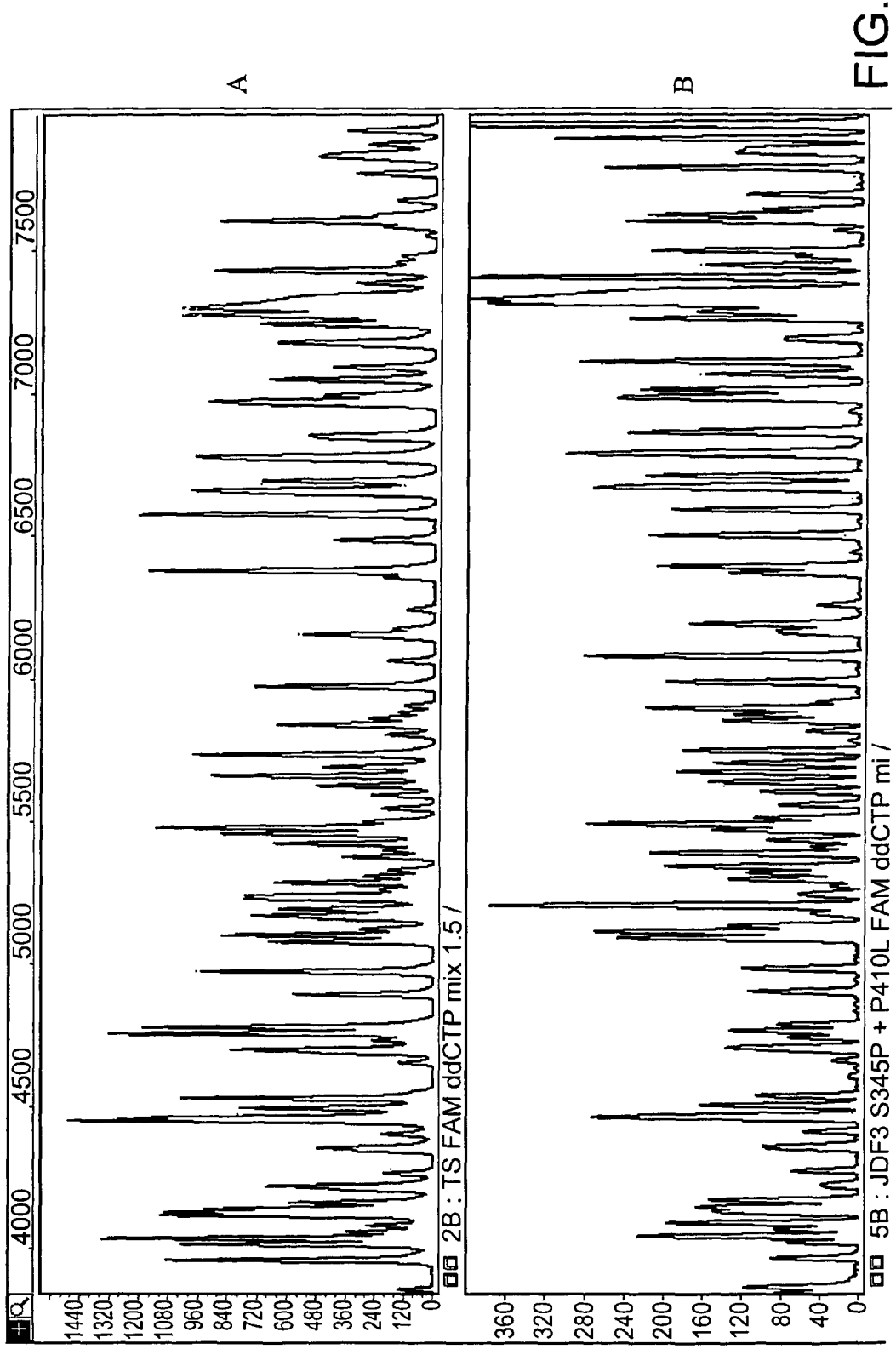
FIG. 11 shows the difference in peak uniformity demonstrated by Thermo Sequenase in Panel A and the double mutant JDF-3 S345P+P410L in Panel B.
Figure 12:
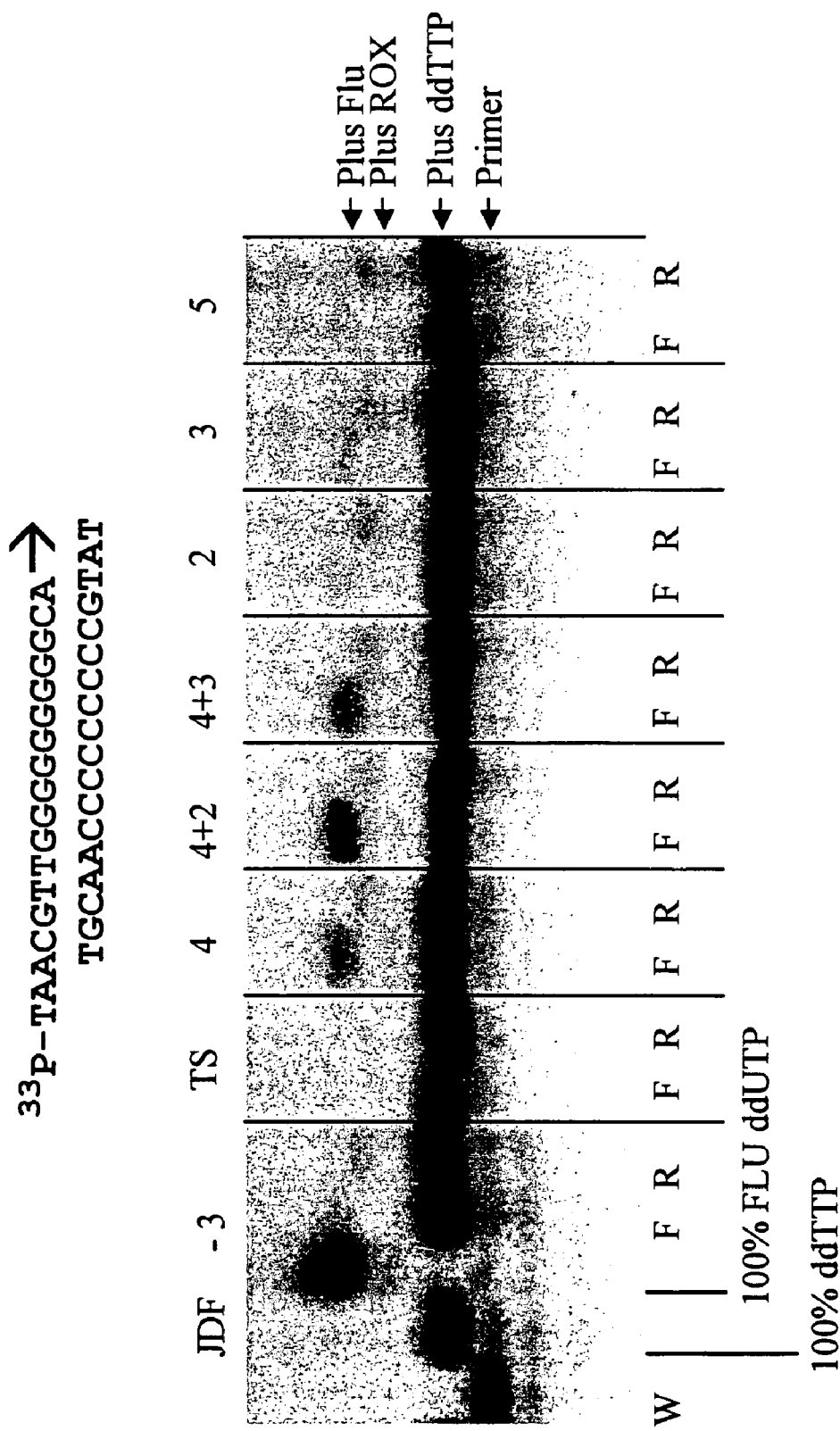
FIG. 12 shows the separated products of 3' extension of a labeled oligonucleotide with the dideoxynucleotide thymidine triphosphate of ROX-ddUTP (New England Nuclear (NEN) NEL476) or Fluorescein-12-ddUTP (NEN NEL401). Mutant 4 is JDF-3 S345P, Mutant 2 is JDF-3 P410L, Mutant 3 is JDF-3 A485T and Mutant 5 is Y496N. F indicates FLU ddUTP and R indicates ROX ddUTP.
Figure 13:
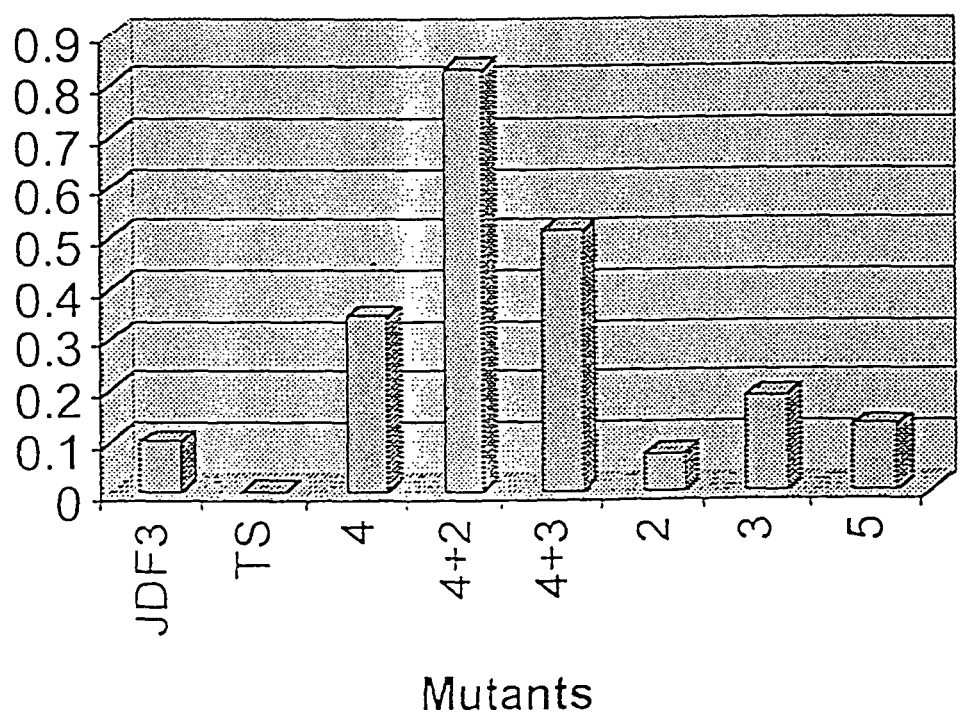
FIG. 13 shows a graphic representation of the relative band intensities form FIG. 12. The numerical values are generated by dividing the intensity value of the ddTTP band into the intensity value for the Fluroescein-12-ddUTP bands.

Background counts per minute (CPM) for the deoxyribonucleotide and the ribonucleotide reactions were subtracted from the respective averaged CPM value of duplicate samples for each enzyme. The background-corrected ribonucleotide CPM value was divided by the background-corrected deoxyribonucleotide CPM value (FIG. 9).

| Polymerase | Ratio NTP/dNTP | Relative to JDF-3 550 |
|---|---|---|
| JDF-3 550 | 0.000165162 | 1 |
| JDF-3 L408H | 0.041087258 | 249 |
| JDF-3 L408F | 0.051703924 | 313 |
| JDF-3 A485T | 0.007628583 | 46 | v. Ribonucleotide Sequencing with JDF-3 Polymerase Mutants.

Ribonucleotides incorporated into a deoxyribonucleotide polymer are susceptible to alkali hydrolysis which can produce a sub-population of polymer lengths. When labeled primer is extended in the presence of a particular ribonucleotide base (for example ATP) and the four deoxyribonucleotide bases, the fragments resulting from alkali hydrolysis create a population of different lengths, which correspond to all the possible positions where ATP was incorporated. When those fragments are size separated, their migration pattern, with respect to other ribonucleotide base (CTP, UTP and GTP) hydrolysis products allows the template sequence to be read. As described previously, most DNA polymerases discriminate against non-conventional deoxynucleotides. A subset of the JDF-3 DNA polymerase mutants which allow improved uptake of the unconventional dideoxynucleotides also show improved tolerance for ribonucleotide incorporation.

100 ng of the 38mer primer was kinased with γ-$^{33}$P according to the instructions in the KINACE-IT™ Kinasing Kit (Stratagene catalog #300390).

38mer primer: 5' GGTTTTCCCAGTCACGACGTTG-TAAAACGACGGCCAGT 3'

The labeled oligonuclcotide was purified from contaminating free nucleotides with a NUC TRAP® Probe Purification Column (Statagene catalog #400701) in 10T.1E (10 mM Tris pH 8.0, 0.1 mM EDTA). Labeled oligonucleotide (~7 picomoles) was annealed to 0.09 pmoles M13 mp18+ by heating to 95° C. then cooling to room temperature in the presence of 0.32 mM MgCl$_2$.

Extension Components

| | |
|---|---|
| 0.054 pM | annealed primer/template |
| 200 µM each | dNTP |
| 1x cPfu | DNA polymerase buffer (Stratagene catalog #200532) |
| 4–200 ATP* | |
| 0.1–5 Units | JDF-3 polymerase* |

*Added separately

Eight microliters of a cocktail containing the first three components listed above were aliquoted into a 0.2 ml tube. 1 µl of polymerase and 1 µl of 2 mM, 0.2 mM or 0.4 mM ATP were added and the reaction was incubated at 72° C. for 15 minutes. The reaction volume was brought to 100 µl with 1×cPfu polymerase buffer and transferred to a 1.5 ml tube. After heating the reactions in the presence of 70mM NaOH for 15 minutes at 100° C., the reaction was neutralized with 70 mM HCl and precipitated through the addition of 10 µl 3M sodium acetate and 327.51 µl of ethanol. The samples were microcentrifuged for 30 minutes at 14 krpm before the supernatant was removed and the pellet washed in 80% ethanol. After vacuum drying, the samples were resuspended in 5 µl of sequencing stop solution (95% formamide, 20 mM EDTA, 0.05% bromophenol blue, 0.05% xylene cyanol FF) and 2.51 µl was loaded on a 6% acylamide-7M urea, 1×TBE CAST-AWAY™ Precast gel (Stratagene catalog numbers 401090 and 401094). The gels were run at 50 watts until the bromophenol blue dye migrated past the bottom of the gel after which the gel was fixed, dried and exposed to film for 72 hours.

Sequencing ladders for JDF-3 550 (wild-type nucleotide incorporation) and all the mutants tested were visible at the 200 µM and 20 µM ATP level. At the 4 µM level, only the L408H and L408F mutants produced ladders (data not shown).

vi. Sequencing with Dye-Dideoxynucleotide Terminators

Primer was extended in the presence of FAM ddCTP (NENNEL481). The sequence reactions were purified and run on an ABI 370.

Reaction conditions for cycle-sequencing were as described below:

1×cPFU buffer, 200 ng pBluescript II KS plasmid, 3 pmole T7 primer, 0.23 mM dCTP, 0.23 mM dATP, 0.23 mM dTTP, 0.23 mM dGTP with 0.046 mM FAM ddCTP. The samples were cycled in a Perkin-Elmer cycler in 10 µl volumes for 25 cycles of the temperatures and times described below:

| | |
|---|---|
| 95° C. | 30 s |
| 55° C. | 30 s |
| 72° C. | 2 min |

The samples were purified using CentriSep columns according to the manufacturer's instructions. After drying, the samples were resuspended in 3 µl of a loading dye comprised of 66.7% deionized formamide, 16.7 mg/ml Blue Dextran, and 8.3 mM EDTA. Samples were heated at 95° C. for three minutes and loaded on a 5% LongRangen gel in an ABI PRISM 377 DNA sequencer.

Data was processed in Gene Scan 2.1.

Example 2

Labeling of DNA.

The modified DNA polymerases of the invention are applicable to labeling of DNA. It is known to those skilled in the art that there are several means by which to label DNA, including the incorporation of radiolabeled nucleotides. One such common means is by random priming, which enables one of skill in the art to generate labeled DNA fragments, typically about 50 to about 1000 bases long. The procedure described herein are adapted from F. Ausubel et al., Short Protocols in Molecular Biology, Third Edition, John Wiley and Sons, Inc., 1995.

As a first step toward random priming DNA, a reaction mix containing 2.5 microliters 0.5 mM 3dNTP (dCTP, dGTP, TTP, each at 0.5 mM), 50 µCi[-$^{32}$P]dATP, 1 microliter of 3 to 8 units/microliter DNA polymerase in 50 mM Tris-HCl, pH 7.5, 10 mM MgCl$_2$, 1 mM dithiothreitol, 0.05 mg/ml bovine serum albumin is prepared in a total volume of 11 microliters and incubated on ice. Next, about 30 to about 100 ng of DNA is mixed with about with 1 to 5 µg of random hexanucleotides in 14 microliters and boiled for 2 to 3 minutes and then placed on ice. The 11 microliter reaction mix is then added to the DNA/random hexamer mix, and the random priming reaction is incubated over 10 minutes to as much as 4 hours at room temperature. To stop the reaction, 1 microliter 0.5 M EDTA, 3 microliters 110 mg/ml tRNA, and 100 microliters 10 mM Tris-HCl, pH 7.4 is added and the mixture is extracted with phenol. The labeled DNA is then separated from unincorporated radioactive precursors by chromatography.

R. Gel Assay for Dye-Dideoxynucleotide Incorporation

A labeled oligonucleotide duplex was extended with a mixture of dideoxynucleotides and dye-dideoxynucleotides. When the duplex was separated on a denaturing 20% Acrylamide/7 M urea gel, labeled oligonucleotides terminated with a dideoxynucleotide could be resolved from oligonucleotides terminated with dye-deoxynucleotides.

Oligonucleotides:

| | |
|---|---|
| 259C | $^{32}$P-TAACGTTGGGGGGGGGCA→ |
| 258C | TGCAACCCCCCCCGTAT |

The 5' end of 259C was labeled and purified as described in Section Q.ii.a except that $^{32}$Pγ-ATP was used. The labeled oligonucleotide 259C was at a concentration of approximately 0.7 ng/µl. The complimentary oligonucleotide (258C) was added as an equal concentration, heated to 95° C. for three minutes, 50° C. for 5 minutes and room temperature for 20 minutes. Heat killed lysates of the relevant mutants were prepared as described in Example section C. The reactions were incubated in a 5 µl volume composed of 30 mM Tris pH 8.0 and 3 mM MgCl$_2$ with a nucleotide mixture totaling 0.1 mM. The ratio of ddTTP to FLU ddUTP or ROXddUTP was 10:1. The dimer was present at a concentration of 1.2 picomoles and 0.5 µl of enzyme or crude lysate or purified enzyme was added to the reaction before incubation at 50° C. in the RobeCycler® Gradient 96 Temperature Cycler with Hot Top. The samples were incubated for 20 s before 3 µl of a formamide based loading dye was added and the samples were heat-denatured at 95° C. for 3 minutes then loaded onto a 20% acrylamide/7 M urea gel and subjected to electrophoresis at a constant 60 watts. The gel was exposed to X-ray film and the film was analyzed in the EagleEye® Eagle Sight software package.

Example 3

The modified DNA polymerases of the invention are also applicable to identify a nucleotide at a given position of a template DNA molecule, i.e., by mini-sequencing. For example, the JDF-3 DNA polymerase P410L/A485T mutant (JDF-3 D141A/E143A/P410L/A485T) generates the longest and most uniform radioactive DNA sequencing ladders using low ddNTP/dNTP ratios (1/100), indicating efficient ddNTP incorporation, minimal base selectivity, and high polymerase activity. This example describe the properties of this JDF-3 DNA polymerase P410L/A485T mutant and a procedure for optimizing the conditions for mini-sequencing using the mutant polymerase.

A. Experimental Protocol i. Materials

StrataPrep PCR columns, StrataPrep DNA gel extraction columns, cold ddNTPs, calf alkaline phosphatase and pBluescript II were from Stratagene. Rhodamine labeled-ddNTPs were purchased from NEN. EDTA/blue dextran, rhodamine dye-matrix standards, and the SNaPshot ddNTP primer extension kit were purchased from Applied Biosystems. ThermoSequenase (Taq F667Y mutant) was from Amersham Pharmacia Biotech. Long Ranger polyacrylamide gels (6%) were purchased from BMA. Shrimp alkaline phosphatase and exonuclease I were from USB corporation. CENTRI-SEP spin columns were purchased from Princeton Separations. Deionized formamide was from Sigma. Oligonucleotides (PAGE purified) whose sequences are listed in Table VII, were purchased from Genset oligos. All other reagents were molecular biology grade.

ii. Primer:Template Formation:

Duplex primer template pairs were formed by annealing the template with 10 fold excess of the appropriate primer in a solution containing 10 mM Tris-HCl (pH 8) and 0.1 mM EDTA using the following temperature regimen: 5 min at 95° C. and then cool slowly to room temperature. Concentrations of the primer:templates are expressed as moles of single stranded templates.

iii. Product Analysis:

The dye labeled products were resolved on 6% polyacrylamide/urea gels and visualized on a Applied Biosystems model 377 DNA sequencer using 3.1.2 GeneScan fragment analysis software for peak identification and fluorescence measurements. A rhodamine dye-matrix was installed on the ABI 377 sequencer according to the manufacturer's protocol.

TABLE VII

| | | Synthetic oligonucleotides |
|---|---|---|
| Temp-A | SEQ ID NO: 50 | 5'-CTCAACTTGGAGCGAACGACCTACACCGAA |
| Temp-T | SEQ ID NO: 51 | 5'-CTCATCTTGGAGCGAACGACCTACACCGAA |
| Temp-G | SEQ ID NO: 52 | 5'-CTCAGCTTGGAGCGAACGACCTACACCGAA |
| Temp-C | SEQ ID NO: 53 | 5'-CTCACCTTGGAGCGAACGACCTACACCGAA |
| *pBL-25C | SEQ ID NO: 54 | 5'-TTCGGTGTAGGTCGTTCGCTCCAAG |
| *pBL-28T | SEQ ID NO: 55 | 5'-AAGTGTAAAGCCTGGGGTGCCTAATGAG |
| *pBL-31G | SEQ ID NO: 56 | 5'-TTCAGCATCTTTTACTTTCACCAGCGTTTCT |
| *pBL-34A | SEQ ID NO: 57 | 5'-AGCTGGCGAAAGGGGATGTGCTGCAAGGCGATT |
| *pPC-41T | SEQ ID NO: 58 | 5'-CGGTACCTCCTGGTGGATACACTGGTTCCTGTAAGCAGAAG |
| *pPC-26G | SEQ ID NO: 59 | 5'-GAGAGCTTGAGGAGAGCAGGAAAGGT |
| *pPC-37A | SEQ ID NO: 60 | 5'-GATCTCCCAGGGCGGCAGTAAGTCTTCAGCATCAGGC |
| *pPC-29C | SEQ ID NO: 61 | 5'-TCCTTTGGACAGGGATGAGGAATAACTGA |

*The numbers indicate the length of the primer before extension by one ddNTP and the succeeding letters show the ddNTP that is incorporated.

iv. Purification and Optimal Reaction Buffer of JDF-3 P410L/A485T DNA Polymerase:

JDF-3 P410L/A485T was expressed in XL-10 Gold and purified as described in the "Purification of JDF-3 P410L/A485T mutant" Product Transfer Document by Brad Scott. One unit of enzyme is defined as the amount that will catalyze the incorporation of 10 mmol of total nucleotide into acid insoluble form in 30 minutes at 72° C. The 10× reaction buffer for JDF-3 P410L/A485T contains: 200 mM Tris-HCl (pH 8.8), 100 mM KCl, 100 mM (NH4)$_2$SO$_4$, 20 mM MgSO$_4$.

v. Enzyme Assays:

a. Kinetic Analysis of Rhodamine Labeled-ddNTP Incorporation and Misincorporation:

$K_m$ and $V_{max}$ values for rhodamine labeled-ddNTP incorporation were measured by incubating 50 nM primer:template with limiting amounts of polymerase (0.1 units or 5 nM) and varying concentrations of rhodamine labeled-ddNTP ranging from 0.1 nM to 500 nM. Samples were incubated at 60° C. for 10 minutes. The reactions were then quenched with ice-cold 0.2 M EDTA (final concentration). Unincorporated rhodamine labeled ddNTPs were removed by purifying the extended primer:templates on CENTRI-SEP spin columns. Reactions were then dried, and the pellets dissolved in 3:1 formamide:EDTA/blue dextran and analyzed by 6% denaturing PAGE on an ABI 377 sequencer. All peak area quantitations were performed using 3.1.2 GeneScan software and $K_m$ and $V_{max}$ values were calculated using Lineweaver-Burk plots.

$K_m$ and $V_{max}$ values for primer:template were measured with limiting amounts of enzyme (0.1 units or 5 nM) in the presence of 100 nM of R110-ddGTP and varying concentrations of primer:template (pBL31G:pBluescript II) ranging from 0.5 to 100 nM. Samples were incubated for 10 minutes at 60° C. The reactions were then quenched, purified from unincorporated rhodamine labeled-ddNTPs, and analyzed as described above.

To determine the kinetics of misinsertion, the steady state Michaelis-Menten $K_m$ and $V_{max}$ parameters were calculated by incubations of limiting amounts of enzyme (0.1 units or 5 nM) in presence of 50 nM primer:template and varying concentrations of non-complementary rhodamine labeled ddNTP (1 nM to 10,000 nM) for 10 minutes at 60° C. Analysis and quantitations were performed as above.

b. Screen for Fidelity:

Reactions (10 μl) contained 1 unit of enzyme in 1× reaction buffer, 15 nM primer template, 25 nM of unlabeled complementary ddNTP, and 25, 100, 500, or 1000 nM of rhodamine labeled non-complementary ddNTP in four separate reactions. The reactions were incubated in a Perkin-Elmer 9600 for 25 cycles as follows: 96° C. for 10 s, 50° C. for 5 s, and 60° C. for 30 s. The reactions were then quenched with ice-cold 0.2 M EDTA (final concentration) and the products were purified from unincorporated rhodamine labeled ddNTPs and analyzed as described above.

c. Assays for Rhodamine Labeled ddNTP Incorporation:

These experiments were performed using 1 unit of enzyme, 15 nM primer:template (pBL25C and Temp-A, Temp-T, Temp-C, or Temp-G in four separate reactions), and 50 nM dye-ddNTP (TAMRA- or R110-labeled). The reactions were incubated at 60° C. for 10 minutes and then quenched with ice-cold 0.2 M EDTA (final concentration). The products were purified from unincorporated dye-labeled ddNTPs and analyzed as described above.

B. Optimization Procedures i. Preparation of DNA Templates for Minisequencing:

Fragments containing the SNP(s) of interest are amplified from genomic DNA using standard PCR conditions. In this study, PCR reactions were carried out using 2.5 units of TaqPlus Precision DNA polymerase blend. A 4 kb fragment of the human alpha-1-antitrypsin gene was amplified from 100 ng human genomic DNA using 10 pmol of the pPC26G and pPC29C primers (Table VII). The following program was used in a Robocycler: 1 cycle of 95° C. for 2 min, 30 cycles of 95° C. for 1 min, 58° C. for 1 min, and 72° C. for 4 min, followed by one cycle at 72° for 7 min.

In order to purify the resulting 4 kb fragment from PCR primers and unincorporated dNTPs, the fragment can be: (1) purified using the StrataPrep DNA gel extraction kit; (2) treated with exoI/SAP; or (3) incubated on StrataPrep columns with SAP or CIAP. To treat the PCR fragment with exoI/SAP, 2 units of each enzyme was added to 4 μl of PCR product, and the mixture was incubated for 1 hour at 37° C., followed by 15 minutes at 72° C. to inactivate the enzymes. To purify the PCR amplified fragment using StrataPrep columns, a 50 μl PCR reaction was loaded on a StrataPrep column and processed as described in the StrataPrep column manual, except that before elution, 1 unit of CIAP in 50 μl 1× corresponding reaction buffer was added to the column. The column was incubated at room temperature for 5 minutes, washed, and the PCR fragment was eluted as described in the manual. The eluate was incubated at 72° C. for 15 minutes to inactivate any remaining CIAP. All of these clean up methods produced DNA templates that were pure enough for subsequent minisequencing.

ii. Minisequencing Protocol Using Plasmids or PCR Amplified Fragments:

Minisequencing of pBluescript (0.25 pmol) was carried out using 0.15 pmol of each primer (e.g. pBL25C), 1 unit enzyme, 0.04 μM of R6G-ddA, R110-ddG, and ROX-ddC, and 0.2 μM of TAMRA-ddU. When using PCR amplified fragments, template concentrations as low as 0.02 pmol/rxn were used. All reactions were performed in 10 μl volumes. The thermal cycling program consisted of 25 cycles of 96° C. for 10 s, 50° C. for 5 s, and 60° C. for 30 s in a Perkin-Elmer 9600 or 25 cycles of 96° C. for 50 s, 50° C. for 50 s, and 60° C. for 50 s in a Robocycler.

In order to purify the labeled primers from unincorporated dye-ddNTPs, samples were either treated with SAP or CIAP, or purified using CENTRI-SEP columns according to manufacturers's recommendations. 1 unit of CIAP or 0.5 unit of SAP was added to each 10 μl reaction and incubated at 37° C. for 60 min, followed by 15 minutes at 72° C. to inactivate alkaline phosphatase. Reactions were then dried and pellets were dissolved in 10 μl of 3:1 formamide:EDTA/blue dextran. 1 μl of each reaction was resolved by 6% denaturing PAGE on an ABI 377 sequencer and analyzed using GeneScan 3.1.2 (Applied Biosystems).

Figure 16A:
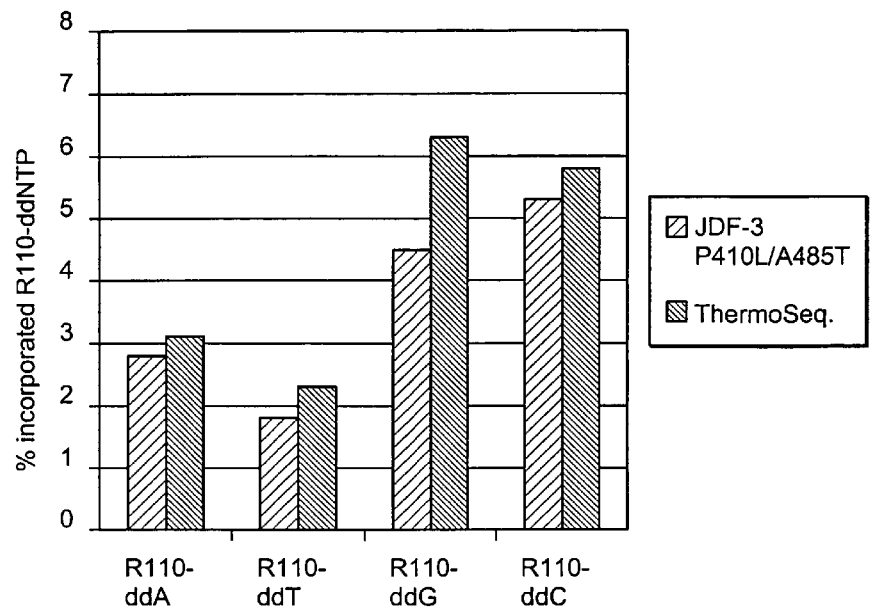
FIG. 16. Incorporation of rhodamine labeled-ddNTPs by JDF-3 P410L/A485T and ThermoSequenase (Taq F667Y). The JDF-3 P410L/A485T and Taq F667Y mutants show slightly different incorporation rates for each of the rhodamine-labeled-ddNTPs. Reactions in panels A and B contained 0.05 µM of either TAMRA- or R110-labeled-ddNTPs, 15 nM primer:template, and 1 unit of enzyme. Reactions were incubated as described in the Experimental Protocol.
Figure 16B:
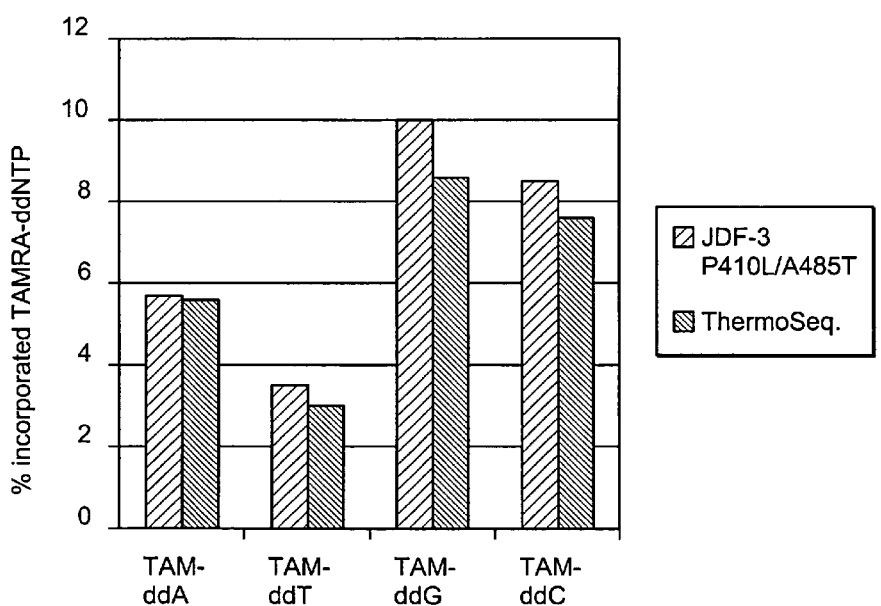
Figure 17A:
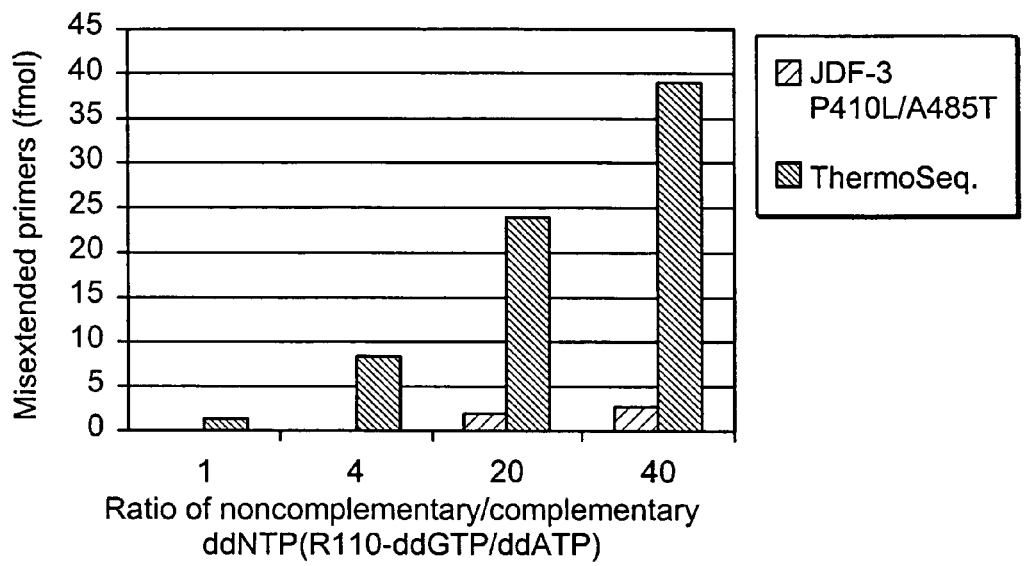
FIG. 17. Misinsertion of rhodamine labeled-ddNTPs by JDF-3 P410L/A485T and ThermoSequenase (Taq F667Y). JDF-3 P410L/A485T shows higher fidelity compared to Taq F667Y when incorporating certain ddNTPs. Reactions in panels A and B contained 1 unit of either JDF-3 P410L/A485T or ThermoSequenase, 15 nM primer:template (panel A: pBluescript:pBL34A; panel B: pBluescript:pBL31 G), and 25 nM of unlabeled complementary ddNTP (panel A: ddATP; panel B: ddGTP) and either 25, 100, 500, or 1000 nM of dye-labeled non-complementary ddNTP (panel A: R110-ddGTP; panel B: R 110-ddUTP) in four separate reactions. Reactions were incubated and analyzed as described in the Experimental Protocol. Panel C shows the sequencing gel from which the data in panel A was derived.
Figure 17B:
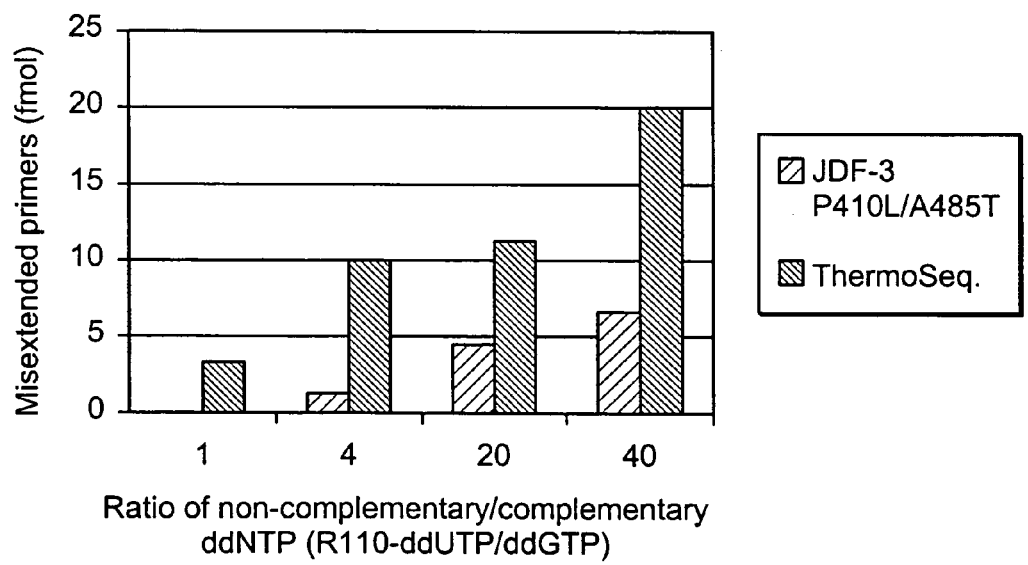

C. Results i. Buffer and Reaction Temperature Optimizations:

Since *Thermococcus* sp. JDF-3 DNA polymerase is closely related to archaeal *P. furiosus* DNA polymerase (Pfu), cloned Pfu buffer (10× buffer: 200 mM Tris-HCl (pH 8.8), 100 mM KCl, 100 mM $(NH_4)_2SO_4$, 20 mM $MgSO_4$, 1% Triton X100, and 1 mg/ml BSA) was used as a starting point for buffer optimization. Changes in enzyme activity due to buffer and reaction temperature alterations were determined by measuring R6G-ddATP incorporation using the pBL34A:pBluescript primer:template system. The presence of Triton X-100 and BSA in this buffer was found to create an artifact (double band effect) in sequencing gels (data not shown). Enzyme activity was measured at pH 8.4 and 9.5, in the presence of varying concentrations of KCl (20, 40 or 80 mM), $(NH_4)_2SO_4$ (5 or 20 mM), and $MgSO_4$ (4 or 8 mM), respectively. None of these changes had a noticable effect on the activity of JDF-3 P410L/A485T. Therefore, cloned Pfu buffer lacking BSA and Triton was identified as the optimal reaction buffer for minisequencing. Furthermore, the activity vs. temperature profile of JDF-3 P410L/A485T showed that nucleotide incorporation did not increase significantly between 60° C. and 72° C. (data not shown). To keep the extension temperature below the melting temperatures of minisequencing primers, all subsequent experiments were performed at 60° C.

ii. Incorporation of Rhodamine-Dideoxyribonucleotides:

Relative incorporation of rhodamine labeled-ddNTPs by the JDF-3 P410L/A485T and Taq F667Y mutants was determined. We used both TAMRA- and R110-labeled ddNTPs, and the amount of incorporated dye-ddNTPs was measured in fluorescense units. These experiments were performed using pBL25C as the primer, and Temp-A, Temp-T, Temp-C, or Temp-G as the complementary template in four separate reactions. The only difference between these four primer:template systems is the SNP site, thereby eliminating the possibility that primer:template sequence has an effect on dye-ddNTP incorporation. FIG. 16 panel B shows that JDF-3 P410L/A485T incorporates TAMRA-ddGTP and TAMRA-ddCTP slightly more efficiently compared to TAMRA-ddATP and TAMRA-ddUTP. ddCTP and ddGTP are also incorporated more efficiently than ddATP and ddUTP when R110 labeled ddNTPs are employed (FIG. 16 panel A). Gardner and Jack had also observed variation in the incorporation of ribonucleotides by the A488L mutant (equivalent to JDF-3 A485) of Vent DNA polymerase (from archaeon *Thermococcus litoralis*)[15]. In fact, the Vent A488L mutant incorporated UMP ~10 fold less efficiently than CMP, GMP, and AMP, and the wild type Vent DNA polymerase showed similar bias against dUMP incorporation.

We performed similar rhodamine labeled-ddNTP incorporation experiments using the same number of units of Taq F667Y. As panels A and B in FIG. 16 indicate, the JDF-3 P410L/A485T and Taq F667Y mutants exhibit similar TAMRA- and R110-ddNTP incorporation efficiencies and limited (<3-fold) base selectivity, with the preference order of: G>C>A>T.

iii. Kinetic Parameters for Polymerization Reaction:

$K_m$ and $V_{max}$ values for primer:template and rhodamine-ddNTPs were determined as described in the Experimental Protocol. These values are reported in Table VIII, which compares the kinetic properties of JDF-3 P410L/A485T and Taq F667Y. This comparison establishes that the JDF-3 P410L/A485T and Taq F667 mutants exhibit similar steady-state kinetic parameters, and therefore, have similar affinities for both primer:template and rhodamine-ddNTP substrates.

Furthermore, kinetic parameters in Table VIII were used to determine incorporation efficiency of TAMRA-ddCTP ($V_{max}/K_m$=3.3/1=3.3) in comparison to TAMRA-ddATP ($V_{max}/K_m$=1.9/0.9=2.1). Incorporation efficiency of TAMRA-ddCTP is 1.5 fold more than TAMRA-ddATP, suggesting that JDF-3 P410L/A485T mutant incorporates different ddNTPs at slightly different rates, confirming the results obtained in FIG. 16.

TABLE VIII

Steady-state kinetic parameters[a] for rhodamine labeled ddNTPs and primer:template.

| Substrate | JDF-3 P410L/A485T mutant | | ThermoSeq. (Taq F667Y mutant) | |
|---|---|---|---|---|
| | $K_m$(nM) | $V_{max}$(fmol/min) | $K_m$(nM) | $V_{max}$(fmol/min) |
| Primer:template[d] | 10 | 7.4 | 8 | 7.4 |
| R6G-ddATP[c] | 0.33 | 6 | 0.35 | 9 |
| TAMRA-ddATP[c] | 0.9 | 1.9 | 0.6 | 1.9 |
| TAMRA-ddCTP[b] | 1 | 3.3 | 0.3 | 2.3 |

Figure 18:
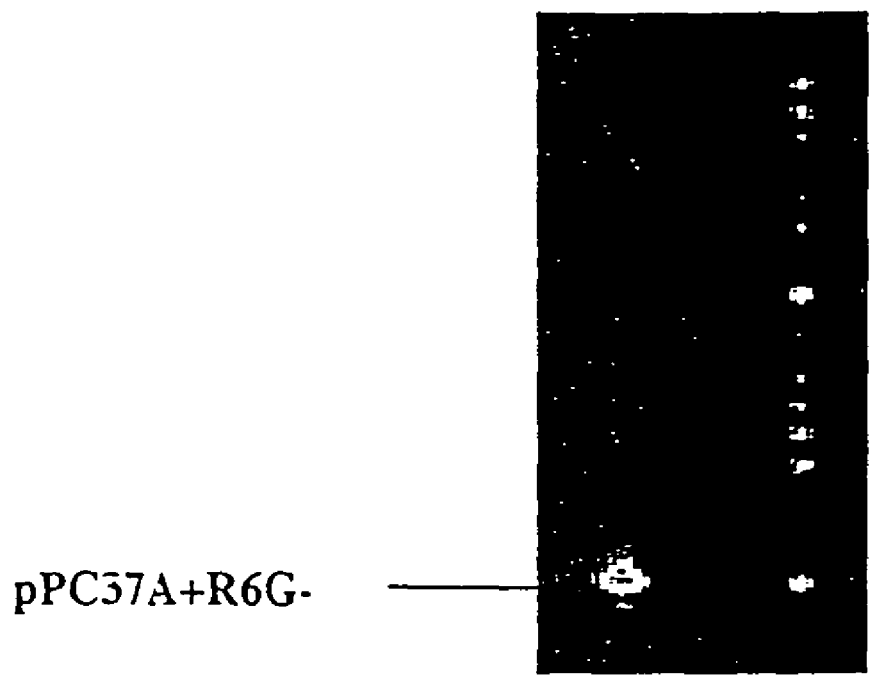
FIG. 18. Incubation of PCR amplified fragments on Strataprep columns with CLAP helps purify fragments prior to minisequencing. 1 unit of JDF-3 P410L/A485T was incubated in presence of 0.05 µM R6G-ddATP, 0.15 pmol pPC37A, and 0.02 pmol of a 4 kb PCR fragment amplified from human genomic DNA. The PCR product was purified on a StrataPrep column, either with (1) or without (2) CIAP treatment, as described in the Experimental Protocol.

[a]All values have ±<30% error and are obtained from at least two independent experiments.
[b]pBL25C:pBluescript
[c]pBL34A:pBluescript
[d]pBL31G:pBluescript iii. Fidelity:

Fidelity was determined as the tendency of a DNA polymerase to incorporate the correct nucleotide in the presence of increasing amounts of a non-complementary nucleotide. These assays employed constant amounts of primer:template, an unlabeled complementary ddNTP and DNA polymerase, and various concentrations of a rhodamine-labeled non-complementary ddNTP, as described in the Experimental Protocol. The amount of misextended primers is plotted against the ratio of rhodamine-labeled incorrect ddNTP/unlabeled correct ddNTP (FIG. 18 panels A and B). We performed similar assays for all possible mispairs (Table IX).

TABLE IX

All possible mispairs.

| ddG:dT | ddT:dC | ddC:dA | ddA:dG |
|--------|--------|------------|--------|
| ddT:dT | ddC:dC | ddA:dA | ddG:dG |

The two mispairs indicated in bold are formed more efficiently by Taq F667Y DNA polymerase compared to JDF-3 P410L/A485T mutant.

The two mispairs, ddT:dC and ddG:dT, are formed at a significantly higher frequency (3 or 20 fold) by Taq F667Y mutants (ThermoSequenase and AmpliTaq FS) compared to JDF-3 P410L/A485T (FIG. 18 panels A and B). The other mispairs are formed less frequently and at a similar rate for JDF-3 P410L/A485T and Taq F667Y.

Similar rates of ddG:dT mispair formation were obtained using AmpliTaqFS (Taq F667Y mutant; ABI). AmpliTaqFS is only available in a mixture containing dye-ddNTPs and reaction buffer (SNaPshot kit; ABI). In order to test AmpliTaqFS, we removed dye-ddNTPs by adding 0.5 unit of SAP to 5 μl of the SnaPshot kit mix, followed by incubations at 37° C. for 30 minutes and at 72° C. for 15 minutes. The resulting mix, free of dye-ddNTPs, was then used in fidelity assays.

In order to establish that this difference in fidelity is not sequence specific, we performed similar experiments with two other primer:template systems (pBL25C:Temp-T and pPC34A:4 kb PCR amplified fragment) and obtained similar misincorporation rates for both enzymes (data not shown). We also obtained similar misincorporation rates using TAMRA-labeled ddNTPs as the incorrect ddNTP (data not shown). Therefore, the lower fidelity exhibited by Taq F667Y DNA polymerase is neither sequence specific nor due to increased misincorporation of R110 dyes.

To gain more insight into the mechanism of lower fidelity, we determined the misinsertion frequency for the mispair ddG:dT, which was evaluated in terms of relative $K_m$ and $V_{max}$ values for the wrong versus correct dye-ddNTP. Efficiency of nucleotide misinsertion was determined opposite a DNA template dT, primed with a 34-nucleotide oligomer (pBL34A). Apparent Michaelis constant ($K_m$) and maximum velocity ($V_{max}$) and relative insertion frequencies were measured for ddATP and ddGTP (Table X).

TABLE X

Kinetic Parameters[a] of TAMRA-ddATP insertion versus TAMRA-ddGTP misinsertion.

| DNA polymerase | I.E.[b] ($V_{max}/K_m$) | M.E.[b] ($V_{max}/K_m$) | M.F.[b] (M.E./I.E.) |
|---|---|---|---|
| JDF-3 P410L/A485T | 1.9/0.9 = 2.1 | 4.7/700 = 0.0067 | 0.003 |
| ThermoSequenase (Taq F667Y) | 1.9/0.6 = 3.2 | 16.9/100 = 0.169 | 0.053 |

[a]All values have ±<30% error and are obtained from 3 independent experiments.
[b]I.E., M.E. and M.F. are insertion efficiency, misinsertion efficiency and misinsertion frequency, respectively.

As shown in Table X, the misinsertion frequency of Taq F667Y for ddG:dT is significantly (~17 fold) higher than that exhibited by JDF-3 P410L/A485T. This difference is mostly due to differences in $K_m$ for the wrong dye-ddNTP•primer:template ternary complex. The Taq F667Y mutant exhibits a 7-fold lower $K_m$ (higher binding affinity) for wrong nucleotide (ddGTP) opposite dT, compared to the JDF-3 P410L/A485T mutant.

iv. Development of a Minisequencing Kit:

There are five major steps involved in SNP detection by minisequencing and gel electrophoresis: (i) extraction of DNA from blood or tissue samples; (ii) PCR amplification of specific fragments of genomic DNA containing SNPs; (iii) treatment of PCR products prior to minisequencing to remove unreacted PCR primers and dNTPs; (iv) minisequencing of PCR products and purification of extended primers; (v) analysis of fluorescent labeled primers using gel electrophoresis and GeneScan software (ABI). Here, we have optimized steps (iii) and (iv), and developed a minisequencing kit containing enzyme, reaction buffer, rhodamine labeled-ddNTPs, and a control primer:template system.

To optimize step iii, we used three different approaches to purify PCR products from unreacted PCR primers and dNTPs prior to minisequencing as described in the Experimental Protocol. We found that DNA templates purified using StrataPrep columns without CIAP treatment were contaminated with enough residual dNTPs to interfere with subsequent minisequencing. In the presence of trace amounts of contaminating dNTPs, sequencing ladders were produced instead of a single extended primer (FIG. 18, lane 2). The same problem was also observed using Qiagen's QIAquick PCR purification columns (data not shown). However, adding CIAP directly to PCR products, bound to StrataPrep columns, effectively removed residual dNTPs, and the eluted DNA after heat treatment (15 minutes at 72° C.) was suitable for minisequencing applications (FIG. 18, lane 1).

Figure 19:
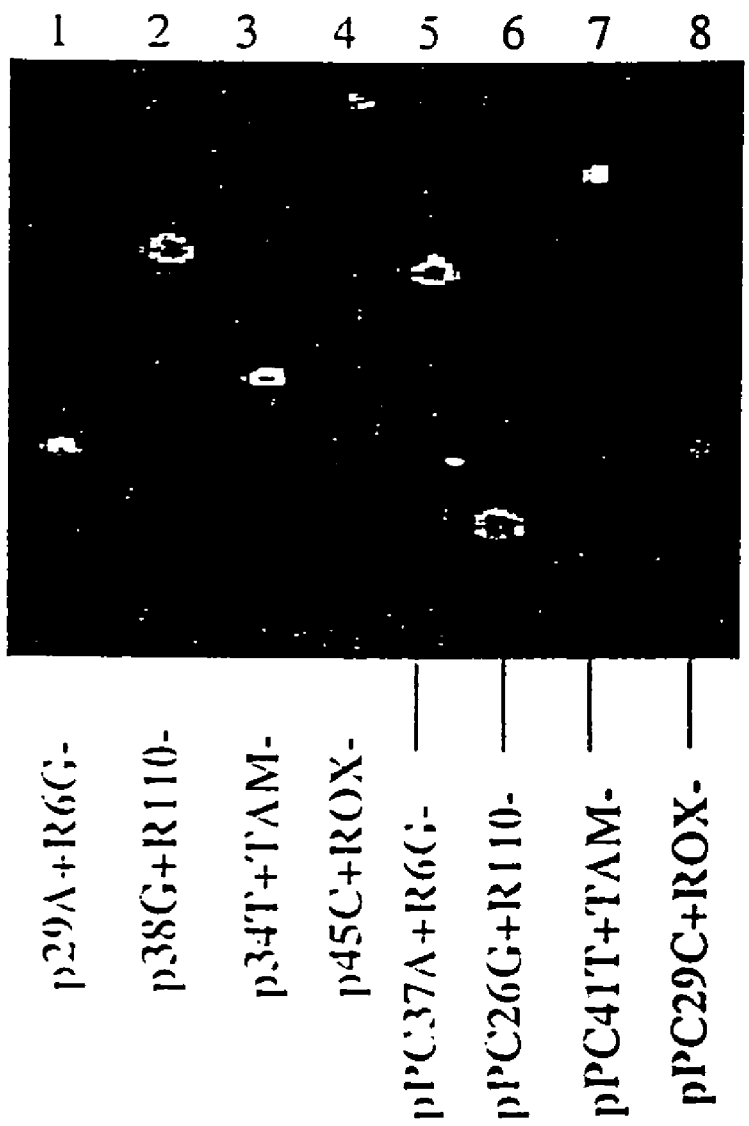
FIG. 19. Minisequencing using JDF-3 P410L/A485T and two different primer:template systems. All reactions contained 1 unit of JDF-3 P410L/A485T, 0.04 µM R6G-ddA, R110-ddG, ROX-ddC, and 0.2 µM TAM-ddU in 1× reaction buffer. Reactions 1 through 4 also contained 0.4 pmol pGEM and 1 µl of p29A, p38G, p34T, and p45C (ABI #4312166), respectively. Reactions 5 through 8 contained 0.02 pmol of 4 kb PCR product and 0.15 pmol pPC37A, pPC26G, pPC41T, and pPC29C, respectively. Reactions were incubated as described in the Experimental Protocol.

Three different primer:template systems were used to optimize the JDF-3 P410L/A485T minisequencing kit, including pBluescript with primers pBL34A, pBL31G, pBL28T, and pBL25C (Table VII) which will be used as the kit controls (FIG. 22); a 4 kb PCR fragment with primers pPC37A, pPC41T, pPC26G, and pPC29C; and pGEM with four control primers (ABI #4312166) (FIG. 19). Our kit protocol employs four rhodamine-labeled ddNTPs in one reaction (see Experimental Protocol section), although it could be adapted in the future for customers interested in performing four separate reactions, each with a different rhodamine labeled-ddNTP (plus three unlabeled ddNTPs).

The concentrations of JDF-3 P410L/A485T, dye-ddNTPs, primer, and template were optimized for minisequencing and fluorescence detection by ABI 377 sequencer (see Experimental protocol for optimized conditions). Higher concentrations of enzyme, dye-ddNTPs, and primer:template will increase the fluorescent signal. However, such increases in signal saturate the ABI 377 detector and result in dye bleedthrough (more than one color showing in one spot).

Figure 20:
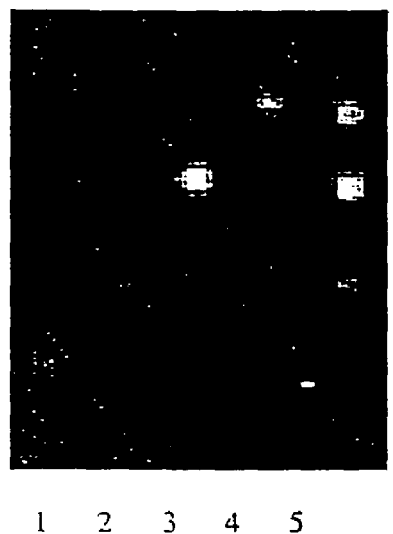
FIG. 20. Multiplexing does not affect the signal strength generated by JDF-3 P410L/A485T. All reactions contained 1 unit of JDF-3 P410L/A485T, 0.25 pmol pBluescript, 0.04 µM R6G-ddA, TAM-ddG, ROX-ddC, and 0.2 µM R110-ddU in 1× reaction buffer. Reactions 1, 2, 3, 4, contained 0.15 pmol pBL25C, pBL28T, pBL31G, and pBL34A, respectively. Reaction 5 contained 0.15 pmol of all four primers. Reactions were incubated as described in the Experimental Protocol.

Different rhodamine dye/ddNTP combinations can be used with JDF-3 P410L/A485T (FIG. 20; TAM-ddG and R110-ddU instead of R110-ddG and TAM-ddUTP). However, the dye/base combination proposed in the Experimental Protocol (R6G-ddATP, R110-ddGTP, ROX-ddCTP, and TAMRA-ddUTP) exihibited the greatest signal uniformity with three different sets of primer:templates. Since JDF-3 P410L/A485T slightly discriminates against incorporation of ddUTP (FIG. 16 panels A and B), ddUTP is used at 5 times the concentration of other ddNTPs. Moreover, preliminary data shows that JDF-3 P410L/A485T can incorporate dyes other than rhodamine (e.g., cyanine dyes). It is imperative to point out that primer:template sequence could also affect the efficiency of dye-ddNTP incorporation and therefore the signal uniformity.

β-testing of JDF-3 P410L/A485T at Stanford genome technology center was performed using Cy3-ddATP and Cy5-ddCTP, and immobolized primers on Zyomyx aldehyde slides.

The following protocol (Applied Biosystems) should be used in designing primers for minisequencing: (1) Since SNP validation by minisequencing is not flexible with respect to the location of the primer, the negative strand (−) of DNA can be used for primer design if positive strand (+) is difficult to assay; (2) Design primers of 18 nucleotides in length or greater with melting temperatures of 45° C. or greater; (3) Check primers for extendable hairpin structures and primer dimer formation; (4) Primers should be PAGE purified; (5) A negative control (lacking DNA template) should be run when evaluating a new primer.

We also tested whether JDF-3 P410L/A485 could be used for multiplexing (several primers with one template in a single reaction) without the signal strength being affected. FIG. 20 indicates that the signal strength remained unaltered when four primers were used to detect four SNPs in the same template DNA. It should be pointed out that we did not optimize the kit for multiplexing, but this application may be further developed in future generations of the kit.

We then determined the amount of SAP or CIAP that can be used to purify minisequencing products from unincorporated rhodamine labeled-ddNTPs. 0.5 unit of SAP or I unit of CIAP in 10 µl minisequencing reactions degrades all unincorporated dye-ddNTPs. Using suboptimal units of alkaline phosphatase could result in fluorescent signal from unincorporated dye-ddNTPs, thereby masking the SNP signal.

Figure 21:
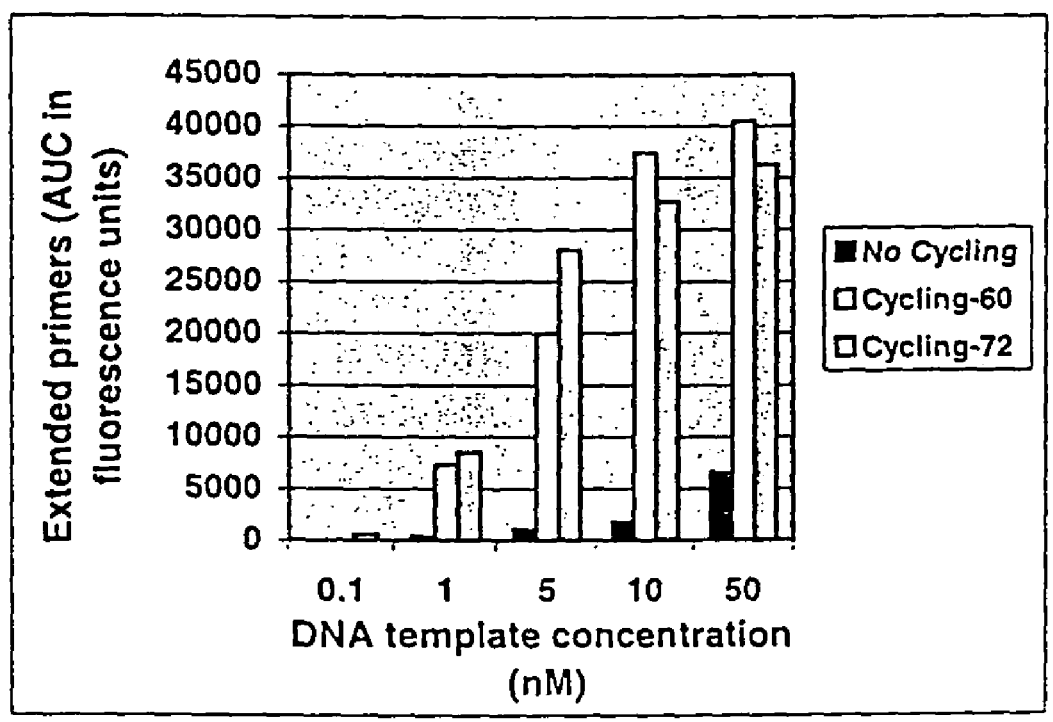
FIG. 21. Thermal cycling improves minisequencing signal significantly. 1 unit of JDF-3 P410L/A485T was incubated in presence of 15 nM pBL25C, 100 nM ROX-ddCTP, and 0.1, 1, 5, 10, or 50 nM pBluescript in five separate reactions. Incubations were performed using a Perkin-Elmer 9600 for one cycle of 96° C. for 2 min, 50° C. for 1 min, and 60° C. for 10 min, or 25 cycles of 96° C. for 10s, 50° C. for 5s, and 60° C. or 72° C. for 30 s. Reactions were purified from unincorporated ROX-ddCTP using SAP treatment and the products were analyzed and quantitated as described in the Experimental Protocol.

In optimizing the kit cycling conditions, we evaluated whether thermal cycling improved product yield. As FIG. 21 indicates, cycling with extension temperatures of 60° C. or 72° C. did not significantly alter enzyme activity. However, thermal cycling did improve the minisequencing signal compared to a single incubation at 60° C. for 10 minutes. The improved signal is expected when the concentration of DNA template is much lower than minisequencing primer. However, as FIG. 21 indicates, even when the minisequencing primer is saturated with DNA template, thermal cycling seems to improve signal, presumably because the minisequencing primer competes with the complementary strand of double-stranded DNA when annealing to the DNA template.

Figure 22A:
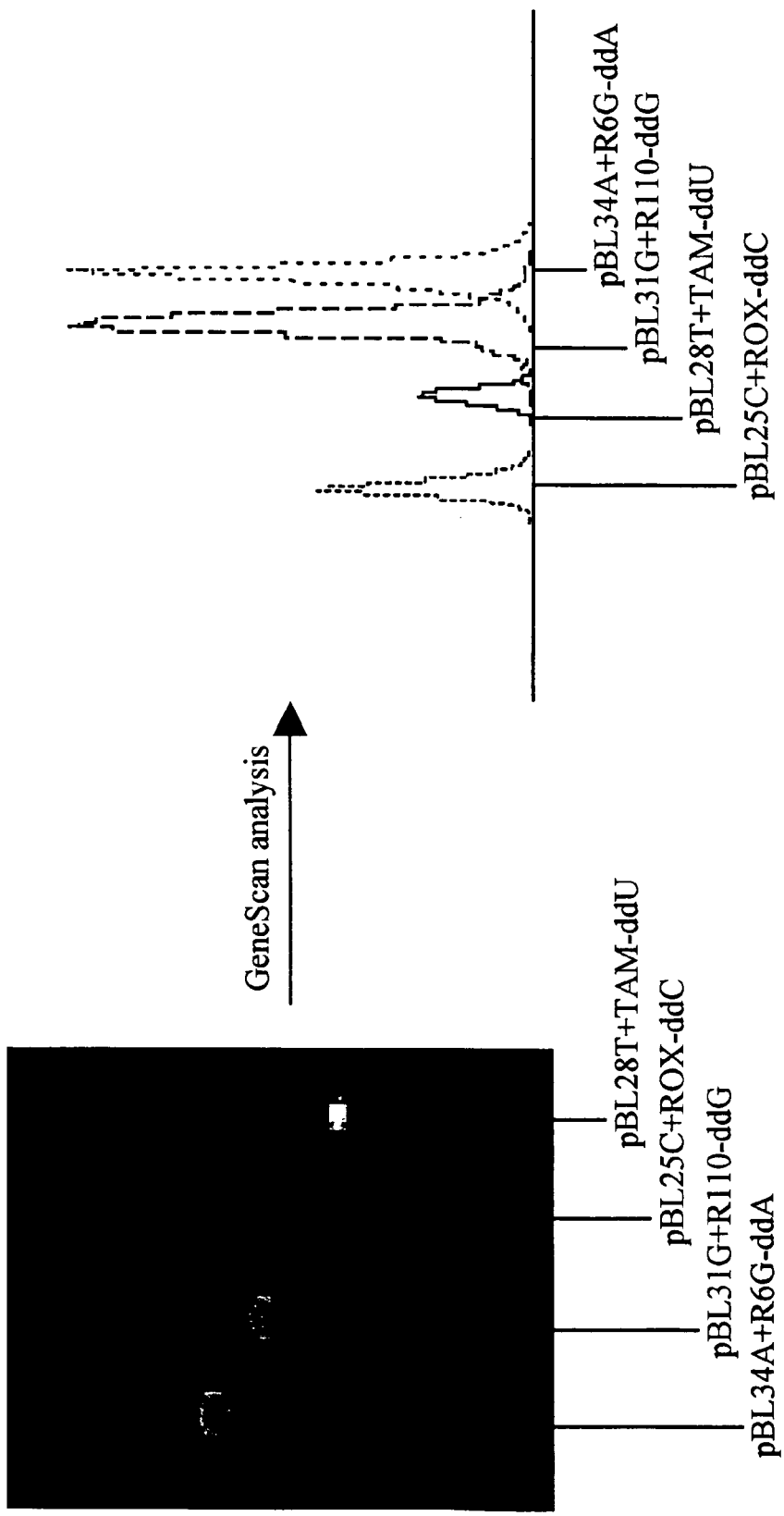
FIG. 22. Performance comparison of our minisequencing kit containing JDF-3 P410L/A485T to the SNaPshot kit from Applied Biosystems. (A) Minisequencing reactions contained 1 unit of JDF-3 P410L/A485T, 0.25 pmol pBluescript, 0.04 µM R6G-ddA, R110-ddG, and ROX-ddC, 0.2 µM TAMRA-ddU, and 0.15 pmol pBL34A, pBL31G, pBL25C, or pBL28T, in four separate reactions respectively. Reactions were incubated, purified and analyzed (using a rhodamine matrix) as described in the Experimental Protocol. (B) The SNaPshot kit was used with the same amount of primer: template as above. Since this kit utilizes dichloro-rhodamine labeled ddNTPs, a dichloro-rhodamine matrix was installed for analysis of the corresponding bands.
Figure 22B:
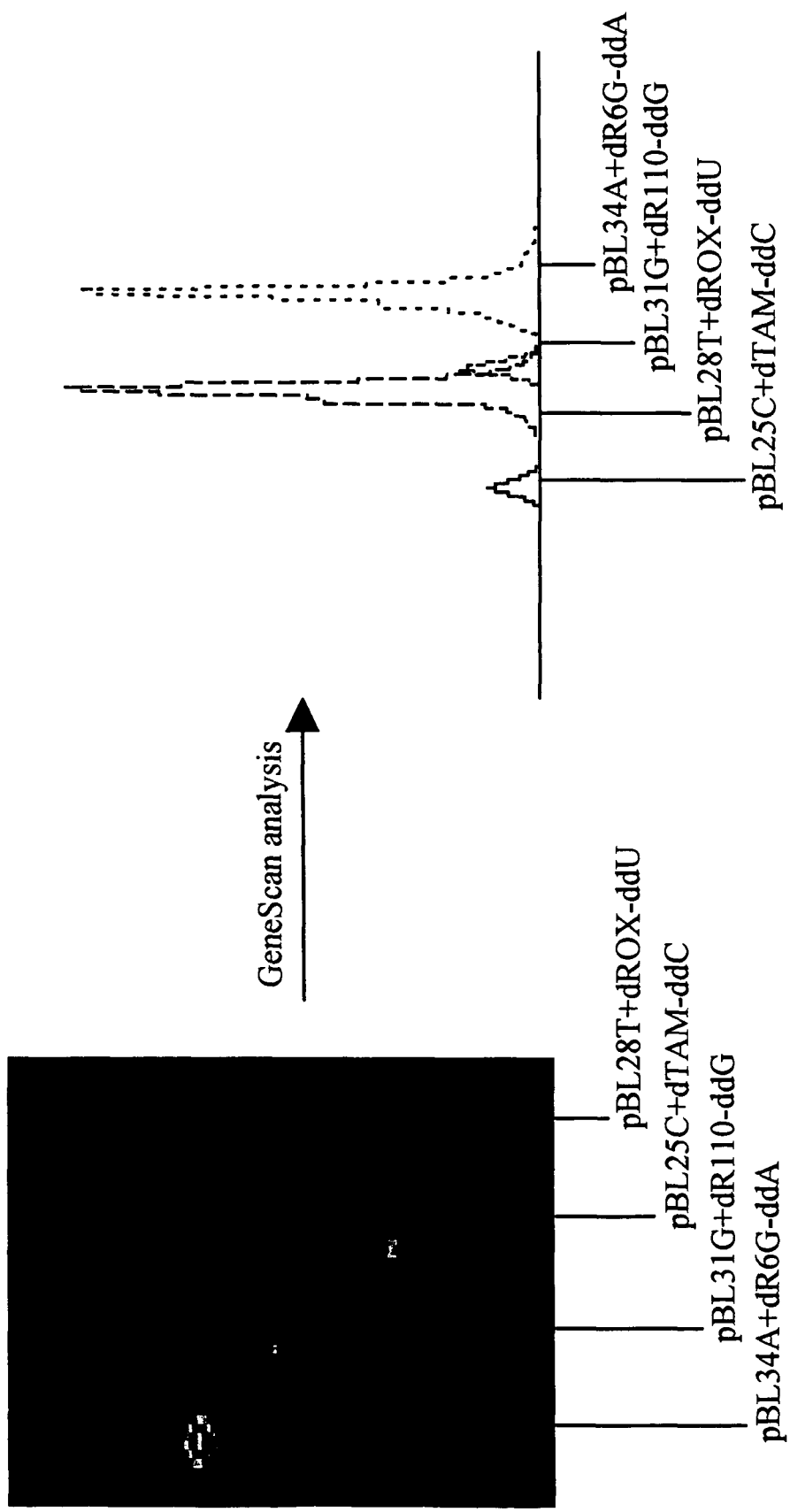

FIG. 22 shows the performance of our minisequencing kit compared to ABI's SNaPshot kit. Since our minisequencing kit employs rhodamine-labeled ddNTPs, a rhodamine dye matrix had to be installed on the ABI 377 sequencer to analyze product bands. In contrast, the SNaPshot kit utilizes dichloro-rhodamine labeled-ddNTPs and a dichloro-rhodamine matrix was installed to analyze the products generated with the SNaPshot kit. As discussed above, our kit employs ROX-ddC and TAMRA-ddU instead of TAMRA-ddC and ROX-ddU (SNaPshot dye-ddNTPs) to improve ddU incorporation by JDF-3 P410L/A485T. ABI does not disclose the concentrations of AmpliTaq FS or dichloro-rhodamine labeled ddNTPs employed in the SNaPshot reaction mixture, so comparisons were simply carried out using the same primer:template amounts and each kit's recommended protocol. As shown in FIG. 22, our kit produces more uniform signals compared to the SnaPshot kit, which generated relatively low signals for ddC and ddG compared to ddA and ddU.

REFERENCES

1. Joyce, C. M., Kelley, W. S. and Grindley N. D. F. (1982) J. Biol. Chem. 257, 1958-1964.
2. Lopes, P. Martinez, S., Diaz, A. Espinosa, M. And Lacks, S. A. (1989) J. Biol. Chem. 264, 4255-4263.
3. Lawyer, F. C., Stoffel, S., Saiki, R. K., Myambo, K. Drummond, R. and Gelfand, D. H. (1989) J. Biol. Chem. 264, 6427-6437.
4. Akhmetzjanov, A. A. and Vakhitov, V. A. (1992) Nucl. Acids Res. 20, 5839.
5. Leavitt, M. C. and Ito, J. (1989) Proc. Acad. Sci. U.S.A. 86, 4465-4469.
6. Dunn, J. J. and Studier, F. W. (1983) J. Mol. Biol. 166, 477-535.
7. Scarlato, V. And Gargano, S. (1992) Gene 118, 109-113.
8. Ràdén, B. And Rutberg, L. (1984) J. Virol. 52, 9-15.
9. Foury, F. (1989) J. Biol. Chem. 264, 20552-20560.
10. Ito, J. And Braithwaite, D. K. (1990) Nucl. Acids Res. 18, 6716.
11. Blanco, L. Bernard, A. And Salas, M. (1991) Nucl. Acids res. 19, 955.
12. Hahn, S. And Rüger, W, (1989) Nucl. Acids Res. 17, 6729.
13. Hollingsworth, H. C. and Nossal, N. G. (1991) J. Biol. Chem. 266, 1888-1897.
14. Kaliman, A. V., Krutilina, A. I., Kryukov, V, M. and Bayev, A. A. (1986) FEBS Lett. 195, 61-64.
15. Iwasaki, H. Ishino, Y., Toh, H. Nakata, A. and Shinagawa, H. (1991) Mol. Gen Genet. 226, 24-33.
16. Jung, G., Leavitt, M. C., Hsieh, J.-C. and Ito, J. (1987) Proc. Natl. Acad. Sci. U.S.A. 84, 8287-8291.
17. Savilahti, H. And Bamford D. H. (1987) Gene 57, 121-130.
18. Yoshikawa, H. And Ito, J. (1982) Gene 17, 323-335.
19. Matsumoto, K., Takano, H., Kim, C. I. and Hirokawa, H. (1989) Gene 84, 247-255.
20. Spicer, E. K., Rush, J. Fung, C., Reha-Krantz, L. J., Karam, J. D. and Konigsberg, W. H. (1988) J. Biol. Chem. 263, 7478-7486.
21. Perler, F. B., Comb, D. G., Jack, W. E., Moran, L. S., Qiang, B., Kucera, R. B., Benner, J., Slatko, B. E., Nwankwo, D. O., Hempstead, S. K., Carlow, C. K. S. and Jannasch, H. (1992) Proc. Natl. Acad. Sci. USA 89, 5577-5581.
22. Mathur, E. J., Adams, M. W., Callen, W. N. and Cline, J. M. (1991) Nucleic. Acids Res. 19, 6952.
23. Pisani, F. W., De Martino, C. and Rossi, M. (1992) Nucl. Acids Res. 20, 2711-2716.
24. Wong S., W. Wahl, A. F., Yuan, P.-M., Arai, N., Pearson, B. E., Arai, K, -i., Korn, D., Hunkapiller, M. W. and Wang, T. S.-F. (1988) EMBO J. 7, 37-47.
25. Pizzagalli, A., Valsasnini, P., Plevani, P. and Lucchini, G. (1988) Porc. Natl. Acad. Sci. U.S.A. 85, 3772-3776.
26. Damagnez, V., Tillit, J., deRecondo, A.-M. and Baldacci, G. (1991) Mol. Gen. Genet. 226, 182-189.
27. Hirose, F., Yamaguchi, M. Nishida, Y., Masutani, M., Miyazawa, H., Hanaoka, F. and Matsukage, A. (1991) Nucl. Acids Res. 19, 4991-4998.
28. Leegwater, P. A. J., Strating, M., Murphy, N. B., Kooy, R. F., van der Vliet, P. C. and Overdulve, J. P. (1991) Nucl. Acids Res. 19, 6441-6447.
29. Chung, D. W., Zhang, J., Tan C.-K., Davie, E. W., So, A. G. and Downey, K. M. (1991) Proc. Natl. Acad. Sci. USA 88, 11197-11201.
30. Yang, C.-L., Chang, L. S., Zhang, P., Hao, H., Zhu, L., Tommey, N. L. and Lee, M. Y. W. T. (1992) Nucl. Acids Res. 20, 735-745.
31. Zhang, J. Chung, D. W., Tan, C.-K., Downey, K. M., Davie, E. W. and So, A. G. (1991) Biochemistry 30, 11742-11750.
32. Morrison, A. and Sugino, A. (1992) Nucl. Acids Res. 20, 375.
33. Pignéde, G., Bouvier, D., deRecondo, A.-M. And Baldacci, G. (1991) J. Mol. Biol. 222, 209-218.

34. Ridley, R. G., White, J. H., McAleese, S. M., Gorman, M., Alano, P., deVies, E. and Kilbey, B. J. (1991) Nucl Acids Res. 19, 6731-6736.
35. Morrison, A., Araki, H., Clark, A. B., Hamatake, R. K. and Sugino, A. (1990) Cell 62, 1143-1151.
36. Morrison, A., Christensen, R. B., Alley, J., Beck, A. K., Bernstine, E. G., Lemontt, J. F. and Lawrence, C. W. (1989) J. Bacteriol. 171, 5659-5667.
37. Gibbs, J. S., Chiou, H. C., Hall, J. D., Mount, D. W., Retondo, M. J., Weller, S. K. and Coen, D. M. (1985) Proc. Natl. Acad. Sci. U.S.A. 82, 7969-7973.
38. Telford, E. A., Watson, M. S., McBride, K. and Davison, A. J. (1992) Virology 189, 304-316.
39. Davison, A. J. and Scott, J. E. (1986) J. Gen. Virol. 67, 1759-1816.
40. Baer, R., Bankier, A. T. Biggin, M. D., Deininger, P. L., Farrell, P. J., Gibson, T. J., Hatfull, G., Hudson, G. S., Satchwell, S. C., Séguin, C., Tuffnell, P. S. and Barrell, B. G. (1984) Nature 310, 207-211.
41. Albrecht, J.-C. and Fleckenstein, B. (1990) Virology 174, 533-542.
42. Kouzarides, T. Bankier, A. T., Satchwell, S. C., Weston, K., Tomlinson, P. and Barrell, B. G. (1987) J. Virol, 61, 125-133.
43. Elliott, R., Clark, C. Jaquish, D. and Spector, D. H. (1991) Virology n185, 169-186.
44. Teo, I. A., Griffin, B. E. and Jones, M. D. (1991) J. Virol. 65, 4670-4680.
45. Davison, A. J. (1992) Virology 186, 9-14.
46. Grabherr, R., Strasser, P. and Van Etten, J. L. (1992) Virology 188, 721-731.
47. Binns, M. M., Stenzler, L. Tomley, F. M., Campbell, J. and Broursnell, M. E. G. (1987) Nucl. Acids Res. 15, 6563-6573.
48. Earl P. L., Jones, E. V. and Moss, B. (1986) Prov. Natl. Acad. Sci. U.S.A. 83, 3659-3663.
49. Mustafa, A. And Yuen, L. (1991) DNA Seq. 2, 39-45.
50. Tomalski, M. D., Wu, J. and Miller, L. K. (1988) Virology 167, 591-600.
51. Bjornson, R. M. and Rohrmann, G. F. (1992) J. Gen. Virol 73, 1499-1504.
52. Gingeras, T. R., Sciaky, D., Gelinas, R. E., Bing-Dong, J., Yen, C. E., Kelly, M. M., Bullock, P. A. Parsons, B. L., O'Neill. K. E. and Roberts, R. J. (1982) J. Biol. Chem, 257, 13475-13491.
53. Engler, J. A., Hoppe, M. S. and van Bree, M. P. (1983) Gene 21, 145-159.
54. Shu, L., Hing, J. S., Wei, Y.-f. and Engler, J. A., (1986) Gene 46, 187-195.
55. Paillard, M., Sederoff, R. R. and Levings, C. S. III (1985) EMBRO J. 4, 1125-1128.
56. Chan, B. S.-S., Court, D. A., Vierula, P. J. and Bertrand, H. (1991) Curr. Genet. 20, 225-237.
57. Kempken, F., Meinhardt, F. and Esser, K. (1989) Mol. Gen. Genet, 218, 623-530.
58. Oester, B. And Tudzynski, P. (1989) Mol. Gen. Genet. 217, 132-140.
59. Court D. A. and Bertrand, H. (1992) Curr. Genet. 22, 385-397.
60. Robison, M. M., Royer, J. C. and Horgen, P. A. (1991) Curr. Genet. 19, 495-502.
61. Stark, M. J. R., Mileham, A. J., Romanos, M. A. and Boyd, A. (1994) Nucl. Acids Res. 12, 6011-6030.
62. Tommasino, M. Ricci, S. and Galeotti, C. L. (1988) Nucl. Acids Res. 16, 5863-5878.
63. Hishinuma, F. and Hirai, K. (1991) J. Gen. Genet. 226, 97-106.
64. Hopfner, K. P. et al. (1999) Proc. Natl. Acad. Sci. U.S.A. 96, 3600-3605.
65. Niehaus, F. et al. (1997) Gene 204, 153-158.
66. Tagaki et al. (1997) Appl. Environ. Microbiol. 63, 4504-4510.
67. Datukishvili, N. et al. (1996) Gene 177, 271-273.
68. Southworth, M. W. et al. (1996) Proc. Natl. Acad. Sci. U.S.A. 93, 5281-5285.
69. Uemori, T. et al. (1995) J. Bacteriol. 177, 2164-2177.
70. Konisky, J. et al. (1994) J. Bacteriol. 176, 6402-6403.
71. Zhao (1999) Structure Fold Des. 7, 1189.
72. Lai, E., Riley, J., Purvis, I. & Roses, A. A 4-Mb high-density single nucleotide polymorphism-based map around human APOE. Genomics 54, 31-8. (1998).
73. Saiki, R. K., Walsh, P. S., Levenson, C. H. & Erlich, H. A. Genetic analysis of amplified DNA with immobilized sequence-specific oligonucleotide probes. Proc Natl Acad Sci USA 86, 6230-4. (1989).
74. Landegren, U., Kaiser, R., Caskey, C. T. & Hood, L. DNA diagnostics—molecular techniques and automation. Science 242, 229-37. (1988).
75. Shi, M. M. Enabling large-scale pharmacogenetic studies by high-throughput mutation detection and genotyping technologies. Clin Chem 47, 164-72. (2001).
76. Livak, K. J., Marmaro, J. & Todd, J. A. Towards fully automated genome-wide polymorphism screening. Nat Genet 9, 341-2. (1995).
77. Tyagi, S., Bratu, D. P. & Kramer, F. R. Multicolor molecular beacons for allele discrimination. Nat Biotechnol 16, 49-53. (1998).
78. Gilles, P. N., Wu, D. J., Foster, C. B., Dillon, P. J. & Chanock, S. J. Single nucleotide polymorphic discrimination by an electronic dot blot assay on semiconductor microchips. Nat Biotechnol 17, 365-70. (1999).
79. Fu, D. J. et al. Sequencing exons 5 to 8 of the p53 gene by MALDI-TOF mass spectrometry. Nat Biotechnol 16, 381-4. (1998).
80. Chen, X. & Kwok, P. Y. Template-directed dye-terminator incorporation (TDI) assay: a homogeneous DNA diagnostic method based on fluorescence resonance energy transfer. Nucleic Acids Res 25, 347-53. (1997).
81. Syvanen, A. C., Aalto-Setala, K., Harju, L., Kontula, K. & Soderlund, H. A primer-guided nucleotide incorporation assay in the genotyping of apolipoprotein E. Genomics 8, 684-92. (1990).
82. Taylor, J. D. et al. Flow cytometric platform for high-throughput single nucleotide polymorphism analysis. Biotechniques 30, 661-6, 668-9. (2001).
83. Chen, X., Zehnbauer, B., Gnirke, A. & Kwok, P. Y. Fluorescence energy transfer detection as a homogeneous DNA diagnostic method. Proc Natl Acad Sci USA 94, 10756-61. (1997).
84. Tabor, S. & Richardson, C. C. A single residue in DNA polymerases of the *Escherichia coli* DNA polymerase I family is critical for distinguishing between deoxy- and dideoxyribonucleotides. Proc Natl Acad Sci USA 92, 6339-43. (1995).
85. Gardner, A. F. & Jack, W. E. Determinants of nucleotide sugar recognition in an archaeon DNA polymerase. Nucleic Acids Res 27, 2545-53. (1999).
86. Evans, S. J. et al. Improving dideoxynucleotide-triphosphate utilisation by the hyper-thermophilic DNA polymerase from the archaeon *Pyrococcus furiosus*. Nucleic Acids Res 28, 1059-66. (2000).

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A composition for identifying a nucleotide at a given position of a template DNA molecule, said composition comprising:
   a Family B DNA polymerase deficient in 3' to 5' exonuclease activity comprising the amino acid sequence of one of SEQ ID NOs: 2 and 62-78, except
   a first mutation at amino acid D or E or both in the exo I (DXE) motif within said SEQ ID NO, and
   a second mutation at an amino acid selected from the group consisting of: amino acid L, P, and both L and P in Region II (DXXSLYPSII, SEQ ID NO:7) within said SEQ ID NO, wherein said second mutation confers a reduction in discrimination.

2. The composition of claim 1, wherein said mutations are selected from the group consisting of: D141A or D141T, E143A, L408H or L408F, and P410L.

3. The composition of claim 2, wherein said mutations are D141A, E143A, and P410L.

4. The composition of claim 1, further comprising a first primer.

5. The composition of claim 4, further comprising at least one chain-terminating nucleotide analog, wherein said chain-terminating nucleotide analog is incorporated into said first primer by said Family B DNA polymerase in a template-dependent manner.

6. The composition of claim 5, wherein at least one chain-terminating nucleotide analog is labeled with a first detectable label.

7. The composition of claim 5, wherein more than one chain-terminating nucleotide analog is labeled, each chain-terminating nucleotide analog being labeled with a different first delectable label.

8. The composition of claim 5, wherein said chain-terminating nucleotide analog is a dideoxynucleotide.

9. The composition of claim 8, wherein said dideoxynucleotide is selected from the group consisting of: ddATP, ddTTP, ddCTP and ddGTP.

10. The composition of claim 6, wherein said first primer is labeled with a second detectable label.

11. The composition of claim 10, wherein first and second detectable labels generate a signal for identifying said nucleotide at the given position of the template DNA molecule.

12. The composition of claim 4, further comprising a second primer, wherein said first primer is labeled with a first detectable label and said second primer is labeled with a second detectable label, said first and second detectable labels generate a signal for identifying said nucleotide at the given position of the template DNA molecule.

13. The composition of claim 12, wherein said second primer anneals to the immediate 5' of said nucleotide at the given position of said template DNA molecule.

14. The composition of claim 13, further comprising a DNA ligase.

15. The composition of claim 1, further comprising a reaction buffer for said Family B DNA polymerase.

16. The composition of claim 1, wherein said template DNA molecule is the product of a polymerase chain reaction or a plasmid DNA.

17. The composition of claim 6, 10, or 12, wherein said first or second detectable label is one selected from the group consisting of: a fluorescent label, an isotope, a chemiluminescent label, a quantum dot label, an antigen, or an affinity moiety.

18. The composition of claim 17, wherein said first detectable label is a rhodamine label or a cyanine label.

19. A kit for identifying a nucleotide at a given position of a template DNA molecule, said kit comprising:
   a Family B DNA polymerase deficient in 3' to 5' exonuclease activity comprising the amino acid sequence of one of SEQ ID NOs: 2 and 62-78, except
   a first mutation at amino acid D or E or both in the exo I (DXE) motif within said SEQ ID NO, and
   a second mutation at an amino acid selected from the group consisting of: amino acid L, P, and both L and P in Region II (DXXSLYPSII, SEQ ID NO:7) within said SEQ ID NO wherein said second mutation confers a reduction in discrimination.

20. The kit of claim 19, wherein said mutations are selected from the group consisting of: D141A or D141T, E143A, L408H or L408F, and P410L.

21. The kit of claim 20, wherein said mutations are D141A, E143A, and P410L.

22. The kit of claim 19, wherein said Family B DNA polymerase has reduced discrimination against a non-conventional nucleotide selected from the group consisting of: dideoxynucleotides, ribonucleotides and conjugated nucleotides.

23. The kit of claim 19, further comprising at least one chain-terminating nucleotide analog, wherein said chain-terminating analog is incorporated into said first primer by said DNA polymerase in a template-dependent manner.

24. The kit of claim 23, wherein said at least one chain-terminating nucleotide analog is labeled with a first detectable label.

25. The kit of claim 23, wherein more than one chain-terminating nucleotide analog is labeled, each chain-terminating nucleotide analog being labeled with a different first detectable label.

26. The kit of claim 23, wherein said chain-terminating nucleotide analog is a dideoxynucleotide.

27. The kit of claim 26, wherein said dideoxynucleotide is selected from the group consisting of: ddATP, ddTTP, ddCTP and ddGTP.

28. The kit of claim 24, further comprising a first primer, wherein said first primer is labeled with a second detectable label.

29. The kit of claim 28, wherein first and second detectable labels generate a signal for identifying said nucleotide at the given position of the template DNA molecule.

30. The kit of claim 19, further comprising a first and a second primer.

31. The kit of claim 30, wherein said first primer is labeled with a first detectable label and said second primer is labeled with a second detectable label, said first and second detectable labels generate a signal for identifying said nucleotide at the given position of the template DNA molecule.

32. The kit of claim 31, wherein said second primer anneals to the immediate 5' of said nucleotide at the given position of said template DNA molecule.

33. The kit of claim 32, further comprising a DNA ligase.

34. The kit of claim 19, further comprising a reaction buffer for said Family B DNA polymerase.

35. The kit of claim 19, wherein said template DNA molecule is the product of a polymerase chain reaction or a plasmid DNA.

36. The kit of claim 28, or 31, wherein said first or second detectable label is one selected from the group consisting of: a fluorescent label, an isotope, a chemiluminescent label, a quantum dot label, an antigen, and an affinity moiety.

37. The kit of claim 36, wherein said first detectable label is a rhodamine label or a cyanine label.

38. The kit of claim 19, 23 or 34, further comprising a control template and/or at least one control primer.

39. The kit of claim 38, comprising a control template and four control primers.

40. A method for identifying a nucleotide at a given position of a template DNA molecule in a sample, said method comprising:
contacting a first primer with said template DNA molecule, wherein said contacting allows said first primer to anneal to the immediate 3' of said nucleotide at the given position of said template DNA molecule, so as to form a duplex between said first primer and said template DNA molecule;
incubating said duplex in the presence of at least one chain-terminating nucleotide analog and a Family B DNA polymerase deficient in 3' to 5' exonuclease activity, said Family B DNA polymerase comprising the amino acid sequence of one of SEQ ID NOs: 2 and 62-78, except a first mutation at amino acid D or E or both in the exo I (DXE) motif within said SEQ ID NO, and
a second mutation at an amino acid selected from the group consisting of: amino acid L, P, and both L and P in Region II (DXXSLYPSII, SEQ ID NO:7) within said SEQ ID NO, wherein said second mutation confers a reduction in discrimination,
wherein said at least one chain-terminating nucleotide analog is labeled with a first detectable label,
wherein said incubating allows the incorporation of a labeled chain-terminating nucleotide analog into said first primer by said DNA polymerase in a template-dependent manner; and
determining the presence or identity of said duplex by a signal generated from said first detectable label as a result of said incubating.

41. The method of claim 40, wherein said mutations are selected from the group consisting of: D141A or D141T, E143A, L408H or L408F, and P410L.

42. The method of claim 41, wherein said one or more amino acid mutations are D141A, E143A, and P410L.

43. The method of claim 40, wherein more than one chain-terminating nucleotide analog is labeled, each chain-terminating nucleotide analog being labeled with a different first detectable label.

44. The method of claim 40, wherein said chain-terminating nucleotide analog is a dideoxynucleotide.

45. The method of claim 44, wherein said dideoxynucleotide is selected from the group consisting of: ddATP, ddTTP, ddCTP and ddGTP.

46. The method of claim 40, wherein said first primer is labeled with a second detectable label.

47. The method of claim 46, wherein the first and second detectable labels generate a signal for identifying said nucleotide at the given position of the template DNA molecule.

48. The method of claim 40, wherein said template DNA molecule is the product of a polymerase chain reaction or a plasmid.

49. The method of claim 48, further comprising removing PCR primers and dNTPs from the PCR product before said contacting a first primer with said template DNA molecule.

50. The method of claim 46, wherein said first or second detectable label is one selected from the group consisting of: a radiolabel, a fluorescent label, a chemiluminescent label, a colorimetric label and an enzymatic label.

51. The method of claim 50, wherein said first detectable label is a rhodamine label or a cyanine label.

52. A DNA polymerase comprising the sequence of SEQ ID NO: 2 except an amino acid mutation at P410 and A485.

53. The DNA polymerase of claim 52, wherein said mutation at position P410 is a P410L mutation.

54. The DNA polymerase of claim 52, wherein said mutation at position A485 is an A485T mutation.

55. The DNA polymerase of claim 52, wherein said mutation at position P410 is a P410L mutation and said mutation at position A485 is a A485T mutation.

56. A DNA polymerase comprising the sequence of SEQ ID NO:2 except amino acid mutations at 1) P410 and A485; and 2) D141, E143, or both.

57. The DNA polymerase of claim 56, wherein the amino acid mutation at D141 is a D141A mutation and the mutation at E143 is a E143A mutation.

58. A composition comprising a DNA polymerase comprising the sequence of SEQ ID NO:2 except mutations at P410 and A485.

59. The composition of claim 58, wherein said mutation at position P410 is a P410L mutation.

60. The composition of claim 58, wherein said mutation at position A485 is an A485T mutation.

61. The composition of claim 58, wherein said mutation at position P410 is a P410L mutation and said mutation at position A485 is an A485T mutation.

62. A DNA polymerase comprising the sequence of SEQ ID NO:2 except a P410L mutation, an A485T mutation, a D141A mutation, and a E143 mutation.

63. The composition of claim 58, further comprising a first primer and at least one chain-terminating nucleotide analog.

64. The composition of claim 63, further comprising two, three, or four chain-terminating nucleotide analogs.

65. The composition of claim 64, wherein at least one said chain-terminating nucleotide analog is labeled with a first detectable label.

66. The composition of claim 65, wherein said first primer is labeled with a second detectable label.

67. The composition of claim 66, wherein said first or second detectable label is one selected from the group consisting of: a fluorescent label, an isotope, a chemiluminescent label, a quantum dot label, an antigen, and an affinity moiety.

68. The composition of claim 67, wherein said detectable label is a rhodamine label or a cyanine label.

69. A kit comprising
a DNA polymerase comprising the sequence of SEQ ID NO:2 except mutations at positions P410 and A485 and optionally at D141 and E143, and
packaging material therefor.

70. The kit of claim 69, wherein said mutation at position P410 is a P410L mutation.

71. The kit of claim 69, wherein said mutation at position A485 is an A485T mutation.

72. The kit of claim 69, wherein said mutation at position P410 is a P410L mutation and said mutation at position A485 is an A485T mutation.

73. The kit of claim 69, wherein said mutations are P410L, A485T, D141A, and E143A.

74. The kit of claim 73, further comprising a first primer which anneals to a template DNA.

75. The kit of claim 74, further comprising at least one chain-terminating nucleotide analog, wherein said chain-terminating nucleotide analog is incorporatable into said first primer by said DNA polymerase in a template-dependent manner.

76. The kit of claim 75, further comprising two, three, or four chain-terminating nucleotide analogs.

77. The kit of claim 75, wherein said at least one said chain-terminating nucleotide analog is labeled with a first detectable label.

78. The kit of claim 77, wherein said first primer is labeled with a second detectable label.

79. The kit of claim 78, wherein said first and said second detectable labels generate a signal for identifying a nucleotide at a given position of said template DNA molecule.

80. The kit of claim 78, wherein said first or second detectable label is one selected from the group consisting of: a fluorescent label, an isotope, a chemiluminescent label, a quantum dot label, an antigen, and an affinity moiety.

81. The kit of claim 80, wherein said detectable label is a rhodamine label or a cyanine label.

82. A DNA polymerase produced by expressing a polynucleotide encoding a DNA polymerase, wherein said DNA polymerase comprises the sequence of SEQ ID NO: 2 except a mutation at P410 and A485.

83. A DNA polymerase produced by the steps:
(a) introducing a mutation into a polynucleotide encoding a wild-type DNA polymerase comprising the sequence of SEQ ID NO:2 to produce a mutant polynucleotide encoding a mutant DNA polymerase comprising the sequence of SEQ ID NO:2 except mutations at positions P410 and A485; and
(b) expressing said mutant polynucleotide to produce said mutant DNA polymerase.

84. The DNA polymerase of claim 82 or 83, wherein said mutation at position P410 is a P410L mutation.

85. The DNA polymerase of claim 82 or 83, wherein said mutation at position A485 is an A485T mutation.

86. The DNA polymerase of claim 82 or 83, wherein said mutation at position P410 is a P410L mutation and said mutation at position A485 is a A485T mutation.

87. A DNA polymerase produced by expressing a polynucleotide encoding a mutant DNA polymerase, wherein said mutant DNA polymerase comprises the sequence of SEQ ID NO: 2 except one or more mutations at D141, E143, P410, and A485.

88. The DNA polymerase of claim 87, wherein said one or more mutations at D141 and E143 are D141A and E143A.

89. A composition comprising a DNA polymerase produced by expressing in said composition a polynucleotide encoding a DNA polymerase comprising the sequence of SEQ ID NO:2 except mutations at P410 and A485 and optionally D141 and E143.

90. A composition comprising a DNA polymerase produced by the steps:
(a) introducing a mutation into a polynucleotide encoding a wild-type DNA polymerase to produce a mutant polynucleotide encoding a mutant DNA polymerase comprising the sequence of SEQ ID NO:2 except mutations at P410 and A485 and optionally D141 and E143; and
(b) expressing said mutant polynucleotide to produce said composition comprising said mutant DNA polymerase.

91. The composition of claim 89 or 90, wherein said mutation at P410 is a P410L mutation.

92. The composition of claim 89 or 90, wherein said mutation at A485 is an A485T mutation.

93. The composition of claim 89 or 90, wherein said mutation at P410 is a P410L mutation and said mutation at A485 is an A485T mutation.

94. The composition of claim 93, wherein said mutation at D141 is a D141A mutation and said mutation at E143 is a E143A mutation.

95. The composition of claim 1, wherein said DNA polymerase has reduced discrimination against a non-conventional nucleotide selected from the group consisting of: dideoxynucleotides, ribonucleotides and conjugated nucleotides.

* * * * *

UNITED STATES PATENT AND TRADEMARK OFFICE
CERTIFICATE OF CORRECTION

PATENT NO. : 8,268,605 B2
APPLICATION NO. : 09/896923
DATED : September 18, 2012
INVENTOR(S) : Sorge et al.

Page 1 of 1

It is certified that error appears in the above-identified patent and that said Letters Patent is hereby corrected as shown below:

IN THE CLAIMS:

In column 220, line 40, in Claim 19, delete "NO" and insert -- NO, --, therefor.

Signed and Sealed this
Thirtieth Day of April, 2013

Teresa Stanek Rea
*Acting Director of the United States Patent and Trademark Office*

SEQUENCE LISTING

<160> NUMBER OF SEQ ID NOS: 78

<210> SEQ ID NO 1
<211> LENGTH: 2331
<212> TYPE: DNA
<213> ORGANISM: Thermococcus sp. JDF-3

<400> SEQUENCE: 1

```
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacgttc cggcaatccg cgacaaaata     300
aggaagcacc ccgcggtcat cgacatctac gagtacgaca tacccttcgc caagcgctac     360
ctcatagaca agggcctaat cccgatggaa ggtgaggaag agcttaaact catgtccttc     420
gacatcgaga cgctctacca cgagggagaa gagtttggaa ccgggccgat tctgatgata     480
agctacgccg atgaaagcga ggcgcgcgtg ataacctgga gaagatcga ccttccttac     540
gttgaggttg tctccaccga gaaggagatg attaagcgct tcttgagggt cgttaaggag     600
aaggacccgg acgtgctgat aacatacaac ggcgacaact tcgacttcgc ctacctgaaa     660
aagcgctgtg agaagcttgg cgtgagcttt acccctggga gggacgggag cgagccgaag     720
atacagcgca tgggggacag gtttgcggtc gaggtgaagg gcagggtaca cttcgacctt     780
tatccagtca taaggcgcac cataaacctc ccgacctaca cccttgaggc tgtatacgag     840
gcggttttcg gcaagcccaa ggagaaggtc tacgccgagg atagccac cgcctgggag     900
accggcgagg ggcttgagag ggtcgcgcgc tactcgatgg aggacgcgag ggttacctac     960
gagcttggca gggagttctt cccgatggag gcccagcttt ccaggctcat cggccaaggc    1020
ctctgggacg tttcccgctc cagcaccggc aacctcgtcg agtggttcct cctaaggaag    1080
gcctacgaga ggaacgaact cgctcccaac aagcccgacg agagggagct ggcgaggaga    1140
aggggggggct acgccggtgg ctacgtcaag gagccggagc ggggactgtg gacaatatc    1200
gtgtatctag actttcgtag tctctaccct tcaatcataa tcacccacaa cgtctcgcca    1260
gatacgctca accgcgaggg gtgtaggagc tacgacgttg ccccgaggt cggtcacaag    1320
ttctgcaagg acttccccgg cttcattccg agcctgctcg aaacctgct ggaggaaagg    1380
cagaagataa agaggaagat gaaggcaact ctcgacccgc tggagaagaa tctcctcgat    1440
tacaggcaac gcgccatcaa gattctcgcc aacagctact acggctacta cggctatgcc    1500
agggcaagat ggtactgcag ggagtgcgcc gagagcgtta cggcatgggg aagggagtac    1560
atcgaaatgg tcatcagaga gcttgaggaa aagttcggtt ttaaagtcct ctatgcagac    1620
acagacggtc tccatgccac cattcctgga gcggacgctg aaacagtcaa gaaaaaggca    1680
atggagttct taaactatat caatcccaaa ctgcccggcc ttctcgaact cgaatacgag    1740
ggcttctacg tcagggggctt cttcgtcacg aagaaaaagt acgcggtcat cgacgaggag    1800
ggcaagataa ccacgcgcgg gcttgagata gtcaggcgcg actggagcga gatagcgaag    1860
gagacgcagg cgagggtttt ggaggcgata ctcaggcacg gtgacgttga agaggccgtc    1920
agaattgtca gggaagtcac cgaaaagctg agcaagtacg aggttccgcc ggagaagctg    1980
gttatccacg agcagataac gcgcgagctc aaggactaca aggccaccgg cccgcacgta    2040
```

-continued

```
gccatagcga agcgtttggc cgccagaggt gttaaaatcc ggcccggaac tgtgataagc    2100
tacatcgttc tgaagggctc cggaaggata ggcgacaggg cgattcccttc cgacgagttc   2160 gacccgacga agcacaagta cgatgcggac tactacatcg agaaccaggt tctgccggca    2220
gttgagagaa tcctcagggc cttcggctac cgcaaggaag acctgcgcta ccagaagacg    2280
aggcaggtcg ggcttggcgc gtggctgaag ccgaagggga agaagaagtg a             2331
```

<210> SEQ ID NO 2
<211> LENGTH: 776
<212> TYPE: PRT
<213> ORGANISM: Thermococcus sp. JDF-3

<400> SEQUENCE: 2

```
Met Ile Leu Asp Val Asp Tyr Ile Thr Glu Asn Gly Lys Pro Val Ile
1               5                  10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335
```

-continued

```
Ile Gly Gln Gly Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asn Leu Leu Glu Glu Arg Gln Lys Ile Lys
450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
                500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
                660                 665                 670

Tyr Lys Ala Thr Gly Pro His Val Ala Ile Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
```

-continued

```
             755                 760                 765
Leu Lys Pro Lys Gly Lys Lys Lys
        770                 775

<210> SEQ ID NO 3
<211> LENGTH: 1300
<212> TYPE: PRT
<213> ORGANISM: Thermococcus sp. JDF-3
<220> FEATURE:
<221> NAME/KEY: MISC_FEATURE
<222> LOCATION: (1015)..(1015)
<223> OTHER INFORMATION: Xaa=Undetermined sequence

<400> SEQUENCE: 3

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335
```

```
Ile Gly Gln Gly Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Leu Leu Pro Gly
                485                 490                 495

Glu Trp Val Ala Val Ile Glu Gly Gly Lys Leu Arg Pro Val Arg Ile
            500                 505                 510

Gly Glu Leu Val Asp Gly Leu Met Glu Ala Ser Gly Glu Arg Val Lys
        515                 520                 525

Arg Asp Gly Asp Thr Glu Val Leu Glu Val Gly Leu Tyr Ala Ser
530                 535                 540

Pro Ser Thr Gly Ser Pro Arg Lys Pro Ala Gln Cys Arg Lys Pro Gly
545                 550                 555                 560

Thr Ala Met Pro Gly Lys Phe Thr Glu Leu Ser Thr Pro Glu Gly Gly
                565                 570                 575

Leu Ser Val Thr Arg Gly His Ser Leu Phe Ala Tyr Arg Asp Ala Ser
            580                 585                 590

Leu Trp Arg Arg Gly Arg Arg Phe Lys Pro Gly Asp Leu Leu Ala
        595                 600                 605

Val Pro Ser Gly Pro Ser Arg Arg Gly Arg Gly Ser Thr Ser Leu
610                 615                 620

Asn Cys Ser Ser Asn Cys Pro Arg Arg Lys Arg Pro Thr Cys His Arg
625                 630                 635                 640

His Ser Gly Lys Gly Arg Lys Asn Phe Phe Arg Gly Met Leu Arg Thr
                645                 650                 655

Leu Arg Trp Ile Phe Gly Glu Glu Lys Thr Gly Gly Arg Pro Gly Ala
            660                 665                 670

Thr Trp Ser Thr Leu Arg Gly Leu Gly Tyr Val Lys Leu Arg Lys Ile
        675                 680                 685

Gly Tyr Gly Val Val Asp Arg Glu Gly Leu Gly Lys Val Pro Arg Phe
            690                 695                 700

Tyr Glu Arg Leu Val Glu Val Ile Arg Tyr Asn Gly Asn Arg Gly Glu
705                 710                 715                 720

Phe Ile Ala Asp Phe Asn Ala Leu Arg Pro Val Leu Arg Leu Met Met
                725                 730                 735

Pro Glu Lys Glu Leu Glu Glu Trp Leu Val Gly Thr Arg Asn Gly Phe
            740                 745                 750

Arg Ile Arg Pro Phe Ile Glu Val Asp Trp Lys Phe Ala Lys Leu Leu
755                 760                 765
```

```
Gly Tyr Tyr Val Ser Glu Gly Ser Ala Gly Lys Trp Lys Asn Arg Thr
    770                 775                 780

Gly Gly Trp Ser Tyr Ser Val Arg Leu Tyr Asn Glu Asp Gly Ser Val
785                 790                 795                 800

Leu Asp Asp Met Glu Arg Leu Ala Arg Ser Ser Leu Gly Ala Ala Arg
                805                 810                 815

Gly Glu Leu Arg Arg Asp Phe Lys Glu Asp Gly Leu His Asn Leu Arg
            820                 825                 830

Gly Ala Leu Arg Phe Thr Gly Arg Glu Gln Glu Gly Ser Val Ala Tyr
        835                 840                 845

Leu His Val Pro Gly Gly Pro Leu Gly Leu Pro Gly Val Leu His Arg
    850                 855                 860

Arg Arg Arg Arg Ser Pro Glu Gln Asp Gly Ser Ala Leu His Gln Glu
865                 870                 875                 880

Arg Ala Ser Gly Arg Pro Arg Pro Ala Pro Glu Leu Ala Gly Arg Leu
                885                 890                 895

Ser Asp Lys Arg Pro Pro Arg Gln Arg Gly Leu Gln Gly Leu Arg Glu
            900                 905                 910

Arg Gly Thr Ala Leu Tyr Arg Val Pro Glu Ala Glu Arg Leu Thr
        915                 920                 925

Tyr Ser His Val Ile Pro Arg Glu Val Leu Glu Thr Ser Ala Gly
    930                 935                 940

Pro Ser Arg Arg Thr Val Thr Gly Asn Ser Gly Ser Trp Trp Lys Ala
945                 950                 955                 960

Gly Ser Ser Thr Arg Lys Gly Pro Val Gly Ala Gly Ser Ser Thr Gly
                965                 970                 975

Ile Ser Ser Thr Gly Ser Arg Lys Ser Gly Arg Lys Ala Thr Arg Gly
            980                 985                 990

Thr Ser Thr Thr Ala Leu Arg Arg Thr Arg Thr Ser Gly Gly Leu Trp
        995                 1000                1005

Val Pro Leu Arg Ala Gln Xaa Ser Tyr Tyr Gly Tyr Tyr Gly Tyr
    1010                1015                1020

Ala Arg Ala Arg Trp Tyr Cys Arg Glu Cys Ala Glu Ser Val Thr
    1025                1030                1035

Ala Trp Gly Arg Glu Tyr Ile Glu Met Val Ile Arg Glu Leu Glu
    1040                1045                1050

Glu Lys Phe Gly Phe Lys Val Leu Tyr Ala Asp Thr Asp Gly Leu
    1055                1060                1065

His Ala Thr Ile Pro Gly Ala Asp Ala Glu Thr Val Lys Lys Lys
    1070                1075                1080

Ala Met Glu Phe Leu Asn Tyr Ile Asn Pro Lys Leu Pro Gly Leu
    1085                1090                1095

Leu Glu Leu Glu Tyr Glu Gly Phe Tyr Val Arg Gly Phe Phe Val
    1100                1105                1110

Thr Lys Lys Lys Tyr Ala Val Ile Asp Glu Glu Gly Lys Ile Thr
    1115                1120                1125

Thr Arg Gly Leu Glu Ile Val Arg Arg Asp Trp Ser Glu Ile Ala
    1130                1135                1140

Lys Glu Thr Gln Ala Arg Val Leu Glu Ala Ile Leu Arg His Gly
    1145                1150                1155

Asp Val Glu Glu Ala Val Arg Ile Val Arg Glu Val Thr Glu Lys
    1160                1165                1170

Leu Ser Lys Tyr Glu Val Pro Pro Glu Lys Leu Val Ile His Glu
```

```
                1175                1180                1185
Gln Ile Thr Arg Glu Leu Lys Asp Tyr Lys Ala Thr Gly Pro His
        1190                1195                1200

Val Ala Ile Ala Lys Arg Leu Ala Ala Arg Gly Val Lys Ile Arg
        1205                1210                1215

Pro Gly Thr Val Ile Ser Tyr Ile Val Leu Lys Gly Ser Gly Arg
        1220                1225                1230

Ile Gly Asp Arg Ala Ile Pro Phe Asp Glu Phe Asp Pro Thr Lys
        1235                1240                1245

His Lys Tyr Asp Ala Asp Tyr Tyr Ile Glu Asn Gln Val Leu Pro
        1250                1255                1260

Ala Val Glu Arg Ile Leu Arg Ala Phe Gly Tyr Arg Lys Glu Asp
        1265                1270                1275

Leu Arg Tyr Gln Lys Thr Arg Gln Val Gly Leu Gly Ala Trp Leu
        1280                1285                1290

Lys Pro Lys Gly Lys Lys Lys
        1295                1300

<210> SEQ ID NO 4
<211> LENGTH: 5255
<212> TYPE: DNA
<213> ORGANISM: Thermococcus sp. JDF-3
<220> FEATURE:
<221> NAME/KEY: misc_feature
<222> LOCATION: (3518)..(3519)
<223> OTHER INFORMATION: n = unknown
<220> FEATURE:
<221> NAME/KEY: misc_feature
<222> LOCATION: (4560)..(4580)
<223> OTHER INFORMATION: n = unknown

<400> SEQUENCE: 4
aattccactg ccgtgtttaa cctttccacc gttgaacttg agggtgatt tctgagcctc      60 ctcaatcact taatcgagac cgcggattac cttgaactgg tacacgttca acgattcggt    120
tcttgtaatg gtcgatactg ggccgtgctg gattttctaa acgtctcaag aacggctttc    180
atcaacggaa actgccacgt ctccgccgtc gtgagggtta aacctgaagt tcaagacttt    240
gcaacggaat ggcgagagaa cggcgactac cccagtggaa gagcttttga agccaaagc     300 cgagcttcag cgaatgtgcg gtgcccttgt tcaagagttg tgagcccttg attgttgttt    360
tctcctcttt tctgataaca tcgatggcga agtttattag ttctcagttc gataatcagg    420
caggtgttgg tcatgatcct tgacgttgat tacatcaccg agaatggaaa gcccgtcatc    480
agggtcttca agaaggagaa cggcgagttc aggattgaat acgaccgcga gttcgagccc    540
tacttctacg cgctcctcag ggacgactct gccatcgaag aaatcaaaaa gataaccgcg    600
gagaggcacg gcagggtcgt taaggttaag cgcgcggaga aggtgaagaa aaagttcctc    660
ggcaggtctg tggaggtctg ggtcctctac ttcacgcacc gcaggacgt tccggcaatc     720 cgcgacaaaa taaggaagca ccccgcggtc atcgacatct acgagtacga catacccttc    780
gccaagcgct acctcataga caagggccta atcccgatgg aaggtgagga agagcttaaa    840
ctcatgtcct tcgacatcga gacgctctac cacgagggag aagagtttgg aaccgggccg    900
attctgatga taagctacgc cgatgaaagc gaggcgcgcg tgataacctg gaagaagatc    960
gaccttcctt acgttgaggt tgtctccacc gagaaggaga tgattaagcg cttcttgagg   1020
gtcgttaagg agaaggaccc ggacgtgctg ataacataca acggcgacaa cttcgacttc   1080
gcctacctga aaaagcgctg tgagaagctt ggcgtgagct ttaccctcgg gagggacggg   1140
```

```
agcgagccga agatacagcg catggggac aggtttgcgg tcgaggtgaa gggcagggta    1200
cacttcgacc tttatccagt cataaggcgc accataaacc tcccgaccta cacccttgag    1260
gctgtatacg aggcggtttt cggcaagccc aaggagaagg tctacgccga ggagatagcc    1320
accgcctggg agaccggcga ggggcttgag agggtcgcgc gctactcgat ggaggacgcg    1380
agggttacct acgagcttgg cagggagttc ttcccgatgg aggcccagct ttccaggctc    1440
atcggccaag gcctctggga cgtttcccgc tccagcaccg gcaacctcgt cgagtggttc    1500
ctcctaagga aggcctacga gaggaacgaa ctcgctccca acaagcccga cgagagggag    1560
ctggcgagga aaggggggg ctacgccggt ggctacgtca aggagccgga gcggggactg    1620
tgggacaata tcgtgtatct agactttcgt agtctctacc cttcaatcat aatcacccac    1680
aacgtctcgc cagatacgct caaccgcgag gggtgtagga gctacgacgt tgccccccgag    1740 gtcggtcaca agttctgcaa ggacttcccc ggcttcattc cgagcctgct cggaaacctg    1800
ctggaggaaa ggcagaagat aaagaggaag atgaaggcaa ctctcgaccc gctggagaag    1860
aatctcctcg attacaggca acgcgccatc aagattctcg ccaacagcct tcttcccggg    1920
gagtgggttg cggtcattga aggggggaaa ctcaggcccg tccgcatcgg cgagctggtt    1980
gatggactga tggaagccag cggggagagg gtgaaaagag acggcgacac cgaggtcctt    2040
gaagtcgagg ggctttacgc ctctccttcg acagggagtc caagaaagcc cgcacaatgc    2100
cggtgaaagc cgtgataagg caccgctatg ccggggaagt ttacagaata gctctcaact    2160
ccggaaggag gattaagcgt gacgcgcggc cacagcctct tcgcgtaccg ggacgcgagc    2220
ttgtggaggt gacggggag gaggaggttc aagcccggcg acctcctggc ggtgccaagc    2280
ggataaccct cccggagagg agggagaggc tcaacatcgt tgaactgctc ctcgaactgc    2340
ccgaggagga aacggccgac atgtcatcga cattccggca agggtagaaa gaacttcttc    2400 agggaatgc tcagaaccct ccgctggatt ttcggggagg agaagaccgg agggcggcca    2460
ggcgctacct ggagcacctt gcgtgggctc ggctacgtga agctgaggaa aatcggctac    2520
ggggtggttg ataggagg actgggaaag gtaccgcgct tctacgagag gctcgtggag    2580
gtaatccgct acaacggcaa caggggggag ttcatcgccg atttcaacgc gctccgcccc    2640
gtcctccgcc tgatgatgcc cgagaaggag cttgaagagt ggctcgttgg gacgaggaac    2700
gggttcagga taaggccgtt catagaggtt gattggaagt tcgcaaagct cctcggctac    2760
tacgtgagcg aggggagcgc cgggaagtgg aaaaaccgga ccggggctg gagctactcg    2820 gtgaggcttt acaacgagga cgggagcgtt ctcgacgaca tggagagact cgcgaggagt    2880
tctttggggg cgtgagcgcg ggggaacta cgtcgagatt tcaaagaaga tggcctacat    2940
aatcttcgag gggctctgcg gttcaccggc cgagaacaag agggttccgt ggcttatctt    3000
cacgtcccct gaggaggtcc gctgggcctt ccttgagggg tacttcatcg gcgacggcga    3060
cgttcacccg agcaagatgg ttcggctctc caccaagagc gagcttctgg ctaacggcct    3120
cgtcctgctc ctgaactcgc tgggcgtctc agcgataaac gtccgccacg acagcgggt    3180 ttacagggtc tacgtgaacg aggaactgcc ctttacagag taccgaaagc ggaagaacgc    3240
ctcacttact cccacgtcat accgagggaa gtgctggagg agacttcggc cgggccttcc    3300
agaagaacat gagtcacggg aaattcaggg agctggtgga agcggggag ctcgacgcgg    3360 aaagggccgg taggataggc tggctcctcg acggggatat agtcctcgac agggtctcgg    3420
aagtcaggaa ggaaagctac gaggggtacg tctacgacct gagcgttgag gaggacgaga    3480
acttctggcg ggctttgggt tcctctacgc gcacaacnna gctactacgg ctactacggc    3540
```

```
tatgccaggg caagatggta ctgcaggag tgcgccgaga gcgttacggc atggggaagg   3600
gagtacatcg aaatggtcat cagagagctt gaggaaaagt tcggttttaa agtcctctat   3660
gcagacacag acggtctcca tgccaccatt cctggagcgg acgctgaaac agtcaagaaa   3720
aaggcaatgg agttcttaaa ctatatcaat cccaaactgc ccggccttct cgaactcgaa   3780
tacgagggct tctacgtcag gggcttcttc gtcacgaaga aaaagtacgc ggtcatcgac   3840
gaggagggca agataaccac gcgcgggctt gagatagtca ggcgcgactg gagcgagata   3900
gcgaaggaga cgcaggcgag ggttttggag gcgatactca ggcacggtga cgttgaagag   3960
gccgtcagaa ttgtcaggga agtcaccgaa aagctgagca agtacgaggt tccgccggag   4020
aagctggtta tccacgagca gataacgcgc gagctcaagg actacaaggc caccggcccg   4080
cacgtagcca tagcgaagcg tttggccgcc agaggtgtta aaatccggcc cggaactgtg   4140
ataagctaca tcgttctgaa gggctccgga aggataggcg acagggcgat tcccttcgac   4200
gagttcgacc cgacgaagca caagtacgat gcggactact acatcgagaa ccaggttctg   4260
ccggcagttg agagaatcct cagggccttc ggctaccgca aggaagacct gcgctaccag   4320
aagacgaggc aggtcgggct tggcgcgtgg ctgaagccga aggggaagaa gaagtgagga   4380
attatctggt ttcttttccc agcattaaat gcttccgaca ttgccttatt tatgaaactc   4440
ctgttgtgcc tgagttttgtg ccagaaaaca gcctgttctg acggcgcttt ttcttgccag   4500
gtctcttgag tttcgcaagg gtcttctcga ccagctcaat ggtcttgtcg tcattgtttn   4560
nnnnnnnnnn nnnnnnnnnn cccggggact tcatactggc ggtaatagac agggattcct   4620
tcctcaagga cttcccggga ggcattggag ttttttggtg gggctttcac aggatttgct   4680
catcttgtgg atttctcgtt cgattgaatc tgtccacttg agggtgtagg tcgagacggt   4740
ggagcgcgta ttccgggagc gggtcttgag gctccatttt tcagtcctcc tccggcgaag   4800
aagtggaact caagccgggt gttagcttat gttatgttcc caactcctcc agcacctcca   4860
ggatcccctc aatcccggaa cctcgaagcc cctctcgtgg atctttctaa cttcctctgc   4920
ctccgggttt atccagaccg cccacatgcc ggctctcagc gcaccctcga atcctccgc    4980
gtaggtgtcg ccgatgtgga ttgcctcgtc cggctcgacc ccgaagcatc gagcggtttt   5040
ctgaacatct cgggcatcgg cttatacgcc agaacctcgt cggcgaagaa ggttccctca   5100
atgtagtcca tcaggccgaa cctctcgagg ggggcccgg tacccaattc gccctatagt   5160
gagtcgatta caattcactg gccgtcgttt tacaacgtcg tgactgggaa aaccctggcg   5220
ttacccaact taagtcgctt tgcagcacat ccccc                             5255
```

<210> SEQ ID NO 5
<211> LENGTH: 9
<212> TYPE: PRT
<213> ORGANISM: Thermococcus sp. JDF-3
<220> FEATURE:
<221> NAME/KEY: MISC_FEATURE
<222> LOCATION: (2)..(4)
<223> OTHER INFORMATION: Xaa is any naturally occuring amino acid
<220> FEATURE:
<221> NAME/KEY: MISC_FEATURE
<222> LOCATION: (7)..(7)
<223> OTHER INFORMATION: Xaa is any naturally occuring amino acid

<400> SEQUENCE: 5

Lys Xaa Xaa Xaa Asn Ser Xaa Tyr Gly
1               5

<210> SEQ ID NO 6
<211> LENGTH: 10

```
<212> TYPE: PRT
<213> ORGANISM: Thermococcus sp. JDF-3
<220> FEATURE:
<221> NAME/KEY: MISC_FEATURE
<222> LOCATION: (2)..(5)
<223> OTHER INFORMATION: Xaa is any naturally occuring amino acid
<220> FEATURE:
<221> NAME/KEY: MISC_FEATURE
<222> LOCATION: (7)..(8)
<223> OTHER INFORMATION: Xaa is any naturally occuring amino acid

<400> SEQUENCE: 6

Lys Xaa Xaa Xaa Xaa Gly Xaa Xaa Tyr Gly
1               5                   10

<210> SEQ ID NO 7
<211> LENGTH: 10
<212> TYPE: PRT
<213> ORGANISM: Thermococcus sp. JDF-3
<220> FEATURE:
<221> NAME/KEY: MISC_FEATURE
<222> LOCATION: (2)..(3)
<223> OTHER INFORMATION: Xaa is any naturally occuring amino acid

<400> SEQUENCE: 7

Asp Xaa Xaa Ser Leu Tyr Pro Ser Ile Ile
1               5                   10

<210> SEQ ID NO 8
<211> LENGTH: 10
<212> TYPE: PRT
<213> ORGANISM: Thermococcus sp. JDF-3

<400> SEQUENCE: 8

Asp Phe Arg Ser Leu Tyr Leu Ser Ile Ile
1               5                   10

<210> SEQ ID NO 9
<211> LENGTH: 10
<212> TYPE: PRT
<213> ORGANISM: Thermococcus sp. JDF-3

<400> SEQUENCE: 9

Asp Phe Arg Ser His Tyr Pro Ser Ile Ile
1               5                   10

<210> SEQ ID NO 10
<211> LENGTH: 10
<212> TYPE: PRT
<213> ORGANISM: Thermococcus sp. JDF-3

<400> SEQUENCE: 10

Asp Phe Arg Ser Phe Tyr Pro Ser Ile Ile
1               5                   10

<210> SEQ ID NO 11
<211> LENGTH: 30
<212> TYPE: DNA
<213> ORGANISM: Artificial
<220> FEATURE:
<223> OTHER INFORMATION: Synthetic oligonucleotide PCR primer

<400> SEQUENCE: 11
gggaaacata tgatccttga cgttgattac                                    30

<210> SEQ ID NO 12
<211> LENGTH: 31
<212> TYPE: DNA
```

```
<213> ORGANISM: Artificial
<220> FEATURE:
<223> OTHER INFORMATION: Synthetic oligonucleotide PCR primer

<400> SEQUENCE: 12
gggaaaggat cctcacttct tcttcccctt c                              31

<210> SEQ ID NO 13
<211> LENGTH: 34
<212> TYPE: DNA
<213> ORGANISM: Artificial
<220> FEATURE:
<223> OTHER INFORMATION: Synthetic oligonucleotide primer

<400> SEQUENCE: 13
tcagatgaat tcgatgatcc ttgacgttga ttac                           34

<210> SEQ ID NO 14
<211> LENGTH: 54
<212> TYPE: DNA
<213> ORGANISM: Artificial
<220> FEATURE:
<223> OTHER INFORMATION: Synthetic oligonucleotide primer

<400> SEQUENCE: 14
gagagaattc ataatgataa ggaggaaaaa attatgatcc ttgacgttga ttac     54

<210> SEQ ID NO 15
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 15
tcagatctcg agtcacttct tcttcccctt c                              31

<210> SEQ ID NO 16
<211> LENGTH: 29
<212> TYPE: DNA
<213> ORGANISM: Artificial
<220> FEATURE:
<223> OTHER INFORMATION: Synthetic oligonucleotide sequencing primer

<400> SEQUENCE: 16
ccagctttcc agactagtcg gccaaggcc                                 29

<210> SEQ ID NO 17
<211> LENGTH: 16
<212> TYPE: DNA
<213> ORGANISM: Artificial
<220> FEATURE:
<223> OTHER INFORMATION: Synthetic oligonucleotide sequencing primer

<400> SEQUENCE: 17
aactctcgac ccgctg                                               16

<210> SEQ ID NO 18
<211> LENGTH: 38
<212> TYPE: DNA
<213> ORGANISM: Artificial
<220> FEATURE:
<223> OTHER INFORMATION: Synthetic oligonucleotide primer

<400> SEQUENCE: 18
ggttttccca gtcacgacgt tgtaaaacga cggccagt                       38
```

<210> SEQ ID NO 19
<211> LENGTH: 18
<212> TYPE: DNA
<213> ORGANISM: Artificial Sequence
<220> FEATURE:
<221> NAME/KEY: misc_feature
<223> OTHER INFORMATION: First strand of synthetic oligonucleotide
      duplex

<400> SEQUENCE: 19
taacgttggg gggggggca                                                      18

<210> SEQ ID NO 20
<211> LENGTH: 18
<212> TYPE: DNA
<213> ORGANISM: Artificial
<220> FEATURE:
<223> OTHER INFORMATION: Second strand of synthetic oligonucleotide
      duplex

<400> SEQUENCE: 20 tgcaacccccc ccccgtat                                                      18

<210> SEQ ID NO 21
<211> LENGTH: 139
<212> TYPE: PRT
<213> ORGANISM: Thermococcus sp. JDF-3
<220> FEATURE:
<221> NAME/KEY: MISC_FEATURE
<222> LOCATION: (6)..(6)
<223> OTHER INFORMATION: Xaa=Undetermined Sequence

<400> SEQUENCE: 21

Leu Val Cys Asn Ala Xaa Ser Thr Gly Asn Leu Val Glu Trp Phe Leu
1               5                   10                  15

Leu Arg Lys Ala Tyr Glu Arg Asn Glu Leu Ala Pro Asn Lys Pro Asp
            20                  25                  30

Glu Arg Glu Leu Ala Arg Arg Gly Gly Tyr Ala Gly Gly Tyr Val
        35                  40                  45

Lys Glu Pro Glu Arg Gly Leu Trp Asp Asn Ile Val Tyr Leu Asp Phe
    50                  55                  60

Arg Ser Leu Tyr Pro Ser Ile Ile Ile Thr His Asn Val Ser Pro Asp
65                  70                  75                  80

Thr Leu Asn Arg Glu Gly Cys Arg Ser Tyr Asp Val Ala Pro Glu Val
                85                  90                  95

Gly His Lys Phe Cys Lys Asp Phe Pro Gly Phe Ile Pro Ser Leu Leu
            100                 105                 110

Gly Asn Leu Leu Glu Glu Arg Gln Lys Ile Lys Arg Lys Met Lys Ala
        115                 120                 125

Thr Leu Asp Pro Leu Glu Lys Asn Leu Leu Asp
    130                 135

<210> SEQ ID NO 22
<211> LENGTH: 140
<212> TYPE: PRT
<213> ORGANISM: Thermococcus sp. JDF-3

<400> SEQUENCE: 22

Val Trp Asp Val Ser Arg Ser Ser Thr Gly Asn Leu Val Glu Arg Phe
1               5                   10                  15

Leu Leu Arg Lys Ala Tyr Glu Arg Asn Glu Leu Ala Pro Asn Lys Pro
            20                  25                  30

```
Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
 50                  55                  60

Phe Arg Ser Leu Tyr Pro Ser Ile Ile Ile Thr His Ser Val Ser Pro
 65                  70                  75                  80

Asp Thr Leu Asp Arg Glu Gly Cys Arg Ser Tyr Asp Val Ala Pro Glu
                 85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
            115                 120                 125

Ala Thr Leu Asp Pro Leu Glu Lys Asn Leu Leu Asp
        130                 135                 140

<210> SEQ ID NO 23
<211> LENGTH: 140
<212> TYPE: PRT
<213> ORGANISM: Thermococcus sp. JDF-3

<400> SEQUENCE: 23

Val Trp Asp Val Ser Arg Ser Ser Thr Gly Asn Leu Val Glu Trp Phe
 1               5                  10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
 50                  55                  60

Phe Arg Ser Leu Tyr Pro Ser Ile Ile Ile Thr His Asn Val Ser Pro
 65                  70                  75                  80

Asp Thr Leu Asn Arg Glu Gly Cys Arg Ser Tyr Asp Val Ala Pro Glu
                 85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
            115                 120                 125

Ala Thr Leu Asp Pro Leu Glu Lys Asn Leu Leu Asp
        130                 135                 140

<210> SEQ ID NO 24
<211> LENGTH: 140
<212> TYPE: PRT
<213> ORGANISM: Thermococcus sp. JDF-3

<400> SEQUENCE: 24

Val Trp Asp Val Ser Arg Ser Ser Thr Gly Asn Leu Val Glu Trp Phe
 1               5                  10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
 50                  55                  60

Phe Arg Ser Leu Tyr Pro Ser Ile Ile Ile Thr His Asn Val Ser Pro
 65                  70                  75                  80

Asp Thr Leu Asn Arg Glu Gly Cys Arg Ser Tyr Asp Val Ala Pro Glu
```

```
                          85                  90                  95
Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Met Lys Met Lys
        115                 120                 125

Ala Thr Leu Asp Pro Leu Glu Lys Asn Leu Leu Asp
    130                 135                 140

<210> SEQ ID NO 25
<211> LENGTH: 140
<212> TYPE: PRT
<213> ORGANISM: Thermococcus sp. JDF-3

<400> SEQUENCE: 25

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 26
<211> LENGTH: 140
<212> TYPE: PRT
<213> ORGANISM: Thermococcus sp. JDF-3
<220> FEATURE:
<221> NAME/KEY: MISC_FEATURE
<222> LOCATION: (5)..(5)
<223> OTHER INFORMATION: Xaa=Undetermined sequence

<400> SEQUENCE: 26

Val Trp Asp Val Xaa Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Gln Trp Asp Asn Ile Ala Tyr Leu Asp
50                  55                  60

Phe Arg Ser Leu Tyr Pro Ser Ile Ile Ile Thr His Asn Val Ser Pro
65                  70                  75                  80

Asp Thr Leu Lys Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
```

```
                    115                 120                 125

Ala Thr Leu Asp Pro Leu Glu Lys Asn Leu Leu Asp
        130                 135                 140

<210> SEQ ID NO 27
<211> LENGTH: 140
<212> TYPE: PRT
<213> ORGANISM: Thermococcus sp. JDF-3

<400> SEQUENCE: 27

Val Trp Asp Val Pro Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
        130                 135                 140

<210> SEQ ID NO 28
<211> LENGTH: 140
<212> TYPE: PRT
<213> ORGANISM: Thermococcus sp. JDF-3
<220> FEATURE:
<221> NAME/KEY: MISC_FEATURE
<222> LOCATION: (92)..(92)
<223> OTHER INFORMATION: Xaa=Undetermined sequence

<400> SEQUENCE: 28

Val Trp Asp Val Ser Arg Ser Ser Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
    50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Xaa Val Ala Pro Glu
                85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
        130                 135                 140
```

-continued

```
<210> SEQ ID NO 29
<211> LENGTH: 140
<212> TYPE: PRT
<213> ORGANISM: Thermococcus sp. JDF-3
<220> FEATURE:
<221> NAME/KEY: MISC_FEATURE
<222> LOCATION: (92)..(92)
<223> OTHER INFORMATION: Xaa=Undetermined Sequence

<400> SEQUENCE: 29

Val Trp Asp Val Ser Arg Ser Ser Thr Gly Asn Leu Val Glu Trp Phe
 1               5                  10                  15

Leu Leu Arg Lys Ala Tyr Glu Arg Asn Glu Leu Ala Pro Asn Lys Pro
             20                  25                  30

Asp Glu Arg Glu Leu Ala Arg Arg Gly Gly Tyr Ala Gly Gly Tyr
         35                  40                  45

Val Lys Glu Pro Glu Arg Gly Pro Trp Asp Asn Ile Val Tyr Leu Asp
     50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Xaa Val Ala Pro Glu
                 85                  90                  95

Val Gly His Lys Phe Cys Lys Asp Phe Pro Gly Phe Ile Pro Ser Leu
            100                 105                 110

Leu Gly Asn Leu Leu Glu Val Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 30
<211> LENGTH: 140
<212> TYPE: PRT
<213> ORGANISM: Thermococcus sp. JDF-3

<400> SEQUENCE: 30

Val Trp Asp Val Ser Arg Ser Ser Thr Gly Asn Leu Val Glu Trp Phe
 1               5                  10                  15

Leu Leu Arg Lys Ala Tyr Glu Arg Asn Lys Leu Ala Pro Asn Lys Pro
             20                  25                  30

Asp Glu Arg Glu Leu Ala Arg Arg Gly Gly Tyr Ala Gly Gly Tyr
         35                  40                  45

Val Lys Glu Pro Glu Arg Gly Leu Trp Asp Asn Ile Val Tyr Leu Asp
     50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                 85                  90                  95

Val Gly His Lys Phe Cys Lys Asp Phe Pro Gly Phe Ile Pro Ser Leu
            100                 105                 110

Leu Gly Asn Leu Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 31
<211> LENGTH: 140
<212> TYPE: PRT
<213> ORGANISM: Thermococcus sp. JDF-3
<220> FEATURE:
<221> NAME/KEY: MISC_FEATURE
```

<222> LOCATION: (4)..(4)
<223> OTHER INFORMATION: Xaa=Undetermined Sequence
<220> FEATURE:
<221> NAME/KEY: MISC_FEATURE
<222> LOCATION: (6)..(6)
<223> OTHER INFORMATION: Xaa=Undetermined Sequence

<400> SEQUENCE: 31

Tyr Trp Ser Xaa Pro Xaa Leu Arg Thr Gly Asn Leu Val Glu Trp Phe
1               5                   10                  15

Leu Leu Arg Lys Ala Tyr Glu Arg Asn Glu Leu Ala Pro Asn Lys Pro
            20                  25                  30

Asp Glu Arg Glu Leu Ala Arg Arg Gly Gly Tyr Ala Gly Gly Tyr
        35                  40                  45

Val Lys Glu Pro Glu Arg Gly Leu Trp Asp Asn Ile Val Tyr Leu Asp
50                  55                  60

Phe Arg Ser Leu Tyr Pro Ser Ile Ile Ile Thr His Asn Val Ser Pro
65                  70                  75                  80

Asp Thr Leu Asn Arg Glu Gly Cys Arg Ser Tyr Asp Val Ala Pro Glu
                85                  90                  95

Val Gly His Lys Phe Cys Lys Asp Phe Pro Gly Phe Ile Pro Ser Leu
            100                 105                 110

Leu Gly Asn Pro Leu Glu Glu Arg Gln Lys Ile Lys Arg Lys Met Lys
        115                 120                 125

Ala Thr Leu Asp Pro Leu Glu Lys Asn Leu Leu Asp
    130                 135                 140

<210> SEQ ID NO 32
<211> LENGTH: 141
<212> TYPE: PRT
<213> ORGANISM: Thermococcus sp. JDF-3
<220> FEATURE:
<221> NAME/KEY: MISC_FEATURE
<222> LOCATION: (5)..(5)
<223> OTHER INFORMATION: Xaa=Undetermined Sequence

<400> SEQUENCE: 32

Val Asp Gly Thr Xaa Pro Arg Ser Ser Thr Gly Asn Leu Val Glu Trp
1               5                   10                  15

Phe Leu Leu Arg Lys Ala Tyr Glu Arg Asn Glu Leu Ala Pro Asn Lys
            20                  25                  30

Pro Asp Glu Arg Glu Leu Ala Arg Arg Gly Gly Tyr Ala Gly Gly
        35                  40                  45

Tyr Val Lys Glu Pro Glu Arg Gly Leu Trp Asp Asn Ile Val Tyr Leu
50                  55                  60

Asp Phe Arg Ser His Tyr Pro Ser Ile Ile Ile Thr His Asn Val Ser
65                  70                  75                  80

Pro Asp Thr Leu Asn Arg Glu Gly Cys Arg Ser Tyr Asp Val Ala Pro
                85                  90                  95

Glu Asp Gly His Lys Phe Cys Lys Asp Phe Pro Gly Phe Ile Pro Ser
            100                 105                 110

Leu Leu Gly Asn Leu Leu Glu Glu Arg Gln Lys Ile Lys Arg Lys Met
        115                 120                 125

Lys Ala Thr Leu Asp Pro Leu Glu Lys Asn His Leu Asp
    130                 135                 140

<210> SEQ ID NO 33
<211> LENGTH: 143
<212> TYPE: PRT
<213> ORGANISM: Thermococcus sp. JDF-3

```
<220> FEATURE:
<221> NAME/KEY: MISC_FEATURE
<222> LOCATION: (1)..(3)
<223> OTHER INFORMATION: Xaa=Undetermined Sequence

<400> SEQUENCE: 33

Xaa Xaa Xaa Phe Trp Asp Val Ser Arg Ser Ser Thr Gly Asn Leu Val
1               5                   10                  15

Glu Trp Phe Leu Leu Arg Lys Ala Tyr Glu Arg Asn Glu Leu Ala Pro
            20                  25                  30

Asn Lys Pro Asp Glu Arg Glu Leu Ala Arg Arg Gly Gly Tyr Ala
            35                  40                  45

Gly Gly Tyr Val Lys Glu Pro Glu Arg Gly Leu Trp Asp Asn Ile Val
50                  55                  60

Tyr Leu Asp Phe Arg Ser Leu Tyr Pro Ser Ile Ile Ile Thr His Asn
65                  70                  75                  80

Val Ser Pro Asp Thr Leu Asn Arg Glu Gly Cys Arg Ser Tyr Asp Val
                85                  90                  95

Ala Pro Glu Val Gly His Lys Phe Cys Lys Asp Phe Pro Gly Phe Ile
            100                 105                 110

Pro Ser Leu Leu Gly Asn Leu Leu Glu Glu Arg Gln Lys Ile Lys Arg
            115                 120                 125

Lys Met Lys Ala Thr Leu Asp Pro Leu Glu Lys Asn Leu Leu Asp
130                 135                 140

<210> SEQ ID NO 34
<211> LENGTH: 180
<212> TYPE: PRT
<213> ORGANISM: Thermococcus sp. JDF-3

<400> SEQUENCE: 34

Thr Gly Glu Gly Leu Glu Arg Val Ala Arg Tyr Ser Met Glu Asp Ala
1               5                   10                  15

Arg Val Thr Tyr Glu Leu Gly Arg Glu Phe Phe Pro Met Glu Ala Gln
            20                  25                  30

Leu Ser Arg Leu Ile Gly Gln Gly Asp Trp Asp Val Ser Arg Ser Ser
            35                  40                  45

Thr Gly Asn Leu Val Glu Trp Phe Leu Leu Arg Lys Ala Tyr Glu Arg
50                  55                  60

Asn Glu Leu Ala Pro Asn Lys Pro Asp Glu Arg Glu Leu Ala Arg Arg
65                  70                  75                  80

Arg Gly Gly Tyr Ala Gly Gly Tyr Val Lys Glu Pro Glu Arg Gly Leu
                85                  90                  95

Trp Asp Asn Ile Val Tyr Leu Asp Phe Arg Ser Leu Tyr Pro Ser Ile
            100                 105                 110

Ile Ile Thr His Asn Val Ser Pro Asp Thr Leu Asn Arg Glu Gly Cys
            115                 120                 125

Arg Ser Tyr Asp Val Ala Pro Glu Val Gly His Lys Phe Cys Lys Asp
            130                 135                 140

Phe Pro Gly Phe Ile Pro Ser Leu Leu Gly Asn Leu Leu Glu Glu Arg
145                 150                 155                 160

Gln Lys Ile Lys Arg Lys Met Lys Ala Thr Leu Asp Pro Leu Glu Lys
                165                 170                 175

Asn Leu Leu Asp
            180

<210> SEQ ID NO 35
```

```
<211> LENGTH: 180
<212> TYPE: PRT
<213> ORGANISM: Thermococcus sp. JDF-3

<400> SEQUENCE: 35

Tyr Arg Gln Arg Ala Ile Lys Ile Leu Ala Asn Ser Tyr Tyr Gly Tyr
1               5                   10                  15

Cys Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
        50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Val Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 36
<211> LENGTH: 180
<212> TYPE: PRT
<213> ORGANISM: Thermococcus sp. JDF-3

<400> SEQUENCE: 36

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
                20                  25                  30

Val Thr Ala Trp Gly Arg Glu Tyr Ile Glu Met Val Ile Arg Glu Leu
            35                  40                  45

Glu Glu Lys Phe Gly Phe Lys Val Leu Tyr Ala Asp Thr Asp Gly Leu
        50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160
```

Arg Ile Val Arg Glu Val Thr Glu Lys Leu Ser Lys Tyr Glu Val Pro
            165                 170                 175

Pro Glu Glu Leu
            180

<210> SEQ ID NO 37
<211> LENGTH: 180
<212> TYPE: PRT
<213> ORGANISM: Thermococcus sp. JDF-3

<400> SEQUENCE: 37

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Lys Val Thr Glu Lys Leu Ser Lys Tyr Glu Val Pro
                165                 170                 175

Pro Glu Lys Leu
            180

<210> SEQ ID NO 38
<211> LENGTH: 180
<212> TYPE: PRT
<213> ORGANISM: Thermococcus sp. JDF-3

<400> SEQUENCE: 38

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Lys Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu

```
                115                 120                 125
Glu Ile Val Arg Arg Asp Trp Ser Glu Ile Ala Lys Glu Thr Gln Ala
            130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 39
<211> LENGTH: 180
<212> TYPE: PRT
<213> ORGANISM: Thermococcus sp. JDF-3

<400> SEQUENCE: 39

Tyr Arg Gln Arg Ala Ile Lys Ile Leu Ala Asn Asn Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Asp Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 40
<211> LENGTH: 180
<212> TYPE: PRT
<213> ORGANISM: Thermococcus sp. JDF-3
<220> FEATURE:
<221> NAME/KEY: MISC_FEATURE
<222> LOCATION: (114)..(114)
<223> OTHER INFORMATION: Xaa=Undetermined Sequence

<400> SEQUENCE: 40

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
```

```
                50                  55                  60
His Ala Thr Ile Pro Gly Ala Asp Ala Glu Thr Val Lys Lys Lys Ala
 65                  70                  75                  80

Met Glu Phe Leu Asn Tyr Ile Asn Leu Lys Leu Pro Gly Leu Leu Glu
                 85                  90                  95

Leu Glu Tyr Glu Gly Phe Tyr Val Arg Gly Phe Phe Val Thr Lys Lys
                100                 105                 110

Lys Xaa Ala Val Ile Asp Glu Gly Lys Ile Thr Thr Arg Gly Leu
                115                 120                 125

Glu Ile Val Arg Arg Asp Trp Ser Lys Ile Ala Lys Glu Thr Gln Ala
                130                 135                 140

Arg Val Leu Glu Ala Ile Leu Arg His Gly Asp Val Glu Glu Ala Ile
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 41
<211> LENGTH: 180
<212> TYPE: PRT
<213> ORGANISM: Thermococcus sp. JDF-3

<400> SEQUENCE: 41

Tyr Arg Gln Arg Ala Ile Lys Ile Leu Ala Asn Ser Tyr Tyr Gly Tyr
  1               5                  10                  15

Tyr Gly Tyr Ala Arg Ala Arg Trp Tyr Cys Arg Glu Cys Ala Glu Ser
                 20                  25                  30

Val Thr Ala Trp Gly Arg Glu Tyr Ile Glu Met Val Ile Arg Glu Leu
                 35                  40                  45

Glu Glu Lys Phe Gly Phe Lys Val Leu Tyr Ala Asp Thr Asp Gly Leu
                 50                  55                  60

His Ala Thr Ile Pro Gly Ala Asp Ala Glu Thr Val Lys Lys Lys Ala
 65                  70                  75                  80

Met Glu Phe Leu Asn Tyr Ile Asn Pro Lys Leu Pro Gly Leu Leu Glu
                 85                  90                  95

Leu Glu Tyr Glu Gly Phe Tyr Val Arg Gly Phe Phe Val Thr Lys Lys
                100                 105                 110

Lys Tyr Ala Val Ile Asp Glu Glu Gly Lys Ile Ala Thr Arg Gly Leu
                115                 120                 125

Glu Ile Val Arg Arg Asp Trp Ser Glu Ile Ala Lys Glu Thr Gln Ala
                130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 42
<211> LENGTH: 180
<212> TYPE: PRT
<213> ORGANISM: Thermococcus sp. JDF-3

<400> SEQUENCE: 42

Tyr Arg Gln Arg Ala Ile Lys Ile Leu Ala Asn Ser Tyr Tyr Gly Tyr
  1               5                  10                  15
```

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Asn Lys Tyr Glu Val Pro
                165                 170                 175

Pro Glu Lys Leu
            180

<210> SEQ ID NO 43
<211> LENGTH: 180
<212> TYPE: PRT
<213> ORGANISM: Thermococcus sp. JDF-3

<400> SEQUENCE: 43

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 44

```
<211> LENGTH: 180
<212> TYPE: PRT
<213> ORGANISM: Thermococcus sp. JDF-3

<400> SEQUENCE: 44

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Pro Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 45
<211> LENGTH: 180
<212> TYPE: PRT
<213> ORGANISM: Thermococcus sp. JDF-3

<400> SEQUENCE: 45

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160
```

Arg Ile Val Arg Glu Val Thr Glu Lys Leu Ser Lys Tyr Glu Val Pro
            165                 170                 175

Pro Val Lys Leu
        180

<210> SEQ ID NO 46
<211> LENGTH: 180
<212> TYPE: PRT
<213> ORGANISM: Thermococcus sp. JDF-3

<400> SEQUENCE: 46

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
    130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Gly Glu Ala
        180

<210> SEQ ID NO 47
<211> LENGTH: 180
<212> TYPE: PRT
<213> ORGANISM: Thermococcus sp. JDF-3

<400> SEQUENCE: 47

Tyr Arg Gln Arg Ala Ile Lys Ile Leu Ala Asn Ser Tyr Tyr Gly Asn
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
    50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu

```
                115                 120                 125
Glu Ile Val Arg Arg Asp Trp Ser Glu Ile Ala Lys Glu Thr Gln Ala
130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 48
<211> LENGTH: 180
<212> TYPE: PRT
<213> ORGANISM: Thermococcus sp. JDF-3

<400> SEQUENCE: 48

Tyr Arg Gln Arg Ala Ile Lys Ile Leu Ala Asn Ser Tyr Tyr Gly Tyr
1               5                   10                  15

Tyr Gly Tyr Ala Arg Ala Arg Trp Tyr Cys Arg Glu Cys Ala Glu Ser
            20                  25                  30

Val Thr Ala Trp Gly Arg Glu Tyr Ile Glu Met Val Ile Arg Glu Leu
        35                  40                  45

Glu Glu Lys Phe Gly Phe Lys Val Leu Tyr Ala Asp Thr Asp Gly Leu
50                  55                  60

His Ala Thr Ile Pro Gly Ala Asp Ala Glu Thr Val Lys Lys Lys Ala
65                  70                  75                  80

Met Glu Phe Leu Asn Tyr Ile Asn Pro Lys Leu Pro Gly Leu Leu Glu
                85                  90                  95

Leu Glu Tyr Glu Gly Phe Tyr Val Arg Gly Phe Phe Val Thr Lys Lys
            100                 105                 110

Lys Tyr Ala Val Ile Asp Glu Glu Gly Lys Ile Thr Thr Arg Gly Leu
        115                 120                 125

Glu Ile Val Arg Arg Asp Trp Ser Glu Ile Ala Lys Glu Thr Gln Ala
130                 135                 140

Arg Val Leu Glu Ala Ile Leu Arg His Gly Asp Val Glu Glu Ala Val
145                 150                 155                 160

Arg Ile Val Arg Glu Val Thr Glu Lys Leu Ser Lys Tyr Glu Val Pro
                165                 170                 175

Pro Glu Lys Leu
            180

<210> SEQ ID NO 49
<211> LENGTH: 6
<212> TYPE: PRT
<213> ORGANISM: Thermococcus barossii

<400> SEQUENCE: 49

Ile Leu Ala Asn Ser Phe
1               5

<210> SEQ ID NO 50
<211> LENGTH: 30
<212> TYPE: DNA
<213> ORGANISM: Artificial
<220> FEATURE:
<223> OTHER INFORMATION: Synthetic oligonucleotide

<400> SEQUENCE: 50
ctcaacttgg agcgaacgac ctacaccgaa                                        30
```

<210> SEQ ID NO 51
<211> LENGTH: 30
<212> TYPE: DNA
<213> ORGANISM: Artificial
<220> FEATURE:
<223> OTHER INFORMATION: Synthetic oligonucleotide

<400> SEQUENCE: 51
ctcatcttgg agcgaacgac ctacaccgaa                            30

<210> SEQ ID NO 52
<211> LENGTH: 30
<212> TYPE: DNA
<213> ORGANISM: Artificial
<220> FEATURE:
<223> OTHER INFORMATION: Synthetic oligonucleotide

<400> SEQUENCE: 52
ctcagcttgg agcgaacgac ctacaccgaa                            30

<210> SEQ ID NO 53
<211> LENGTH: 30
<212> TYPE: DNA
<213> ORGANISM: Artificial
<220> FEATURE:
<223> OTHER INFORMATION: Synthetic oligonucleotide

<400> SEQUENCE: 53
ctcaccttgg agcgaacgac ctacaccgaa                            30

<210> SEQ ID NO 54
<211> LENGTH: 25
<212> TYPE: DNA
<213> ORGANISM: Artificial
<220> FEATURE:
<223> OTHER INFORMATION: Synthetic oligonucleotide

<400> SEQUENCE: 54
ttcggtgtag gtcgttcgct ccaag                                 25

<210> SEQ ID NO 55
<211> LENGTH: 28
<212> TYPE: DNA
<213> ORGANISM: Artificial
<220> FEATURE:
<223> OTHER INFORMATION: Synthetic oligonucleotide

<400> SEQUENCE: 55
aagtgtaaag cctggggtgc ctaatgag                              28

<210> SEQ ID NO 56
<211> LENGTH: 34
<212> TYPE: DNA
<213> ORGANISM: Artificial
<220> FEATURE:
<223> OTHER INFORMATION: Synthetic oligonucleotide

<400> SEQUENCE: 56
agctggcgaa aggggatgt gctgcaaggc gatt                        34

<210> SEQ ID NO 57
<211> LENGTH: 34
<212> TYPE: DNA
<213> ORGANISM: Artificial
<220> FEATURE:
<223> OTHER INFORMATION: Synthetic oligonucleotide

<400> SEQUENCE: 57
agctggcgaa aggggatgt gctgcaaggc gatt                                34

<210> SEQ ID NO 58
<211> LENGTH: 41
<212> TYPE: DNA
<213> ORGANISM: Artificial
<220> FEATURE:
<223> OTHER INFORMATION: Synthetic oligonucleotide

<400> SEQUENCE: 58
cggtacctcc tggtggatac actggttcct gtaagcagaa g                       41

<210> SEQ ID NO 59
<211> LENGTH: 26
<212> TYPE: DNA
<213> ORGANISM: Artificial
<220> FEATURE:
<223> OTHER INFORMATION: Synthetic oligonucleotide

<400> SEQUENCE: 59
gagagcttga ggagagcagg aaaggt                                        26

<210> SEQ ID NO 60
<211> LENGTH: 37
<212> TYPE: DNA
<213> ORGANISM: Artificial
<220> FEATURE:
<223> OTHER INFORMATION: Synthetic oligonucleotide

<400> SEQUENCE: 60
gatctcccag ggcggcagta agtcttcagc atcaggc                            37

<210> SEQ ID NO 61
<211> LENGTH: 29
<212> TYPE: DNA
<213> ORGANISM: Artificial
<220> FEATURE:
<223> OTHER INFORMATION: Synthetic oligonucleotide

<400> SEQUENCE: 61
tcctttggac agggatgagg aataactga                                     29

<210> SEQ ID NO 62
<211> LENGTH: 774
<212> TYPE: PRT
<213> ORGANISM: Thermococcus litoralis

<400> SEQUENCE: 62

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr

```
              100                 105                 110
Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
            165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
            195                 200                 205

Tyr Asn Gly Asp Asn Phe Asp Leu Pro Tyr Leu Ile Lys Arg Ala Glu
            210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
            245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
            275                 280                 285

Lys Ser Lys Leu Gly Ala Glu Glu Ile Ala Ala Ile Trp Glu Thr Glu
            290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
            325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
            355                 360                 365

Leu Ala Pro Asn Lys Pro Asp Glu Glu Glu Tyr Lys Arg Arg Leu Arg
370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile
            405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
            435                 440                 445

Pro Gly Phe Ile Pro Ser Ile Leu Gly Asp Leu Ile Ala Met Arg Gln
            450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
            485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
            515                 520                 525
```

```
Arg Glu Ile Glu Glu Lys Phe Gly Phe Lys Val Leu Tyr Ala Asp Thr
            530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
            595                 600                 605

Arg Gly Leu Glu Val Val Arg Arg Asp Trp Ser Glu Ile Ala Lys Glu
            610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
            675                 680                 685

Leu Ala Ala Arg Gly Ile Lys Val Lys Pro Gly Thr Ile Ile Ser Tyr
690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
            755                 760                 765

Asp Ala Trp Leu Lys Arg
    770

<210> SEQ ID NO 63
<211> LENGTH: 1829
<212> TYPE: PRT
<213> ORGANISM: Thermococcus aggregans
<220> FEATURE:
<221> NAME/KEY: MISC_FEATURE
<222> LOCATION: (1118)..(1118)
<223> OTHER INFORMATION: Xaa=Undetermined Sequence
<220> FEATURE:
<221> NAME/KEY: MISC_FEATURE
<222> LOCATION: (1123)..(1123)
<223> OTHER INFORMATION: Xaa=Undetermined Sequence

<400> SEQUENCE: 63

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
    50                  55                  60

Val Val Asp Ala Val Lys Val Lys Lys Phe Leu Gly Arg Asp Val
65                  70                  75                  80

Glu Val Trp Lys Leu Ile Phe Glu His Pro Gln Asp Val Pro Ala Leu
```

```
                    85                  90                  95
Arg Gly Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Leu Met Ala Phe Asp Ile Glu Thr
                130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
                180                 185                 190

Arg Phe Val Gln Ile Val Arg Glu Lys Asp Pro Asp Val Leu Ile Thr
                195                 200                 205

Tyr Asn Gly Asp Asn Phe Asp Leu Pro Tyr Leu Ile Lys Arg Ala Glu
                210                 215                 220

Lys Leu Gly Val Thr Leu Leu Leu Gly Arg Asp Lys Glu His Pro Glu
225                 230                 235                 240

Pro Lys Ile His Arg Met Gly Asp Ser Phe Ala Val Glu Ile Lys Gly
                245                 250                 255

Arg Ile His Phe Asp Leu Phe Pro Val Val Arg Arg Thr Ile Asn Leu
                260                 265                 270

Pro Thr Tyr Thr Leu Glu Ala Val Tyr Glu Ala Val Leu Gly Lys Thr
                275                 280                 285

Lys Ser Lys Leu Gly Ala Glu Glu Ile Ala Ala Ile Trp Glu Thr Glu
290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
                340                 345                 350

Asn Leu Val Glu Trp Tyr Leu Leu Arg Val Ala Tyr Glu Arg Asn Glu
                355                 360                 365

Leu Ala Pro Asn Lys Pro Asp Glu Glu Tyr Arg Arg Arg Leu Arg
                370                 375                 380

Thr Thr Tyr Leu Gly Gly Tyr Val Lys Glu Pro Glu Arg Gly Leu Trp
385                 390                 395                 400

Glu Asn Ile Ala Tyr Leu Asp Phe Arg Cys His Pro Ala Asp Thr Lys
                405                 410                 415

Val Ile Val Lys Gly Lys Gly Ile Val Asn Ile Ser Asp Val Lys Glu
                420                 425                 430

Gly Asp Tyr Ile Leu Gly Ile Asp Gly Trp Gln Arg Val Lys Lys Val
                435                 440                 445

Trp Lys Tyr His Tyr Glu Gly Lys Leu Ile Asn Ile Asn Gly Leu Lys
450                 455                 460

Cys Thr Pro Asn His Lys Val Pro Val Val Thr Glu Asn Asp Arg Gln
465                 470                 475                 480

Thr Arg Ile Arg Asp Ser Leu Ala Lys Ser Phe Leu Ser Gly Lys Val
                485                 490                 495

Lys Gly Lys Ile Ile Thr Thr Lys Leu Phe Glu Lys Ile Ala Glu Phe
                500                 505                 510
```

```
Glu Lys Asn Lys Pro Ser Glu Glu Ile Leu Lys Gly Glu Leu Ser
        515                 520                 525

Gly Ile Ile Leu Ala Glu Gly Thr Leu Leu Arg Lys Asp Ile Glu Tyr
530                 535                 540

Phe Asp Ser Ser Arg Gly Lys Lys Arg Ile Ser His Gln Tyr Arg Val
545                 550                 555                 560

Glu Ile Thr Ile Gly Glu Asn Glu Lys Glu Leu Leu Glu Arg Ile Leu
                565                 570                 575

Tyr Ile Phe Asp Lys Leu Phe Gly Ile Arg Pro Ser Val Lys Lys
                580                 585                 590

Gly Asp Thr Asn Ala Leu Lys Ile Thr Ala Lys Lys Ala Val Tyr
            595                 600                 605

Leu Gln Ile Glu Glu Leu Leu Lys Asn Ile Glu Ser Leu Tyr Ala Pro
        610                 615                 620

Ala Val Leu Arg Gly Phe Phe Glu Arg Asp Ala Thr Val Asn Lys Ile
625                 630                 635                 640

Arg Ser Thr Ile Val Val Thr Gln Gly Thr Asn Asn Lys Trp Lys Ile
                645                 650                 655

Asp Ile Val Ala Lys Leu Leu Asp Ser Leu Gly Ile Pro Tyr Ser Arg
                660                 665                 670

Tyr Glu Tyr Lys Tyr Ile Glu Asn Gly Lys Glu Leu Thr Lys His Ile
                675                 680                 685

Leu Glu Ile Thr Gly Arg Asp Gly Leu Ile Leu Phe Gln Thr Leu Val
        690                 695                 700

Gly Phe Ile Ser Ser Glu Lys Asn Glu Ala Leu Glu Lys Ala Ile Glu
705                 710                 715                 720

Val Arg Glu Met Asn Arg Leu Lys Asn Asn Ser Phe Tyr Asn Leu Ser
                725                 730                 735

Thr Phe Glu Val Ser Ser Glu Tyr Tyr Lys Gly Glu Val Tyr Asp Leu
                740                 745                 750

Thr Leu Glu Gly Asn Pro Tyr Tyr Phe Ala Asn Gly Ile Leu Thr His
        755                 760                 765

Asn Ser Leu Tyr Pro Ser Ile Ile Val Thr His Asn Val Ser Pro Asp
770                 775                 780

Thr Leu Glu Arg Glu Gly Cys Lys Asn Tyr Asp Val Ala Pro Ile Val
785                 790                 795                 800

Gly Tyr Lys Phe Cys Lys Asp Phe Pro Gly Phe Ile Pro Ser Ile Leu
                805                 810                 815

Gly Glu Leu Ile Thr Met Arg Gln Glu Ile Lys Lys Met Lys Ala
            820                 825                 830

Thr Ile Asp Pro Ile Glu Lys Lys Met Leu Asp Tyr Arg Gln Arg Ala
            835                 840                 845

Val Lys Leu Leu Ala Asn Ser Ile Leu Pro Asn Glu Trp Leu Pro Ile
850                 855                 860

Ile Glu Asn Gly Glu Val Lys Phe Val Lys Ile Gly Glu Phe Ile Asp
865                 870                 875                 880

Arg Tyr Met Glu Glu Gln Lys Asp Lys Val Arg Thr Val Asp Asn Thr
                885                 890                 895

Glu Val Leu Glu Val Asp Asn Ile Phe Ala Phe Ser Leu Asn Lys Glu
                900                 905                 910

Ser Lys Lys Ser Glu Ile Lys Lys Val Lys Ala Leu Ile Arg His Lys
            915                 920                 925

Tyr Lys Gly Glu Ala Tyr Glu Val Glu Leu Asn Ser Gly Arg Lys Ile
930                 935                 940
```

His Ile Thr Arg Gly His Ser Leu Phe Thr Ile Arg Asn Gly Lys Ile
945                 950                 955                 960

Lys Glu Ile Trp Gly Glu Val Lys Val Gly Asp Leu Ile Ile Val
            965                 970                 975

Pro Lys Lys Val Lys Leu Asn Glu Lys Glu Ala Val Ile Asn Ile Pro
                980                 985                 990

Glu Leu Ile Ser Lys Leu Pro Asp Glu Asp Thr Ala Asp Val Val Met
            995                 1000                1005

Thr Thr Pro Val Lys Gly Arg Lys Asn Phe Phe Lys Gly Met Leu
    1010            1015            1020

Arg Thr Leu Lys Trp Ile Phe Gly Glu Glu Ser Lys Arg Ile Arg
    1025            1030            1035

Thr Phe Asn Arg Tyr Leu Phe His Leu Glu Leu Gly Phe Val
    1040            1045            1050

Lys Leu Leu Pro Arg Gly Tyr Glu Val Thr Asp Trp Glu Gly Leu
    1055            1060            1065

Lys Arg Tyr Arg Gln Leu Tyr Glu Lys Leu Val Lys Asn Leu Arg
    1070            1075            1080

Tyr Asn Gly Asn Lys Arg Glu Tyr Leu Val Arg Phe Asn Asp Ile
    1085            1090            1095

Lys Asp Ser Val Ser Cys Phe Pro Arg Lys Glu Leu Glu Glu Trp
    1100            1105            1110

Lys Ile Gly Thr Xaa Lys Gly Phe Arg Xaa Lys Cys Ile Leu Lys
    1115            1120            1125

Val Asp Glu Asp Phe Gly Lys Phe Leu Gly Tyr Tyr Val Ser Glu
    1130            1135            1140

Gly Tyr Ala Gly Ala Gln Lys Asn Lys Thr Gly Gly Met Ser Tyr
    1145            1150            1155

Ser Val Lys Leu Tyr Asn Glu Asn Pro Asn Val Leu Lys Asp Met
    1160            1165            1170

Lys Asn Ile Ala Glu Lys Phe Phe Gly Lys Val Arg Val Gly Lys
    1175            1180            1185

Asn Cys Val Asp Ile Pro Lys Lys Met Ala Tyr Leu Leu Ala Lys
    1190            1195            1200

Ser Leu Cys Gly Val Thr Ala Glu Asn Lys Arg Ile Pro Ser Ile
    1205            1210            1215

Ile Phe Asp Ser Ser Glu Pro Val Arg Trp Ala Phe Leu Arg Ala
    1220            1225            1230

Tyr Phe Val Gly Asp Gly Asp Ile His Pro Ser Lys Arg Leu Arg
    1235            1240            1245

Leu Ser Thr Lys Ser Glu Leu Leu Ala Asn Gln Leu Val Phe Leu
    1250            1255            1260

Leu Asn Ser Leu Gly Val Ser Ser Ile Lys Ile Gly Phe Asp Ser
    1265            1270            1275

Gly Val Tyr Arg Val Tyr Ile Asn Glu Asp Leu Pro Phe Leu Gln
    1280            1285            1290

Thr Ser Arg Gln Lys Asn Thr Tyr Tyr Pro Asn Leu Ile Pro Lys
    1295            1300            1305

Glu Val Leu Glu Glu Ile Phe Gly Arg Lys Phe Gln Lys Asn Ile
    1310            1315            1320

Thr Phe Glu Lys Phe Lys Glu Leu Ala Asp Ser Gly Lys Leu Asp
    1325            1330            1335

Lys Arg Lys Val Lys Leu Leu Asp Phe Leu Leu Asn Gly Asp Ile

```
         1340             1345             1350

Val Leu Asp Arg Val Lys Asn Val Glu Lys Arg Glu Tyr Glu Gly
    1355             1360             1365

Tyr Val Tyr Asp Leu Ser Val Glu Asp Asn Glu Asn Phe Leu Val
    1370             1375             1380

Gly Phe Gly Leu Leu Tyr Ala His Asn Ser Tyr Tyr Gly Tyr Met
    1385             1390             1395

Gly Tyr Pro Lys Ala Arg Trp Tyr Ser Lys Glu Cys Ala Glu Ser
    1400             1405             1410

Val Thr Ala Trp Gly Arg His Tyr Ile Glu Met Thr Ile Lys Glu
    1415             1420             1425

Ile Glu Glu Lys Phe Gly Phe Lys Val Leu Tyr Ala Asp Ser Val
    1430             1435             1440

Thr Gly Asp Thr Glu Ile Ile Val Lys Arg Asn Gly Arg Ile Glu
    1445             1450             1455

Phe Val Pro Ile Glu Lys Leu Phe Glu Arg Val Asp Tyr Arg Ile
    1460             1465             1470

Gly Glu Lys Glu Tyr Cys Ile Leu Glu Asp Val Glu Ala Leu Thr
    1475             1480             1485

Leu Asp Asn Arg Gly Lys Leu Ile Trp Lys Lys Val Pro Tyr Val
    1490             1495             1500

Met Arg His Arg Ala Lys Lys Lys Val Tyr Arg Ile Trp Ile Thr
    1505             1510             1515

Asn Ser Trp Tyr Ile Asp Val Thr Glu Asp His Ser Leu Ile Val
    1520             1525             1530

Ala Glu Asp Gly Leu Lys Glu Ala Arg Pro Met Glu Ile Glu Gly
    1535             1540             1545

Lys Ser Leu Ile Ala Thr Lys Asp Asp Leu Ser Gly Val Glu Tyr
    1550             1555             1560

Ile Lys Pro His Ala Ile Glu Glu Ile Ser Tyr Asn Gly Tyr Val
    1565             1570             1575

Tyr Asp Ile Glu Val Glu Gly Thr His Arg Phe Phe Ala Asn Gly
    1580             1585             1590

Ile Leu Val His Asn Thr Asp Gly Phe Tyr Ala Thr Ile Pro Gly
    1595             1600             1605

Glu Lys Pro Glu Thr Ile Lys Lys Lys Ala Lys Glu Phe Leu Lys
    1610             1615             1620

Tyr Ile Asn Ser Lys Leu Pro Gly Leu Leu Glu Leu Glu Tyr Glu
    1625             1630             1635

Gly Phe Tyr Leu Arg Gly Phe Phe Val Ala Lys Lys Arg Tyr Ala
    1640             1645             1650

Val Ile Asp Glu Glu Gly Arg Ile Thr Thr Arg Gly Leu Glu Val
    1655             1660             1665

Val Arg Arg Asp Trp Ser Glu Ile Ala Lys Glu Thr Gln Ala Lys
    1670             1675             1680

Val Leu Glu Ala Ile Leu Lys Glu Asp Ser Val Glu Lys Ala Val
    1685             1690             1695

Glu Ile Val Lys Asp Val Val Glu Glu Ile Ala Lys Tyr Gln Val
    1700             1705             1710

Pro Leu Glu Lys Leu Val Ile His Glu Gln Ile Thr Lys Asp Leu
    1715             1720             1725

Ser Glu Tyr Lys Ala Ile Gly Pro His Val Ala Ile Ala Lys Arg
    1730             1735             1740
```

```
Leu Ala Ala Lys Gly Ile Lys Val Arg Pro Gly Thr Ile Ile Ser
    1745            1750                1755

Tyr Ile Val Leu Arg Gly Ser Gly Lys Ile Ser Asp Arg Val Ile
    1760            1765                1770

Leu Leu Ser Glu Tyr Asp Pro Lys Lys His Lys Tyr Asp Pro Asp
    1775            1780                1785

Tyr Tyr Ile Glu Asn Gln Val Leu Pro Ala Val Leu Arg Ile Leu
    1790            1795                1800

Glu Ala Phe Gly Tyr Arg Lys Glu Asp Leu Lys Tyr Gln Ser Ser
    1805            1810                1815

Lys Gln Val Gly Leu Asp Ala Trp Leu Lys Lys
    1820            1825

<210> SEQ ID NO 64
<211> LENGTH: 771
<212> TYPE: PRT
<213> ORGANISM: Pyrococcus abyssi

<400> SEQUENCE: 64

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285
```

-continued

```
Lys Val Tyr Ala His Glu Ile Ala Glu Ala Trp Glu Thr Gly Lys Gly
            290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
        435                 440                 445

Phe Ile Pro Ser Leu Leu Gly Asn Leu Leu Glu Glu Arg Gln Lys Ile
    450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
        515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
        675                 680                 685

Lys Gly Val Lys Val Lys Pro Gly Met Val Ile Gly Tyr Ile Val Leu
    690                 695                 700

Arg Gly Asp Gly Pro Ile Ser Lys Arg Ala Ile Ala Ile Glu Glu Phe
705                 710                 715                 720
```

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe
    770

<210> SEQ ID NO 65
<211> LENGTH: 1235
<212> TYPE: PRT
<213> ORGANISM: Pyrococcus horikoshii

<400> SEQUENCE: 65

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Arg Asp Asp Ser Ala Ile
            35                  40                  45

Asp Glu Ile Lys Lys Ile Thr Ala Gln Arg His Gly Lys Val Val Arg
        50                  55                  60

Ile Val Glu Thr Glu Lys Ile Gln Arg Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Lys Leu Thr Phe Leu Ala Val Asp Ile Glu Thr
130                 135                 140

Leu Tyr His Glu Gly Glu Glu Phe Gly Lys Gly Pro Val Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Leu Ile Arg Val Ile Lys Glu Lys Asp Pro Asp Val Ile Ile Thr
        195                 200                 205

Tyr Asn Gly Asp Asn Phe Asp Phe Pro Tyr Leu Leu Lys Arg Ala Glu
210                 215                 220

Lys Leu Gly Ile Lys Leu Leu Leu Gly Arg Asp Asn Ser Glu Pro Lys
225                 230                 235                 240

Met Gln Lys Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
        290                 295                 300

Leu Glu Arg Val Ala Lys Tyr Ser Met Glu Asp Ala Lys Val Thr Tyr
305                 310                 315                 320

```
Glu Leu Gly Arg Glu Phe Phe Pro Met Glu Ala Gln Leu Ala Arg Leu
                325                 330                 335
Val Gly Gln Pro Val Trp Asp Val Ser Arg Ser Thr Gly Asn Leu
            340                 345                 350
Val Glu Trp Phe Leu Leu Arg Lys Ala Tyr Glu Arg Asn Glu Leu Ala
            355                 360                 365
Pro Asn Lys Pro Asp Glu Lys Glu Tyr Glu Arg Arg Leu Arg Glu Ser
        370                 375                 380
Tyr Glu Gly Gly Tyr Val Lys Glu Pro Glu Lys Gly Leu Trp Glu Gly
385                 390                 395                 400
Ile Val Ser Leu Asp Phe Arg Ser Leu Tyr Pro Ser Ile Ile Ile Thr
                405                 410                 415
His Asn Val Ser Pro Asp Thr Leu Asn Arg Glu Gly Cys Glu Glu Tyr
            420                 425                 430
Asp Val Ala Pro Lys Val Gly His Arg Phe Cys Lys Asp Phe Pro Gly
            435                 440                 445
Phe Ile Pro Ser Leu Leu Gly Gln Leu Leu Glu Glu Arg Gln Lys Ile
        450                 455                 460
Lys Lys Arg Met Lys Glu Ser Lys Asp Pro Val Glu Lys Lys Leu Leu
465                 470                 475                 480
Asp Tyr Arg Gln Arg Ala Ile Lys Ile Leu Ala Asn Ser Ile Leu Pro
                485                 490                 495
Asp Glu Trp Leu Pro Ile Val Glu Asn Glu Lys Val Arg Phe Val Lys
            500                 505                 510
Ile Gly Asp Phe Ile Asp Arg Glu Ile Glu Glu Asn Ala Glu Arg Val
        515                 520                 525
Lys Arg Asp Gly Glu Thr Glu Ile Leu Glu Val Lys Asp Leu Lys Ala
530                 535                 540
Leu Ser Phe Asn Arg Glu Thr Lys Lys Ser Glu Leu Lys Lys Val Lys
545                 550                 555                 560
Ala Leu Ile Arg His Arg Tyr Ser Gly Lys Val Tyr Ser Ile Lys Leu
                565                 570                 575
Lys Ser Gly Arg Arg Ile Lys Ile Thr Ser Gly His Ser Leu Phe Ser
            580                 585                 590
Val Lys Asn Gly Lys Leu Val Lys Val Arg Gly Asp Glu Leu Lys Pro
        595                 600                 605
Gly Asp Leu Val Val Val Pro Gly Arg Leu Lys Leu Pro Glu Ser Lys
610                 615                 620
Gln Val Leu Asn Leu Val Glu Leu Leu Leu Lys Leu Pro Glu Glu Glu
625                 630                 635                 640
Thr Ser Asn Ile Val Met Met Ile Pro Val Lys Gly Arg Lys Asn Phe
                645                 650                 655
Phe Lys Gly Met Leu Lys Thr Leu Tyr Trp Ile Phe Gly Glu Gly Glu
            660                 665                 670
Arg Pro Arg Thr Ala Gly Arg Tyr Leu Lys His Leu Glu Arg Leu Gly
        675                 680                 685
Tyr Val Lys Leu Lys Arg Arg Gly Cys Glu Val Leu Asp Trp Glu Ser
            690                 695                 700
Leu Lys Arg Tyr Arg Lys Leu Tyr Glu Thr Leu Ile Lys Asn Leu Lys
705                 710                 715                 720
Tyr Asn Gly Asn Ser Arg Ala Tyr Met Val Glu Phe Asn Ser Leu Arg
                725                 730                 735
Asp Val Val Ser Leu Met Pro Ile Glu Glu Leu Lys Glu Trp Ile Ile
```

```
                    740                 745                 750
Gly Glu Pro Arg Gly Pro Lys Ile Gly Thr Phe Ile Asp Val Asp Asp
                755                 760                 765
Ser Phe Ala Lys Leu Leu Gly Tyr Tyr Ile Ser Ser Gly Asp Val Glu
770                 775                 780
Lys Asp Arg Val Lys Phe His Ser Lys Asp Gln Asn Val Leu Glu Asp
785                 790                 795                 800
Ile Ala Lys Leu Ala Glu Lys Leu Phe Gly Lys Val Arg Arg Gly Arg
                805                 810                 815
Gly Tyr Ile Glu Val Ser Gly Lys Ile Ser His Ala Ile Phe Arg Val
                820                 825                 830
Leu Ala Glu Gly Lys Arg Ile Pro Glu Phe Ile Phe Thr Ser Pro Met
                835                 840                 845
Asp Ile Lys Val Ala Phe Leu Lys Gly Leu Asn Gly Asn Ala Glu Glu
                850                 855                 860
Leu Thr Phe Ser Thr Lys Ser Glu Leu Leu Val Asn Gln Leu Ile Leu
865                 870                 875                 880
Leu Leu Asn Ser Ile Gly Val Ser Asp Ile Lys Ile Glu His Glu Lys
                    885                 890                 895
Gly Val Tyr Arg Val Tyr Ile Asn Lys Lys Glu Ser Ser Asn Gly Asp
                900                 905                 910
Ile Val Leu Asp Ser Val Glu Ser Ile Glu Val Glu Lys Tyr Glu Gly
                915                 920                 925
Tyr Val Tyr Asp Leu Ser Val Glu Asp Asn Glu Asn Phe Leu Val Gly
                930                 935                 940
Phe Gly Leu Leu Tyr Ala His Asn Ser Tyr Tyr Gly Tyr Tyr Gly Tyr
945                 950                 955                 960
Ala Lys Ala Arg Trp Tyr Cys Lys Glu Cys Ala Glu Ser Val Thr Ala
                    965                 970                 975
Trp Gly Arg Gln Tyr Ile Asp Leu Val Arg Arg Glu Leu Glu Ala Arg
                    980                 985                 990
Gly Phe Lys Val Leu Tyr Ile Asp  Thr Asp Gly Leu Tyr  Ala Thr Ile
                995                 1000                1005
Pro Gly Val Lys Asp Trp Glu  Glu Val Lys Arg Arg  Ala Leu Glu
    1010                1015                1020
Phe Val Asp Tyr Ile Asn Ser  Lys Leu Pro Gly Val  Leu Glu Leu
    1025                1030                1035
Glu Tyr Glu Gly Phe Tyr Ala  Arg Gly Phe Phe Val  Thr Lys Lys
    1040                1045                1050
Lys Tyr Ala Leu Ile Asp Glu  Gly Lys Ile Val  Thr Arg Gly
    1055                1060                1065
Leu Glu Ile Val Arg Arg Asp  Trp Ser Glu Ile Ala  Lys Glu Thr
    1070                1075                1080
Gln Ala Arg Val Leu Glu Ala  Ile Leu Lys His Gly  Asn Val Glu
    1085                1090                1095
Glu Ala Val Lys Ile Val Lys  Asp Val Thr Glu Lys  Leu Thr Asn
    1100                1105                1110
Tyr Glu Val Pro Pro Glu Lys  Leu Val Ile Tyr Glu  Gln Ile Thr
    1115                1120                1125
Arg Pro Ile Asn Glu Tyr Lys  Ala Ile Gly Pro His  Val Ala Val
    1130                1135                1140
Ala Lys Arg Leu Met Ala Arg  Gly Ile Leu Val Lys  Pro Gly Met
    1145                1150                1155
```

```
Val Ile Gly Tyr Ile Val Leu Arg Gly Asp Gly Pro Ile Ser Lys
    1160                1165                1170

Arg Ala Ile Ser Ile Glu Glu Phe Asp Pro Arg Lys His Lys Tyr
    1175                1180                1185

Asp Ala Glu Tyr Tyr Ile Glu Asn Gln Val Leu Pro Ala Val Glu
    1190                1195                1200

Arg Ile Leu Lys Ala Phe Gly Tyr Lys Arg Glu Asp Leu Arg Trp
    1205                1210                1215

Gln Lys Thr Lys Gln Val Gly Leu Gly Ala Trp Ile Lys Val Lys
    1220                1225                1230

Lys Ser
    1235

<210> SEQ ID NO 66
<211> LENGTH: 771
<212> TYPE: PRT
<213> ORGANISM: Pyrococcus sp. GE23

<400> SEQUENCE: 66

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
                20                  25                  30

Thr Phe Arg Pro Tyr Ile Tyr Ala Leu Leu Lys Asp Asp Ser Ala Ile
            35                  40                  45

Asp Glu Val Lys Lys Ile Thr Ala Glu Arg His Gly Lys Ile Val Arg
        50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
        275                 280                 285
```

-continued

```
Lys Val Tyr Ala His Glu Ile Ala Glu Ala Trp Glu Thr Gly Lys Gly
            290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Gln Tyr Ile Asp Leu Val Arg Arg Glu
            515                 520                 525

Leu Glu Ser Ser Gly Phe Lys Val Leu Tyr Ile Asp Thr Asp Gly Leu
530                 535                 540

Tyr Ala Thr Ile Pro Gly Ala Lys Pro Asn Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
        595                 600                 605

Glu Ile Val Arg Arg Asp Trp Ser Glu Ile Ala Lys Glu Thr Gln Ala
610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
            675                 680                 685

Lys Gly Val Lys Val Lys Pro Gly Met Val Ile Gly Tyr Ile Val Leu
        690                 695                 700

Arg Gly Asp Gly Pro Ile Ser Lys Arg Ala Ile Ala Ile Glu Glu Phe
705                 710                 715                 720
```

Asp Pro Lys Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Phe
    770

<210> SEQ ID NO 67
<211> LENGTH: 775
<212> TYPE: PRT
<213> ORGANISM: Pyrococcus sp. GB-D

<400> SEQUENCE: 67

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65              70                  75                  80

Glu Val Trp Arg Leu Tyr Phe Glu His Pro Gln Asp Val Pro Ala Ile
            85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145             150                 155                 160

Ser Tyr Ala Asp Glu Glu Glu Ala Lys Val Ile Thr Trp Lys Lys Ile
            165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225             230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305             310                 315                 320

```
Glu Leu Gly Arg Glu Phe Phe Pro Met Glu Ala Gln Leu Ser Arg Leu
            325                 330                 335

Val Gly Gln Pro Leu Trp Asp Val Ser Arg Ser Thr Gly Asn Leu
        340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                    405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                    485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                    565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
        610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                    645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
        690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                    725                 730                 735

Gln Val Leu Pro Ala Val Leu Arg Ile Leu Glu Ala Phe Gly Tyr Arg
```

```
                    740                 745                 750
Lys Glu Asp Leu Arg Trp Gln Lys Thr Lys Gln Thr Gly Leu Thr Ala
                755                 760                 765

Trp Leu Asn Ile Lys Lys Lys
        770                 775

<210> SEQ ID NO 68
<211> LENGTH: 775
<212> TYPE: PRT
<213> ORGANISM: Pyrococcus furiosus

<400> SEQUENCE: 68

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
```

```
                340             345             350
Val Glu Trp Phe Leu Leu Arg Lys Ala Tyr Glu Arg Asn Glu Val Ala
            355                 360             365
Pro Asn Lys Pro Ser Glu Glu Glu Tyr Gln Arg Arg Leu Arg Glu Ser
        370                 375                 380
Tyr Thr Gly Gly Phe Val Lys Glu Pro Glu Lys Gly Leu Trp Glu Asn
385                     390                 395                 400
Ile Val Tyr Leu Asp Phe Arg Ala Leu Tyr Pro Ser Ile Ile Thr
                405                 410                 415
His Asn Val Ser Pro Asp Thr Leu Asn Leu Glu Gly Cys Lys Asn Tyr
                420                 425                 430
Asp Ile Ala Pro Gln Val Gly His Lys Phe Cys Lys Asp Ile Pro Gly
            435                 440                 445
Phe Ile Pro Ser Leu Leu Gly His Leu Leu Glu Glu Arg Gln Lys Ile
        450                 455                 460
Lys Thr Lys Met Lys Glu Thr Gln Asp Pro Ile Glu Lys Ile Leu Leu
465                 470                 475                 480
Asp Tyr Arg Gln Lys Ala Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
                500                 505                 510
Ser Val Thr Ala Trp Gly Arg Lys Tyr Ile Glu Leu Val Trp Lys Glu
            515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Arg Tyr Ala Val Ile Asp Glu Glu Gly Lys Val Ile Thr Arg Gly
            595                 600                 605
Leu Glu Ile Val Arg Arg Asp Trp Ser Glu Ile Ala Lys Glu Thr Gln
        610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
            675                 680                 685
Ala Lys Gly Val Lys Ile Lys Pro Gly Met Val Ile Gly Tyr Ile Val
            690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
            755                 760                 765
```

```
Trp Leu Asn Ile Lys Lys Ser
770                 775

<210> SEQ ID NO 69
<211> LENGTH: 775
<212> TYPE: PRT
<213> ORGANISM: Thermococcus sp. 9oN-7

<400> SEQUENCE: 69

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365
```

```
Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 70
```

<211> LENGTH: 1671
<212> TYPE: PRT
<213> ORGANISM: Pyrococcus sp. KOD-1

<400> SEQUENCE: 70

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
370                 375                 380

Glu Gly Gly Tyr Val Lys Glu Pro Glu Arg Gly Leu Trp Glu Asn Ile
385                 390                 395                 400
```

-continued

```
Val Tyr Leu Asp Phe Arg Cys His Pro Ala Asp Thr Lys Val Val
            405                 410                 415
Lys Gly Lys Gly Ile Ile Asn Ile Ser Glu Val Gln Glu Gly Asp Tyr
            420                 425                 430
Val Leu Gly Ile Asp Gly Trp Gln Arg Val Arg Lys Val Trp Glu Tyr
            435                 440                 445
Asp Tyr Lys Gly Glu Leu Val Asn Ile Asn Gly Leu Lys Cys Thr Pro
        450                 455                 460
Asn His Lys Leu Pro Val Val Thr Lys Asn Glu Arg Gln Thr Arg Ile
465                 470                 475                 480
Arg Asp Ser Leu Ala Lys Ser Phe Leu Thr Lys Val Lys Gly Lys
                485                 490                 495
Ile Ile Thr Thr Pro Leu Phe Tyr Glu Ile Gly Arg Ala Thr Ser Glu
                500                 505                 510
Asn Ile Pro Glu Glu Glu Val Leu Lys Gly Glu Leu Ala Gly Ile Leu
            515                 520                 525
Leu Ala Glu Gly Thr Leu Leu Arg Lys Asp Val Glu Tyr Phe Asp Ser
        530                 535                 540
Ser Arg Lys Lys Arg Arg Ile Ser His Gln Tyr Arg Val Glu Ile Thr
545                 550                 555                 560
Ile Gly Lys Asp Glu Glu Phe Arg Asp Arg Ile Thr Tyr Ile Phe
                565                 570                 575
Glu Arg Leu Phe Gly Ile Thr Pro Ser Ile Ser Glu Lys Lys Gly Thr
            580                 585                 590
Asn Ala Val Thr Leu Lys Val Ala Lys Lys Asn Val Tyr Leu Lys Val
            595                 600                 605
Lys Glu Ile Met Asp Asn Ile Glu Ser Leu His Ala Pro Ser Val Leu
        610                 615                 620
Arg Gly Phe Phe Glu Gly Asp Gly Ser Val Asn Arg Val Arg Arg Ser
625                 630                 635                 640
Ile Val Ala Thr Gln Gly Thr Lys Asn Glu Trp Lys Ile Lys Leu Val
                645                 650                 655
Ser Lys Leu Leu Ser Gln Leu Gly Ile Pro His Gln Thr Tyr Thr Tyr
                660                 665                 670
Gln Tyr Gln Glu Asn Gly Lys Asp Arg Ser Arg Tyr Ile Leu Glu Ile
            675                 680                 685
Thr Gly Lys Asp Gly Leu Ile Leu Phe Gln Thr Leu Ile Gly Phe Ile
        690                 695                 700
Ser Glu Arg Lys Asn Ala Leu Leu Asn Lys Ala Ile Ser Gln Arg Glu
705                 710                 715                 720
Met Asn Asn Leu Glu Asn Gly Phe Tyr Arg Leu Ser Glu Phe Asn
                725                 730                 735
Val Ser Thr Glu Tyr Tyr Glu Gly Lys Val Tyr Asp Leu Thr Leu Glu
            740                 745                 750
Gly Thr Pro Tyr Tyr Phe Ala Asn Gly Ile Leu Thr His Asn Ser Leu
        755                 760                 765
Tyr Pro Ser Ile Ile Ile Thr His Asn Val Ser Pro Asp Thr Leu Asn
        770                 775                 780
Arg Glu Gly Cys Lys Glu Tyr Asp Val Ala Pro Gln Val Gly His Arg
785                 790                 795                 800
Phe Cys Lys Asp Phe Pro Gly Phe Ile Pro Ser Leu Leu Gly Asp Leu
                805                 810                 815
Leu Glu Glu Arg Gln Lys Ile Lys Lys Lys Met Lys Ala Thr Ile Asp
```

-continued

```
              820                 825                 830
Pro Ile Glu Arg Lys Leu Leu Asp Tyr Arg Gln Arg Ala Ile Lys Ile
          835                 840                 845
Leu Ala Asn Ser Ile Leu Pro Glu Glu Trp Leu Pro Val Leu Glu Glu
          850                 855                 860
Gly Glu Val His Phe Val Arg Ile Gly Glu Leu Ile Asp Arg Met Met
865                 870                 875                 880
Glu Glu Asn Ala Gly Lys Val Lys Arg Glu Gly Glu Thr Glu Val Leu
              885                 890                 895
Glu Val Ser Gly Leu Glu Val Pro Ser Phe Asn Arg Arg Thr Asn Lys
              900                 905                 910
Ala Glu Leu Lys Arg Val Lys Ala Leu Ile Arg His Asp Tyr Ser Gly
              915                 920                 925
Lys Val Tyr Thr Ile Arg Leu Lys Ser Gly Arg Arg Ile Lys Ile Thr
              930                 935                 940
Ser Gly His Ser Leu Phe Ser Val Arg Asn Gly Glu Leu Val Glu Val
945                 950                 955                 960
Thr Gly Asp Glu Leu Lys Pro Gly Asp Leu Val Ala Val Pro Arg Arg
              965                 970                 975
Leu Glu Leu Pro Glu Arg Asn His Val Leu Asn Leu Val Glu Leu Leu
              980                 985                 990
Leu Gly Thr Pro Glu Glu Glu Thr Leu Asp Ile Val Met Thr Ile Pro
              995                 1000                1005
Val Lys Gly Lys Lys Asn Phe Phe Lys Gly Met Leu Arg Thr Leu
          1010                1015                1020
Arg Trp Ile Phe Gly Glu Glu Lys Arg Pro Arg Thr Ala Arg Arg
          1025                1030                1035
Tyr Leu Arg His Leu Glu Asp Leu Gly Tyr Val Arg Leu Lys Lys
          1040                1045                1050
Ile Gly Tyr Glu Val Leu Asp Trp Asp Ser Leu Lys Asn Tyr Arg
          1055                1060                1065
Arg Leu Tyr Glu Ala Leu Val Glu Asn Val Arg Tyr Asn Gly Asn
          1070                1075                1080
Lys Arg Glu Tyr Leu Val Glu Phe Asn Ser Ile Arg Asp Ala Val
          1085                1090                1095
Gly Ile Met Pro Leu Lys Glu Leu Lys Glu Trp Lys Ile Gly Thr
          1100                1105                1110
Leu Asn Gly Phe Arg Met Arg Lys Leu Ile Glu Val Asp Glu Ser
          1115                1120                1125
Leu Ala Lys Leu Leu Gly Tyr Tyr Val Ser Glu Gly Tyr Ala Arg
          1130                1135                1140
Lys Gln Arg Asn Pro Lys Asn Gly Trp Ser Tyr Ser Val Lys Leu
          1145                1150                1155
Tyr Asn Glu Asp Pro Glu Val Leu Asp Asp Met Glu Arg Leu Ala
          1160                1165                1170
Ser Arg Phe Phe Gly Lys Val Arg Arg Gly Arg Asn Tyr Val Glu
          1175                1180                1185
Ile Pro Lys Lys Ile Gly Tyr Leu Leu Phe Glu Asn Met Cys Gly
          1190                1195                1200
Val Leu Ala Glu Asn Lys Arg Ile Pro Glu Phe Val Phe Thr Ser
          1205                1210                1215
Pro Lys Gly Val Arg Leu Ala Phe Leu Glu Gly Tyr Phe Ile Gly
          1220                1225                1230
```

```
Asp Gly Asp Val His Pro Asn Lys Arg Leu Arg Leu Ser Thr Lys
    1235                1240                1245

Ser Glu Leu Leu Ala Asn Gln Leu Val Leu Leu Leu Asn Ser Val
    1250                1255                1260

Gly Val Ser Ala Val Lys Leu Gly His Asp Ser Gly Val Tyr Arg
    1265                1270                1275

Val Tyr Ile Asn Glu Glu Leu Pro Phe Val Lys Leu Asp Lys Lys
    1280                1285                1290

Lys Asn Ala Tyr Tyr Ser His Val Ile Pro Lys Glu Val Leu Ser
    1295                1300                1305

Glu Val Phe Gly Lys Val Phe Gln Lys Asn Val Ser Pro Gln Thr
    1310                1315                1320

Phe Arg Lys Met Val Glu Asp Gly Arg Leu Asp Pro Glu Lys Ala
    1325                1330                1335

Gln Arg Leu Ser Trp Leu Ile Glu Gly Asp Val Val Leu Asp Arg
    1340                1345                1350

Val Glu Ser Val Asp Val Glu Asp Tyr Asp Gly Tyr Val Tyr Asp
    1355                1360                1365

Leu Ser Val Glu Asp Asn Glu Asn Phe Leu Val Gly Phe Gly Leu
    1370                1375                1380

Val Tyr Ala His Asn Ser Tyr Tyr Gly Tyr Tyr Gly Tyr Ala Arg
    1385                1390                1395

Ala Arg Trp Tyr Cys Lys Glu Cys Ala Glu Ser Val Thr Ala Trp
    1400                1405                1410

Gly Arg Glu Tyr Ile Thr Met Thr Ile Lys Glu Ile Glu Glu Lys
    1415                1420                1425

Tyr Gly Phe Lys Val Ile Tyr Ser Asp Thr Asp Gly Phe Phe Ala
    1430                1435                1440

Thr Ile Pro Gly Ala Asp Ala Glu Thr Val Lys Lys Lys Ala Met
    1445                1450                1455

Glu Phe Leu Lys Tyr Ile Asn Ala Lys Leu Pro Gly Ala Leu Glu
    1460                1465                1470

Leu Glu Tyr Glu Gly Phe Tyr Lys Arg Gly Phe Phe Val Thr Lys
    1475                1480                1485

Lys Lys Tyr Ala Val Ile Asp Glu Glu Gly Lys Ile Thr Thr Arg
    1490                1495                1500

Gly Leu Glu Ile Val Arg Arg Asp Trp Ser Glu Ile Ala Lys Glu
    1505                1510                1515

Thr Gln Ala Arg Val Leu Glu Ala Leu Leu Lys Asp Gly Asp Val
    1520                1525                1530

Glu Lys Ala Val Arg Ile Val Lys Glu Val Thr Glu Lys Leu Ser
    1535                1540                1545

Lys Tyr Glu Val Pro Pro Glu Lys Leu Val Ile His Glu Gln Ile
    1550                1555                1560

Thr Arg Asp Leu Lys Asp Tyr Lys Ala Thr Gly Pro His Val Ala
    1565                1570                1575

Val Ala Lys Arg Leu Ala Ala Arg Gly Val Lys Ile Arg Pro Gly
    1580                1585                1590

Thr Val Ile Ser Tyr Ile Val Leu Lys Gly Ser Gly Arg Ile Gly
    1595                1600                1605

Asp Arg Ala Ile Pro Phe Asp Glu Phe Asp Pro Thr Lys His Lys
    1610                1615                1620

Tyr Asp Ala Glu Tyr Tyr Ile Glu Asn Gln Val Leu Pro Ala Val
    1625                1630                1635
```

```
Glu Arg Ile Leu Arg Ala Phe Gly Tyr Arg Lys Glu Asp Leu Arg
    1640            1645                1650

Tyr Gln Lys Thr Arg Gln Val Gly Leu Ser Ala Trp Leu Lys Pro
    1655            1660                1665

Lys Gly Thr
    1670

<210> SEQ ID NO 71
<211> LENGTH: 773
<212> TYPE: PRT
<213> ORGANISM: Thermococcus gorgonarius

<400> SEQUENCE: 71

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335
```

Val Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
                420                 425                 430

Val Ala Pro Gln Val Gly His Lys Phe Cys Lys Asp Phe Pro Gly Phe
                435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
            515                 520                 525

Glu Glu Lys Phe Gly Phe Lys Val Leu Tyr Ala Asp Thr Asp Gly Phe
            530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp

```
                755                 760                 765
Leu Lys Pro Lys Thr
        770

<210> SEQ ID NO 72
<211> LENGTH: 1523
<212> TYPE: PRT
<213> ORGANISM: Thermococcus fumicolans

<400> SEQUENCE: 72

Met Ile Leu Asp Thr Asp Tyr Ile Thr Glu Asp Gly Arg Pro Val Ile
1               5                   10                  15

Arg Val Phe Lys Lys Glu Asn Gly Glu Phe Lys Ile Glu Tyr Asp Arg
            20                  25                  30

Asp Phe Glu Pro Tyr Ile Tyr Ala Leu Leu Lys Asp Asp Ser Ala Ile
        35                  40                  45

Glu Asp Val Lys Lys Ile Thr Ala Ser Arg His Gly Thr Thr Val Arg
    50                  55                  60

Val Val Arg Ala Gly Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg His Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Ser Phe Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
```

```
                355                 360                 365
Pro Asn Lys Pro Ser Gly Arg Glu Leu Glu Arg Arg Gly Gly Tyr
    370                 375                 380
Ala Gly Gly Tyr Val Lys Glu Pro Glu Arg Gly Leu Trp Glu Asn Ile
385                 390                 395                 400
Ala Tyr Leu Asp Phe Arg Cys His Pro Ala Asp Thr Lys Val Ile Val
                405                 410                 415
Lys Gly Lys Gly Val Val Asn Ile Ser Glu Val Arg Glu Gly Asp Tyr
            420                 425                 430
Val Leu Gly Ile Asp Gly Trp Gln Lys Val Gln Arg Val Trp Glu Tyr
            435                 440                 445
Asp Tyr Glu Gly Glu Leu Val Asn Ile Asn Gly Leu Lys Cys Thr Pro
    450                 455                 460
Asn His Lys Leu Pro Val Val Arg Arg Thr Glu Arg Gln Thr Ala Ile
465                 470                 475                 480
Arg Asp Ser Leu Ala Lys Ser Phe Leu Thr Lys Lys Val Lys Gly Lys
                485                 490                 495
Leu Ile Thr Thr Pro Leu Phe Glu Lys Ile Gly Lys Ile Glu Arg Glu
            500                 505                 510
Asp Val Pro Glu Glu Glu Ile Leu Lys Gly Glu Leu Ala Gly Ile Ile
    515                 520                 525
Leu Ala Glu Gly Thr Leu Leu Arg Lys Asp Val Glu Tyr Phe Asp Ser
    530                 535                 540
Ser Arg Gly Lys Lys Arg Val Ser His Gln Tyr Arg Val Glu Ile Thr
545                 550                 555                 560
Val Gly Ala Gln Glu Glu Asp Phe Gln Arg Arg Ile Val Tyr Ile Phe
                565                 570                 575
Glu Arg Leu Phe Gly Val Thr Pro Ser Val Tyr Arg Lys Lys Asn Thr
            580                 585                 590
Asn Ala Ile Thr Phe Lys Val Ala Lys Lys Glu Val Tyr Leu Arg Val
            595                 600                 605
Arg Glu Ile Met Asp Gly Ile Glu Asn Leu His Ala Pro Ser Val Leu
    610                 615                 620
Arg Gly Phe Phe Glu Gly Asp Gly Ser Val Asn Lys Val Arg Lys Thr
625                 630                 635                 640
Val Val Val Asn Gln Gly Thr Asn Asn Glu Trp Lys Ile Glu Val Val
                645                 650                 655
Ser Lys Leu Leu Asn Lys Leu Gly Ile Pro His Arg Arg Tyr Thr Tyr
            660                 665                 670
Asp Tyr Thr Glu Arg Glu Lys Thr Met Thr Thr His Ile Leu Glu Ile
            675                 680                 685
Ala Gly Arg Asp Gly Leu Ile Leu Phe Gln Thr Ile Val Gly Phe Ile
    690                 695                 700
Ser Thr Glu Lys Asn Met Ala Leu Glu Glu Ala Ile Arg Asn Arg Glu
705                 710                 715                 720
Val Asn Arg Leu Glu Asn Asn Ala Phe Tyr Thr Leu Ala Asp Phe Thr
                725                 730                 735
Ala Lys Thr Glu Tyr Tyr Lys Gly Lys Val Tyr Asp Leu Thr Leu Glu
            740                 745                 750
Gly Thr Pro Tyr Tyr Phe Ala Asn Gly Ile Leu Thr His Asn Ser Leu
        755                 760                 765
Tyr Pro Ser Ile Ile Ile Ser His Asn Val Ser Pro Asp Thr Leu Asn
    770                 775                 780
```

```
Arg Glu Gly Cys Gly Glu Tyr Asp Glu Ala Pro Gln Val Gly His Arg
785                 790                 795                 800

Phe Cys Lys Asp Phe Pro Gly Phe Ile Pro Ser Leu Leu Gly Asp Leu
            805                 810                 815

Leu Asp Glu Arg Gln Lys Val Lys Lys His Met Lys Ala Thr Val Asp
        820                 825                 830

Pro Ile Glu Lys Lys Leu Leu Asp Tyr Arg Gln Arg Ala Ile Lys Ile
        835                 840                 845

Leu Ala Asn Ser Phe Tyr Gly Tyr Tyr Gly Tyr Ala Lys Ala Arg Trp
850                 855                 860

Tyr Cys Lys Glu Cys Ala Glu Ser Val Thr Ala Trp Gly Arg Gln Tyr
865                 870                 875                 880

Ile Glu Thr Thr Met Arg Glu Ile Glu Lys Phe Gly Phe Lys Val
            885                 890                 895

Leu Tyr Ala Asp Ser Val Thr Gly Asp Thr Glu Val Thr Ile Arg Arg
        900                 905                 910

Asn Gly Arg Ile Glu Phe Val Pro Ile Glu Lys Leu Phe Glu Arg Val
            915                 920                 925

Asp His Arg Val Gly Lys Glu Tyr Cys Val Leu Gly Gly Val Glu
930                 935                 940

Ala Leu Thr Leu Asp Asn Arg Gly Arg Leu Val Trp Lys Lys Val Pro
945                 950                 955                 960

Tyr Val Met Arg His Lys Thr Asp Lys Arg Ile Tyr Arg Val Trp Phe
            965                 970                 975

Thr Asn Ser Trp Tyr Leu Asp Val Thr Glu Asp His Ser Leu Ile Gly
            980                 985                 990

Tyr Leu Asn Thr Ser Lys Val Lys  Pro Gly Lys Pro Leu  Lys Glu Arg
        995                 1000                1005

Leu Val  Glu Val Lys Pro Glu  Glu Leu Gly Gly Lys  Val Lys Ser
    1010                1015                1020

Leu Ile  Thr Pro Asn Arg Pro  Ile Ala Arg Thr Ile  Lys Ala Asn
    1025                1030                1035

Pro Ile  Ala Val Lys Leu Trp  Glu Leu Ile Gly Leu  Leu Val Gly
    1040                1045                1050

Asp Gly  Asn Trp Gly Gly Gln  Ser Asn Trp Ala Lys  Tyr Tyr Val
    1055                1060                1065

Gly Leu  Ser Cys Gly Leu Asp  Lys Ala Glu Ile Glu  Arg Lys Val
    1070                1075                1080

Leu Asn  Pro Leu Arg Glu Ala  Ser Val Ile Ser Asn  Tyr Tyr Asp
    1085                1090                1095

Lys Ser  Lys Lys Gly Asp Val  Ser Ile Leu Ser Lys  Trp Leu Ala
    1100                1105                1110

Gly Phe  Met Val Lys Tyr Phe  Lys Asp Glu Asn Gly  Asn Lys Ala
    1115                1120                1125

Ile Pro  Ser Phe Met Phe Asn  Leu Pro Arg Glu Tyr  Ile Glu Ala
    1130                1135                1140

Phe Leu  Arg Gly Leu Phe Ser  Ala Asp Gly Thr Val  Ser Leu Arg
    1145                1150                1155

Arg Gly  Ile Pro Glu Ile Arg  Leu Thr Ser Val Asn  Arg Glu Leu
    1160                1165                1170

Ser Asp  Ala Val Arg Lys Leu  Leu Trp Leu Val Gly  Val Ser Asn
    1175                1180                1185

Ser Leu  Phe Thr Glu Thr Lys  Pro Asn Arg Asn Tyr  Leu Glu Lys Glu
    1190                1195                1200
```

Ser Gly Thr His Ser Ile His Val Arg Ile Lys Asn Lys His Arg
    1205                1210                1215

Phe Ala Asp Arg Ile Gly Phe Leu Ile Asp Arg Lys Ser Thr Lys
    1220                1225                1230

Leu Ser Glu Asn Leu Gly Gly His Thr Asn Lys Lys Arg Ala Tyr
    1235                1240                1245

Lys Tyr Asp Phe Asp Leu Val Tyr Pro Arg Lys Ile Glu Glu Ile
    1250                1255                1260

Thr Tyr Asp Gly Tyr Val Tyr Asp Ile Glu Val Glu Gly Thr His
    1265                1270                1275

Arg Phe Phe Ala Asn Gly Ile Leu Val His Asn Thr Asp Gly Phe
    1280                1285                1290

Phe Ala Thr Ile Pro Gly Ala Asp Ala Glu Thr Val Lys Lys Lys
    1295                1300                1305

Ala Arg Glu Phe Leu Asn Tyr Ile Asn Pro Lys Leu Pro Gly Leu
    1310                1315                1320

Leu Glu Leu Glu Tyr Glu Gly Phe Tyr Arg Arg Gly Phe Phe Val
    1325                1330                1335

Thr Lys Lys Lys Tyr Ala Val Ile Asp Glu Glu Gly Lys Ile Thr
    1340                1345                1350

Thr Arg Gly Leu Glu Ile Val Arg Arg Asp Trp Ser Glu Val Ala
    1355                1360                1365

Lys Glu Thr Gln Ala Arg Val Leu Glu Ala Ile Leu Arg His Gly
    1370                1375                1380

Asp Val Glu Glu Ala Val Arg Ile Val Lys Glu Val Thr Glu Lys
    1385                1390                1395

Leu Ser Lys Tyr Glu Val Pro Pro Glu Lys Leu Val Ile His Glu
    1400                1405                1410

Gln Ile Thr Arg Glu Leu Lys Asp Tyr Lys Ala Thr Gly Pro His
    1415                1420                1425

Val Ala Ile Ala Lys Arg Leu Ala Ala Arg Gly Ile Lys Val Arg
    1430                1435                1440

Pro Gly Thr Val Ile Ser Tyr Ile Val Leu Lys Gly Ser Gly Arg
    1445                1450                1455

Ile Gly Asp Arg Thr Ile Pro Phe Asp Glu Phe Asp Pro Thr Lys
    1460                1465                1470

His Arg Tyr Asp Ala Glu Tyr Tyr Ile Glu Asn Gln Val Leu Pro
    1475                1480                1485

Ala Val Glu Arg Ile Leu Lys Ala Phe Gly Tyr Lys Lys Glu Asp
    1490                1495                1500

Leu Arg Tyr Gln Lys Thr Arg Gln Val Gly Leu Gly Ala Trp Leu
    1505                1510                1515

Lys Met Gly Lys Lys
    1520

<210> SEQ ID NO 73
<211> LENGTH: 586
<212> TYPE: PRT
<213> ORGANISM: Methanobacterium thermoautotrophicum

<400> SEQUENCE: 73

Met Glu Asp Tyr Arg Met Val Leu Leu Asp Ile Asp Tyr Val Thr Val
1               5                   10                  15

Asp Glu Val Pro Val Ile Arg Leu Phe Gly Lys Asp Lys Ser Gly Gly
                20                  25                  30

```
Asn Glu Pro Ile Ile Ala His Asp Arg Ser Phe Arg Pro Tyr Ile Tyr
         35                   40                  45

Ala Ile Pro Thr Asp Leu Asp Glu Cys Leu Arg Glu Leu Glu Glu Leu
 50                   55                  60

Glu Leu Glu Lys Leu Glu Val Lys Glu Met Arg Asp Leu Gly Arg Pro
 65                   70                  75                  80

Thr Glu Val Ile Arg Ile Glu Phe Arg His Pro Gln Asp Val Pro Lys
                 85                  90                  95

Ile Arg Asp Arg Ile Arg Asp Leu Glu Ser Val Arg Asp Ile Arg Glu
                100                 105                 110

His Asp Ile Pro Phe Tyr Arg Tyr Leu Ile Asp Lys Ser Ile Val
                115                 120                 125

Pro Met Glu Glu Leu Glu Phe Gln Gly Val Glu Val Asp Ser Ala Pro
        130                 135                 140

Ser Val Thr Thr Asp Val Arg Thr Val Glu Val Thr Gly Arg Val Gln
145                 150                 155                 160

Ser Thr Gly Ser Gly Ala His Gly Leu Asp Ile Leu Ser Phe Asp Ile
                165                 170                 175

Glu Val Arg Asn Pro His Gly Met Pro Asp Pro Glu Lys Asp Glu Ile
                180                 185                 190

Val Met Ile Gly Val Ala Gly Asn Met Gly Tyr Glu Ser Val Ile Ser
        195                 200                 205

Thr Ala Gly Asp His Leu Asp Phe Val Glu Val Val Glu Asp Glu Arg
        210                 215                 220

Glu Leu Leu Glu Arg Phe Ala Glu Ile Val Ile Asp Lys Lys Pro Asp
225                 230                 235                 240

Ile Leu Val Gly Tyr Asn Ser Asp Asn Phe Asp Phe Pro Tyr Ile Thr
                245                 250                 255

Arg Arg Ala Ala Ile Leu Gly Ala Glu Leu Asp Leu Gly Trp Asp Gly
                260                 265                 270

Ser Lys Ile Arg Thr Met Arg Arg Gly Phe Ala Asn Ala Thr Ala Ile
                275                 280                 285

Lys Gly Thr Val His Val Asp Leu Tyr Pro Val Met Arg Arg Tyr Met
        290                 295                 300

Asn Leu Asp Arg Tyr Thr Leu Glu Arg Val Tyr Gln Glu Leu Phe Gly
305                 310                 315                 320

Glu Glu Lys Ile Asp Leu Pro Gly Asp Arg Leu Trp Glu Tyr Trp Asp
                325                 330                 335

Arg Asp Glu Leu Arg Asp Glu Leu Phe Arg Tyr Ser Leu Asp Asp Val
                340                 345                 350

Val Ala Thr His Arg Ile Ala Glu Lys Ile Leu Pro Leu Asn Leu Glu
                355                 360                 365

Leu Thr Arg Leu Val Gly Gln Pro Leu Phe Asp Ile Ser Arg Met Ala
370                 375                 380

Thr Gly Gln Gln Ala Glu Trp Phe Leu Val Arg Lys Ala Tyr Gln Tyr
385                 390                 395                 400

Gly Glu Leu Val Pro Asn Lys Pro Ser Gln Ser Asp Phe Ser Ser Arg
                405                 410                 415

Arg Gly Arg Ala Val Gly Gly Tyr Val Lys Glu Pro Glu Lys Gly
                420                 425                 430

Leu His Glu Asn Ile Val Gln Phe Asp Phe Arg Ser Leu Tyr Pro Ser
                435                 440                 445

Ile Ile Ile Ser Lys Asn Ile Ser Pro Asp Thr Leu Thr Asp Asp Glu
```

```
                450                 455                 460
Glu Ser Glu Cys Tyr Val Ala Pro Tyr Gly Tyr Arg Phe Arg Lys
465                 470                 475                 480

Ser Pro Arg Gly Phe Val Pro Ser Val Ile Gly Glu Ile Leu Ser Glu
                485                 490                 495

Arg Val Arg Ile Lys Glu Glu Met Lys Gly Ser Asp Asp Pro Met Glu
                500                 505                 510

Arg Lys Ile Leu Asn Val Gln Gln Glu Ala Leu Lys Arg Leu Ala Asn
                515                 520                 525

Thr Met Tyr Gly Val Tyr Gly Tyr Ser Arg Phe Arg Trp Tyr Ser Met
                530                 535                 540

Glu Cys Ala Glu Ala Ile Thr Ala Trp Gly Arg Asp Tyr Ile Lys Lys
545                 550                 555                 560

Thr Ile Lys Thr Ala Glu Glu Phe Gly Phe His Thr Val Tyr Ala Asp
                565                 570                 575

Thr Asp Gly Phe Tyr Ala Thr Tyr Arg Gly
                580                 585

<210> SEQ ID NO 74
<211> LENGTH: 1634
<212> TYPE: PRT
<213> ORGANISM: Methanococcus jannaschii

<400> SEQUENCE: 74

Met Gly Met Ser Met Gly Lys Ile Lys Ile Asp Ala Leu Ile Asp Asn
1               5                   10                  15

Thr Tyr Lys Thr Ile Glu Asp Lys Ala Val Ile Tyr Leu Tyr Leu Ile
                20                  25                  30

Asn Ser Ile Leu Lys Asp Arg Asp Phe Lys Pro Tyr Phe Tyr Val Glu
                35                  40                  45

Leu His Lys Glu Lys Val Glu Asn Glu Asp Ile Glu Lys Ile Lys Glu
                50                  55                  60

Phe Leu Leu Lys Asn Asp Leu Leu Lys Phe Val Glu Asn Ile Glu Val
65                  70                  75                  80

Val Lys Lys Ile Ile Leu Arg Lys Glu Lys Glu Val Ile Lys Ile Ile
                85                  90                  95

Ala Thr His Pro Gln Lys Val Pro Lys Leu Arg Lys Ile Lys Glu Cys
                100                 105                 110

Glu Ile Val Lys Glu Ile Tyr Glu His Asp Ile Pro Phe Ala Lys Arg
                115                 120                 125

Tyr Leu Ile Asp Asn Glu Ile Ile Pro Met Thr Tyr Trp Asp Phe Glu
                130                 135                 140

Asn Lys Lys Pro Val Ser Ile Glu Ile Pro Lys Leu Lys Ser Val Ala
145                 150                 155                 160

Phe Asp Met Glu Val Tyr Asn Arg Asp Thr Glu Pro Asn Pro Glu Arg
                165                 170                 175

Asp Pro Ile Leu Met Ala Ser Phe Trp Asp Glu Asn Gly Gly Lys Val
                180                 185                 190

Ile Thr Tyr Lys Glu Phe Asn His Pro Asn Ile Glu Val Val Lys Asn
                195                 200                 205

Glu Lys Glu Leu Ile Lys Lys Ile Ile Glu Thr Leu Lys Glu Tyr Asp
                210                 215                 220

Val Ile Tyr Thr Tyr Asn Gly Asp Asn Phe Asp Phe Pro Tyr Leu Lys
225                 230                 235                 240

Ala Arg Ala Lys Ile Tyr Gly Ile Asp Ile Asn Leu Gly Lys Asp Gly
```

-continued

```
            245                 250                 255
Glu Glu Leu Lys Ile Lys Arg Gly Gly Met Glu Tyr Arg Ser Tyr Ile
            260                 265                 270

Pro Gly Arg Val His Ile Asp Leu Tyr Pro Ile Ser Arg Arg Leu Leu
            275                 280                 285

Lys Leu Thr Lys Tyr Thr Leu Glu Asp Val Val Tyr Asn Leu Phe Gly
            290                 295                 300

Ile Glu Lys Leu Lys Ile Pro His Thr Lys Ile Val Asp Tyr Trp Ala
305                 310                 315                 320

Asn Asn Asp Lys Thr Leu Ile Glu Tyr Ser Leu Gln Asp Ala Lys Tyr
                325                 330                 335

Thr Tyr Lys Ile Gly Lys Tyr Phe Phe Pro Leu Glu Val Met Phe Ser
            340                 345                 350

Arg Ile Val Asn Gln Thr Pro Phe Glu Ile Thr Arg Met Ser Ser Gly
            355                 360                 365

Gln Met Val Glu Tyr Leu Leu Met Lys Arg Ala Phe Lys Glu Asn Met
        370                 375                 380

Ile Val Pro Asn Lys Pro Asp Glu Glu Tyr Arg Arg Arg Val Leu
385                 390                 395                 400

Thr Thr Tyr Glu Gly Gly Tyr Val Lys Glu Pro Lys Gly Met Phe
                405                 410                 415

Glu Asp Ile Ile Ser Met Asp Phe Arg Cys His Pro Lys Gly Thr Lys
                420                 425                 430

Val Val Val Lys Gly Lys Gly Ile Val Asn Ile Glu Asp Val Lys Glu
            435                 440                 445

Gly Asn Tyr Val Leu Gly Ile Asp Gly Trp Gln Lys Val Lys Lys Val
            450                 455                 460

Trp Lys Tyr Glu Tyr Glu Gly Glu Leu Ile Asn Val Asn Gly Leu Lys
465                 470                 475                 480

Cys Thr Pro Asn His Lys Ile Pro Leu Arg Tyr Lys Ile Lys His Lys
                485                 490                 495

Lys Ile Asn Lys Asn Asp Tyr Leu Val Arg Asp Ile Tyr Ala Lys Ser
            500                 505                 510

Leu Leu Thr Lys Phe Lys Gly Glu Gly Lys Leu Ile Leu Cys Lys Asp
            515                 520                 525

Phe Glu Thr Ile Gly Asn Tyr Glu Lys Tyr Ile Asn Asp Met Asp Glu
        530                 535                 540

Asp Phe Ile Leu Lys Ser Glu Leu Ile Gly Ile Leu Ala Glu Gly
545                 550                 555                 560

His Leu Leu Arg Arg Asp Ile Glu Tyr Phe Asp Ser Ser Arg Gly Lys
                565                 570                 575

Lys Arg Ile Ser His Gln Tyr Arg Val Glu Ile Thr Val Asn Glu Asp
            580                 585                 590

Glu Lys Asp Phe Ile Glu Lys Ile Lys Tyr Ile Phe Lys Lys Leu Phe
            595                 600                 605

Asn Tyr Glu Leu Tyr Val Arg Arg Lys Gly Thr Lys Ala Ile Thr
        610                 615                 620

Leu Gly Cys Ala Lys Lys Asp Ile Tyr Leu Lys Ile Glu Glu Ile Leu
625                 630                 635                 640

Lys Asn Lys Glu Lys Tyr Leu Pro Asn Ala Ile Leu Arg Gly Phe Phe
                645                 650                 655

Glu Gly Asp Gly Tyr Val Asn Thr Val Arg Arg Ala Val Val Val Asn
            660                 665                 670
```

-continued

```
Gln Gly Thr Asn Asn Tyr Asp Lys Ile Lys Phe Ile Ala Ser Leu Leu
        675                 680                 685

Asp Arg Leu Gly Ile Lys Tyr Ser Phe Tyr Thr Tyr Ser Tyr Glu Glu
    690                 695                 700

Arg Gly Lys Lys Leu Lys Arg Tyr Val Ile Glu Ile Phe Ser Lys Gly
705                 710                 715                 720

Asp Leu Ile Lys Phe Ser Ile Leu Ile Ser Phe Ile Ser Arg Arg Lys
                725                 730                 735

Asn Asn Leu Leu Asn Glu Ile Ile Arg Gln Lys Thr Leu Tyr Lys Ile
            740                 745                 750

Gly Asp Tyr Gly Phe Tyr Asp Leu Asp Asp Val Cys Val Ser Leu Glu
        755                 760                 765

Ser Tyr Lys Gly Glu Val Tyr Asp Leu Thr Leu Glu Gly Arg Pro Tyr
    770                 775                 780

Tyr Phe Ala Asn Gly Ile Leu Thr His Asn Ser Leu Tyr Pro Ser Ile
785                 790                 795                 800

Ile Ile Ser Tyr Asn Ile Ser Pro Asp Thr Leu Asp Cys Glu Cys Cys
                805                 810                 815

Lys Asp Val Ser Glu Lys Ile Leu Gly His Trp Phe Cys Lys Lys Lys
            820                 825                 830

Glu Gly Leu Ile Pro Lys Thr Leu Arg Asn Leu Ile Glu Arg Arg Ile
        835                 840                 845

Asn Ile Lys Arg Arg Met Lys Lys Met Ala Glu Ile Gly Glu Ile Asn
    850                 855                 860

Glu Glu Tyr Asn Leu Leu Asp Tyr Glu Gln Lys Ser Leu Lys Ile Leu
865                 870                 875                 880

Ala Asn Ser Ile Leu Pro Asp Glu Tyr Leu Thr Ile Ile Glu Glu Asp
                885                 890                 895

Gly Ile Lys Val Val Lys Ile Gly Glu Tyr Ile Asp Asp Leu Met Arg
            900                 905                 910

Lys His Lys Asp Lys Ile Lys Phe Ser Gly Ile Ser Glu Ile Leu Glu
        915                 920                 925

Thr Lys Asn Leu Lys Thr Phe Ser Phe Asp Lys Ile Thr Lys Lys Cys
    930                 935                 940

Glu Ile Lys Lys Val Lys Ala Leu Ile Arg His Pro Tyr Phe Gly Lys
945                 950                 955                 960

Ala Tyr Lys Ile Lys Leu Arg Ser Gly Arg Thr Ile Lys Val Thr Arg
                965                 970                 975

Gly His Ser Leu Phe Lys Tyr Glu Asn Gly Lys Ile Val Glu Val Lys
            980                 985                 990

Gly Asp Asp Val Arg Phe Gly Asp Leu Ile Val Val Pro Lys Lys Leu
        995                 1000                1005

Thr Cys Val Asp Lys Glu Val Val Ile Asn Ile Pro Lys Arg Leu
    1010                1015                1020

Ile Asn Ala Asp Glu Glu Glu Ile Lys Asp Leu Val Ile Thr Lys
    1025                1030                1035

His Lys Asp Lys Ala Phe Phe Val Lys Leu Lys Lys Thr Leu Glu
    1040                1045                1050

Asp Ile Glu Asn Asn Lys Leu Lys Val Ile Phe Asp Asp Cys Ile
    1055                1060                1065

Leu Tyr Leu Lys Glu Leu Gly Leu Ile Asp Tyr Asn Ile Ile Lys
    1070                1075                1080

Lys Ile Asn Lys Val Asp Ile Lys Ile Leu Asp Glu Glu Lys Phe
    1085                1090                1095
```

-continued

```
Lys Ala Tyr Lys Lys Tyr Phe Asp Thr Val Ile Glu His Gly Asn
    1100            1105            1110
Phe Lys Lys Gly Arg Cys Asn Ile Gln Tyr Ile Lys Ile Lys Asp
    1115            1120            1125
Tyr Ile Ala Asn Ile Pro Asp Lys Glu Phe Glu Asp Cys Glu Ile
    1130            1135            1140
Gly Ala Tyr Ser Gly Lys Ile Asn Ala Leu Leu Lys Leu Asp Glu
    1145            1150            1155
Lys Leu Ala Lys Phe Leu Gly Phe Phe Val Thr Arg Gly Arg Leu
    1160            1165            1170
Lys Lys Gln Lys Leu Lys Gly Glu Thr Val Tyr Glu Ile Ser Val
    1175            1180            1185
Tyr Lys Ser Leu Pro Glu Tyr Gln Lys Glu Ile Ala Glu Thr Phe
    1190            1195            1200
Lys Glu Val Phe Gly Ala Gly Ser Met Val Lys Asp Lys Val Thr
    1205            1210            1215
Met Asp Asn Lys Ile Val Tyr Leu Val Leu Lys Tyr Ile Phe Lys
    1220            1225            1230
Cys Gly Asp Lys Asp Lys Lys His Ile Pro Glu Glu Leu Phe Leu
    1235            1240            1245
Ala Ser Glu Ser Val Ile Lys Ser Phe Leu Asp Gly Phe Leu Lys
    1250            1255            1260
Ala Lys Lys Asn Ser His Lys Gly Thr Ser Thr Phe Met Ala Lys
    1265            1270            1275
Asp Glu Lys Tyr Leu Asn Gln Leu Met Ile Leu Phe Asn Leu Val
    1280            1285            1290
Gly Ile Pro Thr Arg Phe Thr Pro Val Lys Asn Lys Gly Tyr Lys
    1295            1300            1305
Leu Thr Leu Asn Pro Lys Tyr Gly Thr Val Lys Asp Leu Met Leu
    1310            1315            1320
Asp Glu Val Lys Glu Ile Glu Ala Phe Glu Tyr Ser Gly Tyr Val
    1325            1330            1335
Tyr Asp Leu Ser Val Glu Asp Asn Glu Asn Phe Leu Val Asn Asn
    1340            1345            1350
Ile Tyr Ala His Asn Ser Val Tyr Gly Tyr Leu Ala Phe Pro Arg
    1355            1360            1365
Ala Arg Phe Tyr Ser Arg Glu Cys Ala Glu Ile Val Thr Tyr Leu
    1370            1375            1380
Gly Arg Lys Tyr Ile Leu Glu Thr Val Lys Glu Ala Glu Lys Phe
    1385            1390            1395
Gly Phe Lys Val Leu Tyr Ile Asp Thr Asp Gly Phe Tyr Ala Ile
    1400            1405            1410
Trp Lys Glu Lys Ile Ser Lys Glu Glu Leu Ile Lys Lys Ala Met
    1415            1420            1425
Glu Phe Val Glu Tyr Ile Asn Ser Lys Leu Pro Gly Thr Met Glu
    1430            1435            1440
Leu Glu Phe Glu Gly Tyr Phe Lys Arg Gly Ile Phe Val Thr Lys
    1445            1450            1455
Lys Arg Tyr Ala Leu Ile Asp Glu Asn Gly Arg Val Thr Val Lys
    1460            1465            1470
Gly Leu Glu Phe Val Arg Arg Asp Trp Ser Asn Ile Ala Lys Ile
    1475            1480            1485
Thr Gln Arg Arg Val Leu Glu Ala Leu Leu Val Glu Gly Ser Ile
```

-continued

```
            1490                1495                1500

Glu Lys Ala Lys Lys Ile Ile Gln Asp Val Ile Lys Asp Leu Arg
    1505                1510                1515

Glu Lys Lys Ile Lys Lys Glu Asp Leu Ile Ile Tyr Thr Gln Leu
    1520                1525                1530

Thr Lys Asp Pro Lys Glu Tyr Lys Thr Thr Ala Pro His Val Glu
    1535                1540                1545

Ile Ala Lys Lys Leu Met Arg Glu Gly Lys Arg Ile Lys Val Gly
    1550                1555                1560

Asp Ile Ile Gly Tyr Ile Ile Val Lys Gly Thr Lys Ser Ile Ser
    1565                1570                1575

Glu Arg Ala Lys Leu Pro Glu Glu Val Asp Ile Asp Ile Asp
    1580                1585                1590

Val Asn Tyr Tyr Ile Asp Asn Gln Ile Leu Pro Pro Val Leu Arg
    1595                1600                1605

Ile Met Glu Ala Val Gly Val Ser Lys Asn Glu Leu Lys Lys Glu
    1610                1615                1620

Gly Ala Gln Leu Thr Leu Asp Lys Phe Phe Lys
    1625                1630

<210> SEQ ID NO 75
<211> LENGTH: 803
<212> TYPE: PRT
<213> ORGANISM: Pyrodictium occultum

<400> SEQUENCE: 75

Met Thr Glu Thr Ile Glu Phe Val Leu Leu Asp Ser Ser Tyr Glu Ile
1               5                   10                  15

Leu Gly Lys Glu Pro Val Val Ile Leu Trp Gly Ile Thr Leu Asp Gly
                20                  25                  30

Lys Arg Val Val Leu Leu Asp His Arg Phe Arg Pro Tyr Phe Tyr Ala
            35                  40                  45

Leu Ile Ala Arg Gly Tyr Glu Asp Met Val Glu Glu Ile Ala Ala Ser
        50                  55                  60

Ile Arg Arg Leu Ser Val Val Lys Ser Pro Ile Ile Asp Ala Lys Pro
65                  70                  75                  80

Leu Asp Lys Arg Tyr Phe Gly Arg Pro Arg Lys Ala Val Lys Ile Thr
                85                  90                  95

Thr Met Ile Pro Glu Ser Val Arg His Tyr Arg Glu Ala Val Lys Lys
            100                 105                 110

Ile Glu Gly Val Glu Asp Ser Leu Glu Ala Asp Ile Arg Phe Ala Met
        115                 120                 125

Arg Tyr Leu Ile Asp Lys Arg Leu Tyr Pro Phe Thr Val Tyr Arg Ile
    130                 135                 140

Pro Val Glu Asp Ala Gly Arg Asn Pro Gly Phe Arg Val Asp Arg Val
145                 150                 155                 160

Tyr Lys Val Ala Gly Asp Pro Glu Pro Leu Ala Asp Ile Thr Arg Ile
                165                 170                 175

Asp Leu Pro Pro Met Arg Leu Val Ala Phe Asp Ile Glu Val Tyr Ser
            180                 185                 190

Arg Arg Gly Ser Pro Asn Pro Ala Arg Asp Pro Val Ile Ile Val Ser
        195                 200                 205

Leu Arg Asp Ser Glu Gly Lys Glu Arg Leu Ile Glu Ala Glu Gly His
    210                 215                 220

Asp Asp Arg Arg Val Leu Arg Glu Phe Val Glu Tyr Val Arg Ala Phe
```

```
                225                 230                 235                 240
        Asp Pro Asp Ile Ile Val Gly Tyr Asn Ser Asn His Phe Asp Trp Pro
                        245                 250                 255

Tyr Leu Met Glu Arg Ala Arg Arg Leu Gly Ile Lys Leu Asp Val Thr
                        260                 265                 270

Arg Arg Val Gly Ala Glu Pro Thr Thr Ser Val Tyr Gly His Val Ser
                        275                 280                 285

Val Gln Gly Arg Leu Asn Val Asp Leu Tyr Asp Tyr Ala Glu Glu Met
                        290                 295                 300

Pro Glu Ile Lys Met Lys Thr Leu Glu Glu Val Ala Glu Tyr Leu Gly
        305                 310                 315                 320

Val Met Lys Lys Ser Glu Arg Val Ile Ile Glu Trp Trp Arg Ile Pro
                        325                 330                 335

Glu Tyr Trp Asp Asp Glu Lys Lys Arg Gln Leu Leu Glu Arg Tyr Ala
                        340                 345                 350

Leu Asp Asp Val Arg Ala Thr Tyr Gly Leu Ala Glu Lys Met Leu Pro
                        355                 360                 365

Phe Ala Ile Gln Leu Ser Thr Val Thr Gly Val Pro Leu Asp Gln Val
                        370                 375                 380

Gly Ala Met Gly Val Gly Phe Arg Leu Glu Trp Tyr Leu Met Arg Ala
        385                 390                 395                 400

Ala Tyr Asp Met Asn Glu Leu Val Pro Asn Arg Val Glu Arg Arg Gly
                        405                 410                 415

Glu Ser Tyr Lys Gly Ala Val Val Leu Lys Pro Leu Lys Gly Val His
                        420                 425                 430

Glu Asn Val Val Leu Asp Phe Ser Ser Met Tyr Pro Ser Ile Met
                        435                 440                 445

Ile Lys Tyr Asn Val Gly Pro Asp Thr Ile Val Asp Asp Pro Ser Glu
                        450                 455                 460

Cys Pro Lys Tyr Gly Gly Cys Tyr Val Ala Pro Glu Val Gly His Arg
        465                 470                 475                 480

Phe Arg Arg Ser Pro Pro Gly Phe Phe Lys Thr Val Leu Glu Asn Leu
                        485                 490                 495

Leu Lys Leu Arg Arg Gln Val Lys Glu Lys Met Lys Glu Phe Pro Pro
                        500                 505                 510

Asp Ser Pro Glu Tyr Arg Leu Tyr Asp Glu Arg Gln Lys Ala Leu Lys
                        515                 520                 525

Val Leu Ala Asn Ala Ser Tyr Gly Tyr Met Gly Trp Ser His Ala Arg
                        530                 535                 540

Trp Tyr Cys Lys Arg Cys Ala Glu Ala Val Thr Ala Trp Gly Arg Asn
        545                 550                 555                 560

Leu Ile Leu Thr Ala Ile Glu Tyr Ala Arg Lys Leu Gly Leu Lys Val
                        565                 570                 575

Ile Tyr Gly Asp Thr Asp Ser Leu Phe Val Val Tyr Lys Glu Lys
                        580                 585                 590

Val Glu Lys Leu Ile Glu Phe Val Lys Glu Leu Gly Phe Glu Ile
                        595                 600                 605

Lys Ile Asp Lys Ile Tyr Lys Lys Val Phe Phe Thr Glu Ala Lys Lys
                        610                 615                 620

Arg Tyr Val Gly Leu Leu Glu Asp Gly Arg Ile Asp Ile Val Gly Phe
        625                 630                 635                 640

Glu Ala Val Arg Gly Asp Trp Cys Glu Leu Ala Lys Glu Val Gln Glu
                        645                 650                 655
```

```
Lys Ala Ala Glu Ile Val Leu Asn Thr Gly Asn Val Asp Lys Ala Ile
            660                 665                 670

Ser Tyr Ile Arg Glu Val Ile Lys Gln Leu Arg Glu Gly Lys Val Pro
            675                 680                 685

Ile Thr Lys Leu Ile Ile Trp Lys Thr Leu Ser Lys Arg Ile Glu Glu
            690                 695                 700

Tyr Glu His Asp Ala Pro His Val Met Ala Arg Arg Met Lys Glu
705             710                 715                 720

Ala Gly Tyr Glu Val Ser Pro Gly Asp Lys Val Gly Tyr Val Ile Val
                725                 730                 735

Lys Gly Ser Gly Ser Val Ser Ser Arg Ala Tyr Pro Tyr Phe Met Val
            740                 745                 750

Asp Pro Ser Thr Ile Asp Val Asn Tyr Tyr Ile Asp His Gln Ile Val
            755                 760                 765

Pro Ala Ala Leu Arg Ile Leu Ser Tyr Phe Gly Val Thr Glu Lys Gln
            770                 775                 780

Leu Lys Ala Ala Ala Thr Val Gln Arg Ser Leu Phe Asp Phe Phe Ala
785             790                 795                 800

Ser Lys Lys

<210> SEQ ID NO 76
<211> LENGTH: 784
<212> TYPE: PRT
<213> ORGANISM: Aeropyrum pernix

<400> SEQUENCE: 76

Met Arg Gly Ser Thr Pro Val Ile Ile Leu Trp Gly Arg Gly Ala Asp
1               5                   10                  15

Gly Ser Arg Val Val Phe Tyr Gly Glu Phe Arg Pro Tyr Phe Tyr
            20                  25                  30

Val Leu Pro Asp Gly Ser Val Gly Leu Asp Gln Leu Ala Ala Met Ile
            35                  40                  45

Arg Arg Leu Ser Arg Pro Ser Ser Pro Ile Leu Ser Val Glu Arg Val
            50                  55                  60

Arg Arg Arg Phe Ile Gly Arg Glu Val Glu Ala Leu Lys Val Thr Thr
65              70                  75                  80

Leu Val Pro Ala Ser Val Arg Glu Tyr Arg Glu Ala Val Arg Arg Leu
                85                  90                  95

Gly Gly Val Arg Asp Val Leu Glu Ala Asp Ile Pro Phe Ala Leu Arg
            100                 105                 110

Phe Ile Ile Asp Phe Asn Leu Tyr Pro Met Arg Trp Tyr Val Ala Glu
            115                 120                 125

Val Arg Glu Val Ala Val Pro His Gly Tyr Ser Val Asp Arg Ala Tyr
            130                 135                 140

Thr Leu Ser Gly Asp Ile Arg Glu Asp Glu Thr Arg Ile Gln Glu Asp
145             150                 155                 160

Pro Leu Lys Gly Leu Arg Val Met Ala Phe Asp Ile Glu Val Tyr Ser
                165                 170                 175

Lys Met Arg Thr Pro Asp Pro Lys Lys Asp Pro Val Ile Met Ile Gly
            180                 185                 190

Leu Gln Gln Ala Gly Gly Glu Ile Glu Ile Leu Glu Ala Glu Asp Arg
            195                 200                 205

Ser Asp Lys Lys Val Ile Ala Gly Phe Val Glu Arg Val Lys Ser Ile
            210                 215                 220

Asp Pro Asp Val Ile Val Gly Tyr Asn Gln Asn Arg Phe Asp Trp Pro
```

```
                 225                 230                 235                 240

Tyr Leu Val Glu Arg Ala Arg Val Leu Gly Val Lys Leu Ala Val Gly
                        245                 250                 255

Arg Arg Ser Val Glu Pro Gln Pro Gly Leu Tyr Gly His Tyr Ser Val
                        260                 265                 270

Ser Gly Arg Leu Asn Val Asp Leu Leu Asp Phe Ala Glu Glu Leu His
                        275                 280                 285

Glu Val Lys Val Lys Thr Leu Glu Glu Val Ala Asp Tyr Leu Gly Val
                        290                 295                 300

Val Lys Ile Gly Glu Arg Val Thr Leu Glu Trp Trp Gln Ile Gly Glu
        305                 310                 315                 320

Tyr Trp Asp Asp Pro Ser Lys Arg Glu Ile Leu Arg Lys Tyr Leu Arg
                        325                 330                 335

Asp Asp Val Arg Ser Thr Met Gly Leu Ala Glu Lys Phe Leu Pro Phe
                        340                 345                 350

Gly Ala Glu Leu Ser Gln Val Ser Gly Leu Pro Leu Asp Gln Val Met
                        355                 360                 365

Ala Ala Ser Val Gly Phe Arg Leu Glu Trp Arg Leu Ile Arg Glu Ala
                        370                 375                 380

Ala Lys Leu Gly Glu Leu Val Pro Asn Arg Val Glu Arg Ser Glu Gly
        385                 390                 395                 400

Arg Tyr Ala Gly Ala Ile Val Leu Arg Pro Lys Pro Gly Val His Glu
                        405                 410                 415

Asp Ile Ala Val Leu Asp Phe Ala Ser Met Tyr Pro Asn Ile Met Val
                        420                 425                 430

Lys Tyr Asn Val Gly Pro Asp Thr Leu Val Arg Pro Gly Glu Glu Tyr
                        435                 440                 445

Gly Glu Glu Val Tyr Thr Ala Pro Glu Val Gly His Lys Phe Arg
                        450                 455                 460

Lys Ser Pro Pro Gly Phe Phe Lys Lys Ile Leu Glu Arg Phe Leu Ser
        465                 470                 475                 480

Trp Arg Arg Gln Ile Arg Ser Glu Met Lys Lys His Pro Pro Asp Ser
                        485                 490                 495

Pro Glu Tyr Lys Leu Leu Asp Glu Arg Gln Lys Ala Ile Lys Leu Leu
                        500                 505                 510

Ala Asn Ala Ser Tyr Gly Tyr Met Gly Trp Pro His Ala Arg Trp Tyr
                        515                 520                 525

Cys Arg Glu Cys Ala Glu Ala Val Thr Ala Trp Gly Arg Ser Ile Ile
                        530                 535                 540

Arg Thr Ala Ile Arg Lys Ala Gly Glu Leu Gly Leu Glu Val Ile Tyr
        545                 550                 555                 560

Gly Asp Thr Asp Ser Leu Phe Val Lys Asn Asp Pro Glu Lys Val Glu
                        565                 570                 575

Arg Leu Ile Arg Phe Val Glu Glu Leu Gly Phe Asp Ile Lys Val
                        580                 585                 590

Asp Lys Val Tyr Arg Arg Val Phe Phe Thr Glu Ala Lys Lys Arg Tyr
                        595                 600                 605

Val Gly Leu Thr Val Asp Gly Lys Ile Asp Val Val Gly Phe Glu Ala
                        610                 615                 620

Val Arg Gly Asp Trp Ser Glu Leu Ala Lys Glu Thr Gln Phe Lys Val
        625                 630                 635                 640

Ala Glu Ile Val Leu Lys Thr Gly Ser Val Asp Glu Ala Val Asp Tyr
                        645                 650                 655
```

-continued

```
Val Arg Asn Ile Ile Glu Lys Leu Arg Arg Gly Gln Val Asp Met Arg
                660                 665                 670

Lys Leu Val Ile Trp Lys Thr Leu Thr Arg Pro Pro Ser Met Tyr Glu
            675                 680                 685

Ala Arg Gln Pro His Val Thr Ala Ala Leu Leu Met Glu Arg Ala Gly
        690                 695                 700

Ile Lys Val Glu Pro Gly Ala Lys Ile Gly Tyr Val Thr Lys Gly
705                 710                 715                 720

Ser Gly Pro Leu Tyr Thr Arg Ala Lys Pro Tyr Phe Met Ala Ser Lys
                725                 730                 735

Glu Glu Val Asp Val Glu Tyr Tyr Val Asp Lys Gln Val Pro Ala
            740                 745                 750

Ala Leu Arg Ile Leu Gln Tyr Phe Gly Val Thr Glu Lys Arg Leu Lys
        755                 760                 765

Gly Gly Gly Arg Gln Ser Thr Leu Leu Asp Phe Met Arg Gly Lys
770                 775                 780

<210> SEQ ID NO 77
<211> LENGTH: 781
<212> TYPE: PRT
<213> ORGANISM: Archaeoglobus fulgidus

<400> SEQUENCE: 77

Met Glu Arg Val Glu Gly Trp Leu Ile Asp Ala Asp Tyr Glu Thr Ile
1               5                   10                  15

Gly Gly Lys Ala Val Val Arg Leu Trp Cys Lys Asp Asp Gln Gly Ile
            20                  25                  30

Phe Val Ala Tyr Asp Tyr Asn Phe Asp Pro Tyr Phe Tyr Val Ile Gly
        35                  40                  45

Val Asp Glu Asp Ile Leu Lys Asn Ala Ala Thr Ser Thr Arg Arg Glu
    50                  55                  60

Val Ile Lys Leu Lys Ser Phe Glu Lys Ala Gln Leu Lys Thr Leu Gly
65                  70                  75                  80

Arg Glu Val Glu Gly Tyr Ile Val Tyr Ala His His Pro Gln His Val
                85                  90                  95

Pro Lys Leu Arg Asp Tyr Leu Ser Gln Phe Gly Asp Val Arg Glu Ala
            100                 105                 110

Asp Ile Pro Phe Ala Tyr Arg Tyr Leu Ile Asp Lys Asp Leu Ala Cys
        115                 120                 125

Met Asp Gly Ile Ala Ile Glu Gly Glu Lys Gln Gly Gly Val Ile Arg
    130                 135                 140

Ser Tyr Lys Ile Glu Lys Val Glu Arg Ile Pro Arg Met Glu Phe Pro
145                 150                 155                 160

Glu Leu Lys Met Leu Val Phe Asp Cys Glu Met Leu Ser Ser Phe Gly
                165                 170                 175

Met Pro Glu Pro Glu Lys Asp Pro Ile Ile Val Ile Ser Val Lys Thr
            180                 185                 190

Asn Asp Asp Asp Glu Ile Ile Leu Thr Gly Asp Glu Arg Lys Ile Ile
        195                 200                 205

Ser Asp Phe Val Lys Leu Ile Lys Ser Tyr Pro Asp Ile Ile Val
    210                 215                 220

Gly Tyr Asn Gln Asp Ala Phe Asp Trp Pro Tyr Leu Arg Lys Arg Ala
225                 230                 235                 240

Glu Arg Trp Asn Ile Pro Leu Asp Val Gly Arg Asp Gly Ser Asn Val
                245                 250                 255
```

-continued

```
Val Phe Arg Gly Gly Arg Pro Lys Ile Thr Gly Arg Leu Asn Val Asp
            260                 265                 270

Leu Tyr Asp Ile Ala Met Arg Ser Asp Ile Lys Ile Lys Lys Leu
        275                 280                 285

Glu Asn Val Ala Glu Phe Leu Gly Thr Lys Ile Glu Ile Ala Asp Ile
        290                 295                 300

Glu Ala Lys Asp Ile Tyr Arg Tyr Trp Ser Arg Gly Glu Lys Glu Lys
305                 310                 315                 320

Val Leu Asn Tyr Ala Arg Gln Asp Ala Ile Asn Thr Tyr Leu Ile Ala
                325                 330                 335

Lys Glu Leu Leu Pro Met His Tyr Glu Leu Ser Lys Met Ile Arg Leu
            340                 345                 350

Pro Val Asp Asp Val Thr Arg Met Gly Arg Gly Lys Gln Val Asp Trp
        355                 360                 365

Leu Leu Leu Ser Glu Ala Lys Lys Ile Gly Glu Ile Ala Pro Asn Pro
    370                 375                 380

Pro Glu His Ala Glu Ser Tyr Glu Gly Ala Phe Val Leu Glu Pro Glu
385                 390                 395                 400

Arg Gly Leu His Glu Asn Val Ala Cys Leu Asp Phe Ala Ser Met Tyr
                405                 410                 415

Pro Ser Ile Met Ile Ala Phe Asn Ile Ser Pro Asp Thr Tyr Gly Cys
            420                 425                 430

Arg Asp Asp Cys Tyr Glu Ala Pro Glu Val Gly His Lys Phe Arg Lys
        435                 440                 445

Ser Pro Asp Gly Phe Phe Lys Arg Ile Leu Arg Met Leu Ile Glu Lys
    450                 455                 460

Arg Arg Glu Leu Lys Val Glu Leu Lys Asn Leu Ser Pro Glu Ser Ser
465                 470                 475                 480

Glu Tyr Lys Leu Leu Asp Ile Lys Gln Gln Thr Leu Lys Val Leu Thr
                485                 490                 495

Asn Ser Phe Tyr Gly Tyr Met Gly Trp Asn Leu Ala Arg Trp Tyr Cys
            500                 505                 510

His Pro Cys Ala Glu Ala Thr Thr Ala Trp Gly Arg His Phe Ile Arg
        515                 520                 525

Thr Ser Ala Lys Ile Ala Glu Ser Met Gly Phe Lys Val Leu Tyr Gly
    530                 535                 540

Asp Thr Asp Ser Ile Phe Val Thr Lys Ala Gly Met Thr Lys Glu Asp
545                 550                 555                 560

Val Asp Arg Leu Ile Asp Lys Leu His Glu Leu Pro Ile Gln Ile
                565                 570                 575

Glu Val Asp Glu Tyr Tyr Ser Ala Ile Phe Phe Val Gly Lys Lys Arg
            580                 585                 590

Tyr Ala Gly Leu Thr Glu Asp Gly Arg Leu Val Val Lys Gly Leu Glu
        595                 600                 605

Val Arg Arg Gly Asp Trp Cys Glu Leu Ala Lys Lys Val Gln Arg Glu
    610                 615                 620

Val Ile Glu Val Ile Leu Lys Lys Asn Pro Glu Lys Ala Leu Ser
625                 630                 635                 640

Leu Val Lys Asp Val Ile Leu Arg Ile Lys Glu Gly Lys Val Ser Leu
                645                 650                 655

Glu Glu Val Val Ile Tyr Lys Gly Leu Thr Lys Lys Pro Ser Lys Tyr
            660                 665                 670

Glu Ser Met Gln Ala His Val Lys Ala Ala Leu Lys Ala Arg Glu Met
        675                 680                 685
```

```
Gly Ile Ile Tyr Pro Val Ser Ser Lys Ile Gly Tyr Val Ile Val Lys
            690                 695                 700

Gly Ser Gly Asn Ile Gly Asp Arg Ala Tyr Pro Ile Asp Leu Ile Glu
705                 710                 715                 720

Asp Phe Asp Gly Glu Asn Leu Arg Ile Lys Thr Lys Ser Gly Ile Glu
            725                 730                 735

Ile Lys Lys Leu Asp Lys Asp Tyr Tyr Ile Asp Asn Gln Ile Ile Pro
            740                 745                 750

Ser Val Leu Arg Ile Leu Glu Arg Phe Gly Tyr Thr Glu Ala Ser Leu
            755                 760                 765

Lys Gly Ser Ser Gln Met Ser Leu Asp Ser Phe Phe Ser
            770                 775                 780

<210> SEQ ID NO 78
<211> LENGTH: 773
<212> TYPE: PRT
<213> ORGANISM: Desulfurococcus sp. Tok

<400> SEQUENCE: 78

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asp Tyr Asp Arg
                20                  25                  30

Asp Phe Glu Pro Tyr Ile Tyr Ala Leu Leu Lys Asp Asp Ser Ala Ile
            35                  40                  45

Glu Asp Ile Lys Lys Ile Thr Ala Glu Arg His Gly Thr Thr Val Arg
50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
            115                 120                 125

Met Glu Gly Asp Glu Glu Leu Arg Met Leu Ala Phe Asp Ile Glu Thr
130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Met Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Pro Val Phe Gly Gln Pro Lys Glu
            275                 280                 285
```

-continued

```
Lys Val Tyr Ala Glu Glu Ile Ala Arg Ala Trp Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Asp Val Ala
        355                 360                 365

Pro Asn Lys Pro Asp Glu Arg Glu Leu Ala Arg Arg Thr Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Ala Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Asn Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg His Glu Val Pro
                645                 650                 655

Pro Glu Lys Leu Val Ile Tyr Glu Gln Ile Thr Arg Asp Leu Arg Ser
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Pro Gly Arg Val Gly Asp Arg Ala Ile Pro Phe Asp Glu Phe
```

-continued

```
            705                 710                 715                 720
Asp Pro Ala Lys His Arg Tyr Asp Ala Glu Tyr Tyr Ile Glu Asn Gln
                    725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Lys Gln Ala Gly Leu Gly Ala Trp
            755                 760                 765

Leu Lys Pro Lys Thr
        770
```